US012551549B2

(12) United States Patent
Stamatatos et al.

(10) Patent No.: US 12,551,549 B2
(45) Date of Patent: Feb. 17, 2026

(54) METHODS OF ELICITING ANTIBODIES THAT BIND TO FULL-LENGTH GLYCOSYLATED HIV-1 ENV USING MULTIMERIZED ENV CORES

(71) Applicant: FRED HUTCHINSON CANCER CENTER, Seattle, WA (US)

(72) Inventors: Leonidas Stamatatos, Seattle, WA (US); Andrew McGuire, Seattle, WA (US); Katherine Rachael Parks, Seattle, WA (US); Matthew D. Gray, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 18/402,480

(22) Filed: Jan. 2, 2024

(65) Prior Publication Data

US 2024/0238405 A1 Jul. 18, 2024

Related U.S. Application Data

(63) Continuation of application No. 17/269,199, filed as application No. PCT/US2019/048825 on Aug. 29, 2019, now Pat. No. 11,883,485.

(60) Provisional application No. 62/724,555, filed on Aug. 29, 2018.

(51) Int. Cl.
*A61K 39/21* (2006.01)
*A61K 39/02* (2006.01)
*A61K 39/00* (2006.01)

(52) U.S. Cl.
CPC .............. *A61K 39/21* (2013.01); *A61K 39/02* (2013.01); *A61K 2039/545* (2013.01); *C12N 2740/16034* (2013.01); *C12N 2740/16134* (2013.01)

(58) Field of Classification Search
CPC .......... A61K 39/21; C12N 2740/16034; C12N 2740/16134
See application file for complete search history.

(56) References Cited

U.S. PATENT DOCUMENTS

| | | | |
|---|---|---|---|
| 2006/0251679 | A1 | 11/2006 | Carter et al. |
| 2009/0233377 | A1 | 9/2009 | Iwahori |
| 2011/0038025 | A1 | 2/2011 | Naitou et al. |
| 2011/0262474 | A1 | 10/2011 | Du et al. |
| 2016/0272948 | A1 | 9/2016 | Dubrovskaya et al. |
| 2017/0080082 | A1 | 3/2017 | Haynes et al. |

FOREIGN PATENT DOCUMENTS

| | | | |
|---|---|---|---|
| WO | WO201615442 | A1 | 9/2016 |
| WO | WO2016145102 | A1 | 9/2016 |
| WO | WO2016205704 | A2 | 12/2016 |

OTHER PUBLICATIONS

Gerhardt, M., et al., Jul. 2005, In-Depth, Longitudinal Analysis of Viral Quasispecies from an Individual Triply Infected with Late-Stage Human Immunodeficiency Virus Type 1, Using a Multiple PCR Primer Approach, J. Virol. 79(13):8249-8261.*

Arnaout, et al., "High-Resolution Description of Antibody Heavy-Chain Repertoires in Humans," PLoS One, vol. 6, No. 8, 2011, 8 pages.

Bern, et al., "Chapter 13: Byonic: advanced peptide and protein identification software," Current Protocols in Bioinformatics, vol. 40, No. 1, 2012, 14 pages.

Bonsignori, et al., "Maturation Pathway from Germline to Broad HIV-1 Neutralizer of a CD4-Mimic Antibody," Cell, vol. 165, No. 2, 2016, pp. 449-463.

Briney, et al., "Tailored Immunogens Direct Affinity Maturation toward HIV Neutralizing Antibodies," Cell, vol. 166, No. 6, 2016, pp. 1459-1470.e11.

Dosenovic, et al., "Immunization for HIV-1 Broadly Neutralizing Antibodies in Human Ig Knockin Mice," Cell, vol. 161, No. 7, 2015, pp. 1505-1515.

Emsley & Cowtan, "Coot: model-building tools for molecular graphics," Acta Crystallographica Section D, vol. 60, No. 12, 2004, pp. 2126-2132.

Escolano, et al., "Sequential Immunization Elicits Broadly Neutralizing Anti-HIV-1 Antibodies in Ig Knockin Mice," Cell, vol. 166, No. 6, 2016, pp. 1445-1458.e12.

Gautam, et al., "A single injection of anti-HIV-1 antibodies protects against repeated SHIV challenges," Nature, vol. 533, No. 7601, 2016, pp. 105-109.

GenBank [Internet]. Bethesda (MD): National Library of Medicine (US), National Center for Biotechnology Information; [1982]—GenBank Accession No. MN087228, Mus musculus clone N-p4a9-LC immunoglobulin light chain variable region mRNA, partial cds, [cited Mar. 4, 2021]. Available from: https://www.ncbi.nlm.nih.gov/nuccore/MN087228.

GenBank [Internet]. Bethesda (MD): National Library of Medicine (US), National Center for Biotechnology Information; [1982]—GenBank Accession No. MN087231, Mus musculus clone P-p1g2-LC immunoglobulin light chain variable region mRNA, partial cds, [cited Mar. 4, 2021]. Available from: https://www.ncbi.nlm.nih.gov/nuccore/MN087231.

GenBank [Internet]. Bethesda (MD): National Library of Medicine (US), National Center for Biotechnology Information; [1982]—GenBank Accession No. MN087234, Mus musculus clone P-p1d3-LC immunoglobulin light chain variable region mRNA, partial cds, [cited Mar. 4, 2021]. Available from: https://www.ncbi.nlm.nih.gov/nuccore/MN087234.

GenBank [Internet]. Bethesda (MD): National Library of Medicine (US), National Center for Biotechnology Information; [1982]—GenBank Accession No. MN087239, Mus musculus clone B-p2e1-LC immunoglobulin light chain variable region mRNA, partial cds, [cited Mar. 4, 2021]. Available from: https://www.ncbi.nlm.nih.gov/nuccore/MN087239.

(Continued)

*Primary Examiner* — Jeffrey S Parkin

(74) *Attorney, Agent, or Firm* — C. Rachal Winger; Lee & Hayes PC

(57) ABSTRACT

Sequential immunization strategies to guide the maturation of antibodies against the human immunodeficiency virus (HIV) are described. The sequential immunization strategies utilize an HIV envelope protein (Env) that binds germline (gl) B cells as a first (prime) immunization and an Env with a functional glycosylated N276 as a second (boost) immunization. The sequential immunization strategies successfully elicit neutralizing antibodies against HIV.

20 Claims, 61 Drawing Sheets

Specification includes a Sequence Listing.

(56) References Cited

OTHER PUBLICATIONS

GenBank [Internet]. Bethesda (MD): National Library of Medicine (US), National Center for Biotechnology Information; [1982]—GenBank Accession No. MN087243, Mus musculus clone B-p1f2-LC immunoglobulin light chain variable region mRNA, partial cds, [cited Mar. 4, 2021]. Available from: https://www.ncbi.nlm.nih.gov/nuccore/MN087243.
GenBank [Internet]. Bethesda (MD): National Library of Medicine (US), National Center for Biotechnology Information; [1982]—GenBank Accession No. MN087247, Mus musculus clone B-p1c10-LC immunoglobulin light chain variable region mRNA, partial cds, [cited Mar. 4, 2021]. Available from: https://www.ncbi.nlm.nih.gov/nuccore/MN087247.
GenBank [Internet]. Bethesda (MD): National Library of Medicine (US), National Center for Biotechnology Information; [1982]—GenBank Accession No. MN087251, Mus musculus clone B-p1a9-LC immunoglobulin light chain variable region mRNA, partial cds, [cited Mar. 4, 2021]. Available from: https://www.ncbi.nlm.nih.gov/nuccore/MN087251.
GenBank [Internet]. Bethesda (MD): National Library of Medicine (US), National Center for Biotechnology Information; [1982]—GenBank Accession No. MN087254, Mus musculus clone P-p1c4-LC immunoglobulin light chain variable region mRNA, partial cds, [cited Mar. 4, 2021]. Available from: https://www.ncbi.nlm.nih.gov/nuccore/MN087254.
GenBank [Internet]. Bethesda (MD): National Library of Medicine (US), National Center for Biotechnology Information; [1982]—GenBank Accession No. MN087261, Mus musculus clone P-p1f2-LC immunoglobulin light chain variable region mRNA, partial cds, [cited Mar. 4, 2021]. Available from: https://www.ncbi.nlm.nih.gov/nuccore/MN087261.
GenBank [Internet]. Bethesda (MD): National Library of Medicine (US), National Center for Biotechnology Information; [1982]—GenBank Accession No. MN087268, Mus musculus clone P-p1f1-LC immunoglobulin light chain variable region mRNA, partial cds, [cited Mar. 4, 2021]. Available from: https://www.ncbi.nlm.nih.gov/nuccore/MN087268.
GenBank [Internet]. Bethesda (MD): National Library of Medicine (US), National Center for Biotechnology Information; [1982]—GenBank Accession No. MN087275, Mus musculus clone P-p1g2-HC immunoglobulin heavy chain variable region mRNA, partial cds, [cited Mar. 4, 2021]. Available from: https://www.ncbi.nlm.nih.gov/nuccore/MN087275.
GenBank [Internet]. Bethesda (MD): National Library of Medicine (US), National Center for Biotechnology Information; [1982]—GenBank Accession No. MN087277, Mus musculus clone P-p1e3-HC immunoglobulin heavy chain variable region mRNA, partial cds, [cited Mar. 4, 2021]. Available from: https://www.ncbi.nlm.nih.gov/nuccore/MN087277.
GenBank [Internet]. Bethesda (MD): National Library of Medicine (US), National Center for Biotechnology Information; [1982]—GenBank Accession No. MN087282, Mus musculus clone B-p2e2-HC immunoglobulin heavy chain variable region mRNA, partial cds, [cited Mar. 4, 2021]. Available from: https://www.ncbi.nlm.nih.gov/nuccore/MN087282.
GenBank [Internet]. Bethesda (MD): National Library of Medicine (US), National Center for Biotechnology Information; [1982]—GenBank Accession No. MN087286, Mus musculus clone B-p1f8-HC immunoglobulin heavy chain variable region mRNA, partial cds, [cited Mar. 4, 2021]. Available from: https://www.ncbi.nlm.nih.gov/nuccore/MN087286.
GenBank [Internet]. Bethesda (MD): National Library of Medicine (US), National Center for Biotechnology Information; [1982]—GenBank Accession No. MN087290, Mus musculus clone B-p1c11-HC immunoglobulin heavy chain variable region mRNA, partial cds, [cited Mar. 4, 2021]. Available from: https://www.ncbi.nlm.nih.gov/nuccore/MN087290.
GenBank [Internet]. Bethesda (MD): National Library of Medicine (US), National Center for Biotechnology Information; [1982]—GenBank Accession No. MN087294, Mus musculus clone B-p1a11-HC immunoglobulin heavy chain variable region mRNA, partial cds, [cited Mar. 4, 2021]. Available from: https://www.ncbi.nlm.nih.gov/nuccore/MN087294.
GenBank [Internet]. Bethesda (MD): National Library of Medicine (US), National Center for Biotechnology Information; [1982]—GenBank Accession No. MN087296, Mus musculus clone B-p1a9-HC immunoglobulin heavy chain variable region mRNA, partial cds, [cited Mar. 4, 2021]. Available from: https://www.ncbi.nlm.nih.gov/nuccore/MN087296.
GenBank [Internet]. Bethesda (MD): National Library of Medicine (US), National Center for Biotechnology Information; [1982]—GenBank Accession No. MN087302, Mus musculus clone P-p2b7-HC immunoglobulin heavy chain variable region mRNA, partial cds, [cited Mar. 4, 2021]. Available from: https://www.ncbi.nlm.nih.gov/nuccore/MN087302.
GenBank [Internet]. Bethesda (MD): National Library of Medicine (US), National Center for Biotechnology Information; [1982]—GenBank Accession No. MN087307, Mus musculus clone P-p4c5-HC immunoglobulin heavy chain variable region mRNA, partial cds, [cited Mar. 4, 2021]. Available from: https://www.ncbi.nlm.nih.gov/nuccore/MN087307.
GenBank [Internet]. Bethesda (MD): National Library of Medicine (US), National Center for Biotechnology Information; [1982]—GenBank Accession No. MN087312, Mus musculus clone P-p1f1-HC immunoglobulin heavy chain variable region mRNA, partial cds, [cited Mar. 4, 2021]. Available from: https://www.ncbi.nlm.nih.gov/nuccore/MN087312.
GenBank [Internet]. Bethesda (MD): National Library of Medicine (US), National Center for Biotechnology Information; [1982]—GenBank Accession No. MN087313, Mus musculus clone P-p1e7-HC immunoglobulin heavy chain variable region mRNA, partial cds, [cited Mar. 4, 2021]. Available from: https://www.ncbi.nlm.nih.gov/nuccore/MN087313.
GenBank [Internet]. Bethesda (MD): National Library of Medicine (US), National Center for Biotechnology Information; [1982]—GenBank Accession No. MN087314, Mus musculus clone P-p1d1-HC immunoglobulin heavy chain variable region mRNA, partial cds, [cited Mar. 4, 2021]. Available from: https://www.ncbi.nlm.nih.gov/nuccore/MN087314.
GenBank [Internet]. Bethesda (MD): National Library of Medicine (US), National Center for Biotechnology Information; [1982]—GenBank Accession No. MN179663, Synthetic construct 93TH057 WT Core gp120 C4b multimer protein gene, complete cds, [cited Mar. 4, 2021]. Available from: https://www.ncbi.nlm.nih.gov/nuccore/MN179663.
GenBank [Internet]. Bethesda (MD): National Library of Medicine (US), National Center for Biotechnology Information; [1982]—GenBank Accession No. MN179667, Synthetic construct Q168a2 WT Core gp120 protein gene, complete cds, [cited Mar. 4, 2021]. Available from: https://www.ncbi.nlm.nih.gov/nuccore/MN179667.
Kanekiyo, et al., "Rational Design of an Epstein-Barr Virus Vaccine Targeting the Receptor-Binding Site," Cell, vol. 162, No. 5, 2015, pp. 1090-1100.
Kwong, & Mascola, "Human Antibodies that Neutralize HIV-1: Identification, Structures, and B Cell Ontogenies," Immunity, vol. 37, No. 3, 2012, pp. 412-425.
Liao, et al., "Co-evolution of a broadly neutralizing HIV-1 antibody and founder virus," Nature, vol. 496, No. 7446, 2013, pp. 469-476.
Mcguire, et al., "Specifically modified Env immunogens activate B-cell precursors of broadly neutralizing HIV-1 antibodies in transgenic mice," Nature Communications, vol. 7, No. 10618, 2016, 9 pages.
Medina-Ramírez, et al., "Design and crystal structure of a native-like HIV-1 envelope trimer that engages multiple broadly neutralizing antibody precursors in vivo," Journal of Experimental Medicine, vol. 214, No. 9, 2017, pp. 2573-2590.
Parks, et al., "Overcoming Steric Restrictions of VRC01 HIV-1 Neutralizing Antibodies through Immunization," Cell Reports, vol. 29, No. 10, 2019, pp. 3060-3072.e7.

(56) References Cited

OTHER PUBLICATIONS

Pegu, et al., "Neutralizing antibodies to HIV-1 envelope protect more effectively in vivo than those to the CD4 receptor," Science Translational Medicine, vol. 6, No. 243, 2014, 9 pages.
Scharf, et al., "Structural basis for HIV-1 gp120 recognition by a germ-line version of a broadly neutralizing antibody," Pnas USA, vol. 110, No. 15, 2013, pp. 6049-6054.
Scheid, et al., "Sequence and Structural Convergence of Broad and Potent HIV Antibodies That Mimic CD4 Binding," Science, vol. 333, No. 6049, 2011, pp. 1633-1637.
Scheres, "A Bayesian view on cryo-EM structure determination," Journal of Molecular Biology, vol. 415, No. 2, 2012, pp. 406-418.
Scheres, "RELION: Implementation of a Bayesian approach to cryo-EM structure determination," Journal of Structural Biology, vol. 180, No. 3, 2012, pp. 519-530.
Shingai, et al., "Passive transfer of modest titers of potent and broadly neutralizing anti-HIV monoclonal antibodies block SHIV infection in macaques," Journal of Experimental Medicine, vol. 211, No. 10, 2014, pp. 2061-2074.
Sok, et al., "Priming HIV-1 broadly neutralizing antibody precursors in human Ig loci transgenic mice," Science, vol. 353, No. 6307, 2016, pp. 1557-1560.
Suloway, et al., "Automated molecular microscopy: The new Leginon system," Journal of Structural Biology, vol. 151, No. 1, 2005, pp. 41-60.
Veesler, et al., "Single-particle EM reveals plasticity of interactions between the adenovirus penton base and integrin ALPHA-v BETa-3," PNAS USA, vol. 111, No. 24, 2014, pp. 8815-8819.
Voss, et al., "DoG Picker and TiltPicker: Software tools to facilitate particle selection in single particle electron microscopy," Journal of Structural Biology, vol. 166, No. 2, 2009, pp. 205-213.
Weidle, et al., "Crystal structure of glycosylated 426c HIV-1 gp120 core G459C in complex with glVRC01 A60C heavy chain," World Wide Protein Data Bank, 2020, 49 pages.
Wu, et al., "Rational Design of Envelope Identifies Broadly Neutralizing Human Monoclonal Antibodies to HIV-1," Science, vol. 329, No. 5993, 2010, pp. 856-861.
Bachmann, et al., "Neutralizing Antiviral B Cell Responses," Annual Review of Immunology, vol. 15, 1997, pp. 235-270.
Balazs, et al., "Antibody-based protection against HIV infection by vectored immunoprophylaxis," Nature, vol. 481, 2012, pp. 81-84.
Blom, et al., "Complement inhibitor C4b-binding protein-friend or foe in the innate immune system?," Molecular Immunology, vol. 40, No. 18, 2004, pp. 1333-1346.
Bonsignori, et al., "Inference of the HIV-1 VRC01 Antibody Lineage Unmutated Common Ancestor Reveals Alternative Pathways to Overcome a Key Glycan Barrier," Immunity, vol. 49, No. 6, 2018, pp. 1162-1174.e8.
Dintzis, et al., "Molecular determinants of immunogenicity: the immunon model of immune response," PNAS USA, vol. 73, No. 10, 1976, pp. 3671-3675.
Escolano, et al., "Immunization expands B cells specific to HIV-1 V3 glycan in mice and macaques," Nature, vol. 570, 2019, pp. 468-473.
Forbes, et al., "T Cell Responses Induced by Adenoviral Vectored Vaccines Can be Adjuvanted by Fusion of Antigen to the Oligomerization Domain of C4b-binding Protein," PLoS One, vol. 7, No. 9, 2012, 12 pages.
GenBank [Internet]. Bethesda (MD): National Library of Medicine (US), National Center for Biotechnology Information; [1982]—GenBank Accession No. MN087229, Mus musculus clone N-p3g9-LC immunoglobulin light chain variable region mRNA, partial cds, [cited Mar. 4, 2021]. Available from: https://www.ncbi.nlm.nih.gov/nuccore/MN087229.
GenBank [Internet]. Bethesda (MD): National Library of Medicine (US), National Center for Biotechnology Information; [1982]—GenBank Accession No. MN087232, Mus musculus clone P-p1e5-LC immunoglobulin light chain variable region mRNA, partial cds, [cited Mar. 4, 2021]. Available from: https://www.ncbi.nlm.nih.gov/nuccore/MN087232.
GenBank [Internet]. Bethesda (MD): National Library of Medicine (US), National Center for Biotechnology Information; [1982]—GenBank Accession No. MN087233, Mus musculus clone P-p1e3-LC immunoglobulin light chain variable region mRNA, partial cds, [cited Mar. 4, 2021]. Available from: https://www.ncbi.nlm.nih.gov/nuccore/MN087233.
GenBank [Internet]. Bethesda (MD): National Library of Medicine (US), National Center for Biotechnology Information; [1982]—GenBank Accession No. MN087235, Mus musculus clone P-p1d1-C-LC immunoglobulin light chain variable region mRNA, partial cds, [cited Mar. 4, 2021]. Available from: https://www.ncbi.nlm.nih.gov/nuccore/MN087235.
GenBank [Internet]. Bethesda (MD): National Library of Medicine (US), National Center for Biotechnology Information; [1982]—GenBank Accession No. MN087238, Mus musculus clone B-p2e1-LC immunoglobulin light chain variable region mRNA, partial cds, [cited Mar. 4, 2021]. Available from: https://www.ncbi.nlm.nih.gov/nuccore/MN087238.
GenBank [Internet]. Bethesda (MD): National Library of Medicine (US), National Center for Biotechnology Information; [1982]—GenBank Accession No. MN087244, Mus musculus clone B-p1d12-LC immunoglobulin light chain variable region mRNA, partial cds, [cited Mar. 4, 2021]. Available from: https://www.ncbi.nlm.nih.gov/nuccore/MN087244.
GenBank [Internet]. Bethesda (MD): National Library of Medicine (US), National Center for Biotechnology Information; [1982]—GenBank Accession No. MN087248, Mus musculus clone B-p1b11-LC immunoglobulin light chain variable region mRNA, partial cds, [cited Mar. 4, 2021]. Available from: https://www.ncbi.nlm.nih.gov/nuccore/MN087248.
GenBank [Internet]. Bethesda (MD): National Library of Medicine (US), National Center for Biotechnology Information; [1982]—GenBank Accession No. MN087253, Mus musculus clone P-p1d1-B-LC immunoglobulin light chain variable region mRNA, partial cds, [cited Mar. 4, 2021]. Available from: https://www.ncbi.nlm.nih.gov/nuccore/MN087253.
GenBank [Internet]. Bethesda (MD): National Library of Medicine (US), National Center for Biotechnology Information; [1982]—GenBank Accession No. MN087258, Mus musculus clone P-p2b7-LC immunoglobulin light chain variable region mRNA, partial cds, [cited Mar. 4, 2021]. Available from: https://www.ncbi.nlm.nih.gov/nuccore/MN087258.
GenBank [Internet]. Bethesda (MD): National Library of Medicine (US), National Center for Biotechnology Information; [1982]—GenBank Accession No. MN087262, Mus musculus clone P-p1d8-LC immunoglobulin light chain variable region mRNA, partial cds, [cited Mar. 4, 2021]. Available from: https://www.ncbi.nlm.nih.gov/nuccore/MN087262.
GenBank [Internet]. Bethesda (MD): National Library of Medicine (US), National Center for Biotechnology Information; [1982]—GenBank Accession No. MN087267, Mus musculus clone P-p1f10-LC immunoglobulin light chain variable region mRNA, partial cds, [cited Mar. 4, 2021]. Available from: https://www.ncbi.nlm.nih.gov/nuccore/MN087267.
GenBank [Internet]. Bethesda (MD): National Library of Medicine (US), National Center for Biotechnology Information; [1982]—GenBank Accession No. MN087269, Mus musculus clone P-p1e7-LC immunoglobulin light chain variable region mRNA, partial cds, [cited Mar. 4, 2021]. Available from: https://www.ncbi.nlm.nih.gov/nuccore/MN087269.
GenBank [Internet]. Bethesda (MD): National Library of Medicine (US), National Center for Biotechnology Information; [1982]—GenBank Accession No. MN087272, Mus musculus clone N-p4a9-HC immunoglobulin heavy chain variable region mRNA, partial cds, [cited Mar. 4, 2021]. Available from: https://www.ncbi.nlm.nih.gov/nuccore/MN087272.
GenBank [Internet]. Bethesda (MD): National Library of Medicine (US), National Center for Biotechnology Information; [1982]—GenBank Accession No. MN087273, Mus musculus clone N-p3g9-HC immunoglobulin heavy chain variable region mRNA, partial cds, partial cds, [cited Mar. 4, 2021]. Available from: https://www.ncbi.nlm.nih.gov/nuccore/MN087273.

(56) References Cited

OTHER PUBLICATIONS

GenBank [Internet]. Bethesda (MD): National Library of Medicine (US), National Center for Biotechnology Information; [1982]—GenBank Accession No. MN087274, Mus musculus clone P-p1h2-HC immunoglobulin heavy chain variable region mRNA, partial cds, [cited Mar. 4, 2021]. Available from: https://www.ncbi.nlm.nih.gov/nuccore/MN087274.
GenBank [Internet]. Bethesda (MD): National Library of Medicine (US), National Center for Biotechnology Information; [1982]—GenBank Accession No. MN087276, Mus musculus clone P-p1e5-HC immunoglobulin heavy chain variable region mRNA, partial cds, [cited Mar. 4, 2021]. Available from: https://www.ncbi.nlm.nih.gov/nuccore/MN087276.
GenBank [Internet]. Bethesda (MD): National Library of Medicine (US), National Center for Biotechnology Information; [1982]—GenBank Accession No. MN087279, Mus musculus clone P-p1d1-C-HC immunoglobulin heavy chain variable region mRNA, partial cds, [cited Mar. 4, 2021]. Available from: https://www.ncbi.nlm.nih.gov/nuccore/MN087279.
GenBank [Internet]. Bethesda (MD): National Library of Medicine (US), National Center for Biotechnology Information; [1982]—GenBank Accession No. MN087281, Mus musculus clone P-p1a6-HC immunoglobulin heavy chain variable region mRNA, partial cds, [cited Mar. 4, 2021]. Available from: https://www.ncbi.nlm.nih.gov/nuccore/MN087281.
GenBank [Internet]. Bethesda (MD): National Library of Medicine (US), National Center for Biotechnology Information; [1982]—GenBank Accession No. MN087284, Mus musculus clone B-p2d6-HC immunoglobulin heavy chain variable region mRNA, partial cds, [cited Mar. 4, 2021]. Available from: https://www.ncbi.nlm.nih.gov/nuccore/MN087284.
GenBank [Internet]. Bethesda (MD): National Library of Medicine (US), National Center for Biotechnology Information; [1982]—GenBank Accession No. MN087287, Mus musculus clone B-p1f2-HC immunoglobulin heavy chain variable region mRNA, partial cds, [cited Mar. 4, 2021]. Available from: https://www.ncbi.nlm.nih.gov/nuccore/MN087287.
GenBank [Internet]. Bethesda (MD): National Library of Medicine (US), National Center for Biotechnology Information; [1982]—GenBank Accession No. MN087295, Mus musculus clone B-p1a10-HC immunoglobulin heavy chain variable region mRNA, partial cds, [cited Mar. 4, 2021]. Available from: https://www.ncbi.nlm.nih.gov/nuccore/MN087295.
GenBank [Internet]. Bethesda (MD): National Library of Medicine (US), National Center for Biotechnology Information; [1982]—GenBank Accession No. MN087303, Mus musculus clone P-p2b5-HC immunoglobulin heavy chain variable region mRNA, partial cds, [cited Mar. 4, 2021]. Available from: https://www.ncbi.nlm.nih.gov/nuccore/MN087303.
GenBank [Internet]. Bethesda (MD): National Library of Medicine (US), National Center for Biotechnology Information; [1982]—GenBank Accession No. MN087309, Mus musculus clone P-p3b3-HC immunoglobulin heavy chain variable region mRNA, partial cds, [cited Mar. 4, 2021]. Available from: https://www.ncbi.nlm.nih.gov/nuccore/MN087309.
GenBank [Internet]. Bethesda (MD): National Library of Medicine (US), National Center for Biotechnology Information; [1982]—GenBank Accession No. MN179668, Synthetic construct 45_01dH1 WT Core gp120 protein gene, complete cds, [cited Mar. 4, 2021]. Available from: https://www.ncbi.nlm.nih.gov/nuccore/MN179668.
GenBank [Internet]. Bethesda (MD): National Library of Medicine (US), National Center for Biotechnology Information; [1982]—GenBank Accession No. MN179671, Synthetic construct HxB2 WT Core gp120 C4b multimer with 2W1S tag protein gene, complete cds, [cited Mar. 4, 2021]. Available from: https://www.ncbi.nlm.nih.gov/nuccore/MN179671.
Hoot, et al., "Recombinant HIV envelope proteins fail to engage germline versions of anti-CD4bs bNAbs," PLoS Pathogen, vol. 9, No. 1, 2013, 14 pages.
Kanekiyo, et al., "Self-assembling influenza nanoparticle vaccines elicit broadly neutralizing H1N1 antibodies," Nature, vol. 499, 2013, pp. 102-106.
Klein, et al., "Somatic Mutations of the Immunoglobulin Framework are Generally Required for Broad and Potent HIV-1 Neutralization," Cell, vol. 153, No. 1, 2013, pp. 126-138.
Ludtke, et al., "EMAN: semiautomated software for high-resolution single-particle reconstructions," Journal of Structural Biology, vol. 128, No. 1, 1999, pp. 82-97.
Lynch, et al., "HIV-1 Fitness Cost Associated with Escape from the VRC01 Class of CD4 Binding Site Neutralizing Antibodies," Journal of Virology, vol. 89, No. 8, 2015, pp. 4201-4213.
McGuire, et al., "Engineering HIV envelope protein to activate germline B cell receptors of broadly neutralizing anti-CD4 binding site antibodies," Journal of Experimental Medicine, vol. 210, No. 4, 2013, pp. 655-663.
Mohan, et al., "Sequential Immunization with a panel of HIV-1 Env virus-like particles coach immune system to make broadly neutralizing antibodies," Scientific Reports, vol. 8, No. 7, 2018, 12 pages.
Otwinowski and Minor, "[20] Processing of X-ray diffraction data collected in oscillation mode," Methods in Enzymology, vol. 376, 1997, pp. 307-326.
Search Report and Written Opinion Dated Feb. 6, 2020 for International Application No. PCT/US2019/048825, 14 pages.
Stamatatos, et al., "Germline Targeting Immunogens," Immunol. Rev., vol. 275, No. 1, 2017, pp. 203-216.
Tian, et al., "Induction of HIV Neutralizing Antibody Lineages in Mice with Diverse Precursor Repertoires," Cell, vol. 166, No. 6, 2016, pp. 1471-1484.e188.
West, et al., "Structural basis for germ-line gene usage of a potent class of antibodies targeting the CD4-binding site of HIV-1 gp120," PNAS USA, vol. 109, No. 30, 2012, pp. E2083-E2090.
Wickham, "Tidyverse: Version 1.3.0.9000," retrieved on Mar. 12, 2021, at << https://tidyverse.tidyverse.org/>>, Tidyverse, Nov. 19, 2019, 4 pages.
Wu, et al., "Focused evolution of HIV-1 neutralizing antibodies revealed by structures and deep sequencing," Science, vol. 333, No. 6049, 2011, pp. 1593-1602.
Xiao, et al., "Germline-like predecessors of broadly neutralizing antibodies lack measurable binding to HIV-1 envelope glycoproteins: Implications for evasion of immune responses and design of vaccine immunogens," Biochemical and Biophysical Research Communications, vol. 390, No. 3, 2009, pp. 404-409.
Yamashita, et al., "Ferritin in the field of nanodevices," Biochimica et Biophysica Acta, vol. 1800, No. 8, 2010, pp. 846-857.
Zhou, et al., "Multidonor analysis reveals structural elements, genetic determinants, and maturation pathway for HIV-1 neutralization by VRC01-class antibodies," Immunity, vol. 39, No. 2, 2013, pp. 245-258.
Zhou, et al., "Structural Repertoire of HIV-1-Neutralizing Antibodies Targeting the CD4 Supersite in 14 Donors," Cell, vol. 161, No. 6, 2015, pp. 1280-1292.
Adams, et al., "Recent developments in the PHENIX software for automated crystallographic structure determination," Journal of Synchrotron Radiation, vol. 11, No. 1, 2004, pp. 53-55.
Balazs, et al., "Vectored immunoprophylaxis protects humanized mice from mucosal HIV transmission," Nature Medicine, vol. 20, 2014, pp. 296-300.
Borst, et al., "Germline VRC01 antibody recognition of a modified clade C HIV-1 envelope trimer and a glycosylated HIV-1 gp120 core," eLife: Structural Biology and Molecular Biophysics, vol. 7, 2018, 32 pages.
Doria-Rose, et al., "Developmental pathway for potent V1V2-directed HIV-neutralizing antibodies," Nature, vol. 509, No. 7498, 2014, pp. 55-62.
Frese, et al., "Unambiguous phosphosite localization using electron-transfer/higher-energy collision dissociation (EThcD)," Journal of Proteome Research, vol. 12, No. 3, 2013, pp. 1520-1525.
Freund, et al., "A New Glycan-Dependent CD4-Binding Site Neutralizing Antibody Exerts Pressure on HIV-1 In Vivo," vol. 11, No. 10, 2015, 19 pages.
GenBank [Internet]. Bethesda (MD): National Library of Medicine (US), National Center for Biotechnology Information; [1982]—

(56) References Cited

OTHER PUBLICATIONS

GenBank Accession No. MN087236, Mus musculus clone P-p1a7-LC immunoglobulin light chain variable region mRNA, partial cds, [cited Mar. 4, 2021]. Available from: https://www.ncbi.nlm.nih.gov/nuccore/MN087236.
GenBank [Internet]. Bethesda (MD): National Library of Medicine (US), National Center for Biotechnology Information; [1982]—GenBank Accession No. MN087237, Mus musculus clone P-p1a6-LC immunoglobulin light chain variable region mRNA, partial cds, [cited Mar. 4, 2021]. Available from: https://www.ncbi.nlm.nih.gov/nuccore/MN087237.
GenBank [Internet]. Bethesda (MD): National Library of Medicine (US), National Center for Biotechnology Information; [1982]—GenBank Accession No. MN087240, Mus musculus clone B-p2d6-LC immunoglobulin light chain variable region mRNA, partial cds, [cited Mar. 4, 2021]. Available from: https://www.ncbi.nlm.nih.gov/nuccore/MN087240.
GenBank [Internet]. Bethesda (MD): National Library of Medicine (US), National Center for Biotechnology Information; [1982]—GenBank Accession No. MN087241, Mus musculus clone B-p2c5-LC immunoglobulin light chain variable region mRNA, partial cds, [cited Mar. 4, 2021]. Available from: https://www.ncbi.nlm.nih.gov/nuccore/MN087241.
GenBank [Internet]. Bethesda (MD): National Library of Medicine (US), National Center for Biotechnology Information; [1982]—GenBank Accession No. MN087242, Mus musculus clone B-p1f8-LC immunoglobulin light chain variable region mRNA, partial cds, [cited Mar. 4, 2021]. Available from: https://www.ncbi.nlm.nih.gov/nuccore/MN087242.
GenBank [Internet]. Bethesda (MD): National Library of Medicine (US), National Center for Biotechnology Information; [1982]—GenBank Accession No. MN087250, Mus musculus clone B-p1a10-LC immunoglobulin light chain variable region mRNA, partial cds, [cited Mar. 4, 2021]. Available from: https://www.ncbi.nlm.nih.gov/nuccore/MN087250.
GenBank [Internet]. Bethesda (MD): National Library of Medicine (US), National Center for Biotechnology Information; [1982]—GenBank Accession No. MN087252, Mus musculus clone B-p1a11-LC immunoglobulin light chain variable region mRNA, partial cds, [cited Mar. 4, 2021]. Available from: https://www.ncbi.nlm.nih.gov/nuccore/MN087252.
GenBank [Internet]. Bethesda (MD): National Library of Medicine (US), National Center for Biotechnology Information; [1982]—GenBank Accession No. MN087256, Mus musculus clone P-p1b2-LC immunoglobulin light chain variable region mRNA, partial cds, [cited Mar. 4, 2021]. Available from: https://www.ncbi.nlm.nih.gov/nuccore/MN087256.
GenBank [Internet]. Bethesda (MD): National Library of Medicine (US), National Center for Biotechnology Information; [1982]—GenBank Accession No. MN087259, Mus musculus clone P-p2b5-LC immunoglobulin light chain variable region mRNA, partial cds, [cited Mar. 4, 2021]. Available from: https://www.ncbi.nlm.nih.gov/nuccore/MN087259.
GenBank [Internet]. Bethesda (MD): National Library of Medicine (US), National Center for Biotechnology Information; [1982]—GenBank Accession No. MN087263, Mus musculus clone P-p4c5-LC immunoglobulin light chain variable region mRNA, partial cds, [cited Mar. 4, 2021]. Available from: https://www.ncbi.nlm.nih.gov/nuccore/MN087263.
GenBank [Internet]. Bethesda (MD): National Library of Medicine (US), National Center for Biotechnology Information; [1982]—GenBank Accession No. MN087265, Mus musculus clone P-p3b3-LC immunoglobulin light chain variable region mRNA, partial cds, [cited Mar. 4, 2021]. Available from: https://www.ncbi.nlm.nih.gov/nuccore/MN087265.
GenBank [Internet]. Bethesda (MD): National Library of Medicine (US), National Center for Biotechnology Information; [1982]—GenBank Accession No. MN087271, Mus musculus clone P-p1a8-LC immunoglobulin light chain variable region mRNA, partial cds, [cited Mar. 4, 2021]. Available from: https://www.ncbi.nlm.nih.gov/nuccore/MN087271.
GenBank [Internet]. Bethesda (MD): National Library of Medicine (US), National Center for Biotechnology Information; [1982]—GenBank Accession No. MN087278, Mus musculus clone P-p1d3-HC immunoglobulin heavy chain variable region mRNA, partial cds, [cited Mar. 4, 2021]. Available from: https://www.ncbi.nlm.nih.gov/nuccore/MN087278.
GenBank [Internet]. Bethesda (MD): National Library of Medicine (US), National Center for Biotechnology Information; [1982]—GenBank Accession No. MN087280, Mus musculus clone P-p1a7-HC immunoglobulin heavy chain variable region mRNA, partial cds, [cited Mar. 4, 2021]. Available from: https://www.ncbi.nlm.nih.gov/nuccore/MN087280.
GenBank [Internet]. Bethesda (MD): National Library of Medicine (US), National Center for Biotechnology Information; [1982]—GenBank Accession No. MN087285, Mus musculus clone B-p2c5-HC immunoglobulin heavy chain variable region mRNA, partial cds, [cited Mar. 4, 2021]. Available from: https://www.ncbi.nlm.nih.gov/nuccore/MN087285.
GenBank [Internet]. Bethesda (MD): National Library of Medicine (US), National Center for Biotechnology Information; [1982]—GenBank Accession No. MN087289, Mus musculus clone B-p1d7-HC immunoglobulin heavy chain variable region mRNA, partial cds, [cited Mar. 4, 2021]. Available from: https://www.ncbi.nlm.nih.gov/nuccore/MN087289.
GenBank [Internet]. Bethesda (MD): National Library of Medicine (US), National Center for Biotechnology Information; [1982]—GenBank Accession No. MN087291, Mus musculus clone B-p1c10-HC immunoglobulin heavy chain variable region mRNA, partial cds, [cited Mar. 4, 2021]. Available from: https://www.ncbi.nlm.nih.gov/nuccore/MN087291.
GenBank [Internet]. Bethesda (MD): National Library of Medicine (US), National Center for Biotechnology Information; [1982]—GenBank Accession No. MN087292, Mus musculus clone B-p1b11-HC immunoglobulin heavy chain variable region mRNA, partial cds, [cited Mar. 4, 2021]. Available from: https://www.ncbi.nlm.nih.gov/nuccore/MN087292.
GenBank [Internet]. Bethesda (MD): National Library of Medicine (US), National Center for Biotechnology Information; [1982]—GenBank Accession No. MN087298, Mus musculus clone P-p1c4-HC immunoglobulin heavy chain variable region mRNA, partial cds, [cited Mar. 4, 2021]. Available from: https://www.ncbi.nlm.nih.gov/nuccore/MN087298.
GenBank [Internet]. Bethesda (MD): National Library of Medicine (US), National Center for Biotechnology Information; [1982]—GenBank Accession No. MN087301, Mus musculus clone P-p2b11-HC immunoglobulin heavy chain variable region mRNA, partial cds, [cited Mar. 4, 2021]. Available from: https://www.ncbi.nlm.nih.gov/nuccore/MN087301.
GenBank [Internet]. Bethesda (MD): National Library of Medicine (US), National Center for Biotechnology Information; [1982]—GenBank Accession No. MN087304, Mus musculus clone P-p2a5-HC immunoglobulin heavy chain variable region mRNA, partial cds, [cited Mar. 4, 2021]. Available from: https://www.ncbi.nlm.nih.gov/nuccore/MN087304.
GenBank [Internet]. Bethesda (MD): National Library of Medicine (US), National Center for Biotechnology Information; [1982]—GenBank Accession No. MN087305, Mus musculus clone P-p1f2-HC immunoglobulin heavy chain variable region mRNA, partial cds, [cited Mar. 4, 2021]. Available from: https://www.ncbi.nlm.nih.gov/nuccore/MN087305.
GenBank [Internet]. Bethesda (MD): National Library of Medicine (US), National Center for Biotechnology Information; [1982]—GenBank Accession No. MN087306, Mus musculus clone P-p1d8-HC immunoglobulin heavy chain variable region mRNA, partial cds, [cited Mar. 4, 2021]. Available from: https://www.ncbi.nlm.nih.gov/nuccore/MN087306.
GenBank [Internet]. Bethesda (MD): National Library of Medicine (US), National Center for Biotechnology Information; [1982]—GenBank Accession No. MN179660, Synthetic construct QH0692

(56) References Cited

OTHER PUBLICATIONS

WT Core gp120 C4b multimer protein gene, complete cds, [cited Mar. 4, 2021]. Available from: https://www.ncbi.nlm.nih.gov/nuccore/MN179660.
GenBank [Internet]. Bethesda (MD): National Library of Medicine (US), National Center for Biotechnology Information; [1982]—GenBank Accession No. MN179662, Synthetic construct 45_01dH1 WT Core gp120 C4b multimer protein gene, complete cds, [cited Mar. 4, 2021]. Available from: https://www.ncbi.nlm.nih.gov/nuccore/MN179662.
GenBank [Internet]. Bethesda (MD): National Library of Medicine (US), National Center for Biotechnology Information; [1982]—GenBank Accession No. MN179666, Synthetic construct QH0692 WT Core gp120 protein gene, complete cds, [cited Mar. 4, 2021]. Available from: https://www.ncbi.nlm.nih.gov/nuccore/MN179666.
Havenar-Daughton, et al., "The human naive B cell repertoire contains distinct subclasses for a germline-targeting HIV-1 vaccine immunogen," Science Translational Medicine, vol. 10, No. 448, 2018, 15 pages.
Invitation to Pay Additional Fees Dated Nov. 27, 2019, for International Application No. PCT/US2019/048825, 3 pages.
Jardine, et al., "HIV-1 broadly neutralizing antibody precursor B cells revealed by germline-targeting immunogen," Science, vol. 351, No. 6280, 2016, pp. 1458-1463.
Jardine, et al., "Priming a broadly neutralizing antibody response to HIV-1 using a germline-targeting immunogen," Science, vol. 349, No. 6244, 2015, pp. 156-161.
Kask, et al., "Structural requirements for the intracellular subunit polymerization of the complement inhibitor C4b-binding protein," Biochemistry, vol. 41, No. 30, 2002, pp. 9349-9357.
Kimanius, et al., "Accelerated cryo-EM structure determination with parallelisation using GPUs in RELION-2," eLife: Structural Biology and Molecular Biophysics, 2016, 21 pages.
Lander, et al., "Appion: An integrated, database-driven pipeline to facilitate EM image processing," Journal of Structural Biology, vol. 166, No. 1, 2009, pp. 95-102.
Maclean, et al., "Skyline: an open source document editor for creating and analyzing targeted proteomics experiments," Bioinformatics, vol. 26, No. 7, 2010, pp. 966-968.
Mindell and Grigorieff, "Accurate determination of local defocus and specimen tilt in electron microscopy," Journal of Structural Biology, vol. 142, No. 3, 2003, pp. 334-347.
Montefiori, "Chapter 26: Measuring HIV Neutralization in a Luciferase Reporter Gene Assay," Methods in Molecular Biology, vol. 485, 2009, pp. 395-405.
Office Action Dated Dec. 22, 2022 for U.S. Appl. No. 17/269,199, 10 pages.
Pages, et al., "Biostrings: Version 3.12," retrieved on (Mar. 12, 2021) at <<https://bioconductor.org/packages/release/bioc/html/Biostrings.html>>, Bioconductor, 2020, 5 pages.
Sajadi, et al., "Identification of Near-Pan-neutralizing Antibodies against HIV-1 by Deconvolution of Plasma Humoral Responses," Cell, vol. 173, No. 7, 2018, pp. 1783-1795.e14.
Scharf, et al., "Structural basis for germline antibody recognition of HIV-1 immunogens," eLife: Structural Biology and Molecular BiophysicsImmunology and Inflammation, 2016, 24 pages.
Tsai, et al., "Exposure to MF59-adjuvanted Influenza Vaccines During Pregnancy—A Retrospective Analysis," Vaccine, vol. 28, No. 7, 2010, pp. 1877-1880.
Umotoy, et al., "Rapid and Focused Maturation of a VRC01-Class HIV Broadly Neutralizing Antibody Lineage Involves Both Binding and Accommodation of the N276-Glycan," Immunity, vol. 51, No. 1, 2019, pp. 141-154.e6.
Yacoob, et al., "Differences in Allelic Frequency and CDRH3 Region Limit the Engagement of HIV Env Immunogens by Putative VRC01 Neutralizing Antibody Precursors," Cell Reports, vol. 17, No. 6, 2016, pp. 1560-1570.
Zivanov, et al., "New tools for automated high-resolution cryo-EM structure determination in RELION-3," Elife, vol. 7, No. 42166, 2018, 22 pages.
Charif, et al., "Online synonymous codon usage analyses with the ade4 and seqinR packages," Bioinformatics, vol. 21, No. 4, 2005, pp. 545-547.
Dekosky, et al., "In-depth determination and analysis of the human paired heavy- and light-chain antibody repertoire," Nature Medicine, vol. 21, 2015, pp. 86-91.
Diskin, et al., "Increasing the Potency and Breadth of an HIV Antibody by Using Structure-Based Rational Design," Science, vol. 334, No. 6060, 2011, pp. 1289-1293.
GenBank [Internet]. Bethesda (MD): National Library of Medicine (US), National Center for Biotechnology Information; [1982]—GenBank Accession No. MN087230, Mus musculus clone P-p1h2-LC immunoglobulin light chain variable region mRNA, partial cds, [cited Mar. 4, 2021]. Available from: https://www.ncbi.nlm.nih.gov/nuccore/MN087230.
GenBank [Internet]. Bethesda (MD): National Library of Medicine (US), National Center for Biotechnology Information; [1982]—GenBank Accession No. MN087245, Mus musculus clone B-p1d7-LC immunoglobulin light chain variable region mRNA, partial cds, [cited Mar. 4, 2021]. Available from: https://www.ncbi.nlm.nih.gov/nuccore/MN087245.
GenBank [Internet]. Bethesda (MD): National Library of Medicine (US), National Center for Biotechnology Information; [1982]—GenBank Accession No. MN087246, Mus musculus clone B-p1c11-LC immunoglobulin light chain variable region mRNA, partial cds, [cited Mar. 4, 2021]. Available from: https://www.ncbi.nlm.nih.gov/nuccore/MN087246.
GenBank [Internet]. Bethesda (MD): National Library of Medicine (US), National Center for Biotechnology Information; [1982]—GenBank Accession No. MN087249, Mus musculus clone B-p1b5-LC immunoglobulin light chain variable region mRNA, partial cds, [cited Mar. 4, 2021]. Available from: https://www.ncbi.nlm.nih.gov/nuccore/MN087249.
GenBank [Internet]. Bethesda (MD): National Library of Medicine (US), National Center for Biotechnology Information; [1982]—GenBank Accession No. MN087255, Mus musculus clone P-p1b5-LC immunoglobulin light chain variable region mRNA, partial cds, [cited Mar. 4, 2021]. Available from: https://www.ncbi.nlm.nih.gov/nuccore/MN087255.
GenBank [Internet]. Bethesda (MD): National Library of Medicine (US), National Center for Biotechnology Information; [1982]—GenBank Accession No. MN087257, Mus musculus clone P-p2b11-LC immunoglobulin light chain variable region mRNA, partial cds, [cited Mar. 4, 2021]. Available from: https://www.ncbi.nlm.nih.gov/nuccore/MN087257.
GenBank [Internet]. Bethesda (MD): National Library of Medicine (US), National Center for Biotechnology Information; [1982]—GenBank Accession No. MN087260, Mus musculus clone P-p2a5-LC immunoglobulin light chain variable region mRNA, partial cds, [cited Mar. 4, 2021]. Available from: https://www.ncbi.nlm.nih.gov/nuccore/MN087260.
GenBank [Internet]. Bethesda (MD): National Library of Medicine (US), National Center for Biotechnology Information; [1982]—GenBank Accession No. MN087264, Mus musculus clone P-p4e4-LC immunoglobulin light chain variable region mRNA, partial cds, [cited Mar. 4, 2021]. Available from: https://www.ncbi.nlm.nih.gov/nuccore/MN087264.
GenBank [Internet]. Bethesda (MD): National Library of Medicine (US), National Center for Biotechnology Information; [1982]—GenBank Accession No. MN087266, Mus musculus clone P-p3a2-LC immunoglobulin light chain variable region mRNA, partial cds, [cited Mar. 4, 2021]. Available from: https://www.ncbi.nlm.nih.gov/nuccore/MN087266.
GenBank [Internet]. Bethesda (MD): National Library of Medicine (US), National Center for Biotechnology Information; [1982]—GenBank Accession No. MN087270, Mus musculus clone P-p1d1-LC immunoglobulin light chain variable region mRNA, partial cds, [cited Mar. 4, 2021]. Available from: https://www.ncbi.nlm.nih.gov/nuccore/MN087270.
GenBank [Internet]. Bethesda (MD): National Library of Medicine (US), National Center for Biotechnology Information; [1982]—GenBank Accession No. MN087283, Mus musculus clone B-p2e1-

(56) References Cited

OTHER PUBLICATIONS

HC immunoglobulin heavy chain variable region mRNA, partial cds, [cited Mar. 4, 2021]. Available from: https://www.ncbi.nlm.nih.gov/nuccore/MN087283.
GenBank [Internet]. Bethesda (MD): National Library of Medicine (US), National Center for Biotechnology Information; [1982]—GenBank Accession No. MN087288, Mus musculus clone B-p1d12-HC immunoglobulin heavy chain variable region mRNA, partial cds, [cited Mar. 4, 2021]. Available from: https://www.ncbi.nlm.nih.gov/nuccore/MN087288.
GenBank [Internet]. Bethesda (MD): National Library of Medicine (US), National Center for Biotechnology Information; [1982]—GenBank Accession No. MN087293, Mus musculus clone B-p1b5-HC immunoglobulin heavy chain variable region mRNA, partial cds, [cited Mar. 4, 2021]. Available from: https://www.ncbi.nlm.nih.gov/nuccore/MN087293.
GenBank [Internet]. Bethesda (MD): National Library of Medicine (US), National Center for Biotechnology Information; [1982]—GenBank Accession No. MN087297, Mus musculus clone P-p1d1-B-HC immunoglobulin heavy chain variable region mRNA, partial cds, [cited Mar. 4, 2021]. Available from: https://www.ncbi.nlm.nih.gov/nuccore/MN087297.
GenBank [Internet]. Bethesda (MD): National Library of Medicine (US), National Center for Biotechnology Information; [1982]—GenBank Accession No. MN087299, Mus musculus clone P-p1b5-HC immunoglobulin heavy chain variable region mRNA, partial cds, [cited Mar. 4, 2021]. Available from: https://www.ncbi.nlm.nih.gov/nuccore/MN087299.
GenBank [Internet]. Bethesda (MD): National Library of Medicine (US), National Center for Biotechnology Information; [1982]—GenBank Accession No. MN087300, Mus musculus clone P-p1b2-HC immunoglobulin heavy chain variable region mRNA, partial cds, [cited Mar. 4, 2021]. Available from: https://www.ncbi.nlm.nih.gov/nuccore/MN087300.
GenBank [Internet]. Bethesda (MD): National Library of Medicine (US), National Center for Biotechnology Information; [1982]—GenBank Accession No. MN087308, Mus musculus clone P-p4e4-HC immunoglobulin heavy chain variable region mRNA, partial cds, [cited Mar. 4, 2021]. Available from: https://www.ncbi.nlm.nih.gov/nuccore/MN087308.
GenBank [Internet]. Bethesda (MD): National Library of Medicine (US), National Center for Biotechnology Information; [1982]—GenBank Accession No. MN087310, Mus musculus clone P-p3a2-HC immunoglobulin heavy chain variable region mRNA, partial cds, [cited Mar. 4, 2021]. Available from: https://www.ncbi.nlm.nih.gov/nuccore/MN087310.
GenBank [Internet]. Bethesda (MD): National Library of Medicine (US), National Center for Biotechnology Information; [1982]—GenBank Accession No. MN087311, Mus musculus clone P-p1f10-HC immunoglobulin heavy chain variable region mRNA, partial cds, [cited Mar. 4, 2021]. Available from: https://www.ncbi.nlm.nih.gov/nuccore/MN087311.
GenBank [Internet]. Bethesda (MD): National Library of Medicine (US), National Center for Biotechnology Information; [1982]—GenBank Accession No. MN087315, Mus musculus clone P-p1a8-HC immunoglobulin heavy chain variable region mRNA, partial cds, [cited Mar. 4, 2021]. Available from: https://www.ncbi.nlm.nih.gov/nuccore/MN087315.
GenBank [Internet]. Bethesda (MD): National Library of Medicine (US), National Center for Biotechnology Information; [1982]—GenBank Accession No. MN179661, Synthetic construct Q168a2 WT Core gp120 C4b multimer protein gene, complete cds, [cited Mar. 4, 2021]. Available from: https://www.ncbi.nlm.nih.gov/nuccore/MN179661.
GenBank [Internet]. Bethesda (MD): National Library of Medicine (US), National Center for Biotechnology Information; [1982]—GenBank Accession No. MN179664, Synthetic construct 426c WT Core gp120 protein gene, complete cds, [cited Mar. 4, 2021]. Available from: https://www.ncbi.nlm.nih.gov/nuccore/MN179664.
GenBank [Internet]. Bethesda (MD): National Library of Medicine (US), National Center for Biotechnology Information; [1982]—GenBank Accession No. MN179665, Synthetic construct HxB2 WT Core gp120 protein gene, complete cds, [cited Mar. 4, 2021]. Available from: https://www.ncbi.nlm.nih.gov/nuccore/MN179665.
GenBank [Internet]. Bethesda (MD): National Library of Medicine (US), National Center for Biotechnology Information; [1982]—GenBank Accession No. MN179669, Synthetic construct 93TH057 WT Core gp120 protein gene, complete cds, [cited Mar. 4, 2021]. Available from: https://www.ncbi.nlm.nih.gov/nuccore/MN179669.
GenBank [Internet]. Bethesda (MD): National Library of Medicine (US), National Center for Biotechnology Information; [1982]—GenBank Accession No. MN179670, Synthetic construct HxB2 WT Core gp120 C4b multimer protein gene, complete cds, [cited Mar. 4, 2021]. Available from: https://www.ncbi.nlm.nih.gov/nuccore/MN179670.
Gerhardt, M., et al., Jul. 2005, In-depth, longitudinal analysis of viral quasispecies from an individual triply infected with late-stage human immunodeficiency virus type 1, using a multiple PCR primer approach, J. Viral. 79(13):8249-8261. 13 pages.
Giudicelli & Lefranc, "IMGT/V-QUEST: IMGT Standardized Analysis of the Immunoglobulin (IG) and T Cell Receptor (TR) Nucleotide Sequences," Cold Spring Harbor Laboratory Press, 2011, 10 pages.
Guenaga, et al., "Structure-Guided Redesign Increases the Propensity of HIV Env to Generate Highly Stable Soluble Trimers," Journal of Virology, vol. 90, No. 6, 2015, pp. 2806-2817.
Heikkinen, et al., "Safety of MF59-adjuvanted A/H1N1 influenza vaccine in pregnancy: a comparative cohort study," American Journal of Obstetrics and Gynecology, vol. 207, No. 3, 2012, pp. 177.e1-177.e8.
Hofmeyer, et al., "Arranged Sevenfold: Structural Insights into the C-Terminal Oligomerization Domain of Human C4b- Binding Protein," Journal of Molecular Biology, vol. 425, No. 8, 2013, pp. 1302-1317.
Huang, et al., "Identification of a CD4-Binding-Site Antibody to HIV that Evolved Near-Pan Neutralization Breadth," Immunity, vol. 45, No. 5, 2015, pp. 1108-1121.
Jardine, et al., "Rational HIV immunogen design to target specific germline B cell receptors," Science, vol. 340, No. 6133, 2013, pp. 711-716.
Joyce, et al., "Soluble Prefusion Closed DS-SOSIP.664-Env Trimers of Diverse HIV-1 Strains," Cell Reports, vol. 21, No. 10, 2017, pp. 2992-3002.
LaBranche, et al., "HIV-1 Envelope Glycan Modifications that Permit Neutralization by Germline-Reverted VRC01-Class Broadly Neutralizing Antibodies," PloS Pathogens, vol. 14, No. 11, 2018, 21 pages.
Li, et al., "Ferritin nanoparticle technology A new platform for antigen presentation and vaccine development," Industrial Biotechnology, vol. 2, No. 2, 2006, pp. 143-147.
McGuire, et al., "HIV antibodies. Antigen modification regulates competition of broad and narrow neutralizing HIV antibodies," Science, vol. 346, No. 6215, 2014, pp. 1380-1383.
Meldrum, et al., "Magnetoferritin: in vitro synthesis of a novel magnetic protein," Science, vol. 257, No. 5069, 1992, pp. 522-523.
Mouquet, et al., "Polyreactivity increases the apparent affinity of anti-HIV antibodies by heteroligation," Nature, vol. 467, No. 7315, 2010, pp. 591-595.
Ogun, et al., "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, 2008, pp. 3817-3823.
Snijder, et al., "An Antibody Targeting the Fusion Machinery Neutralizes Dual-Tropic Infection and Defines a Site of Vulnerability on Epstein-Barr Virus," Immunity, vol. 48, No. 4, 2018, pp. 799-811.e9.
Zhou, et al., "Structural basis for broad and potent neutralization of HIV-1 by antibody VRC01," Science, vol. 329, No. 5993, 2010, pp. 811-817.

* cited by examiner

FIG. 7A

| | | |
|---|---|---|
| KI Sequence | QVQLVQSGAEVKKPGASVKVSC[redacted]WVRQAPGQGLEWMG[redacted]RVTMTRDTSISTAYMELSRLRSDDTAVYYC[redacted]WGQGTLVTVSS | SEQ ID NO. 273 |
| P-p1a8 | .................................N.........P.......................I.....................V............................. | SEQ ID NO. 1 |
| P-p1f10 | .................................N..................K.................................................................. | SEQ ID NO. 2 |
| P-p4c5 | .................................N..................K.................................................................. | SEQ ID NO. 2 |
| P-p1e7 | .................................N..................................................................................... | SEQ ID NO. 4 |
| P-p1f1 | .................................N..................................................................................... | SEQ ID NO. 4 |
| P-p3b3 | .................................I..................R............................................I....T................ | SEQ ID NO. 6 |
| P-p3a2 | .................................N..................K.............................................T.................... | SEQ ID NO. 7 |
| P-p1d8 | ................................FL..................Y......F................V.......................................... | SEQ ID NO. 8 |
| P-p2a5 | .................................N...................................I................................................. | SEQ ID NO. 9 |
| P-p1d1 | .................................N..................................................................................... | SEQ ID NO. 4 |
| P-p2b11 | ......................E......I...N..........................................V.......................................... | SEQ ID NO. 11 |
| P-p2b5 | .................................N..........................................V.......................................... | SEQ ID NO. 12 |
| P-p2b7 | ..................R.....Y.......IN..................................................................................... | SEQ ID NO. 13 |
| P-p1f2 | ........................T.......IN..................................................................................... | SEQ ID NO. 14 |
| P-p4e4 | .................................D..................G.................................................................. | SEQ ID NO. 15 |
| P-1c4 | .................................N..................K.............I.................................................... | SEQ ID NO. 16 |
| P-p1b2 | .................................L..................R.................................................T................ | SEQ ID NO. 17 |
| P-p1b5 | ..................................................................................................DT..I................ | SEQ ID NO. 18 |
| P-p1d1-8 | ...............................Q.N..................R.................................................................. | SEQ ID NO. 19 |
| P-p1a6 | .................................N..................H.................................................................. | SEQ ID NO. 20 |
| P-p1a7 | .................................N..................K.................................................................. | SEQ ID NO. 2 |
| P-p1d1-C | ....................................................................................................................... | SEQ ID NO. 273 |
| P-p1d3 | .................................N..................................................................................... | SEQ ID NO. 4 |
| P-p1e3 | ....................................................................................................................... | SEQ ID NO. 273 |

FIG. 7A cont'd

| | | |
|---|---|---|
| P-pie5 | ...................................D..................K................................................D..................... | SEQ ID NO. 25 |
| P-pig2 | .................................M.N......................................................................................... | SEQ ID NO. 26 |
| P-pih2 | ...................................N...................R..................................................................... | SEQ ID NO. 27 |
| B-pic10 | ........................T....IID...N...................R.......K...............N.V.L......................................... | SEQ ID NO. 28 |
| B-pia10 | .................MR............D..VN..................TR...I.....................................F...E....................... | SEQ ID NO. 29 |
| B-pid12 | ........................T....IID...N...................R.......K...............N.V.L..N...................................... | SEQ ID NO. 30 |
| B-pif2 | ................A........F.........N...................K.........................V.L......................F.................. | SEQ ID NO. 31 |
| B-pib11 | ........................T....IID...N...................K.........................V.S......................................... | SEQ ID NO. 32 |
| B-pib5 | .................MR............D..VN..................TR...V.....................................F........................... | SEQ ID NO. 33 |
| B-pid7 | ...................................N..................TR.........................................F........................... | SEQ ID NO. 34 |
| B-pif8 | ...................................N...................R.......................N......T................T..................... | SEQ ID NO. 35 |
| B-pia9 | ........................T.....IA...N..................FR.........................VFL..S...................................... | SEQ ID NO. 36 |
| B-pia11 | ........................T.....IA...N..................FR.........................V.L......................................... | SEQ ID NO. 37 |
| B-pic11 | ........................T.....IA...N..................FR.........................V.L......................................... | SEQ ID NO. 37 |
| B-p2e2 | ...............................D...N..............L...KT...PI..................................I............................. | SEQ ID NO. 198 |
| B-p2e1 | ...............................D...N..............L...KT...P...R..........................F....I............................. | SEQ ID NO. 199 |
| B-p2d6 | ...................................N...................R......................S.............................................. | SEQ ID NO. 200 |
| B-p2c5 | ...............................D...N..............L...KT...P...................................I............................. | SEQ ID NO. 201 |
| N-p3g9 | ...................A......................................................................................................... | SEQ ID NO. 202 |
| N-p4a9 | ............................................................................................................................. | SEQ ID NO. 273 |

FIG. 7B

| | | |
|---|---|---|
| Mouse 8-30*01 | DIVMSQSPSSLAVSVGEKVTMSC[redacted]WYQQKPGQSPKLLIY[redacted]GVPDRFTGSGSGTDFTLTISSVKAEDLAVYYC[redacted] | SEQ ID NO. 204 |
| P-p1a3 | ......................N.........T..E...........................................................ET | SEQ ID NO. 205 |
| P-p1f10 | ............................F...N..............................................................ET | SEQ ID NO. 206 |
| P-p4c5 | .............V.........................................................................Q.......ET | SEQ ID NO. 207 |
| P-p1e7 | ................................................................................................K | SEQ ID NO. 208 |
| P-p1f1 | ...............................................................................................EM | SEQ ID NO. 209 |
| P-p2b3 | ...............................................................................................ET | SEQ ID NO. 210 |
| P-p3a2 | ............................P...T..............................................................ET | SEQ ID NO. 211 |
| P-p1d8 | .................................D.E......R....................................................ET | SEQ ID NO. 212 |
| P-p2a5 | ...................................E............................................................K | SEQ ID NO. 213 |
| P-p1d1 | .................................D........................A....................................EM | SEQ ID NO. 214 |
| P-p2b11 | ...................................E............................................................K | SEQ ID NO. 215 |
| P-p2b5 | ..............................D........................................E........................K | SEQ ID NO. 216 |
| P-p2b7 | ...........G..................D.C..E............................................................K | SEQ ID NO. 217 |
| P-p1f2 | ................................................................................................K | SEQ ID NO. 208 |
| P-p4e4 | ...................................E............................................................. | SEQ ID NO. 219 |
| P-p1c4 | ..................I............G...........................W....................................K | SEQ ID NO. 220 |
| P-p1b2 | ...............................................................................................ET | SEQ ID NO. 221 |
| P-p1b8 | ..................................EE...........................A................................K | SEQ ID NO. 222 |
| P-p1d1-8 | ....................................................................................T...........K | SEQ ID NO. 223 |
| P-p1a6 | ...............................................................................................EM | SEQ ID NO. 209 |
| P-p1a7 | ..................................E............................................................ET | SEQ ID NO. 225 |
| P-p1d3 | .....................................................................A....................L.....K | SEQ ID NO. 226 |
| P-p1e5 | ..............I................................................................................ET | SEQ ID NO. 227 |

FIG. 7B cont'd

| | | |
|---|---|---|
| P-p1g2 | ...................................E..............................................................K | SEQ ID NO. 228 |
| P-p1h2 | .....................N.............E..............................................................K | SEQ ID NO. 229 |
| B-p1c10 | ..........................................................S......................................ET | SEQ ID NO. 230 |
| B-p1a10 | ...........................N......EE.................................................V...........ET | SEQ ID NO. 231 |
| B-p1d12 | .............................F............................S......................................ET | SEQ ID NO. 232 |
| B-p1f2 | ....................L........S..N.E...............................................................K | SEQ ID NO. 233 |
| B-p1b11 | ..............I.....L...............................................I...............E............ET | SEQ ID NO. 234 |
| B-p1b5 | .........F.................N......ED.............................................................ET | SEQ ID NO. 235 |
| B-p1d7 | ..................................EN.....................................................V.......ET | SEQ ID NO. 236 |
| B-p1f8 | .....................N.....NV....D........................I.......................................K | SEQ ID NO. 237 |
| B-p1a9 | ..........................................................S......E...................T...........ET | SEQ ID NO. 238 |
| B-p1a11 | ..........................................................S......E...................T...........ET | SEQ ID NO 238 |
| B-p1c11 | ...........................N......EE.................................................V...........ET | SEQ ID NO. 240 |
| B-p2e8 | ..........................L...DWN........................FI.......................................Q | SEQ ID NO. 241 |
| B-p2e1 | ...........T..............L...DWN.........................S.......................................Q | SEQ ID NO. 242 |
| B-p2d6 | ...........V..L.....L..............E...................S.........................................ET | SEQ ID NO. 243 |
| B-p2c5 | ....T......V..............L...DWN........................FI.......................................Q | SEQ ID NO. 243 |
| N-p4a9 | .................................................................................................WT | SEQ ID NO. 245 |

| | | |
|---|---|---|
| mouse 4-72*01 | QIVLSQSPAILSASPGEKVTMTC[redacted]WYQQKPGSSPKPWIY[redacted]GVPARFSGSGSGTSYSLTISRVEAEDAATYYC[redacted] | SEQ ID NO. 246 |
| F-p1d1-C | ...........................................................................................T | SEQ ID NO. 247 |

| | | |
|---|---|---|
| mouse 12-46*01 | DIQMTQSPASLSVSVGETVTITC[redacted]WYQQKQGKSPQLLVY[redacted]GVPSRFSGSGSGTQYSLKINSLQSEDFGSYYC[redacted] | SEQ ID NO. 248 |
| F-p1e3 | ...........................................................................................VT | SEQ ID NO. 249 |

| | | |
|---|---|---|
| mouse 12-44*01 | DIQMTQSPASLSASVGETVTITC[redacted]WYQQKQGKSPQLLVY[redacted]GVPSRFSGSGSGTQFSLKINSLQPEDFGSYYC[redacted] | SEQ ID NO. 250 |
| N-p3g9 | ..V.S........................................................................................ | SEQ ID NO. 251 |

FIG. 8B

```
                                          CDR H1                 CDR H2
                  1        10        20         30        40        5052A     60
glVRC01 Heavy     QVQLVQSGAEVKKPGASVKVSCKASGYTFTGYYMHWVRQAPGQGLEWMGWINPNSGGTNYAQKFQ
P-p1f1 Heavy      ..................................N..............................
P-p3b3 Heavy      .................................I....................R.....C....
VRC01c-HuGL2      .................................................................
glVRC01 contacts                             * *  * *           * *   **********  *
P-p1f1 contacts                                  * *           * *  ***********  *
P-p3b3 contacts                             ****  * *           ***   **********  *

                                                         CDR H3
                     70        8082ABC     90        100ABCD       110
glVRC01 Heavy     GRVTMTRDTSISTAYMELSRLRSDDTAVYYCARGKNSDYNWDFQHWGQGTLVT
P-p1f1 Heavy      .....................................................
P-p3b3 Heavy      ..................................I....T.............
VRC01c-HuGL2      .................................KISG.---YS.D........
glVRC01 contacts    *** * ** *                       *****
P-p1f1 contacts         *                             ****
P-p3b3 contacts         * *                          *****
```

| |
|---|
| SEQ ID NO. 252 |
| SEQ ID NO. 253 |
| SEQ ID NO. 254 |
| SEQ ID NO. 255 |

FIG. 8C

```
                                                CDR L1                                CDR L2
                    1       10        20      27         30        40        50         60
                                                ABCDEF
glVRC01 K3-20 Light EIVLTQSPGTLSLSPGERATLSCRASQSV------SSSYLAWYQQKPGQAPRLLIYGASSRATGIPDRFS
      P-p1f1 Light  D..MS...SS.AV.V..KV.M..KS...LLYSSNQKN...........S.K....W..T.ES.V.D..T
      P-p3b3 Light  D..MS...SS.AV.V..KV.M..KS...LLYSSNQKN...........S.K....W..T.ES.V.D..T
      VRC01c-HuGL2  D..MT...DS.AV.L.....IN.KS...VLYSSNNKN...........P.K....W..T.RS.V.D..S
  glVRC01 contacts  ***                     ***       *  *
   P-p1f1 contacts  **                      *         *  *
   P-p3b3 contacts                                   **

                                                   CDR L3
                          70        80          9096   100
glVRC01 K3-20 Light SGSGTDFTLTISRLEPEDFAVYYCQQYEFFGQGTKLEI   SEQ ID NO. 256
      P-p1f1 Light  .............VKA..L.........M..G......   SEQ ID NO. 257
      P-p3b3 Light  .............VKA..L.........TL.S......   SEQ ID NO. 258
      VRC01c-HuGL2  ..............QA..V........YS..G...V..   SEQ ID NO. 259
  glVRC01 contacts     *                        *****
   P-p1f1 contacts                              ****
   P-p3b3 contacts                               ***
```

FIG. 9

| | P-p1f1 with eOD-GT8 | P-p3b3 with 426c core |
|---|---|---|
| **Data collection** | | |
| Space group | P22121 | C222 |
| Cell dimensions | | |
| *a*, *b*, *c* (Å) | 60.879, 92.406, 223.498 | 146.796, 176.755, 108.573, |
| *α*, *β*, *γ* (Å) | 90, 90, 90 | 90, 90, 90 |
| Resolution (Å) | 50.00-3.20 (3.26-3.2)* | 50.00–3.59 (3.65-3.59)* |
| $^{R}$sym $^{or}$ $^{R}$merge | 0.227 (1.089)* | 0.105 (0.573)* |
| *I*/s*I* | 7.89 (1.58)* | 7.75 (1.075)* |
| Completeness (%) | 98.7 (99.7)* | 82.5 (75.8)* |
| Redundancy | 6.2 (5.8)* | 2.8 (2.4)* |
| $^{CC}$1/2 | 0.970 (0.659)* | 0.990 (0.801)* |
| **Refinement** | | |
| Resolution (Å) | (41.16-3.202) (3.317-3.202)* | 50.00-3.594 (3.723-3.594)* |
| No. reflections | 20643 (1702)* | 11541 (469) |
| $^{R}$work$^{/R}$free | 22.61/28.72 (29.79/37.28)* | 23.25/26.86 (27.39/24.22)* |
| No. atoms | 8755 | 5868 |
| Protein | 8677 | 5638 |
| Water | 49 | 12 |
| Ligand | 29 | 218 |
| B-factors (Å$^2$) | 65.00 | 95.24 |
| Protein | 65.06 | 94.33 |
| Water | 30.62 | 41.70 |
| Ligand | 104.2 | 121.72 |
| R.m.s deviations | | |
| Bond lengths (Å) | 0.005 | 0.009 |
| Bond angles (°) | 1.02 | 1.09 |
| Ramachadran Favored % | 92.35 | 93.79 |
| Ramachadran Outliers % | 0.00 | 0.13 |
| MolProbity all-atoms clashscore | 5.88 | 5.38 |
| **PDB ID** | **6P8N** | **6P8M** |

* Statistics for the highest-resolution shell are shown in parentheses.

FIG. 10E

| | WT 426c | | 426c Δ276 | |
|---|---|---|---|---|
| **Antibody** | **293T** | **GnTI -/-** | **293T** | **GnTI -/-** |
| P-p1e7 | >50 | >50 | >50 | >50 |
| P-p1f1 | >50 | >50 | >50 | 2.98 |
| P-p3b3 | >50 | >50 | >50 | 1.62 |
| P-p3a2 | >50 | >50 | >50 | 3.46 |
| Mature VRC01 | 2.19 | 0.11 | 0.1 | <0.002 |
| glVRC01 | *nt* | >100 | *nt* | *nt* |

| | WT 426c | |
|---|---|---|
| **Antibody** | **293T** | **GnTI-/-** |
| B-p1c10 | >100 | >100 |
| B-p1d12 | >100 | >100 |
| B-p1f2 | >100 | >100 |
| B-p1b5 | >100 | **32.05** |
| Mature VRC01 | **1.7** | **0.08** |
| glVRC01 | *nt* | >100 |

Fig. 16A

| 426c WT Core | Average Kinetic Values | | | | | | |
|---|---|---|---|---|---|---|---|
| | KD (M) | KD Error | kon(1/Ms) | kon Error | kdis(1/s) | kdis Error | Full R^2 |
| gl VRC01 | 1.67E-05 | 3.74E-07 | 3.45E+02 | 8.65E+00 | 5.33E-03 | 2.41E-05 | 0.9933 |
| N-p3g9 | N.B. | | | | | | |
| N-p4a9 | N.B. | | | | | | |
| P-p1e7 | N.B. | | | | | | |
| P-p2b7 | N.B. | | | | | | |
| P-p1f1 | 5.66E-05 | 9.76E-05 | 2.00E+02 | 4.31E+01 | 6.09E-03 | 8.94E-05 | 0.9537 |
| P-p3a2 | 1.20E-05 | 1.03E-06 | 5.72E+02 | 5.48E+01 | 6.44E-03 | 9.20E-05 | 0.9608 |
| P-p1d1 | 6.25E-06 | 1.16E-06 | 8.17E+02 | 4.28E+01 | 3.69E-03 | 2.73E-05 | 0.9757 |
| P-p3b3 | 5.32E-06 | 3.25E-07 | 1.67E+03 | 6.08E+01 | 1.24E-02 | 1.13E-04 | 0.9981 |
| B-p1f8 | 3.57E-06 | 8.15E-08 | 2.11E+03 | 5.11E+01 | 5.46E-03 | 3.30E-05 | 0.9886 |
| B-p1f2 | 3.53E-06 | 8.10E-08 | 2.39E+03 | 5.89E+01 | 6.02E-03 | 3.76E-05 | 0.9901 |
| B-p1a10 | 3.04E-07 | 5.64E-09 | 4.36E+03 | 5.19E+01 | 1.21E-03 | 5.29E-06 | 0.9879 |
| B-p1a11 | 1.74E-07 | 2.42E-09 | 6.43E+03 | 7.26E+01 | 1.06E-03 | 6.39E-06 | 0.9790 |
| B-p1b5 | 3.86E-08 | 1.39E-09 | 9.79E+03 | 1.30E+02 | 2.64E-04 | 7.64E-06 | 0.9713 |

FIG. 16B

| HxB2 WT Core | Average Kinetic Values | | | | | | |
|---|---|---|---|---|---|---|---|
| | KD (M) | KD Error | kon(1/Ms) | kon Error | kdis(1/s) | kdis Error | Full R^2 |
| gl VRC01 | 2.82E-05 | 8.01E-08 | 3.69E+03 | 1.22E+02 | 1.28E-01 | 3.62E-03 | 0.9677 |
| N-p3g9 | N.B. | | | | | | |
| N-p4a9 | N.B. | | | | | | |
| P-p1e7 | N.B. | | | | | | |
| P-p2b7 | N.B. | | | | | | |
| P-p1f1 | 1.15E-05 | 1.10E-06 | 2.09E+03 | 2.01E+02 | 2.24E-02 | 1.01E-03 | 0.9577 |
| P-p3a2 | 4.75E-06 | 1.89E-07 | 3.58E+03 | 2.11E+02 | 1.37E-02 | 2.26E-04 | 0.9801 |
| P-p1d1 | 7.42E-06 | 4.23E-07 | 2.75E+03 | 1.89E+02 | 1.72E-02 | 3.73E-04 | 0.9736 |
| P-p3b3 | 4.90E-06 | 2.61E-07 | 4.71E+03 | 3.56E+02 | 1.75E-02 | 3.85E-04 | 0.9735 |
| B-p1f8 | 1.08E-05 | 1.34E-06 | 3.31E+03 | 2.55E+02 | 3.99E-02 | 1.28E-03 | 0.9725 |
| B-p1f2 | 8.72E-06 | 7.74E-07 | 4.21E+03 | 4.08E+02 | 3.22E-02 | 1.07E-03 | 0.9683 |
| B-p1a10 | 2.91E-06 | 9.59E-08 | 7.16E+03 | 2.82E+02 | 8.39E-03 | 9.05E-05 | 0.9764 |
| B-p1a11 | 2.46E-08 | 5.92E-10 | 9.64E+03 | 5.98E+01 | 1.90E-04 | 3.86E-06 | 0.9857 |
| B-p1b5 | 6.38E-08 | 1.37E-09 | 5.94E+03 | 4.52E+01 | 2.98E-04 | 4.44E-06 | 0.9966 |

FIG. 17

| | | Prime Antibodies | | | | Boost Antibodies | | | | controls | |
|---|---|---|---|---|---|---|---|---|---|---|---|
| Virus | Cell Type | P-p1f1 | P-p1e7 | P-p3a2 | P-p3b3 | B-p1c10 | B-p1d12 | B-p1f2 | B-p1b5 | Mature VRC01 | glVRC01 |
| WT 426c | 293T | >50 | >50 | >50 | >50 | >100 | >100 | >100 | >100 | 1.7 | nt |
| | GnTI-/- | >50 | >50 | >50 | >50 | >100 | >100 | >100 | 32.05 | 0.08 | >100 |
| 426c Δ276, 460, 463 | 293T | >50 | >50 | >50 | 28.89 | 16.80 | 18.34 | 0.17 | 0.04 | <0.01 | nt |
| | GnTI-/- | 1.36 | 0.36 | 1.84 | 0.45 | 0.04 | 0.04 | 0.01 | 0.01 | 0.01 | 0.642 |
| 426c Δ276, 460, 463 D279K | GnTI-/- | nt | nt | nt | nt | >50 | >50 | >50 | >50 | >25 | nt |
| 426c Δ276 | 293T | >50 | >50 | >50 | >50 | >50 | >50 | >50 | 0.64 | 0.20 | nt |
| | GnTI-/- | 2.98 | >50 | 3.46 | 1.62 | 0.89 | 1.25 | >50 | <0.02 | <0.01 | nt |
| 426c Δ276 D279K | GnTI-/- | nt | nt | nt | nt | >50 | >50 | >50 | >50 | >25 | nt |
| 426c Δ460, 463 | 293T | >50 | >50 | >50 | >50 | nt | nt | nt | nt | 0.29 | nt |
| | GnTI-/- | >50 | >50 | >50 | >50 | nt | nt | nt | nt | 0.03 | nt |
| CH0505TF | 293T | nt | nt | nt | nt | >100 | >100 | >100 | >100 | 0.12 | nt |

FIG. 17 cont'd

| | | | | | | | | | | | |
|---|---|---|---|---|---|---|---|---|---|---|---|
| | GnTI-/- | nt | nt | nt | nt | >100 | >100 | >100 | >100 | <0.02 | nt |
| CH0505TF Δ197, 276, 362, 461/462 | 293T | nt | nt | nt | nt | >100 | >100 | >100 | >100 | <0.02 | nt |
| | GnTI-/- | nt | nt | nt | nt | >100 | >100 | >100 | 8.93 | <0.02 | nt |
| CH0505TF Δ197, 362, 461/462 | 293T | nt | nt | nt | nt | >100 | >100 | >100 | >100 | <0.02 | nt |
| | GnTI-/- | nt | nt | nt | nt | >100 | >100 | >100 | >100 | <0.02 | nt |
| CH0505TF Δ276, 362, 461/462 | 293T | nt | nt | nt | nt | >100 | >100 | >100 | >100 | <0.02 | nt |
| | GnTI-/- | nt | nt | nt | nt | >100 | >100 | >100 | 2.21 | <0.02 | nt |
| CH0505TF Δ197, 276, 362 | 293T | nt | nt | nt | nt | >100 | >100 | >100 | >100 | 1.61 | nt |
| | GnTI-/- | nt | nt | nt | nt | >100 | >100 | >100 | >100 | <0.02 | nt |

*nt, not tested

FIG. 20

| Name | Sequence | Forward/Reverse | First/Second | Heavy/Light | Source | |
|---|---|---|---|---|---|---|
| 5' L-Vκ_3 | TGCTGCTGCTCTGGGTTCCAG | Forward | First | Light | Tiller et al., 2009, Journal of Immunological Methods 350, 183-189 | SEQ ID NO. 265 |
| 5' L-Vκ_4 | ATTWTCAGCTTCCTGCTAATC | Forward | First | Light | | SEQ ID NO. 266 |
| 5' L-Vκ_5 | TTTTGCTTTTCTGGATTYCAG | Forward | First | Light | | SEQ ID NO. 267 |
| 5' L-Vκ_6 | TCGTGTTKCTSTGGTTGTCTG | Forward | First | Light | | SEQ ID NO. 268 |
| 5' L-Vκ_6,8,9 | ATGGAATCACAGRCYCWGGT | Forward | First | Light | | SEQ ID NO. 269 |
| 5' L-Vκ_14 | TCTTGTTGCTCTGGTTYCCAG | Forward | First | Light | | SEQ ID NO. 270 |
| 5' L-Vκ_19 | CAGTTCCTGGGGCTCTTGTTGTTC | Forward | First | Light | | SEQ ID NO. 271 |
| 5' L-Vκ_20 | CTCACTAGCTCTTCTCCTC | Forward | First | Light | | SEQ ID NO. 272 |
| 3' mCk | GATGGTGGGAAGATGGATACAGTT | Reverse | First | Light | | SEQ ID NO. 22 |
| 3' BsiWI P-mJK01 | GCCACCGTACGTTTGATTTCCAGCTTGGTG | Reverse | Second | Light | | SEQ ID NO. 23 |
| 3' BsiWI P-mJK02 | GCCACCGTACGTTTTATTTCCAGCTTGGTC | Reverse | Second | Light | | SEQ ID NO. 24 |

FIG. 20 cont'd

| | | | | | | |
|---|---|---|---|---|---|---|
| 3' BsiWI P-mJK03 | GCCACCGTACGTTTTATTTCCAACTTTGTC | Reverse | Second | Light | | SEQ ID NO. 38 |
| 3' BsiWI P-mJK04 | GCCACCGTACGTTTCAGCTCCAGCTTGGTC | Reverse | Second | Light | | SEQ ID NO. 203 |
| 5' mVkappa | GAYATTGTGMTSACMCARWCTMCA | Forward | Second | Light | | SEQ ID NO. 218 |
| 5' Mouse leader | CTCTTCCTCCTGTCAGTAACTGAAGGTGTCC | Forward | First | Heavy | N/A | SEQ ID NO. 224 |
| 3' KI Rev | TGAGGAGACGGTGACCAGGGTGCC | Reverse | First/Second | Heavy | N/A | SEQ ID NO. 239 |
| 5' glVRC01 | CAGGTGCAGCTGGTGCAGTCTGG | Forward | Second | Heavy | Jardine et al., 2015. Science 349, 156–524 161 | SEQ ID NO. 244 |

FIG. 21

| Temperature (C) | Time | |
|---|---|---|
| 94 | 5 min | |
| 94 | 30 sec | Repeat 50X |
| X (IgH 1st round: 56, IgH 2nd round: 60, IgK 1st round: 50, IgK 2nd round: 45) | 30 sec | |
| 72 | 55 sec | |
| 72 | 10 min | |
| 4 | Infinity | |

FIG. 22

>426c WT core-gp120.
MDAMKRGLCCVLLLCGAVFVSPSASVWKEAKTTLFCASDAKAYEKECHNVWATHACVPTDPN
PQEVVLENVTENFNMWKNDMVDQMQEDVISIWDQCLKPCVKLTNTSTLTQACPKVTFDPIPIH
YCAPAGYAILKCNNKTFNGKGPCNNVSTVQCTHGIKPVVSTQLLLNGSLAEEEIVIRSKNLSDNA
KIIIVQLNKSVEIVCTRPNNGGSGSGGDIRQAYCNISGRNWSEAVNQVKKKLKEHFPHKNISFQS
SSGGDLEITTHSFNCGGEFFYCNTSGLFNDTISNATIMLPCRIKQIINMWQEVGKAIYAPPIKGNI
TCKSDITGLLLLRDGGNTTNNTEIFRPGGGDMRDNWRSELYKYKVVEIKPL (SEQ ID NO: 39)

>eOD-GT8-hisavi.
MDAMKRGLCCVLLLCGAVFVSPSASDTITLPCRPAPPPHCSSNITGLILTRQGGYSNDNTVIFRP
SGGDWRDIARCQIAGTVVSTQLFLNGSLAEEEVVIRSE*DWRD*NAKSICVQLNTSVEINCTGAGH
CNISRAKWNNTLKQIASKLREQYGNKTIIFKPSSGG*D*PEFVNHSFNCGGEFFYCDSTQLFNSTW
FNST (SEQ ID NO: 40)

>426c BG505_WT-Sosip.
MPMGSLQPLATLYLLGMLVASVLAAENLWVTVYYGVPVWKEAKTTLFCASDAKAYEKEVHNV
WATHACVPTDPNPQEVVLENVTENFNMWKNDMVDQMQEDVISIWDQSLKPCVKLTPLCVTLN
CTNVNVTSNSTNVNSSSTDNTTLGEIKNCSFDITTEIRDKTRKEYALFYRLDIVPLDNSSNPNSS
NTYRLINCNTSTCTQACPKVTFDPIPIHYCAPAGYAILKCNNKTFNGKGPCNNVSTVQCTHGIKP
VVSTQLLLNGSLAEEEIVIRSKNLSDNAKIIIVQLNKSVEIVCTRPNNNTRRSIRIGPGQTFYATDII
GDIRQAYCNISGRNWSEAVNQVKKKLKEHFPHKNISFQSSSGGDLEITTHSFNCGGEFFYCNT
SGLFNDTISNATIMLPCRIKQIINMWQEVGKCIYAPPIKGNITCKSDITGLLLLRDGGNTTNNTEIF
RPGGGDMRDNWRSELYKYKVVKIEPLGVAPTRCKRRVVGRRRRRRAVGIGAVFLGFLGAAGS
TMGAASMTLTVQARNLLSGIVQQQSNLLRAPEAQQHLLKLTVWGIKQLQARVLAVERYLRDQQ
LLGIWGCSGKLICCTNVPWNSSWSNRNLSEIWDNMTWLQWDKEISNYTQIIYGLLEESQNQQE
KNEQDLLALD (SEQ ID NO: 41)

>426c:BG505_TM-Sosip (S278A/T462A/T465A)
MPMGSLQPLATLYLLGMLVASVLAAENLWVTVYYGVPVWKEAKTTLFCASDAKAYEKEVHNV
WATHACVPTDPNPQEVVLENVTENFNMWKNDMVDQMQEDVISIWDQSLKPCVKLTPLCVTLN
CTNVNVTSNSTNVNSSSTDNTTLGEIKNCSFDITTEIRDKTRKEYALFYRLDIVPLDNSSNPNSS
NTYRLINCNTSTCTQACPKVTFDPIPIHYCAPAGYAILKCNNKTFNGKGPCNNVSTVQCTHGIKP
VVSTQLLLNGSLAEEEIVIRSKNLADNAKIIIVQLNKSVEIVCTRPNNNTRRSIRIGPGQTFYATDII
GDIRQAYCNISGRNWSEAVNQVKKKLKEHFPHKNISFQSSSGGDLEITTHSFNCGGEFFYCNT
SGLFNDTISNATIMLPCRIKQIINMWQEVGKCIYAPPIKGNITCKSDITGLLLLRDGGNTANNAEIF
RPGGGDMRDNWRSELYKYKVVKIEPLGVAPTRCKRRVVGRRRRRRAVGIGAVFLGFLGAAGS
TMGAASMTLTVQARNLLSGIVQQQSNLLRAPEAQQHLLKLTVWGIKQLQARVLAVERYLRDQQ
LLGIWGCSGKLICCTNVPWNSSWSNRNLSEIWDNMTWLQWDKEISNYTQIIYGLLEESQNQQE
KNEQDLLALD (SEQ ID NO: 42)

FIG. 22 cont'd 426c dGly N276 SOSIP
>426c:BG505_SM-Sosip. S278A
MGSLQPLATLYLLGMLVASVLAAENLWVTVYYGVPVWKEAKTTLFCASDAKAYEKEVHNVWA
THACVPTDPNPQEVVLENVTENFNMWKNDMVDQMQEDVISIWDQSLKPCVKLTPLCVTLNCT
NVNVTSNSTNVNSSSTDNTTLGEIKNCSFDITTEIRDKTRKEYALFYRLDIVPLDNSSNPNSSNT
YRLINCNTSTCTQACPKVTFDPIPIHYCAPAGYAILKCNNKTFNGKGPCNNVSTVQCTHGIKPVV
STQLLLNGSLAEEEIVIRSKNLADNAKIIVQLNKSVEIVCTRPNNNTRRSIRIGPGQTFYATDIIGDI
RQAYCNISGRNWSEAVNQVKKKLKEHFPHKNISFQSSSGGDLEITTHSFNCGGEFFYCNTSGL
FNDTISNATIMLPCRIKQIINMWQEVGKCIYAPPIKGNITCKSDITGLLLLRDGGNTTNNTEIFRPG
GGDMRDNWRSELYKYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARVLAVERYLRDQQLLGI
WGCSGKLICCTNVPWNSSWSNRNLSEIWDNMTWLQWDKEISNYTQIIYGLLEESQNQQEKNE
QDLLALD (SEQ ID NO: 43)

>45_01dG5core-gp120.
MDAMKRGLCCVLLLCGAVFVSPSASVWKEATATLFCASDAKAYETECHNVWATHACVPTDPN
PQEVVLENVTENFNMWKNNMVEQMHEDIISLWDQCLKPCVKLTNTSVITQACPKISFEPIPIHYC
APAGFAILKCNDKKFNGTGPCTNVSTVQCTHGIRPVVSTQLLLNGSLAEEEIVIRSENIKDNAKIII
VQLNETVEINCTRPNNGGSGSGGDIRQAHCNISKAKWENTLKQIARKLREHFKNETIAFNQSSG
GDPEIVMHSFNCGGEFFYCNSTQLFNSTWTWNDTEVVNNTEKNINITLPCRIKQIINMWQEVGK
AMYAPPIKGQIRCSSNITGLLLTRDGGSSTNGTTETFRPGGGDMRDNWRSELYKYKVVKIEPL
(SEQ ID NO: 44)

>45_01dH1core-gp120
MDAMKRGLCCVLLLCGAVFVSPSASVWKEASTTLFCASDAKAYDTECHNVWATHACVPTDPN
PQEVVLENVTEKFNMWKNNMVEQMHEDIISLWDQCLKPCVKLTNTSVITQACPKISFEPIPIHYC
APAGFAILKCNDKKFNGTGKCTNVSTVQCTHGIRPVVSTQLLLNGSLAEEEIIIRSENLTDNAKTL
IVQLNETVAINCTRPNNGGSGSGGNIRQAHCNISETDWNNTLKQVARKLRELFNKTIVFNQSSG
GDPEIVMHSFNCGGEFFYCNTTQLFNSTWHGNETEESSITKDNKTITLPCRIKQIVNRWQEVGK
AMYAPPIEGLIRCSSNITGLLLTRDGGNITNETTTETFRPGGGNMRDNWRSELYKYKVVKIEPL
(SEQ ID NO: 45)

426C dGly V5 SOSIP
>426c:BG505_DM-Sosip. T462A/T465A
MGSLQPLATLYLLGMLVASVLAAENLWVTVYYGVPVWKEAKTTLFCASDAKAYEKEVHNVWA
THACVPTDPNPQEVVLENVTENFNMWKNDMVDQMQEDVISIWDQSLKPCVKLTPLCVTLNCT
NVNVTSNSTNVNSSSTDNTTLGEIKNCSFDITTEIRDKTRKEYALFYRLDIVPLDNSSNPNSSNT
YRLINCNTSTCTQACPKVTFDPIPIHYCAPAGYAILKCNNKTFNGKGPCNNVSTVQCTHGIKPVV
STQLLLNGSLAEEEIVIRSKNLSDNAKIIVQLNKSVEIVCTRPNNNTRRSIRIGPGQTFYATDIIGDI
RQAYCNISGRNWSEAVNQVKKKLKEHFPHKNISFQSSSGGDLEITTHSFNCGGEFFYCNTSGL
FNDTISNATIMLPCRIKQIINMWQEVGKCIYAPPIKGNITCKSDITGLLLLRDGGNTANNAEIFRPG
GGDMRDNWRSELYKYKVVKIEPLGVAPTRCKRRVVGRRRRRRAVGIGAVFLGFLGAAGSTMG
AASMTLTVQARNLLSGIVQQQSNLLRAPEAQQHLLKLTVWGIKQLQARVLAVERYLRDQQLLGI
WGCSGKLICCTNVPWNSSWSNRNLSEIWDNMTWLQWDKEISNYTQIIYGLLEESQNQQEKNE
QDLLALD (SEQ ID NO: 46)

FIG. 22 cont'd

>HxB2 core-gp120 (without multimerization)
MDAMKRGLCCVLLLCGAVFVSPSASVWKEATTTLFCASDAKAYDTECHNVWATHACVPTDPN
PQEVVLVNVTENFNMWKNDMVEQMHEDIISLWDQCLKPCVKLTNTSVITQACPKVSFEPIPIHY
CAPAGFAILKCNNKTFNGTGPCTNVSTVQCTHGIRPVVSTQLLLNGSLAEEEVVIRSVNFTDNA
KTIIVQLNTSVEINCTRPNNGGSGSGGNMRQAHCNISRAKWNNTLKQIASKLREQFGNNKTIIFK
QSSGGDPEIVTHSFNCGGEFFYCNSTQLFNSTWFNSTWSTEGSNNTEGSDTITLPCRIKQIINM
WQKVGKAMYAPPISGQIRCSSNITGLLLTRDGGNSNNESEIFRPGGGDMRDNWRSELYKYKV
VKIEPL (SEQ ID NO: 47)

>QH0692core-gp120.
MDAMKRGLCCVLLLCGAVFVSPSASVWKEATTTLFCASDAKAYETECHNVWATHACVPTDPN
PQEVVLGNVTENFNMWKNNMVEQMHEDIISLWDECLKPCVKLTNTSVITQACPKVSFEPIPIHY
CAPAGFAILKCNNKTFNGTGPCTNVSTVQCTHGIRPVVSTQLLLNGSLAEEEVVIRSENFTNNA
KTIIVHLKKSVEINCTRPGNGGSGSGGDIRQAHCNLSSVQWNDTLKQIVIKLGEQFGTNKTIAFN
QSSGGDPEIVMHSFNCGGEFFYCNTTQLFNSTWEFHGNWTRSNFTESNSTTITLPCRIKQIVN
MWQEVGKAMYAPPIRGQIRCSSNITGLLLTRDGGVNGTRETFRPGGGDMRDNWRSELYKYKV
VKIEPL (SEQ ID NO: 48)

>426c_WTcore-C4b.
VWKEAKTTLFCASDAKAYEKECHNVWATHACVPTDPNPQEVVLENVTENFNMWKNDMVDQM
QEDVISIWDQCLKPCVKLTNTSTLTQACPKVTFDPIPIHYCAPAGYAILKCNNKTFNGKGPCNNV
STVQCTHGIKPVVSTQLLLNGSLAEEEIVIRSKNLSDNAKIIIVQLNKSVEIVCTRPNNGGSGSGG
DIRQAYCNISGRNWSEAVNQVKKKLKEHFPHKNISFQSSSGGDLEITTHSFNCGGEFFYCNTS
GLFNDTISNATIMLPCRIKQIINMWQEVGKAIYAPPIKGNITCKSDITGLLLLRDGGNTTNNTEIFR
PGGGDMRDNWRSELYKYKVVEIKPLGSSKKQGDADVCGEVAYIQSVVSDCHVPTAELRTLLEI
RKLFLEIQKLKVELQGLSKE- (SEQ ID NO: 49)

>Cterm-C4b.
SKKQGDADVCGEVAYIQSVVSDCHVPTAELRTLLEIRKLFLEIQKLKVELQGLSKE (SEQ ID NO: 50)

>Cterm-Ferritin.
ESQVRQQFSKDIEKLLNEQVNKEMQSSNLYMSMSSWCYTHSLDGAGLFLFDHAAEEYEHAKK
LIIFLNENNVPVQLTSISAPEHKFEGLTQIFQKAYEHEQHISESINNIVDHAIKSKDHATFNFLQWY
VAEQHEEEVLFKDILDKIELIGNENHGLYLADQYVKGIAKSRKSGS (SEQ ID NO: 51)

B6 MAb (full name: 021418-p1b5-G28-CC4b-Hx4b-eO) Heavy Chain:
QVQLVQSGAEVKKPGASMRVSCKASGYTFTDYYVNWVRQAPGQGLEWMGWINPTRGGVNY
AQKFQGRVTMTRDTSISTAYMELSRLRSDDTAVYFCARGKNSDYNWDFQHWGQGTLVTVSS
(SEQ ID NO: 52)

B6 MAb Light Chain:
DIVMSQSPSPLAVSVGEKVTMSCKSSQNLLYSSNEENYLAWYQQKPGQSPKLLIYWASTRES
GVPDRFTGSGSGTDFTLTISSVKAEDLAVYYCQQYETFGGGTKLEIK (SEQ ID NO: 53)

FIG. 22 cont'd

>Exemplary wt gp120 protein; GENBANK® Accession AAB05604
MRVKGIRKSYQYLWKGGTLLLGILMICSAVEKLWVTVYYGVPVWKEATTTLFCASDAKAYDTEV
HNVWATHACVPTDPNPQEVVLENVTEHFNMWKNNMVEQMQEDIISLWDQSLKPCVKLTPLCV
TLNCKDVNATNTTNDSEGTMERGEIKNCSFNITTSIRDEVQKEYALFYKLDVVPIDNNNTSYRLI
SCDTSVITQACPKISFEPIPIHYCAPAGFAILKCNDKTFNGKGPCKNVSTVQCTHGIRPVVSTQLL
LNGSLAEEEVVIRSDNFTNNAKTIIVQLKESVEINCTRPNNNTRKSIHIGPGRAFYTTGEIIGDIRQ
AHCNISRAKWNDTLKQIVIKLREQFENKTIVFNHSSGGDPEIVMHSFNCGGEFFYCNSTQLFNS
TWNNNTEGSNNTEGNTITLPCRIKQIINMWQEVGKAMYAPPIRGQIRCSSNITGLLLTRDGGINE
NGTEIFRPGGGDMRDNWRSELYKYKVVKIEPLGVAPTKAKRRVVQREKRAVGIGAVFLGFLGA
AGSTMGAASMTLTVQARLLLSGIVQQQNNLLRAIEAQQRMLQLTVWGIKQLQARVLAVERYLG
DQQLLGIWGCSGKLICTTAVPWNASWSNKSLDRIWNNMTWMEWEREIDNYTSEIYTLIEESQN
QQEKNEQELLELDKWASLWNWFDITKWLWYIKIFIMIVGGLVGLRLVFTVLSIVNRVRQGYSPLS
FQTLLPAPRGPDRPEGIEEEGGERDRDRSGRLVNGFLALIWVDLRSLCLFSYHRLRDLLLTVTR
IVELLGRRGWEVLKYWWNLLQYWSQELKNSAVSLLNATAIAVAEGTDRIIEALQRTYRAILHIPT
RIRQGLERALL (SEQ ID NO: 54)

>Exemplary wt gp120 protein; GENBANK® Accession AAD12142
MRVKEKYQHLWRWGWRWGTMLLGMLMICSATEKLWVTVYYGVPVWKEATTTLFCASDAKAY
DTEVHNVWATHACVPTDPNPQEVVLVNVTENFNMWKNDMVEQMHEDIISLWDQSLKPCVKLT
PLCVSLNCTDLKNDTNTNSSSGRMIMEKGEIKNCSFNISTSIRGKVQKEYAFFYKLDIIPIDNDTT
SYTLTSCNTSVISQACPKVSFEPIPIHYCAPAGFAILKCNNKTFNGTGPCTNVSTVQCTHGIRPV
VSTQLLLNGSLAEEEVVIRSVNFMDNAKTIIVQLNTSVEINCTRPSNNTIKRIRIQRGPGRAFVTM
GKIGDMRQAHCNISRAKWNNTLKQIASKLREQFGNNKTIIFKQSSGGDPEIVTHSFNCGGEFFY
CNSTQLFNSTWFNSTWSTEGSNNTEGSDTITLPCRIKQIINMWQKVGKAMYAPPISGQIRCSSN
ITGLLLTRDGGKGNNESEIFRPGGGDMRDNWRSELYKYKVVKIEPLGVAPTKAKRRVVQREKR
AVGIGALFLGFLGAAGSTMGAASMTLTVQARQLLSGIVQQQNNLLRAIEAQQHLLQLTVWGIKQ
LQARILAVERYLKDQQLLGIWGCSGKLICTTAVPWNASWSNKSLEQIWNHMTWMEWDREINN
YTSLIHSLIEESQNQQEKNEQELLELDKWASLWNWFDITNWLWYIKLFIMIVGGLVGLRIVFAVL
SIVNRVRQGYSPLSFQTHLPTPRGPDRPEGIEEEGGERDRDRSIRLVNGSLALIWDDLRSLCLF
SYHRLRDLLLIVTRIVELLGRRGWEALKYWWNLLQYWSQELKNSAVSLLNATAIAVAEGTDRVI
EVVQGACRAIRHIPRRIRQGLERILL (SEQ ID NO: 55)

>426ccore WT gp120 without signal sequence (mutation positions bolded)
VWKEAKTTLFCASDAKAYEKECHNVWATHACVPTDPNPQEVVLENVTENFNMWKNDMVDQM
QEDVISIWDQCLKPCVKLTNTSTLTQACPKVTFDPIPIHYCAPAGYAILKCNNKTFNGKGPCNNV
STVQCTHGIKPVVSTQLLLNGSLAEEEIVIRSKNLSDNAKIIVQLNKSVEIVCTRPNNGGSGSGG
DIRQAYCNISGRNWSEAVNQVKKKLKEHFPHKNISFQSSSGGDLEITTHSFNCGGEFFYCNTS
GLFNDTISNATIMLPCRIKQIINMWQEVGKAIYAPPIKGNITCKSDITGLLLLRDGGNTTNNTEIFR
PGGGDMRDNWRSELYKYKVVEIKPL (SEQ ID NO: 175)

>eOD-GT8-hisavi without signal sequence
DTITLPCRPAPPPHCSSNITGLILTRQGGYSNDNTVIFRPSGGDWRDIARCQIAGTVVSTQLFLN
GSLAEEEVVIRSE*DWRD*NAKSICVQLNTSVEINCTGAGHCNISRAKWNNTLKQIASKLREQYGN
KTIIFKPSSGG*D*PEFVNHSFNCGGEFFYCDSTQLFNSTWFNST (SEQ ID NO: 176)

FIG. 22 cont'd

>426c:BG505_WT-Sosip. without signal sequence
ENLWVTVYYGVPVWKEAKTTLFCASDAKAYEKEVHNVWATHACVPTDPNPQEVVLENVTENF
NMWKNDMVDQMQEDVISIWDQSLKPCVKLTPLCVTLNCTNVNVTSNSTNVNSSSTDNTTLGEI
KNCSFDITTEIRDKTRKEYALFYRLDIVPLDNSSNPNSSNTYRLINCNTSTCTQACPKVTFDPIPI
HYCAPAGYAILKCNNKTFNGKGPCNNVSTVQCTHGIKPVVSTQLLLNGSLAEEEIVIRSKNLSDN
AKIIIVQLNKSVEIVCTRPNNNTRRSIRIGPGQTFYATDIIGDIRQAYCNISGRNWSEAVNQVKKKL
KEHFPHKNISFQSSSGGDLEITTHSFNCGGEFFYCNTSGLFNDTISNATIMLPCRIKQIINMWQE
VGKCIYAPPIKGNITCKSDITGLLLLRDGGNTTNNTEIFRPGGGDMRDNWRSELYKYKVVKIEPL
GVAPTRCKRRVVGRRRRRRAVGIGAVFLGFLGAAGSTMGAASMTLTVQARNLLSGIVQQQSN
LLRAPEAQQHLLKLTVWGIKQLQARVLAVERYLRDQQLLGIWGCSGKLICCTNVPWNSSWSNR
NLSEIWDNMTWLQWDKEISNYTQIIYGLLEESQNQQEKNEQDLLALD (SEQ ID NO: 177)

>426c:BG505_TM-Sosip. S278A/T462A/T465A without signal sequence
ENLWVTVYYGVPVWKEAKTTLFCASDAKAYEKEVHNVWATHACVPTDPNPQEVVLENVTENF
NMWKNDMVDQMQEDVISIWDQSLKPCVKLTPLCVTLNCTNVNVTSNSTNVNSSSTDNTTLGEI
KNCSFDITTEIRDKTRKEYALFYRLDIVPLDNSSNPNSSNTYRLINCNTSTCTQACPKVTFDPIPI
HYCAPAGYAILKCNNKTFNGKGPCNNVSTVQCTHGIKPVVSTQLLLNGSLAEEEIVIRSKNLAD
NAKIIIVQLNKSVEIVCTRPNNNTRRSIRIGPGQTFYATDIIGDIRQAYCNISGRNWSEAVNQVKK
KLKEHFPHKNISFQSSSGGDLEITTHSFNCGGEFFYCNTSGLFNDTISNATIMLPCRIKQIINMW
QEVGKCIYAPPIKGNITCKSDITGLLLLRDGGNTANNAEIFRPGGGDMRDNWRSELYKYKVVKI
EPLGVAPTRCKRRVVGRRRRRRAVGIGAVFLGFLGAAGSTMGAASMTLTVQARNLLSGIVQQ
QSNLLRAPEAQQHLLKLTVWGIKQLQARVLAVERYLRDQQLLGIWGCSGKLICCTNVPWNSSW
SNRNLSEIWDNMTWLQWDKEISNYTQIIYGLLEESQNQQEKNEQDLLALD (SEQ ID NO: 178)

426c dGly N276 SOSIP without signal sequence
>426c:BG505_SM-Sosip. S278A without signal sequence
ENLWVTVYYGVPVWKEAKTTLFCASDAKAYEKEVHNVWATHACVPTDPNPQEVVLENVTENF
NMWKNDMVDQMQEDVISIWDQSLKPCVKLTPLCVTLNCTNVNVTSNSTNVNSSSTDNTTLGEI
KNCSFDITTEIRDKTRKEYALFYRLDIVPLDNSSNPNSSNTYRLINCNTSTCTQACPKVTFDPIPI
HYCAPAGYAILKCNNKTFNGKGPCNNVSTVQCTHGIKPVVSTQLLLNGSLAEEEIVIRSKNLAD
NAKIIIVQLNKSVEIVCTRPNNNTRRSIRIGPGQTFYATDIIGDIRQAYCNISGRNWSEAVNQVKK
KLKEHFPHKNISFQSSSGGDLEITTHSFNCGGEFFYCNTSGLFNDTISNATIMLPCRIKQIINMW
QEVGKCIYAPPIKGNITCKSDITGLLLLRDGGNTTNNTEIFRPGGGDMRDNWRSELYKYKVVKIE
PLGVAPTRCKRRVVGRRRRRRAVGIGAVFLGFLGAAGSTMGAASMTLTVQARNLLSGIVQQQ
SNLLRAPEAQQHLLKLTVWGIKQLQARVLAVERYLRDQQLLGIWGCSGKLICCTNVPWNSSWS
NRNLSEIWDNMTWLQWDKEISNYTQIIYGLLEESQNQQEKNEQDLLALD (SEQ ID NO: 179)

>45_01dG5core-gp120 without signal sequence
VWKEATATLFCASDAKAYETECHNVWATHACVPTDPNPQEVVLENVTENFNMWKNNMVEQM
HEDIISLWDQCLKPCVKLTNTSVITQACPKISFEPIPIHYCAPAGFAILKCNDKKFNGTGPCTNVS
TVQCTHGIRPVVSTQLLLNGSLAEEEIVIRSENIKDNAKIIIVQLNETVEINCTRPNNGGSGSGGDI
RQAHCNISKAKWENTLKQIARKLREHFKNETIAFNQSSGGDPEIVMHSFNCGGEFFYCNSTQLF
NSTWTWNDTEVVNNTEKNINITLPCRIKQIINMWQEVGKAMYAPPIKGQIRCSSNITGLLLTRDG
GSSTNGTTETFRPGGGDMRDNWRSELYKYKVVKIEPL (SEQ ID NO: 180)

FIG. 22 cont'd

>45_01dH1core-gp120 without signal sequence
VWKEASTTLFCASDAKAYDTECHNVWATHACVPTDPNPQEVVLENVTEKFNMWKNNMVEQM
HEDIISLWDQCLKPCVKLTNTSVITQACPKISFEPIPIHYCAPAGFAILKCNDKKFNGTGKCTNVS
TVQCTHGIRPVVSTQLLLNGSLAEEEIIIRSENLTDNAKTLIVQLNETVAINCTRPNNGGSGSGGN
IRQAHCNISETDWNNTLKQVARKLRELFNKTIVFNQSSGGDPEIVMHSFNCGGEFFYCNTTQLF
NSTWHGNETEESSITKDNKTITLPCRIKQIVNRWQEVGKAMYAPPIEGLIRCSSNITGLLLTRDG
GNITNETTTETFRPGGGNMRDNWRSELYKYKVVKIEPL (SEQ ID NO: 181)

426C dGly V5 SOSIP without signal sequence
>426c:BG505_DM-Sosip. T462A/T465A without signal sequence
ENLWVTVYYGVPVWKEAKTTLFCASDAKAYEKEVHNVWATHACVPTDPNPQEVVLENVTENF
NMWKNDMVDQMQEDVISIWDQSLKPCVKLTPLCVTLNCTNVNVTSNSTNVNSSSTDNTTLGEI
KNCSFDITTEIRDKTRKEYALFYRLDIVPLDNSSNPNSSNTYRLINCNTSTCTQACPKVTFDPIPI
HYCAPAGYAILKCNNKTFNGKGPCNNVSTVQCTHGIKPVVSTQLLLNGSLAEEEIVIRSKNLSDN
AKIIIVQLNKSVEIVCTRPNNNTRRSIRIGPGQTFYATDIIGDIRQAYCNISGRNWSEAVNQVKKKL
KEHFPHKNISFQSSSGGDLEITTHSFNCGGEFFYCNTSGLFNDTISNATIMLPCRIKQIINMWQE
VGKCIYAPPIKGNITCKSDITGLLLLRDGGNTANNAEIFRPGGGDMRDNWRSELYKYKVVKIEPL
GVAPTRCKRRVVGRRRRRRAVGIGAVFLGFLGAAGSTMGAASMTLTVQARNLLSGIVQQQSN
LLRAPEAQQHLLKLTVWGIKQLQARVLAVERYLRDQQLLGIWGCSGKLICCTNVPWNSSWSNR
NLSEIWDNMTWLQWDKEISNYTQIIYGLLEESQNQQEKNEQDLLALD (SEQ ID NO: 182)

>Hxb2core-gp120 without multimerization and without signal sequence
VWKEATTTLFCASDAKAYDTECHNVWATHACVPTDPNPQEVVLVNVTENFNMWKNDMVEQM
HEDIISLWDQCLKPCVKLTNTSVITQACPKVSFEPIPIHYCAPAGFAILKCNNKTFNGTGPCTNVS
TVQCTHGIRPVVSTQLLLNGSLAEEEVVIRSVNFTDNAKTIIVQLNTSVEINCTRPNNGGSGSGG
NMRQAHCNISRAKWNNTLKQIASKLREQFGNNKTIIFKQSSGGDPEIVTHSFNCGGEFFYCNST
QLFNSTWFNSTWSTEGSNNTEGSDTITLPCRIKQIINMWQKVGKAMYAPPISGQIRCSSNITGLL
LTRDGGNSNNESEIFRPGGGDMRDNWRSELYKYKVVKIEPL (SEQ ID NO: 183)

>QH0692core-gp120 without multimerization and without signal sequence
VWKEATTTLFCASDAKAYETECHNVWATHACVPTDPNPQEVVLGNVTENFNMWKNNMVEQM
HEDIISLWDECLKPCVKLTNTSVITQACPKVSFEPIPIHYCAPAGFAILKCNNKTFNGTGPCTNVS
TVQCTHGIRPVVSTQLLLNGSLAEEEVVIRSENFTNNAKTIIVHLKKSVEINCTRPGNGGSGSGG
DIRQAHCNLSSVQWNDTLKQIVIKLGEQFGTNKTIAFNQSSGGDPEIVMHSFNCGGEFFYCNTT
QLFNSTWEFHGNWTRSNFTESNSTTITLPCRIKQIVNMWQEVGKAMYAPPIRGQIRCSSNITGL
LLTRDGGVNGTRETFRPGGGDMRDNWRSELYKYKVVKIEPL (SEQ ID NO: 184)

>CDRL1 of light chain of glVRC/NIH VRC01-class antibody
RASQSVSSYLA (SEQ ID NO: 185)

>CDRL2 of light chain of glVRC/NIH VRC01-class antibody
DASNRAT (SEQ ID NO: 186)

>CDRL3 of light chain of glVRC/NIH VRC01-class antibody
QQYEF (SEQ ID NO: 187)

>CDRL1 of light chain of glI2A21 VRC01-class antibody
QASQDISNYLN (SEQ ID NO: 188)

FIG. 22 cont'd

>CDRL2 of light chain of gll2A21 VRC01-class antibody
DASNLET (SEQ ID NO: 189)

>CDRL3 of light chain of gll2A21 VRC01-class antibody
AVLEF (SEQ ID NO: 190)

>CDRL1 of light chain of g13BNC60 VRC01-class antibody
QASQDISNYLN (SEQ ID NO: 188)

>CDRL2 of light chain of g13BNC60 VRC01-class antibody
DASNLET (SEQ ID NO: 189)

>CDRL3 of light chain of g13BNC60 VRC01-class antibody
QQYEF (SEQ ID NO: 187)

>CDRL1 of light chain of g1VRC-CH31 VRC01-class antibody
QASQDISNYLN (SEQ ID NO: 188)

>CDRL2 of light chain of g1VRC-CH31 VRC01-class antibody
DASNLET (SEQ ID NO: 189)

>CDRL3 of light chain of g1VRC-CH31 VRC01-class antibody
QQYET (SEQ ID NO: 191)

>CDRL1 of light chain of g1PGV04 VRC01-class antibody
RASQSVSSSYLA (SEQ ID NO: 192)

>CDRL2 of light chain of g1PGV04 VRC01-class antibody
GASSRAT (SEQ ID NO: 193)

>CDRL3 of light chain of g1PGV04 VRC01-class antibody
QQLEF (SEQ ID NO: 194)

>CDRL1 of light chain of glPGV19/20 VRC01-class antibody
TGTSSDVGGYNYVS (SEQ ID NO: 195)

>CDRL2 of light chain of glPGV19/20 VRC01-class antibody
EVSNRPS (SEQ ID NO: 196)

>CDRL3 of light chain of glPGV19/20 VRC01-class antibody
SSYEF (SEQ ID NO: 197)

FIG. 22 cont'd

Annotated Hxb2_core_C4b nanoparticle (this sequence starts at V44 (Hxb2 numbering) and terminates at L494)
VWKEATTTLFCASDAKAYDTECHNVWATHACVPTDPNPQEVVLVNVTENFNMWKNDMVEQM
HEDIISLWDQCLKPCVKLTΔNTSVITQACPKVSFEPIPIHYCAPAGFAILKCNNKTFNGTGPCTNV
STVQCTHGIRPVVSTQLLLNGSLAEEEVVIRSVNFTDNAKTIIVQLNTSVEINCTRPNN*GGSGSG*
*G*NMRQAHCNISRAKWNNTLKQIASKLREQFGNNKTIIFKQSSGGDPEIVTHSFNCGGEFFYCN
STQLFNSTWFNSTWSTEGSNNTEGSDTITLPCRIKQIINMWQKVGKAMYAPPISGQIRCSSNIT
GLLLTRDGGNSNNESEIFRPGGGDMRDNWRSELYKYKVVKIEPL*GS*SKKQGDADVCGEVAYI
QSVVSDCHVPTAELRTLLEIRKLFLEIQKLKVELQGLSKE (SEQ ID NO: 119)

> Δ: The delta symbol represents where V1/V2 would be if not removed. The delta symbol is not part of the sequence but provided for annotation purposes;
> N: N276 glycan;
> *GGSGSGG*: V3 Linker (SEQ ID NO: 120);
> L: L494;
> *GS:* short linker;
> SKKQGDADVCGEVAYIQSVVSDCHVPTAELRTLLEIRKLFLEIQKLKVELQGLSKE: C4b Multimerization Domain (SEQ ID NO: 50).

Unannotated Hxb2_core_C4b nanoparticle (this sequence starts at V44 (Hxb2 numbering) and terminates at L494)
VWKEATTTLFCASDAKAYDTECHNVWATHACVPTDPNPQEVVLVNVTENFNMWKNDMVEQM
HEDIISLWDQCLKPCVKLTNTSVITQACPKVSFEPIPIHYCAPAGFAILKCNNKTFNGTGPCTNVS
TVQCTHGIRPVVSTQLLLNGSLAEEEVVIRSVNFTDNAKTIIVQLNTSVEINCTRPNNGGSGSGG
NMRQAHCNISRAKWNNTLKQIASKLREQFGNNKTIIFKQSSGGDPEIVTHSFNCGGEFFYCNST
QLFNSTWFNSTWSTEGSNNTEGSDTITLPCRIKQIINMWQKVGKAMYAPPISGQIRCSSNITGLL
LTRDGGNSNNESEIFRPGGGDMRDNWRSELYKYKVVKIEPLGSSKKQGDADVCGEVAYIQSV
VSDCHVPTAELRTLLEIRKLFLEIQKLKVELQGLSKE (SEQ ID NO: 119)

METHODS OF ELICITING ANTIBODIES THAT BIND TO FULL-LENGTH GLYCOSYLATED HIV-1 ENV USING MULTIMERIZED ENV CORES

CROSS-REFERENCE TO RELATED APPLICATIONS

This application is a continuation of U.S. Non-provisional Patent Application Ser. No. 17/269,199, filed Feb. 17, 2021, which is a 371 National Phase Application of PCT Application No. PCT/US2019/048825, filed Aug. 29, 2019, which claims priority to U.S. Provisional Patent Application No. 62/724,555 filed on Aug. 29, 2018, all of which are incorporated by reference in their entirety as if fully set forth herein.

STATEMENT REGARDING FEDERALLY SPONSORED RESEARCH OR DEVELOPMENT

This invention was made with government support under AI127249, AI104384, AI138212 and AI109632, awarded by the National Institutes of Health. The government has certain rights in the invention.

REFERENCE TO SEQUENCE LISTING

The Sequence Listing associated with this application is provided in xml format in lieu of a paper copy, and is hereby incorporated by reference into the specification. The name of the text file containing the Sequence Listing is 44738821_xml. The text is 273000 bytes, was created on Jan. 2, 2024, and is being submitted electronically via Patent Center.

FIELD OF THE DISCLOSURE

The current disclosure provides sequential immunization strategies to guide the maturation of antibodies against the human immunodeficiency virus (HIV). The sequential immunization strategies utilize an HIV envelope protein (Env) that binds germline (gl) B cells as a first (prime) immunization and an Env with a glycosylated N276 as a second (boost) immunization. The sequential immunization strategies successfully elicited neutralizing antibodies against HIV.

BACKGROUND OF THE DISCLOSURE

Acquired Immunodeficiency Syndrome (AIDS) is characterized by immunosuppression that results in opportunistic infections and malignancies; wasting syndromes; and central nervous system degeneration. Destruction of CD4+ T-cells, which are critical to immune defense, is a major cause of the progressive immune dysfunction that is the hallmark of AIDS disease progression. The loss of CD4+ T cells seriously impairs the body's ability to fight most pathogens, but it has a particularly severe impact on the defenses against viruses, fungi, parasites and certain bacteria, including mycobacteria.

AIDS is caused by infection with the human immunodeficiency virus (HIV). HIV infection begins when a portion of the virus' envelope protein (Env), gp120, binds to CD4 and other receptors on the surface of an infected individual's CD4+ T-cells and other immune system cells. The bound virus then fuses with the bound infected individual's cell and reverse transcribes its RNA genome. The resulting viral DNA integrates into the infected individual's cell's genome and begins to produce new viral RNA, resulting in new viral proteins and virions. The virions leave the originally infected cell to infect new cells. This process kills the originally infected cell.

Antibodies are proteins that can provide protection against pathogens, such as viruses. In some instances, antibodies are protective because they bind to an invading pathogen and interfere with its normal function. For example, many protective antibodies bind to a portion of a virus that blocks its ability to bind to and/or enter an infected individual's cells.

Vaccines are designed to increase the immunity of a subject against a particular pathogen by exposing individuals to an innocuous form or portion of the pathogen that will not lead to an active and/or on-going infection. Exposure to the form or portion of the pathogen stimulates B cells to produce antibodies against the targeted pathogen.

Each B cell expresses a unique antibody with unique specificity for a particular epitope on a protein. The unique antibody expressed by each B cell is generated randomly through genetic recombination. A germline (gl) B cell refers to an immature B cell before it has come into contact with its epitope. gl B cells express membrane-bound antibodies (also called B cell receptors or BCR). When a BCR encounters and binds its particular epitope, the B cell begins to rapidly proliferate and mature. During proliferation and maturation, the B cell's antibody genes undergo somatic hypermutation, which serves to increase the affinity of the B cell's antibody to its initial epitope even more. The increase in affinity of epitope binding that occurs during B cell maturation is required for effective protection against the pathogen. A single gl B cell is able to undergo dozens of cell divisions to create thousands of antibody-secreting B cells and memory B cells expressing the same antibody, or a related antibody that has been mutated to improve binding to the pathogen.

For decades, researchers have been trying to develop a vaccine that can induce B cells to produce antibodies that are effective to protect against HIV. But all efforts to induce protective antibodies to date have failed.

VRC01-class antibodies are among the most broad and potent neutralizing antibodies known against HIV. Balazs et al., Nature. 2012; 481(7379):81-4; Balazs et al., Nature Medicine. 2014; 20(3):296-300; Shingai et al., Journal of Experimental Medicine. 2014; 211(10):2061-74. It is believed that VRC01-class broadly neutralizing antibodies (bNAbs) could be an important component of protective immune responses elicited by an effective HIV-1 vaccine. The development of an immunization protocol that would reproducibly elicit VRC01-like bNAbs will be of high clinical significance to the development of such a vaccine.

Engineered HIV Env proteins that bind to gl BCRs (including gl VRC01 BCRs) and activate B cells have been developed. Dosenovic et al., Cell. 2015; 161(7): 1505-15; Jardine et al., Science. 2013; 340(6133):711-6; McGuire et al., Nature communications. 2016; 7:10618; Jardine et al., Science. 2015; 349(6244): 156-61. WO2016/154422 describes an engineered Env protein (the '426c core') that binds and activates the inferred gl forms of BCR, including diverse VRC01-class bNAbs. This protein was derived from the Clade C virus 426, which was isolated from an HIV patient 90 days post-infection. WO2016/205704 describes "engineered outer domain" or "eOD" Env proteins that can bind glVRC01 BCR. While immunization with these engineered HIV Env proteins stimulate gl BCR that can lead to broadly-neutralizing antibodies against HIV, the stimulated gl BCR did not sufficiently mature to create broadly-neutralizing antibodies.

One of the important reasons for the lack of success is due to the fact that the appropriate maturation of gl BCRs (including VRC01 BCRs) requires that somatic hypermutations during maturation effectively circumvent steric binding constraints on HIV's Env protein. For example, HIV-1 has evolved to avoid detection by gl VRC01 B cells. HIV-1 avoids detection by these gl VRC01 B cells through the presence of specific N-linked glycosylation sites (NLGS) within the gp120 protein. One such NLGS is found at position 276 of the Env. As a consequence, recombinant Env proteins derived from diverse HIV-1 isolates are ineffective in binding to and stimulating B cells that express the glBCR forms of VRC01-class bNAbs. Targeted disruption of certain conserved NLGS, however, permits binding and activation gl B cell lines expressing BCRs of two clonally-related VRC01-class bNAbs, VRC01 and NIH45-46. These two BCRs represent a small subset of potential VRC01-class antibody progenitors. Thus, designing immunogens capable of recognizing a larger group of gl BCR, including glVRC01-class BCRs should increase the chances of activating rare, naïve gl B cells during human immunization.

An even newer approach in the on-going attempt to elicit bNAbs against HIV through vaccination is based on the 'germline-targeting' approach described in the preceding paragraph combined with subsequently guiding the maturation of the first wave of germline antibodies towards their broad neutralizing form along specific evolutionary pathways, using specifically designed 'booster' engineered Env. Several attempts have been made to guide the maturation of gl BCR stimulated with engineered Env. These strategies are depicted in FIG. 1 and include, for example, Tian et al., (2016 Cell, 166, 1471-1484) who administered:

(i) multimerized eOD, followed by
(ii) multimerized 426c core, followed by
(iii) 426c core monomer glycosylated at N463, followed by
(iv) 426c core monomer glycosylated at N463 and N460, followed by
(v) 426c core monomer glycosylated at N463, N460, and N276 followed by
(vi) a soluble wild-type trimeric 426c (i.e., a natural HIV Env); and Briney et al., (2016 Cell 166, 1459-1470) who administered either:

(A-i) multimerized eOD, followed by
(A-ii) multimerized BG505 GTC core (this protein is similar to the 426c core, but generated from a different strain of HIV) followed by
(A-iii) a soluble wild-type trimeric BG505, but for removal of the NLGS site at N276, followed by
(A-iv) a repeat administration of the soluble wild-type trimeric BG505, but for removal of the NLGS site at N276 or (B-i) multimerized eOD, followed by
(B-ii) a soluble wild-type trimeric BG505, but for removal of NLGS sites N460, N463, and N276 followed by
(B-iii) a soluble wild-type trimeric BG505, but for removal of the NLGS site at N276, followed by
(B-iv) a repeat administration of the soluble wild-type trimeric BG505, but for removal of the NLGS site at N276.

Unfortunately, none of these approaches elicited the maturation of antibodies capable of broadly neutralizing HIV. Tian et al., Cell. 2016; 166(6):1471-84 e18; Briney et al., (2016 Cell 166, 1459-1470).

SUMMARY OF THE DISCLOSURE

The current disclosure provides sequential immunization strategies that successfully guide the maturation of antibodies against human immunodeficiency virus (HIV). The sequential immunization strategies have two key components: (i) administration of an engineered HIV envelope protein (Env) capable of stimulating germline (gl) B cells (including gl VRC01 B cells) that can mature to produce broadly neutralizing antibodies against HIV; and (ii) a next administration of an HIV Env that includes a glycan-occupied N-linked glycosylation site (NLGS) at position 276 of the Env protein, wherein no other Env proteins are administered between step (i) and step (ii).

This approach differs from previous attempts to guide the maturation of antibodies against HIV by using an engineered Env with an NLGS at position 276 as the first immunization boost. Previously, it was believed that the first wave of Abs elicited by the 'germline-binding' engineered Env could not bind in the presence of glycans in Loop D (N276). Thus, immunogenic boosts with Env having an NLGS at position 276 were not administered until, for example, step (v) in Trian et al. Without being bound by theory, within the teachings of the current disclosure, however, delaying exposure to an Env with NLGS at 276 leads to a massive expansion of B cells that cannot bypass N276 glycans. Neutralization analysis of the antibodies elicited in Trian and Briney support this hypothesis. Based on the foregoing, the current disclosure provides for administration of an Env that includes an N276 glycan as the first immunogen boost following an engineered HIV envelope (Env) protein capable of stimulating gl B cells (e.g., gl VRC01 class B cells). As described in more detail herein, this approach successfully guided the maturation of antibodies against human immmunodeficiency virus (HIV).

BRIEF DESCRIPTION OF THE SEVERAL VIEWS OF THE DRAWINGS

Many of the drawings submitted herein are better understood in color. Applicant considers the color versions of the drawings as part of the original submission and reserves the right to present color images of the drawings in later proceedings.

FIGS. 7A, 7B. Amino acid sequences of the isolated antibodies. (7A) Amino acid alignment of the VH1-2*02 domains. The sequence of the knocked-in human glVRC01 gene is indicated at the top. (7B) Amino acid alignment of the mouse VL domains. The prefix 'P' indicates antibodies isolated following the prime immunization, the prefix 'B' indicates antibodies isolated following the boost immunization, and the prefix 'N' indicates antibodies isolated from naïve animals. The sequences of the mouse genes from which the VL sequences were derived from are indicated. CDRs are highlighted in dark gray in the reference sequences.

FIGS. 8A-8C. Structural information of VRC01-like antibodies isolated after immunization with the 426c Core Env. (8A) Structures of P-p1f1 in complex with eOD-GT8 and P-p3b3 in complex with 426c Core superimposed onto the structure of glVRC01 bound to 426c WT Core (PDB ID: 6MFT). The structures are shown in ribbon representation and only the Fv portion of the Fab is shown for clarity. The glycan present at N276 in the structure of 426c WT Core bound to glVRC01 is shown in stick. Zoom insets of important contact residues in the heavy chain of glVRC01 and VRC01-like mouse antibodies are shown at bottom. Zoom insets of the light chain N-terminus, CDRL1 and CDRL3 contacts are shown at right. (8B) Heavy chain sequence alignments of glVRC01, P-p1f1, P-p3b3 and VRC01c690 HuGL2. Residues within 5 Å of each respective antigen are shown with an asterisk under the alignment. (8C) Light chain sequence alignments of glVRC01 (k3-20), P-p1f1, P-p3b3 and VRC01c-HuGL2. Residues within 5 Å of each respective antigen are shown with an asterisk under the alignment. Zoom insets of the light chain N-terminus, CDRL1 and CDRL3 contacts. The glycan at N276 present in the structure of glVRC01 bound to 426c Core is shown in sticks (PDB ID 6MFT). Disordered CDRL1s are drawn in dotted lines.

FIG. 9. Data collection and refinement statistics for P-p1f1 with eOD-GT8 and P-p3b3 with 426c core.

FIGS. 10A-10E. Trimeric Env-binding and neutralizing properties of VRC01-like antibodies elicited by the 426c Core germline-targeting immunogen. The binding of eight VRC01-like antibodies generated following the prime immunization against (10A) the autologous 426c WT DS-SOSIP; (10B) its variant that lacks the N276, N460 and N463 NLGS (426c DS-SOSIP D3); (10C) a variant that only lacks the N276 glycan (426c A276 DS-SOSIP); and (10D) the heterologous 45_01 dG5 native flexibly linked (NFL) which also lacks the N276 NLGS, was determined using Biolayer interferometry (BLI). (10E) EC50 neutralizing titers (μg/ml) of four mAbs tested against the autologous WT 426c virus and its variant lacking the 276 NLGS, grown in either 293T cells or in 293S GnTI−/− cells. Mature VRC01 and glVRC01 mAbs were used as controls during these experiments.

FIGS. 16A-16D. Binding kinetics of antibody Fabs isolated from naïve and immunized mice. BLI was used to determine affinity of Fabs for Env. Kinetic values determined for each Fab for (16A) 426c WT Core, (16B) H×b2 WT Core, and the BLI traces used to determine these values (16C, 16D).

FIG. 17. Neutralization of monoclonal antibodies isolated following immunization.

FIG. 20. Primers used to amplify heavy and light chains of murine antigen-specific specific B cells.

FIG. 21. Cycling conditions used for PCR.

FIG. 22. Sequences supporting the disclosure including: the 426ccore-gp 120 (SEQ ID NO. 39); eOD-GT8-hisavi (SEQ ID NO. 40); 426c:BG505_WT-SOSIP (SEQ ID NO. 41); 426c:BG505_TM-SOSIP. S278A/T462A/T465A (SEQ ID NO. 42); 426c:BG505_SM-SOSIP. S278A (SEQ ID NO. 43); 45_01 dG5core-gp120 (SEQ ID NO. 44); 45_01 dH1core-gp120 (SEQ ID NO. 45); 426c:BG505_DM-SOSIP. T462A/T465A (SEQ ID NO. 46); Hxb2core-gp 120 (SEQ ID NO. 47); QH0692core-gp 120 (SEQ ID NO. 48); 426c_WTcore-C4b (SEQ ID NO. 49); Cterm-C4b (SEQ ID NO. 50); Cterm-Ferritin (SEQ ID NO. 51); B6 MAb (full name: 021418-p1b5-G28-CC4b-Hx4b-eO) Heavy Chain (SEQ ID NO. 52); B6 Mab (Light Chain) (SEQ ID NO. 53); exemplary wt gp120 protein, GenBank® (U.S. Department of Health and Human Services, United States) Accession AAB05604 (SEQ ID NO. 54); exemplary wt gp120 protein; GenBank® Accession AAD12142 (SEQ ID NO. 55); the 426ccore-gp120 without signal sequence (SEQ ID NO. 175); eOD-GT8-hisavi without signal sequence (SEQ ID NO. 176); 426c:BG505_WT-SOSIP without signal sequence (SEQ ID NO. 177); 426c:BG505_TM-SOSIP.S278A/T462A/T465A without signal sequence (SEQ ID NO. 178); 426c:BG505_SM-SOSIP.S278A without signal sequence (SEQ ID NO. 179); 45_01 dG5core-gp120 without signal sequence (SEQ ID NO. 180); 45_01 dH1core-gp120 without signal sequence (SEQ ID NO. 181); 426c:BG505_DM-SOSIP.T462A/T465A without signal sequence (SEQ ID NO. 182); Hxb2core-gp 120 without signal sequence (SEQ ID NO. 183); QH0692core-gp120 without signal sequence (SEQ ID NO. 184); CDRL1 of light chain of gIVRC/NIH VRC01-class antibody (SEQ ID NO. 185); CDRL2 of light chain of gIVRC/NIH VRC01-class antibody (SEQ ID NO. 186); CDRL3 of light chains of gIVRC/NIH and g13BNC60 VRC01-class antibodies (SEQ ID NO. 187); CDRL1 of light chains of gII2A21, g13BNC60, and g1VRC-CH31 VRC01-class antibodies (SEQ ID NO. 188); CDRL2 of light chains of gll2A21, g13BNC60, and g1VRC-CH31 VRC01-class antibodies (SEQ ID NO. 189); CDRL3 of light chain of gll2A21 VRC01-class antibody (SEQ ID NO. 190); CDRL3 of light chain of g1VRC-CH31 VRC01-class antibody (SEQ ID NO. 191); CDRL1 of light chain of g1PGV04 VRC01-class antibody (SEQ ID NO. 192); CDRL2 of light chain of g1PGV04 VRC01-class antibody (SEQ ID NO. 193); CDRL3 of light chain of g1PGV04 VRC01-class antibody (SEQ ID NO. 194); CDRL1 of light chain of g1PGV19/20 VRC01-class antibody (SEQ ID NO. 195); CDRL2 of light chain of g1PGV19/20 VRC01-class antibody (SEQ ID NO. 196); CDRL3 of light chain of gPGV19/20 VRC01-class antibody (SEQ ID NO. 197). Signal sequences are underlined and shaded. Bold amino acid residues indicate the S278, N460, T462, N463, and T465 wild type residues that remain wild type in particular mutant proteins. Bold and underlined amino acid residues indicate that an A (Alanine) was introduced to replace a S (Serine) or a T (Threonine) amino acid that is normally present at that position. The glycosylation motif includes N-x-S/T, and the N is glycosylated. By replacing the S/T with an A, the N is no longer glycosylated. The N276 is not glycosylated if the S278 is replaced by an 'A". The N460 and N463 positions are glycosylated if there are Ts at positions 462 and 465. The italicized DWRD residues in eOD-GT8 indicate the D loop sequence. The italicized and underlined D (Aspartic acid) residue in eOD-GT8 indicates the original N463D (V5) mutation in eOD, which also contains a mutation in a downstream S/T selected for during yeast display. The shaded GS sequence in 426c_WTcore-C4b represents the linker between the Env protein and the C4b multimerization domain. Additionally, annotated and unannotated forms of a H×b2_core_C4b nanoparticle (SEQ ID NO: 119).

DETAILED DESCRIPTION

Figure 1A:
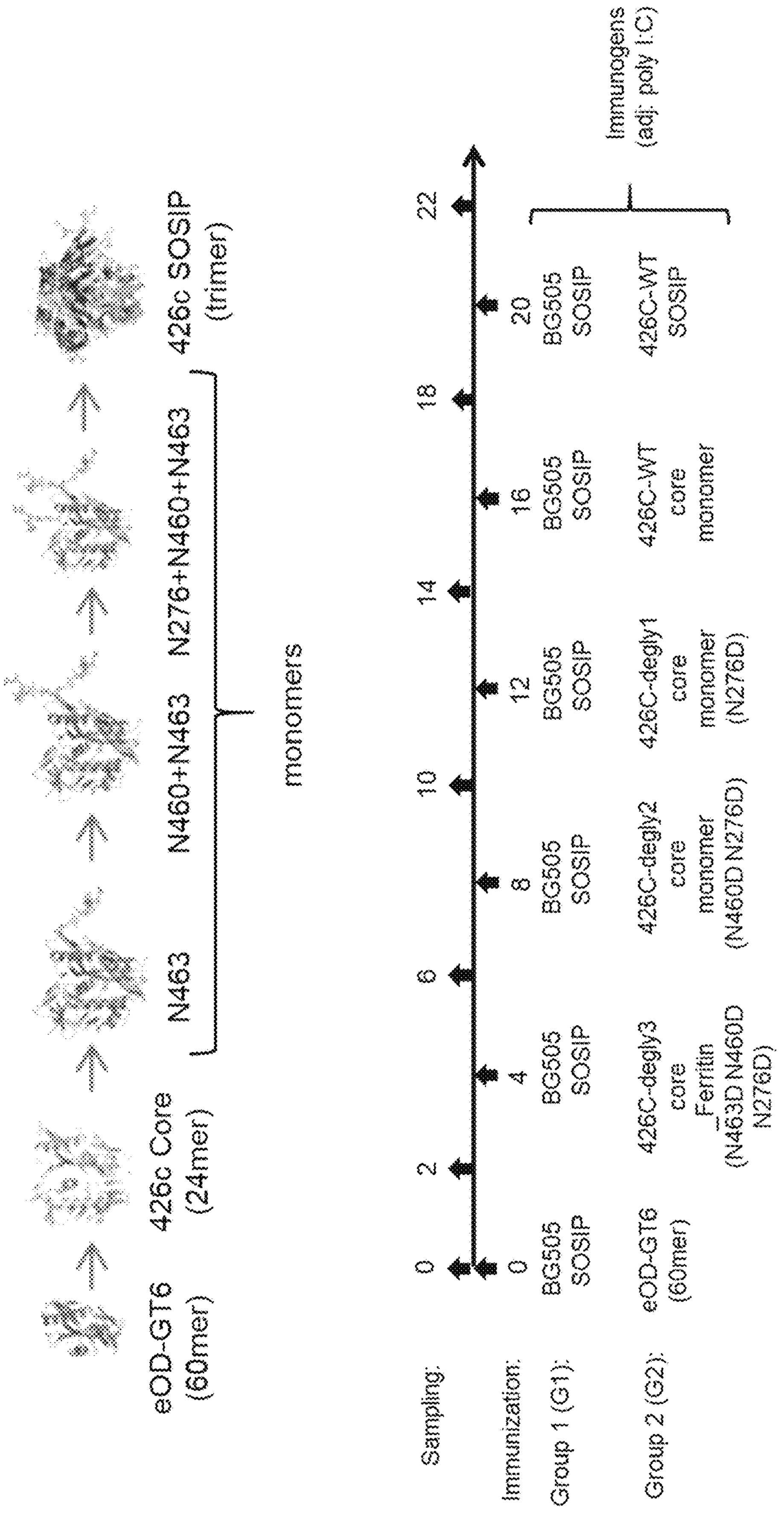
FIGS. 1A, 1B. Depiction of previous attempts to guide maturation of gl VRCO1 B cells to produce antibodies against HIV compared to present approach to guide maturation of gl VRCO1 B cells: (1A) Tian et al., (2016 Cell, 166, 1471-1484); (1B) Briney et al., (2016 Cell 166, 1459-1470).
Figure 1B:
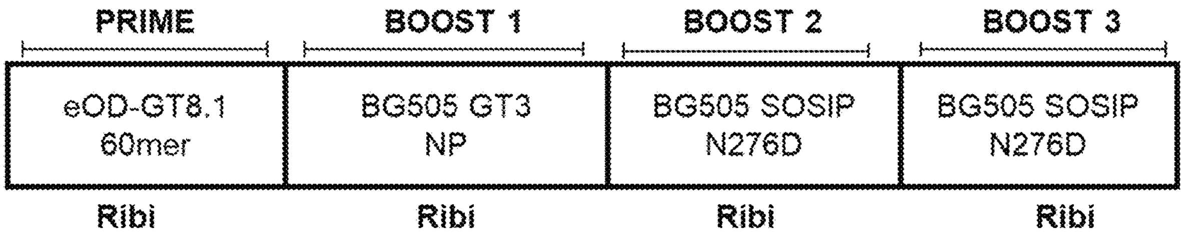

Acquired Immunodeficiency Syndrome (AIDS) is characterized by immunosuppression that results in opportunistic infections and malignancies; wasting syndromes; and central nervous system degeneration. Destruction of CD4+ T-cells, which are critical to immune defense, is a major cause of the progressive immune dysfunction that is the hallmark of AIDS disease progression. The loss of CD4+ T cells seriously impairs the body's ability to fight most pathogens, but it has a particularly severe impact on the defenses against viruses, fungi, parasites and certain bacteria, including mycobacteria.

AIDS is caused by infection with human immunodeficiency virus (HIV). The HIV genome encodes several structural proteins. The env gene encodes the viral envelope glycoprotein (Env), a 160-kilodalton (kDa) protein. Env is cleaved into an external 120-kDa envelope glycoprotein (gp120) and a transmembrane 41-kDa envelope glycoprotein (gp41). Gp120 and gp41 are required for HIV to infect cells.

Mature gp120 wildtype (wt) proteins have 500 amino acids in the primary sequence. gp120 is heavily N-glycosylated giving rise to an apparent molecular weight of 120 kD. The protein includes five conserved regions (C1-$C_5$) and five regions of high variability (V1-V5). Exemplary sequences of wt gp120 proteins are found in GenBank®, for example accession numbers AAB05604 (SEQ ID NO. 54) and AAD12142 (SEQ ID NO. 55). It is understood that there are numerous variations in the sequence of gp120 from what is given in these examples. In particular embodiments, and based on the H×b2 sequence, V5 includes residues 458-466. One of ordinary skill in the art recognizes, however, that V5 varies among different strains in its precise length, amino acid composition, and glycosylation sites. Reference to residues and mutation positions herein refer to H×b2 numbering, unless clearly noted to the contrary.

HIV infection begins when gp120, binds to CD4 and other receptors on the surface of a host's target immune system cells (e.g., CD4+ T-cells, macrophages and dendritic cells). The bound virus then fuses with the target cell and reverse transcribes its RNA genome. The resulting viral DNA integrates into the host cell's genome and begins to produce new viral RNA, resulting in new viral proteins and virions. The virions leave the originally infected cell to then infect new cells. This process kills the originally infected cell.

Antibodies are proteins that can provide protection against pathogens. Antibodies can bind to a pathogen and are protective when this binding interferes with the normal function of a pathogen. For example, many protective antibodies bind to a portion of a pathogen that blocks the pathogen from entering cells. Antibodies can be attached to the surface of B cells (known as B cell receptors or BCR) but exert most of their protective functions when secreted into the blood.

HIV-1 neutralizing antibodies are antibodies capable of neutralizing HIV's infection of host cells. HIV antibodies target four major areas of the Env protein: (i) the portion of gp41 that is external to the cell, but proximal to the cell membrane; (ii) the CD4 receptor-binding site (CD4-BS) of gp120; (iii) two sites including both carbohydrate and amino acid moieties, one at the base of the "V3" loop and another on the "V1/V2" loops of the gp120 subunit; and (iv) regions spanning elements of both gp 120 and gp41.

Based on their ontogenies and mode of recognition, CD4-BS bNAbs are grouped into two major types: (i) heavy chain complementary determining region three (CDRH3)-dominated; and (ii) variable heavy (VH)-gene-restricted. Antibodies that make contact primarily through their CDRH3 regions are further subdivided into the CH103, HJ16, VRC13 and VRC16 classes while the VH-gene-restricted Abs include the VRC01- and the 8ANC131-class antibodies.

Vaccines are designed to increase the immunity of a subject against a particular infection by stimulating B cells to produce antibodies against the targeted infectious agent. Each B cell expresses a unique antibody with unique epitope specificity. The unique antibody expressed by each B cell is generated randomly through genetic recombination. A germline (gl) B cell refers to a B cell that has not yet come in contact with its epitope. Germline B cells express membrane-bound BCR. When a BCR binds its particular epitope, the B cell can rapidly proliferate and mature. During proliferation and maturation, the antibody genes undergo somatic hypermutation, which serves to increase the affinity of epitope binding. The increase in affinity of epitope binding that occurs during B cell maturation is required for effective protection against the pathogen. A single naïve B cell is able to undergo dozens of cell divisions to create thousands of antibody-secreting B cells and memory B cells expressing the same antibody, or a related antibody that has been mutated to improve binding to the pathogen. This binding can lead to activation of the B cell and production of protective antibodies.

For decades, researchers have been trying to develop a vaccine that can induce B cells to produce antibodies that are effective to protect against HIV. But all efforts to induce protective antibodies to date have failed.

One of the many important reasons for the lack of success is thought to be the inability of the Env proteins used as immunogens to engage gl B cell BCRs that encode, for example, the gl of VRC01-class antibodies (e.g., "immature" or not fully developed Abs). Indeed, maturation of these antibodies to full neutralizing Abs requires that they circumvent steric constraints on Env through extensive somatic hypermutation. For example, HIV-1 has evolved to avoid detection by gl B cells that give rise to VRC01-class bNAbs through development of specific N-linked glycosylation sites (NLGS) (for example, in Loop D and V5 of the gp120 subunit). As a consequence, recombinant Env proteins derived from diverse HIV-1 isolates are ineffective in binding to and stimulating B cells engineered to express the glBCR forms of VRC01-class bNAbs in vitro. Targeted disruption of conserved NLGS at position 276 in Loop D, and at positions 460 and 463 in V5 of the 426c clade C Env, however, permits binding and activation gl B cell lines expressing BCRS of two clonally-related VRC01-class bNAbs, VRC01 and NIH45-46 in vitro. These two BCRs represent a small subset of potential VRC01-class antibody progenitors. Thus, designing immunogens capable of recognizing a larger group of glVRC01-class BCRs should increase the chances of activating rare, naïve glVRC01-class B cells during human immunization. In particular embodiments, loop D includes residues 275-283.

During the past decade, the generation of novel reagents for the isolation of individual B cells and the establishment of high-throughput methodologies led to the characterization of a plethora of new bNAbs from HIV-1-infected subjects. The structural characterization of such antibodies, combined with information of their ontogenies, have vastly improved the understanding on how such antibodies are generated during natural infection and how they interact with Env. For example, when the VH and VL domains of certain bNAbs (b12, 2G12 and 2F5) are reverted to their predicted, inferred germline forms (from here onward termed 'germline' for brevity, unless otherwise noted), those Abs no longer bound the dual-tropic 89.4 Env. Xiao et al., Biochemical and Biophysical Research Communications. 2009; 390(3):404-9. This was true for many of the bNAbs that have been isolated since, irrespective of their epitope-specificity and their VH/VL-derivation. Jardine et al., Science. 2013; 340(6133):711-6; McGuire et al., Journal of Experimental Medicine. 2013; 210(4):655-63; Hoot et al., PLOS Pathogens. 2013; 9(1):e1003106; Klein et al., Cell. 2013; 153(1): 126-38; Diskin et al., Science. 2011; 334 (6060): 1289-93.

A hypothesis was put forth that commonly available recombinant Envs are ineffective in eliciting bNAbs because they do not initiate the very first step of that process. Jardine et al., Science. 2013; 340(6133):711-6; McGuire et al., Journal of Experimental Medicine. 2013; 210(4):655-63. It was also hypothesized that during natural HIV-1 infection, rare viral clones that express Envs with particular features emerge and that they are the ones that initiate the activation of naïve B cells that express germline BCRs that eventually produce bNAbs. This was confirmed through studies showing that Env clones with particular features can emerge during infection and engage the germline BCRs of bNAbs and activate the corresponding naïve B cells. Liao et al., Nature. 2013; 496(7446): 469-76; Doria-Rose et al., Nature. 2014; 509(7498):55-62. The subsequent maturation of these germline antibodies into their broad neutralizing forms requires the emergence of viruses expressing Env variants of the original 'germline-binding' one. In cases where the 'natural' Envs that are linked with the development of a particular type of bNAb are known, an immunization scheme can be developed based on those 'natural' Envs. In many cases however, such natural Envs are not known. Such is the case of the VRC01-class bNAbs. In those cases, de novo Env immunogens must be designed.

Figure 2:
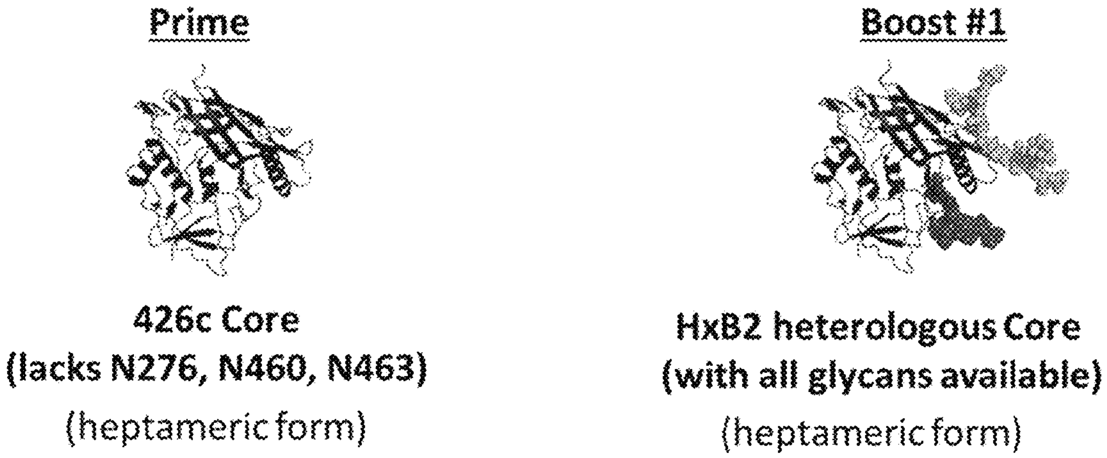
FIG. 2. Exemplary sequential prime-boost immunization scheme disclosed herein.
Figure 3:
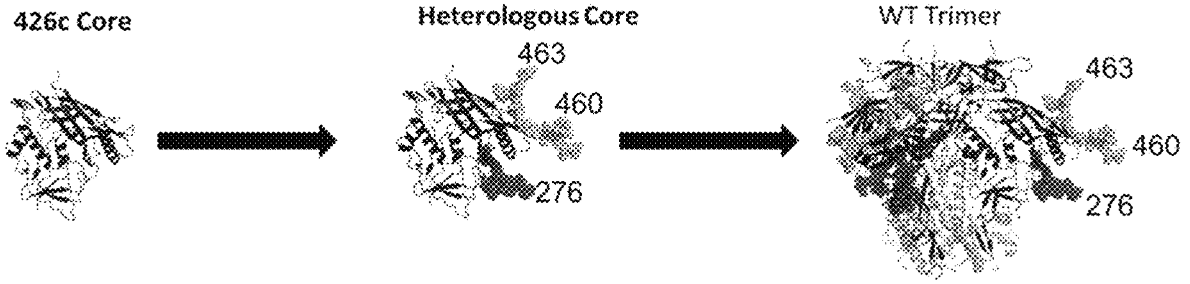
FIG. 3. Additional exemplary sequential prime-boost immunization scheme for the elicitation of cross-neutralizing VRC01-like antibodies.

The 426c core activates B cells expressing the germline BCR of a VRC01-class antibody, called 3BNC60 (Dosenovic et al., Cell. 2015; 161(7): 1505-15; McGuire et al., Nature communications. 2016; 7:10618), among other gl BCR that produce CD4-BS antibodies. The 426c core includes modifications to the clade C 426c Env to allow binding the gl forms of BCR, including VRC01-class antibodies. McGuire et al., Nature communications. 2016; 7:10618. The version of the 426c core utilized in the studies described in Example 1 is based on the gp120 subunit of the 426c Env; it lacks the variable regions 1, 2 and 3 and lacks three key, conserved NLGS (position N276 in Loop D and positions N460 and N463 in V5). Thus, the 426c core includes elements of both the inner and outer domains of gp120. In that, it differs from the engineered outer domain of gp 120 (eOD) construct, which only expresses elements of the outer gp120 domain. Jardine et al., Science. 2013; 340(6133):711-6. The structures of 426c core bound to germline 3BNC60 and germline NIH45-46 are reported in Scharf et al., eLife. 2016; 5. doi: 10.7554/eLife. 13783 and a high resolution structure (2.4 Å) of the germline VRC01 antibody bound to the 426c core was recently obtained (FIG. 2A).

Although a single immunization of transgenic, knock-in mice expressing gl3BNC60 or glVRC01 BCRs with 426c core activates the desired B cells, the secreted antibodies are not neutralizing tier 2 WT viruses (Dosenovic et al., Cell. 2015; 161(7): 1505-15; Jardine et al., Science. 2015; 349 (6244): 156-61. Repeat immunizations with 'germline-binding' proteins fail to drive somatic hympermutations (SHM) that lead to neutralizing antibodies (Tian et al., Cell. 2016; 166(6):1471-84 e18; Dosenovic et al., Cell. 2015; 161(7): 1505-15; Briney et al., Cell. 2016; 166(6): 1459-70 e11). However, the sequential 'prime-boost' immunization strategies disclosed herein show a successful sequential immunization scheme to instigate the maturation of germline VRC01-antibody responses towards their broad neutralizing antibody forms. The key to this immunization strategy is to administer an engineered Env that activates the desired gl B cells followed by a first boost with an engineered Env with N276 NLGS.

Aspects of the disclosure are now described in more detail as follows: (i) Antibodies and Epitopes; (ii) VRC01 Antibodies [(ii-a) The Heavy Chain (HC) of VRC01-Class Antibodies; (ii-b) The Light Chain (LC) of VRC01-Class Antibodies]; (iii) Prime and Boost Env; (iv) Multimerization of Env; (v) Vaccine Adjuvants; (vi) Compositions; (vii) Kits; (viii) Methods of Use; (ix) Exemplary Embodiments; (x) Experimental Examples; and (xi) Closing Paragraphs.

(i) Antibodies and Epitopes. Naturally occurring antibody structural units include a tetramer. Each tetramer includes two pairs of polypeptide chains, each pair having one light chain and one heavy chain. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk, J. Mol. Biol., 196:901-917 (1987); Chothia et al., Nature, 342:878-883 (1989). Kabat numbering is used herein unless specifically noted otherwise. FIG. 2B shows amino acid alignment of the light chain variable regions of gl VRC01-class antibodies. Gray areas indicate (Kabat) CDRL regions. Bold letters indicate negatively charged amino acids and underlined letters indicate positively charged amino acids.

The carboxy-terminal portion of each chain defines a constant region that can be responsible for effector function. Examples of effector functions include: Clq binding and complement dependent cytotoxicity (CDC); antibody-dependent cell-mediated cytotoxicity (ADCC); antibody-dependent phagocytosis (ADCP); down regulation of cell surface receptors (e.g. B cell receptors); and B cell activation.

Within full-length light and heavy chains, the variable and constant regions are joined by a “J” region of amino acids, with the heavy chain also including a “D” region of amino acids. See, e.g., Fundamental Immunology, Ch. 7 (Paul, W., ed., 2nd ed. Raven Press, N.Y. (1989).

Human light chains are classified as kappa (κ) and lambda (Λ) light chains. Heavy chains are classified as mu, delta, gamma, alpha, or epsilon, and define the antibody’s isotype as IgM, IgD, IgG, IgA, and IgE, respectively. IgG has several subclasses, including, IgG1, IgG2, IgG3, and IgG4. IgM has subclasses including IgM1 and IgM2. IgA is similarly subdivided into subclasses including IgA1 and IgA2.

Antibodies bind epitopes on antigens. An antigen refers to a molecule or a portion of a molecule capable of being bound by an antibody. An epitope is a region of an antigen that is bound by the variable region of an antibody. An epitope includes specific amino acids that contact the variable region of an antibody. Epitope determinants can include chemically active surface groupings of molecules such as amino acids, sugar side chains, phosphoryl or sulfonyl groups, and can have specific three-dimensional structural characteristics, and/or specific charge characteristics.

An “epitope” includes any determinant capable of being bound by an antibody. An epitope is a region of molecule that is bound by an antibody that targets that region of molecule, and when that region of molecule is a protein, includes specific residues that directly contact the binding protein. In particular embodiments, an “epitope” denotes the binding site on a protein target bound by a corresponding antibody. The antibody either binds to a linear epitope, (e.g., an epitope including a stretch of 5 to 12 consecutive amino acids), or the antibody binds to a three-dimensional structure formed by the spatial arrangement of several short stretches of the protein target. Three-dimensional epitopes recognized by an antibody, e.g., by the epitope recognition site or paratope of an antibody or antibody fragment, can be thought of as three-dimensional surface features of an epitope molecule. These features fit precisely (in)to the corresponding binding site of the antibody and thereby binding between the antibody and its target protein is facilitated. In particular embodiments, an epitope can be considered to have two levels: (i) the “covered patch” which can be thought of as the shadow an antibody would cast; and (ii) the individual participating side chains and backbone residues. Binding is then due to the aggregate of ionic interactions, hydrogen bonds, and hydrophobic interactions.

(ii) VRC01-Class Antibodies. As indicated previously, based on their ontogenies and mode of recognition, CD4-BS bNAbs are grouped into two major types: CDRH3-dominated (the most common way Abs bind their epitopes) and VH-gene-restricted. Zhou et al., Cell. 2015; 161(6): 1280-92. Antibodies that make contact primarily through their CDRH3 regions are further subdivided into the CH103, HJ16, VRC13 and VRC16 classes, while the VH-gene-restricted antibodies, which make contact primarily through their CDRH2 domains, include the VRC01- and the 8ANC131-classes (derived from VH1-2 and VH1-46, respectively).

At least 29 VRC01-class antibodies have been isolated from at least nine HIV-1+ subjects. Diskin et al., Science. 2011; 334(6060): 1289-93; Wu et al., Science. 2011; 333 (6049): 1593-602; Zhou et al., Immunity. 2013; 39(2): 245-58; Huang et al., Immunity. 2016; 45(5): 1108-21; Zhou et al., Cell. 2015; 161(6): 1280-92; Kwong & Mascola, Immunity. 2012; 37(3):412-25; Sajadi et al., Cell. 2018; 173(7): 1783-1795; Umotoy et al., Immunity. 2019; 51(1): 141-154.

(ii-a) The Heavy Chain (HC) of VRC01-Class Abs. All known VRC01-class Abs are derived from one of the five VH1-2 alleles, the VH1-2*02 allele. Three amino acids, Trp50HC, Asn58HC and Arg71HC, present in the CDRH2 domain of VRC01-class antibodies (i.e., they are encoded by the germline VH1-2 gene segment) make key contacts with Env. Scharf et al., Proceedings of the National Academy of Sciences of the United States of America. 2013; 110(15): 6049-54; West et al., Proceedings of the National Academy of Sciences of the United States of America. 2012; 109(30): E2083-90; Zhou et al., Immunity. 2013; 39(2):245-58. Structural information has revealed the reasons why these three amino acids are critically important for the interaction of the *02 allele with Env: Trp50HC makes contact with the conserved amino acid in Loop D, Asn280; Asn58HC makes contact with the conserved amino acid Arg456 in V5; and Arg71HC makes a key contact with amino acid Asp368 in the CD4-BS. Despite the extensive amino acid changes that occur during affinity maturation of these Abs, these three key HC amino acids remain unaltered. Scharf et al., Proceedings of the National Academy of Sciences of the United States of America. 2013; 110(15):6049-54; Zhou et al., Cell. 2015; 161(6):1280-92; Scharf et al., eLife. 2016; 5. doi: 10.7554/eLife. 13783. In addition to allele *02, alleles *03 and *04 also express these three amino acids.

It is also noteworthy that all known mature VRC01-class Abs have an 11-18 amino acid long CDRH3 and almost always have a Trp that is located 5 amino acids before the start of FW4 (Trp100BHC on VRC01 numbering). This Trp interacts with Asn279 gp120 via hydrogen-bonding. Scharf et al., Proceedings of the National Academy of Sciences of the United States of America. 2013; 110(15):6049-54. This TRP is present in the germline CDRH3 of VRC01-class Abs and are expressed on naïve B cells in HIV-1$^-$ subjects. Yacoob et al., Cell Reports. 2016; 17(6): 1560-70.

(ii-b) The Light Chain (LC) of VRC01-Class Abs. Only a few LC families (K3-20, K3-15, K1-33, K1-5, and \2-14) are presently known to pair with VH1-2*02 to generate VRC01-class antibodies. Importantly, all the LCs associated with VRC01-class bNAbs express an unusually short (5 amino acid long) CDRL3 region. Zhou et al., Immunity. 2013; 39(2):245-58; Zhou et al., Cell. 2015; 161(6): 1280-92; Kwong & Mascola, Immunity. 2012; 37(3):412-25. Less than 0.05% of LCs with these properties are present in the human naïve B cell repertoire. Jardine et al., Science. 2016; 351(6280): 1458-63; Sok et al., Science. 2016; 353(6307): 1557-60. The particular angle of approach of VRC01-class Abs requires such a short CDRL3; otherwise these Abs will not bind Env because of steric clashes with Loop D and V5. Thus, without being bound by theory, the short CDRL3 is presently believed not to be the result of somatic hypermutation but has to exist in the germline form of these antibodies. Zhou et al., Immunity. 2013; 39(2):245-58. Accordingly, one of the main goals of ‘germline-targeting’ immunogens is to select for B cells expressing VH1-2*02 VH paired with LCs with 5 amino acid long CDRL3s. Within the 5 amino acid stretch, a key feature of the mature VRC01 Abs is the presence of a negatively charge amino acid, Glutamic, at position 96 (QQYE). Glu96LC makes key contacts with the V5 loop and Loop D and is one of the amino acids that are linked with the neutralizing activities of VRC01-class Abs. So, ideally, a targeting immunogen should select for LCs with 5 amino acid long CDRL3 that include a Glu96. The CDRL1 domains of the mature VRC01-class Abs are also involved in the interaction of these Abs with Env. The mature CDRL1 domains are either shorter (by 2-6 AA) than the corresponding germline domains or contain multiple glycines which provide chain flexibility. Scharf et al., Proceedings of the National Academy of Sciences of the United States of America. 2013; 110(15):6049-54; Zhou et al., Immunity. 2013; 39(2):245-58; Scharf et al., eLife. 2016; 5. doi: 10.7554/eLife. 13783. The combination of an unusually short CDRL3 (present at the germline level) with a shortening of the CDRL1 (acquired during affinity maturation) allows the mature VRC01-class antibodies to bypass several key steric clashes with Env, in particular carbohydrate moieties that are located in Loop D (conserved position N276). New information from the structural analysis of several germline VRC01-class antibodies bound to Env-derived proteins, suggests that the CDRL1 amino acid shortening may not be important for the recognition of Env by glVRC01-class antibodies. In sum, VRC01-class germline antibodies exhibit preformed antigen-binding and conformations and affinity maturation that result in increased induced-fit recognition. Scharf et al., eLife. 2016; 5. doi: 10.7554/eLife. 13783.

(iii) Prime and Boost Env. According to the current disclosure, prime Env must be capable of binding and activating gl VRC01 B cells. Boost Env must have NLGS at position 276.

One disclosed prime engineered HIV Env includes the "426c core". In particular embodiments, the 426c core includes an HIV Env protein with the following mutations, modifications, and characteristics: N460D; N463D; S278R; G471S; V65C; S115C; no mutation at position 276; removal of V1 and V2; V3 replacement with a flexible linker; an N-terminal truncation before 44, and a C-terminal truncation after 494. These modifications result in: VWKEAKTTLFCASDAKAYEKECHNVWATHACVPTDPNPQEVVLENVTENFNMWKNDMVDQM QEDVISIWDQCLKPCVKLTNTSTLTQACPKVTFDPIPIHYCAPAGYAILKCNNKTFNGKGPCNNV STVQCTHGIKPVVSTQLLLNGSLAEEEIVIRSKNLRDNAKIIIVQLNKSVEIVCTRPNNGGSGSGG DIRQAYCNISGRNWSEAVNQVKKKLKEHFPHKNISFQSSSGGDLEITTHSFNCGGEFFYCNTS GLFNDTISNATIMLPCRIKQIINMWQEVGKAIYAPPIKGNITCKSDITGLLLLRDGGDTTDNTEIFR PSGGDMRDNWRSELYKYKVVEIKPL (SEQ ID NO. 56).

Particular embodiments of the engineered Env include the following mutations: N460D; N463D; S278R; G471S; V65C; S115C; removal of V1 and V2; V3 replacement with a flexible linker; and an N-terminal truncation and a C-terminal truncation. In particular forms of these embodiments, the engineered Env does not include a mutation at position 276.

Particular embodiments of the engineered Env include the following mutations: N460D; N463D; S278R; and G471S; removal of V1 and V2; V3 replacement with a flexible linker; and an N-terminal truncation and a C-terminal truncation. In particular forms of these embodiments, the engineered Env does not include a mutation at position 276. V65C and S115C can optionally be included to stabilize the Env following removal of the V1 and V2 loops.

Particular embodiments of the engineered Env include the following mutations: N460D; N463D; S278R; G471S; V65C; S115C; removal of V1 and V2; V3 replacement with a flexible linker; and an N-terminal truncation. In particular embodiments, V1 refers to 131-152 and V2 refers to 161-196. In particular embodiments, removal of V1 and V2 loops includes removal of 123-196. In particular embodiments, V3 refers to 296-331. In particular embodiments, removal of V3 with a flexible linker replacement includes removal of 301-323 and replacement with GGSGSG (SEQ ID NO. 57). Particular embodiments exclude a mutation at position 276. In the presence of the S278R mutation, the unmutated 276 position is not glycosylated. Exclusion of a mutation at this position was unexpected because as previously stated, this position is an important NLGS site used by HIV to avoid B cell detection. Particular embodiments disclosed herein present the outer domain and the inner domain.

In addition to SEQ ID NO. 57, a number of flexible linkers can be used to replace V3. The linker sequence should not be significantly deleterious to the immunogenicity of the engineered Env and may even be beneficial to immunogenicity. Particular exemplary linkers include flexible Gly-Ser linkers. Such linkers are known to those of skill in the art. One exemplary Gly-Ser linker includes Ac-Cys-Gly-Gly-Gly (SEQ ID NO. 58). Additional Gly-Ser linkers include GSTSGSGKPGSGEGSTKG (SEQ ID NO. 59) and SGRAHAG (SEQ ID NO. 60). Further examples include a linker that includes (Gly)n, where n=1 to 10 (e.g., n=1, 2, 3, 4, 5, 6, 7, 8, 9, or 10; SEQ ID NO. 61); (Ser)n, where n=1 to 10 (e.g., n=1, 2, 3, 4, 5, 6, 7, 8, 9, or 10; SEQ ID NO. 62), (Ala)n, where n=1 to 10 (e.g., n=1, 2, 3, 4, 5, 6, 7, 8, 9, or 10; SEQ ID NO. 63), (Gly-Ser)n, where n=1 to 10 (e.g., n=1, 2, 3, 4, 5, 6, 7, 8, 9, or 10; SEQ ID NO. 64), (Gly-Ser-Ser-Gly)n, where n=1 to 10 (e.g., n=1, 2, 3, 4, 5, 6, 7, 8, 9, or 10; SEQ ID NO. 65), (Gly-Ser-Gly)n, where n=1 to 10 (e.g., n=1, 2, 3, 4, 5, 6, 7, 8, 9, or 10; SEQ ID NO. 66), (Gly-Ser-Ser)n, where n=1 to 10 (e.g., n=1, 2, 3, 4, 5, 6, 7, 8, 9, or 10; SEQ ID NO. 67), $(Gly\text{-}Ala)_n$, where n=1 to 10 (e.g., n=1, 2, 3, 4, 5, 6, 7, 8, 9, or 10; SEQ ID NO. 68), or any combination thereof.

An N-terminal truncation refers to a truncation at the N-terminal end of a naturally-occurring Env. In particular embodiments, the N-terminal truncation is before residue 49, 48, 47, 46, 45, 44, 43, 42, 41, 40 or 39. In particular embodiments, the N-terminal truncation is before residue 46, 45, 44, 43 or 42. In particular embodiments, the N-terminal truncation is before residue 44.

Particular embodiments include a C-terminal truncation. In particular embodiments, the C-terminal truncation is after residue 499, 498, 497, 496, 495, 494, 493, 492, 491, 490 or 389. In particular embodiments, the C-terminal truncation is after residue 496, 495, 494, 493 or 492. In particular embodiments, the C-terminal truncation is after residue 494.

In particular embodiments, the key mutation on the 426c core that is required for glVRC01 binding knocks-out N276. In particular embodiments, the NLGS at position N460 should also be eliminated. In particular embodiments, the N463 on the 426c core may be retained as, without being bound by theory, it appears that the glycans at N463 can stabilize the binding of glVRC01 to the 426c core that lacks N276. One reason why glVRC01 binds the 426c core once N276 is knocked out is because the 426c Env naturally lacks a conserved NLGS at position 234. It is possible that N234, when glycosylated, may block the binding of gIVRC01 even when N276 is knocked out.

Particular engineered Env sequences useful as a prime immunogen within the present disclosure also include those that (i) maintain high affinity for broadly neutralizing VRC01 class antibodies; (ii) bind with little or no detectable affinity to non-neutralizing CD4bs antibodies such as b6, b13, F105, 15e, m14 or m18; (iii) lack the V3 loop and beta20/21 hairpin and are minimal in size (175 residues compared to 230 for wild-type outer domain); (iv) display no or low evidence of aggregation; (v) have N and C termini located distal from the CD4bs to allow coupling, by chemical or genetic means, to larger particles for the purpose of multimeric display; and/or (vi) may be expressed with a minimum of only two (2) glycans which may be useful for manipulating immune responses.

In particular embodiments, high affinity means that a binding domain associates with its target epitope with a dissociation constant ($K_D$) of $10^{-5}$ M or less, in one embodiment of from $10^{-5}$ M to $10^{-13}$ M, or in one embodiment of from $10^{-5}$ M to $10^{-10}$ M. In particular embodiments, high affinity means that a binding domain associates with its target epitope with a dissociation constant ($K_D$) of $10^{-7}$ M or less, or in one embodiment of from $10^{-7}$ M to $10^{-12}$ M, or in one embodiment of from $10^{-7}$ M to $10^{-15}$ M.

In particular embodiments, little or no detectable affinity means that the binding domain associates with its target epitope with a dissociation constant ($K_D$) of $10^{-4}$ M or more, in one embodiment of from $10^{-4}$ M to 1 M.

Exemplary engineered Env that can be as a prime immunogen in the sequential immunization strategies disclosed herein because they are designed to bind gl BCR include:

| SEQ ID NO. | Sequence |
|---|---|
| 69 | RPVVSTQLLLNGSLAEEEVVIRSVNFTDNAKTIIVQLNTSVEINCTGAGHCNISRAK WNNTLKQIASKLREQFGNNKTIIFKQSSGGDPEIVTHSFNCGGEFFYCDSTQLFNS TWFNSTWSTEGSNNTEGSDTITLPCRPAPPPHCSSNITGLLLTRDGGNSNNESEIF RPGGGDMRDNWRSE |
| 70 | RPVVSTQLLLNGSLAEEEVVIRSVNFTDNAKTIIVQLNTSVEINCTGAGHCNISRAK WNNTLKQIASKLREQFGNNKTIIFKQSSGGDPEIVTHSFNCGGEFFYCNSTQLFNS TWFNSTWSTEGSNNTEGSDTITLPCRPAPPPHCSSNITGLLLTRDGGNSNNESEIF RPGGGDMRDNWRSE |
| 71 | DTITLPCRPAPPPHCSSNITGLLLTRDGGNSNNESEIFRPGGGDMRDNWRSGLSG PVVSTQLLLNGSLAEEEVVIRSVNFTDNAKTIIVQLNTSVEINCTGAGHCNISRAKW NNTLKQIASKLREQFGNNKTIIFKQSSGGDPEIVTHSFNCGGEFFYCDSTQLFNST WFNSTWS |
| 72 | GEFFYCDSTQLFNSTWFNSTWSTEGSNNTEGSDTITLPCRPAPPPHCSSNITGLL LTRDGGNSNNESEIFRPGGGDMRDNWRSGLSGPVVSTQLLLNGSLAEEEVVIRS VNFTDNAKTIIVQLNTSVEINCTGAGHCNISRAKWNNTLKQIASKLREQFGNNKTIIF KQSSGGDPEIVTHSFNCG |
| 73 | DTITLPCRPAPPPHCSSNITGLILTRDGGNSNNESEIFRPGGGDMRDIARCQIAGTV VSTQLLLNGSLAEEEVVIRSVNFTDNAKSICVQLNTSVEINCTGAGHCNISRAKWN NTLKQIASKLREQFGNNKTIIFKQSSGGDPEIVTHSFNCGGEFFYCDSTQLFNSTW FNSTWS |
| 74 | DTITLPCRPAPPPHCSSNITGLILTRDGGNSNNESEIFRPGGGDMRDIARCQIAGTV VSTQLLLNGSLAEEEVVCRSVNFTDNAKSICVQLNTSVEINCTGAGHCNISRAKWN NTLKQIASCLREQFGNNKTIIFKQSSGGDPEIVTHSFNCGGEFFYCDSTQLFNSTW FNSTWS |
| 75 | DTITLPCRPAPPPHCSSNITGLILTRDGGNSNNESEIFRPGGGDMAGMPRCGGGA VSTQLLLNGSLAEEEVVCRSVNFTDNAKSICVQLNTSVEINCTGAGHCNISRAKWN NTLKQIASCLREQFGNNKTIIFKQSSGGDPEIVTHSFNCGGEFFYCDSTQLFNSTWF |
| 76 | DTITLPCRPAPPPHCSSNITGLILTRDGGNSNDESEIFRPGGGDMRDIARCQIAGTV VSTQLLLNGSLAEEEVVIRSVDFTDNAKSICVQLDTSVEIDCTGAGHCDISRAKWD NTLKQIASKLREQFGNDKTIIFKQSSGGDPEIVTHSFNCGGEFFYCDSTQLFDSTW FDSTWS |
| 77 | GEFFYCDSTQLFNSTWFNSTWSTEGSNNTEGSDTITLPCRPAPPPHCSSNITGLIL TRDGGNSNNESEIFRPGGGDMRDIARCQIAGTVVSTQLLLNGSLAEEEVVIRSVNF TDNAKSICVQLNTSVEINCTGAGHCNISRAKWNNTLKQIASKLREQFGNNKTIIFKQ SSGGDPEIVTHSFNCG |
| 78 | GEFFYCDSTQLFNSTWFNSTWSTEGSNNTEGSDTITLPCRPAPPPHCSSNITGLIL TRDGGNSNNESEIFRPGGGDMRCGARSGIAGTVVSTQLLLNGSLAEEEVVIRSVN FTDNAKCIIVQLNTSVEINCTGAGHCNISRAKWNNTLKQIASKLREQFGNNKTIIFKQ SSGGDPEIVTHSFNCG |
| 79 | GEFFYCDSTQLFNSTWFNSTWSTEGSNNTEGSDTITLPCRPAPPPHCSSNITGLIL TRDGGNSNNESEIFRPGGGDMRDIARCQIAGTVVSTQLLLNGSLAEEEVVCRSVN FTDNAKSICVQLNTSVEINCTGAGHCNISRAKWNNTLKQIASCLREQFGNNKTIIFK QSSGGDPEIVTHSFNCG |

-continued

| SEQ ID NO. | Sequence |
|---|---|
| 80 | DTITLPCRPAPPPHCSSNITGLILTRDGGTSDDKTEIFRPGGGDMRDIARCQIAGTV VSTQLLLNGSLAEEEVVIRSEDFRDNAKSICVQLNTSVEINCTGAGHCNISRAKWN NTLKQIASKLREQFGNKTIIFKQSSGGDPEFVTHSFNCGGEFFYCDSTQLFDSTWF DSTWS |
| 81 | DTITLPCRPAPPPHCSSNITGLILTRGGGISDDKTEIFRPGGGDMRDIARCQIAGTV VSTQLLLNGSLAEEEVVIRSEDFRDNSKSICVQLNTSVEINCTGAGHCNISRAKWN NTLKQIASKLREQFGNKTIIFSQSLGGDPEFVTHSFNCGGEFFYCDSTQLFDSTWF DSTWS |
| 82 | DTITLPCRPAPPPHCSSNITGLILTRGGGISDDKTEIFRPGGGDMRDIARCQIAGTV VSTQLLLNGSLAEEEVVIRSENFTDNSKSICVQLNTSVEINCTGAGHCNISRAKWN NTLKQIASKLREQFGNKTIIFSQSLGGDPEFVTHSFNCGGEFFYCDSTQLFDSTWF DSTWS |
| 83 | DTITLPCRPAPPPHCSSNITGLILTRGGGISDDKTEIFRPSGGDMRDIARCQIAGTV VSTQLLLNGSLAEEEVVIRSEDFRDNSKSICVQLNTSVEINCTGAGHCNISRAKWN NTLKQIASKLREQFGNKTIIFSQSLGGDPEFVTHSFNCGGEFFYCDSTQLFDSTWF DSTW |
| 84 | DTITLPCRPAPPPHCSSNITGLILTRGGGISDDKTEIFRPGGGDMRDIARCQIAGTV VSTQLLLNGSLAEEEVVIRSEDFRDNSKSICVQLNTSVEINCTGAGHCNISRAKWN NTLKQIASKLREQFGNRTIIFSQSLGGDPEFVTHSFNCGGEFFYCDSTQLFDSTWF DSTW |
| 85 | DTITLPCRPAPPPHCSSNITGLILTRGGGISDDDTEIFRPSGGDMRDIARCQIAGTV VSTQLFLNGSLAEEEVVIRSEDFRDNSKSICVQLNTSVEINCTGAGHCNISRAKWN NTLKQIASKLREQFGNRTIIFSQSLGGDPEFVTHSFNCGGEFFYCDSTQLFDSTWF DSTW |
| 86 | DTITLPCRPAPPPHCSSNITGLILTRAGGISDDNTEIFRPSGGDMRDIARCQIAGTVV STQLFLNGSLAEEEVVIRSEDFRDNSKSICVQLNTSVEINCTGAGHCNISRAKWNN TLKQIASKLREQFGNRTIIFSQSLGGDPEFVTHSFNCGGEFFYCDSTQLFDSTWFD STW |
| 87 | DTITLPCRPAPPPHCSSNITGLILTRGGGISDDNTEIFRPSGGDMRDIARCQIAGTV VSTQLLLNGSLAEEEVVIRSEDFRDNSKSICVQLNTSVEINCTGAGHCNISRAKWN NTLKQIASKLREQFGNRTIIFSQSLGGDPEFVTHSFNCGGEFFYCDSTQLFDSTWF DSTW |
| 88 | DTITLPCRPAPPPHCSSNITGLILTRGGGVSDDDTEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFSQSSGGDPEFVTHSFNCGGEFFYCDSTQLFDSTWF DSTW |
| 89 | DTITLPCRPAPPPHCSSNITGLILTRGGGVSDDDTEIFRPAGGDMRDIARCQIAGTV VSTQLFLNGSLAEEEVVIRSVDFRDNAKSICVQLNTSVEINCTGAGHCNISRAKWN NTLKQIASKLREQFGNRTIIFSQSSGGDPEFVTHSFNCGGEFFYCDSTQLFDSTWF DSTW |
| 90 | DTITLPCRPAPPPHCSSNITGLILTRGGGVSDDDTEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFSQSSGGDPEFVTHSFNCGGEFFYCDSTQLFDSTWFD |
| 91 | DTITLPCRPAPPPHCSSNITGLILTRDGGVSNDETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCDSTQLFNSTWF NST |
| 92 | DTITLPCRPAPPPHCSSNITGLILTRDGGNSNDETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCDSTQLFNSTWF NST |
| 93 | DTITLPCRPAPPPHCSSNITGLILTRDGGVSNDESEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCDSTQLFNSTWF NST |
| 94 | DTITLPCRPAPPPHCSSNITGLILTRDGGVSNDETEIFRPGGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCDSTQLFNSTWF NST |

-continued

| SEQ ID NO. | Sequence |
|---|---|
| 95 | DTITLPCRPAPPPHCSSNITGLILTRDGGVSNDETEIFRPSGGDMRDIARCQIAGTV VSTQLLLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCDSTQLFNSTWF NST |
| 96 | DTITLPCRPAPPPHCSSNITGLILTRDGGVSNDETEIFRPSGGDMRDIARCQIAGTV VSTQLFLNGSLAEEEVVIRSVDFTDNAKSICVQLNTSVEINCTGAGHCNISRAKWN NTLKQIASKLREQFGNRTIIFKQSSGGDPEFVTHSFNCGGEFFYCDSTQLFNSTWF NST |
| 97 | DTITLPCRPAPPPHCSSNITGLILTRDGGVSNDETEIFRPSGGDMRDIARCQIAGTV VSTQLFLNGSLAEEEVVIRSVDFRDNAKSICVQLNTSVEINCTGAGHCNISRAKWN NTLKQIASKLREQFGNKTIIFKQSSGGDPEFVTHSFNCGGEFFYCDSTQLFNSTWF NST |
| 98 | DTITLPCRPAPPPHCSSNITGLILTRDGGVSNDETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEIVTHSFNCGGEFFYCDSTQLFNSTWF NST |
| 99 | DTITLPCRPAPPPHCSSNITGLILTRDGGVSNDETEIFRPSGGDMRDIARCQIAGTV VSTQLFLNGSLAEEEVVIRSVDFRDNAKSICVQLDTSVEIDCTGAGHCDISRAKWD NTLKQIASKLREQFGDRTIIFKQSSGGDPEFVTHSFNCGGEFFYCDSTQLFDSTWF DST |
| 100 | DTITLPCRPAPPPHCSSNITGLILTRDGGVSNNETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCNSTQLFNSTWF NST |
| 101 | DTITLPCRPAPPPHCSSNITGLILTRDGGNSNNETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCNSTQLFNSTWF NST |
| 102 | DTITLPCRPAPPPHCSSNITGLILTRDGGVSNNETEIFRPGGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCNSTQLFNSTWF NST |
| 103 | DTITLPCRPAPPPHCSSNITGLILTRDGGVSNNETEIFRPSGGDMRDIARCQIAGTV VSTQLLLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCNSTQLFNSTWF NST |
| 104 | DTITLPCRPAPPPHCSSNITGLILTRDGGVSNNETEIFRPSGGDMRDIARCQIAGTV VSTQLFLNGSLAEEEVVIRSVDFTDNAKSICVQLNTSVEINCTGAGHCNISRAKWN NTLKQIASKLREQFGNRTIIFKQSSGGDPEFVTHSFNCGGEFFYCNSTQLFNSTWF NST |
| 105 | DTITLPCRPAPPPHCSSNITGLILTRDGGVSNNETEIFRPSGGDMRDIARCQIAGTV VSTQLFLNGSLAEEEVVIRSVDFRDNAKSICVQLNTSVEINCTGAGHCNISRAKWN NTLKQIASKLREQFGNKTIIFKQSSGGDPEFVTHSFNCGGEFFYCNSTQLFNSTWF NST |
| 106 | DTITLPCRPAPPPHCSSNITGLILTRDGGVSNNETEIFRPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEIVTHSFNCGGEFFYCNSTQLFNSTWF NST |
| 107 | DTITLPCRPAPPPHCSSNITGLILTRDGGVSNNETEIFRPSGGDMRDIARCQIAGTV VSTQLFLNGSLAEEEVVIRSVNFTDNAKSICVQLNTSVEINCTGAGHCNISRAKWN NTLKQIASKLREQFGNRTIIFKQSSGGDPEFVTHSFNCGGEFFYCNSTQLFNSTWF NST |
| 108 | DTITLPCRPAPPPHCSSNITGLILTRAGGVSDNNTEIFFPSGGDMRDIARCQIAGTV VSTQLFLNGSLAEEEVVIRSVDFRDNAKSICVQLNTSVEINCTGAGHCNISRAKWN NTLKQIASKLREQFGNRTIIFSQSTGGDPEFVTHSFNCGGEFFYCNSTQLFNSTWF NST |
| 109 | DTITLPCRPAPPPHCSSNITGLILGRAGGASDDNTEIFYPSGGDMRDIARCQIAGTV VSTQLFLNGSLAEEEVVIRSVDFRDNAKSICVQLNTSVEINCTGAGHCNISRAKWN NTLKQIASKLREQFGNRTIIFSQSTGGDPEIVTHSFNCGGEFFYCNSTQLFNSTWF NSTW |

-continued

| SEQ ID NO. | Sequence |
|---|---|
| 110 | DTITLPCRPAPPPHCSSNITGLILTRAGGVSNNETEIFFPSGGDMRDIARCQIAGTV VSTQLFLNGSLAEEEVVIRSVDFRDNAKSICVQLNTSVEINCTGAGHCNISRAKWN NTLKQIASKLREQFGNRTIIFKQSSGGDPEFVTHSFNCGGEFFYCNSTQLFNSTWF NST |
| 111 | VWKEATTTLFCASDAKAYDTEVHNVWATHACVPTDPNPQEVELENVTENFNMWK NNMVEQMHEDIISLWDQSLKPCVKLTGGSVITQACPKISFEPIPIHYCAPAGFAILK CKDKKFNGKGPCSNVSTVQCTHGIRPVVSTQLLLNGSLAEEEVVIRSENFADNAK TIIVQLNESVEINCTRPNNGGSGSGGDIRQAHCNLSRAKWNDTLNKIVIKLREQFG NKTIVFKHSSGGDPEIVTHSFNCGGEFFYCNSTQLFNSTWNVTEESNNTVENNTIT LPCRIKQIINMWQKVGRAMYAPPIRGQIRCSSNITGLLLTRDGGPEDNKTEVFRPG GGDMRDNWRSELYKYKVVKIE |
| 112 | VWKDATTTLFCASDAKAHETEVHNVWATHACVPTDPNPQEVELKNVTENFNMW KNNMVEQMHEDIISLWDQSLKPCVKLTGGSVITQACPKVSFEPIPIHYCAPAGFAIL KCKDKKFNGKGPCSNVSTVQCTHGIRPVVSTQLLLNGSLAEEEVVIRSEDFRNNA KIIIVQLNESVEINCTGAGHCNLSRAKWNDTLNKIVIKLREQFGNKTIVFKHSSGGDP EIVTHSFNCGGEFFYCNSTQLFNSTWNVTEESNNTVENNTITLPCRIKQIINMWQE VGRAMYAPPIRGQIRCSSNI |

Within these examples, SEQ ID NOs. 69-79 are advantageous for the elicitation of CD4-binding site (CD4bs)-directed broadly-neutralizing antibodies (bNAbs), while SEQ ID NOs. 80-112 are advantageous for improving binding to gl VRC01 and/or other VI-11-2 antibodies.

Boost Env are selected to include a functional NLGS at position 276. "Functional" means that not only does the Boost Env have the appropriate amino acid sequence that is a signal that position 276 is an NLGS (i.e., N-x-T/S) but it also must have carbohydrate molecules on the asparagine (N). The exact number and type of carbohydrates at position NLGS varies. For example, while some may include 3 carbohydrates, others may include 5, 6, 7, or more. Particularly useful examples of boost Env include H×B2, QH0692, and 45_01 dH1.

In particular embodiments, the Boost Env is heterologous to the Prime Env. In particular embodiments, the Boost Env is autologous to the Prime Env with the Boost Env having NLGS at position 276 re-introduced. In particular embodiments, a Boost Env that is heterologous to the Prime Env is preferred so that the activation of B cells that target unwanted epitopes is minimized.

Examples of Env proteins with NLGS at position 276 that can be used as Boost Env include: SEQ ID NO. 69, SEQ ID NO. 70, SEQ ID NO. 71, SEQ ID NO. 72, SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 82, and SEQ ID NO. 107. Additional examples of Boost Env with N276 glycosylation include:

| SEQ ID NO.: | Sequence |
|---|---|
| 113 | DTITLPCRPAPPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 114 | DTITLPCRPAPPPHCSSNITGLILTRDGGNSNNESEIFRPGGGDMRDIARCQIAGT VVSTQLFLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 115 | DTITLPCRPAPPPHCSSNITGLILTRDGGNSNNESEIFRPGGGDMRDNARCQIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |
| 116 | DTITLPCRPAPPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLREQFGNKTIIFKQSSGGDPEIVTHSFNCGGEFFYCNSTQLFNST WFNSTWS |
| 117 | DTITLPCRPAPPPHCSSNITGLILTRDGGNSNNESEIFRPGGGDMRDIARCQIAGT VVSTQLLLNGSLAEEEIVIRSVNFTDNAKSICVQLNTSVE1NCTGAGHCNISRAKW NNTLKQIASKLREQFGNNKTIIFKQSSGGDPEIVTHSFNCGGEFFYCNSTQLFNST WFNSTWS |
| 118 | DTITLPCRPAPPPHCSSNITGLILTRDGGNSNNESEIFRPGGGDMRDIARCQIAGT VVSSQLFLNGSLAEEEVVIRSVNFTDNAKSICVQLNTSVEINCTGAGHCNISRAKW NNTLKQIASKLREQFGNNKTIIFKQSSGGDPEIVTHWFNCGGEFFYCNSTQLFNS TWFNSTWS |

-continued

| SEQ ID NO.: | Sequence |
|---|---|
| 121 | DTITLPCRPAPPPHCSSNITGLILTRDGGNSNNESEIFRPGGGDMRDIANCSIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 122 | DTITLPCRPAPPPHCSSNITGLILTRDGGNSNNESEIFRPGGGDMRDIARCQNAS TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |
| 123 | DTITLPCRPAPPPHCSSNITGLILTRDGGNSNNESEIFRPGGGDMRDIARCQIAGN VTSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 124 | DTITLPCRPAPPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLRENFSNNKTIIFKQSSGGDPEIVTHSFNCGGEFFYCNSTQLFNST WFNSTWS |
| 125 | DTITLPCNPSPPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 126 | DTITLPCRNATPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGGEFFYCNSTQLFNST WFNSTWS |
| 127 | DTITLPCRPAPPPHCSSNITGLILTRDGGNSNNESEIFRPGGGDMRDIARCQIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGNETFYCNSTQLFNST WFNSTWS |
| 128 | DTITLPCNPSPPPHCSSNITGLILTRDGGNSNNESEIFRPGGGDMRDIARCQNAS TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGNETFYCNSTQLFN STWFNSTWS |
| 129 | DTITLPCNPSPPPHCSSNITGLILTRDGGNSNNESEIFRPGGGDMRDIANCSIAGT VVSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGNETFYCNSTQLFNST WFNSTWS |
| 130 | DTITLPCNPSPPPHCSSNITGLILTRDGGNSNNESEIFRPGGGDMRDIANCSIAGN VTSTQLLLNGSLAEEEVVIRSVNFTDNAKSICVQLNTSVEINCTGAGHCNISRAKW NNTLKQIASKLREQFGNNKTIIFKQSSGGDPEIVTHSFNCGNETFYCNSTQLFNST WFNSTWS |
| 131 | DTITLPCNPSPPPHCSSNITGLILTRDGGNSNNESEIFRPGGGDMRDIANCSIAGT VVSTQLLLNGSLAEEEVVIRSVNFTDNAKSICVQLNTSVEINCTGAGHCNISRAKW NNTLKQIASKLRENFSNNKTIIFKQSSGGDPEIVTHSFNCGNETFYCNSTQLFNST WFNSTWS |
| 132 | DTITLPCNPSPPPHCSSNITGLILTRDGGNSNNESEIFRPGGGDMRDIANCSIAGN VTSTQLLLNGSLAEEEVVIRSVNFTDNAKSICVQLNTSVEINCTGAGHCNISRAKW NNTLKQIASKLRENFSNNKTIIFKQSSGGDPEIVTHSFNCGNETFYCNSTQLFNST WFNSTWS |

(iv) Multimerization of Env. A multimerized engineered Env refers to an assembly of two or more Env. Multimerization can enhance the immunogenicity of administered Env. In particular embodiments, multimers include trimers, tetramers, and octamers using coiled-coil multimerization domains. From the trimers and tetramers, octamers, 24mers, 60mers, and 180mers or other larger order -mers can be formed.

Particular embodiments can utilize ferritin as a multimerization domain. Ferritin is an iron storage protein found in almost all living organisms, and has been extensively studied and engineered for a number of biochemical/biomedical purposes (US 20090233377; Meldrum, et al. Science 257, 522-523 (1992); U.S. 20110038025; Yamashita, Biochim Biophys Acta 1800, 846-857 (2010), including as a multimerizing vaccine platform for displaying peptide epitopes (US 20060251679 (2006); Li, et al. Industrial Biotechnology 2, 143-147 (2006)). Ferritin is particularly useful for multimerizing vaccine epitopes because of its self-assembly and multivalent presentation of the epitopes which induces stronger B cell responses than monovalent forms as well as induce T-cell independent antibody responses. Bachmann et al., Annual Review of Immunology 15, 235-270 (1997); Dintzis et al. Proceedings of the National Academy of Sciences of the United States of America 73, 3671-3675 (1976). Further, the molecular architecture of ferritin, which can include 24 subunits assembling into an octahedral cage with 432 symmetry has the potential to display multimeric antigens on its surface.

Particular embodiments utilize a monomeric ferritin subunit protein linked to an Env. The monomeric ferritin subunit protein can include a domain that allows the fusion protein to self-assemble into particles. The monomeric ferritin subunit protein can be selected from a bacterial ferritin, a plant ferritin, an algal ferritin, an insect ferritin, a fungal ferritin and a mammalian ferritin or can be a monomeric subunit of a *Helicobacter pylori* ferritin protein.

An exemplary ferritin fusion sequence includes, for example the *Helicobacter pylori* bullfrog fusion described in, PMID 26279189. In particular embodiments, a ferritin sequence includes

| SEQ ID NO. | Sequence |
|---|---|
| 51 | ESQVRQQFSKDIEKLLNEQVNKEMQSSNLYMSMSSWCYTHSLDGAGLFLFDHAA<br>EEYEHAKKLIIFLNENNVPVQLTSISAPEHKFEGLTQIFQKAYEHEQHISESINNIVD<br>HAIKSKDHATFNFLQWYVAEQHEEEVLFKDILDKIELIGNENHGLYLADQYVKGIAK<br>SRKSGS |
| 133 | VWKEAKTTLFCASDAKAYEKECHNVWATHACVPTDPNPQEVVLENVTENFNMW<br>KNDMVDQMQEDVISIWDQCLKPCVKLTNTSTLTQACPKVTFDPIPIHYCAPAGYAI<br>LKCNNKTFNGKGPCNNVSTVQCTHGIKPVVSTQLLLNGSLAEEEIVIRSKNLRDNA<br>KIIIVQLNKSVEIVCTRPNNGGSGSGGDIRQAYCNISGRNWSEAVNQVKKKLKEHF<br>PHKNISFQSSSGGDLEITTHSFNCGGEFFYCNTSGLFNDTISNATIMLPCRIKQIINM<br>WQEVGKAIYAPPIKGNITCKSDITGLLLLRDGGDTTDNTEIFRPSGGDMRDNWRSE<br>LYKYKVVEIKPLGSGGSGESQVRQQFSKDIEKLLNEQVNKEMQSSNLYMSMSSW<br>CYTHSLDGAGLFLFDHAAEEYEHAKKLIIFLNENNVPVQLTSISAPEHKFEGLTQIF<br>QKAYEHEQHISESINNIVDHAIKSKDHATFNFLQWYVAEQHEEEVLFKDILDKIELIG<br>NENHGLYLADQYVKGIAKSRKSGS |
| 134 | DIIKLLNEQVNKEMNSSNLYMSMSSWCYTHSLDGAGLFLFDHAAEEYEHAKKLIIF<br>LNENNVPVQLTSISAPEHKFEGLTQIFQKAYEHEQHISESINNIVDHAIKSKDHATFN<br>FLQWYVAEQHEEEVLFKDILDKIELIGNENHGLYLADQYVKGIAKSRKS |
| 135 | LNEQVNKEMNSSNLYMSMSSWCYTHSLDGAGLFLFDHAAEEYEHAKKLIIFLNEN<br>NVPVQLTSISAPEHKFEGLTQIFQKAYEHEQHISESINNIVDHAIKSKDHATFNFLQ<br>WYVAEQHEEEVLFKDILDKIELIGNENHGLYLADQYVKGIAKSRKS |
| 136 | DIIKLLNEQVNKEMQSSNLYMSMSSWCYTHSLDGAGLFLFDHAAEEYEHAKKLIIF<br>LNENNVPVQLTSISAPEHKFEGLTQIFQKAYEHEQHISESINNIVDHAIKSKDHATFN<br>FLQWYVAEQHEEEVLFKDILDKIELIGNENHGLYLADQYVKGIAKSRKS |

The following sequence provides an exemplary 426c core+linker+ferritin construct:

| SEQ ID NO. | Sequence |
|---|---|
| 137 | VWKEAKTTLFCASDAKAYEKECHNVWATHACVPTDPNPQEVVLENVTENFNMW<br>KNDMVDQMQEDVISIWDQCLKPCVKLTNTSTLTQACPKVTFDPIPIHYCAPAGYAI<br>LKCNNKTFNGKGPCNNVSTVQCTHGIKPVVSTQLLLNGSLAEEEIVIRSKNLRDNA<br>KIIIVQLNKSVEIVCTRPNNGGSGSGGDIRQAYCNISGRNWSEAVNQVKKKLKEHF<br>PHKNISFQSSSGGDLEITTHSFNCGGEFFYCNTSGLFNDTISNATIMLPCRIKQIINM<br>WQEVGKAIYAPPIKGNITCKSDITGLLLLRDGGDTTDNTEIFRPSGGDMRDNWRSE<br>LYKYKVVEIKPL**GSGGSG***ESQVRQQFSKDIEKLLNEQVNKEMQSSNLYMSMSSW*<br>*CYTHSLDGAGLFLFDHAAEEYEHAKKLIIFLNENNVPVQLTSISAPEHKFEGLTQIF*<br>*QKAYEHEQHISESINNIVDHAIKSKDHATFNFLQWYVAEQHEEEVLFKDILDKIELIG*<br>*NENHGLYLADQYVKGIAKSRKSGS* |

In particular embodiments, Env can be multimerized with a C4b multimerization domain. C4 binding protein (C4b) is the major inhibitor of the classical complement and lectin pathway. The complement system is a major part of innate immunity and is the first line of defense against invading microorganisms. Orchestrated by more than 60 proteins, its major task is to discriminate between host cells and pathogens and to initiate immune responses when necessary. It also recognizes necrotic or apoptotic cells. Hofmeyer et al., Journal of Molecular Biology. 2013 Apr. 26; 425(8): 1302-17.

Full-length native C4b includes seven α-chains linked together by a multimerization (i.e., heptamerization) domain at the C-terminus of the α-chains. Blom et al., (2004) Molecular Immunology 40: 1333-1346. One of the α-chains can be replaced by a ß-chain in humans. The wild-type C4b multimerization domain is 57 amino acid residues in humans and 54 amino acid residues in mice. Forbes et al., PLOS One. 2012; 7(9): e44943. It contains an amphipathic a-helix region, which is necessary and sufficient for heptamerization, as well as two cysteine residues which stabilize the structure. Kask et al., (2002) Biochemistry 41: 9349-9357.

The sequences of a number of C4b domain proteins are available in the art. These include human C4b multimerization domains as well as a number of homologues of human C4b multimerization domain available in the art. There are two types of homologues: orthologues and paralogues. Orthologues are defined as homologous genes in different organisms, i.e. the genes share a common ancestor coincident with the speciation event that generated them. Paralogues are defined as homologous genes in the same organism derived from a gene, chromosome or genome duplication, i.e. the common ancestor of the genes occurred since the last speciation event.

GenBank® indicates mammalian C4b multimerization domain homologues in species including chimpanzees, rhesus monkeys, rabbits, rats, dogs, horses, mice, guinea pigs, pigs, chicken, and cattle. Further C4b multimerization domains may be identified by searching databases of DNA or protein sequences, using commonly available search programs such as BLAST.

Particular C4b multimerization domains that can be used include:

| SEQ ID NO. | Sequence |
|---|---|
| 138 | SGRAHAGWETPEGCEQVLTGKRLMQCLPNPEDVKMALEVYKLSLEIEQLELQRDS ARQSTLDKELVPR |
| 139 | KKQGDADVCGEVAYIQSVVSDCHVPTAELRTLLEIRKLFLEIQKLKVELQGLSKE |
| 140 | ETPEGCEQVLTGKRLMQCLPNPEDVKMALEVYKLSLEIEQLELQRDSARQSTLDKEL |
| 141 | WETPEGCEQVLTGKRLMQCLPNPEDVKMALEVYKLSLEIEQLELQRDSARQSTLD KEL |
| 142 | CEQVLTGKRLMQCLPNPEDVKMALEVYKLSLEIEQLELQRDSARQSTLDKEL |
| 143 | ETPEGCEQVLTGKRLMQCLPNPEDVKMALEVYKLSLEIEQLELQRDSARQYTLDKEL |
| 144 | ETPEGCEQVLAGKRLMQCLPNPEDVKMALEVYKLSLEIEQLELQRDRARQSTLDK EL |
| 145 | ETPEGCEQVLAGKRLMQCLPNPEDVKMALEVYKLSLEIEQLELQRDRARQSTWDK EL |
| 146 | EVPEGCEQVQAGRRLMQCLADPYEVKMALEVYKLSLEIELLELQRDKARKSSVLR QL |
| 147 | VVPEGCEHILKGRKTMQCLPNPEDVKMALEIYKLSLDIELLELQRDRAKESTVQSPV |
| 148 | EVPKDCEHVFAGKKLMQCLPNSNDVKMALEVYKLTLEIKQLQLQIDKAKHVDREL |
| 149 | EYPEDCEQVHEGKKLMQCLPNLEEIKLALELYKLSLETKLLELQIDKEKKAKAKYSI |
| 150 | EYPEDCEQVHEGKKLMECLPTLEEIKLALALYKLSLETNLLELQIDKEKKAKAKYST |
| 151 | EIAEGCEQVLAGRKIMQCLPKPEDVRTALELYKLSLEIKQLEKKLEKEEKCTPEVQE |
| 152 | EYPEGCEQVVTGRKLLQCLSRPEEVKLALEVYKLSLEIEILQTNKLKKEAFLLRERE K NVTCDFNPE |
| 153 | EYPEGCEQVVTGRKLLKCLSRPEEVKLALEVYKLSLEIALLELQIDKPKDAS |
| 154 | EVPENCEQVIVGKKLMKCLSNPDEAQMALQLYKLSLEAELLRLQIVKARQGS |
| 155 | EASEDLKPALTGNKTMQYVPNSHDVKMALEIYKLTLEVELLQLQIQKEKHTEAH |
| 156 | VSAEVCEAVFKGQKLLKCLPNAMEVKMALEVYKLSLEIEKLEQEKRKLEIA |
| 157 | EVPEECKQVAAGRKLLECLPNPSDVKMALEVYKLSLEIEQLEKEKYVKIQEKFSKKE MKQLTSALH |
| 158 | EVLEDCRIVSRGAQLLHCLSSPEDVHRALKVYKLFLEIERLEHQKEKWIQLHRKPQS MK |
| 159 | EGPEDCEIVNKGRQLLQCLSSPEDVQRALEVYKLSLEIERLEQQREKRTSVHRKAH YTKVDGP |
| 160 | EAPEGCEQVLTGRKLMQCLPSPEDVKVALEVYKLSLEIKQLEKERDKLMNTHQKFS EKEEMKDLFFP |
| 161 | EVPEGCEQVLTGKKLMQCLPNPEDVKMALEVYKLSLEIELLELQIDKARQGS |
| 162 | GCEQVLTGKRLMQCLPNPEDVKMALEVYKLSLEIEQLELQRDSARQS |
| 163 | ETPEGCEQVLTGKRLMQCLPNPEDVKMALEVYKLSLEIEQLELQRDSARQS |
| 164 | GSEQVLTGKRLMQSLPNPEDVKMALEVYKLSLEIEQLELQRDSARQSTLDKEL |
| 165 | ETPEGCEQVLTGKRLMQCLPNPEDVKMALEIYKLTLEIEQLELQRDSARQSTLDKEL |
| 166 | ETPEGCEQVLTGKRLMQCLPNPEDVKMALEIYKLSLEIKQLELQRDSARQSTLDKEL |
| 167 | EGCEQILTGKRLMQCLPDPEDVKMALEIYKLSLEIKQLELQRDRARQSTL |

-continued

| SEQ ID NO. | Sequence |
|---|---|
| 168 | ETPEGCEQVLTGKRLMQCLPNPEDVKMALEVYKLSLEIKQLELQRDRARQSTLDKEL |
| 169 | EGCEQILTGKRLMQCLPNPEDVKMALEIYKLSLEIEQLELQRDRARQSTLDK |
| 170 | WETPEGCEQVLTGKRLMQCLPNPEDVKMALEVYKLSLEIEQLELQRDSARQSTLD KELVPR |

In particular embodiments, the C4b multimerization domain will be a multimerization domain which includes (i) glycine at position 12, (ii) alanine at position 28, (iii) leucines at positions 29, 34, 36, and/or 41; (iv) tyrosine at position 32; (v) lysine at position 33; and/or (vi) cysteine at positions 6 and 18. In particular embodiments, the C4b multimerization domain will be a multimerization domain which includes (i) glycine at position 12, (ii) alanine at position 28, (iii) leucines at positions 29, 34, 36, and 41; (iv) tyrosine at position 32; (v) lysine at position 33; and (vi) cysteine at positions 6 and 18.

C4b multimerization domains can include any of SEQ ID NOs. 138-170 with an N-terminal deletion of at least 1 consecutive amino acid residues (eg. at least 2, 3, 4, 5, 6, 7, 8, 9, 10 consecutive amino acid residues) in length. Additional embodiments can include a C-terminal deletion of at least 1 consecutive amino acid residues (eg. at least 2, 3, 4, 5, 6, 7, 8, 9, 10 consecutive amino acid residues) in length.

Particular C4b multimerization domain embodiments will retain or will be modified to include at least 1 of the following residues: A6; E11; A13; D21; C22; P25; A27; E28; L29; R30; T31; L32; L33; E34; 135; K37; L38; L40; E41; 142; Q43; K44; L45; E48; L49; or Q50. Further embodiments will retain or will be modified to include A6; E11; A13; D21; C22; P25; A27; E28; L29; R30; T31; L32; L33; E34; 135; K37; L38; L40; E41; 142; Q43; K44; L45; E48; L49; and Q50. Particular C4b multimerization domain embodiments will include the amino acid sequence "AELR".

Particular embodiments can utilize a heptamerization domain such as:

| SEQ ID NO. | Sequence |
|---|---|
| 171 | AHAGWETPEGCEQVLTGKRLMQCLPNPEDVKMALEVYKLSLEIEQLELQRDSARQ STLDKEL (Human) |
| 172 | SKKQGDADVCGEVAYIQSVVSDCHVPTEDVKTLLEIRKLFLEIQKLKVELQGLSKE (Chicken) |
| 50 | SKKQGDADVCGEVAYIQSVVSDCHVPT<u>**AELR**</u>TLLEIRKLFLEIQKLKVELQGLSKE (Modified Chicken) |

Particular embodiments of engineered 426c core Envs, GS linkers, and C4b multimerization domains include:

| SEQ ID NO. | Sequence |
|---|---|
| 174 | VWKEAKTTLFCASDAKAYEKECHNVWATHACVPTDPNPQEVVLENVTENFNMWK NDMVDQMQEDVISIWDQCLKPCVKLTNTSTLTQACPKVTFDPIPIHYCAPAGYAILK CNNKTFNGKGPCNNVSTVQCTHGIKPVVSTQLLLNGSLAEEEIVIRSKNLRDNAKIII VQLNKSVEIVCTRPNNGGSGSGGDIRQAYCNISGRNWSEAVNQVKKKLKEHFPHK NISFQSSSGGDLEITTHSFNCGGEFFYCNTSGLFNDTISNATIMLPCRIKQIINMWQE VGKAIYAPPIKGNITCKSDITGLLLLRDGGDTTDNTEIFRPSGGDMRDNWRSELYKY KVVEIKPLSGSGRAHAGWETPEGCEQVLTGKRLMQCLPNPEDVKMALEVYKLSLEI EQLELQRDSARQSTLDKELVPR |
| 274 | VWKEAKTTLFCASDAKAYEKECHNVWATHACVPTDPNPQEVVLENVTENFNMWK NDMVDQMQEDVISIWDQCLKPCVKLTNTSTLTQACPKVTFDPIPIHYCAPAGYAILK CNNKTFNGKGPCNNVSTVQCTHGIKPVVSTQLLLNGSLAEEEIVIRSKNLRDNAKIII VQLNKSVEIVCTRPNNGGSGSGGDIRQAYCNISGRNWSEAVNQVKKKLKEHFPHK NISFQSSSGGDLEITTHSFNCGGEFFYCNTSGLFNDTISNATIMLPCRIKQIINMWQE VGKAIYAPPIKGNITCKSDITGLLLLRDGGDTTDNTEIFRPSGGDMRDNWRSELYKY KVVEIKPLGSSKKQGDADVCGEVAYIQSVVSDCHVPTAELRTLLEIRKLFLEIQKLKV ELQGLSKE |

These engineered Env include: the following mutations: N460D; N463D; S278R; G471S; V65C; S115C; removal of V1 and V2; V3 replacement with a flexible linker; an N-terminal truncation before 44, a C-terminal truncation after 494 and a C4b multimerization domain. This engineered Env excludes a mutation at position 276, but nonetheless lacks N276 glycosylation due to the S278R mutation.

(v) Vaccine Adjuvants. Vaccines are often administered with vaccine adjuvants. The term "adjuvant" refers to material that enhances the immune response to an antigen and is used herein in the customary use of the term. The precise mode of action is not understood for all adjuvants, but such lack of understanding does not prevent their clinical use for a wide variety of vaccines.

Exemplary vaccine adjuvants, include any kind of Toll-like receptor ligand or combinations thereof (e.g. CpG, Cpg-28 (a TLR9 agonist), Polyriboinosinic polyribocytidylic acid (Poly(I:C)), Adjuplex (a biodegradable matrix of carbomer homopolymer-Carbopol- and nanoliposomes), α-galactoceramide, MPLA, Motolimod (VTX-2337, a novel TLR8 agonist developed by VentiRx), IMO-2055 (EMD1201081), TMX-101 (imiquimod), MGN1703 (a TLR9 agonist), Ribi (a TLR4 agonist), G100 (a stabilized emulsion of the TLR4 agonist glucopyranosyl lipid A), GLA-LSQ (a Glucopyranosyl lipid adjuvant in a liposomal formulation with QS21). Entolimod (a derivative of *Salmonella* flagellin also known as CBLB502), Hiltonol (a TLR3 agonist), and Imiquimod), and/or inhibitors of heat-shock protein 90 (Hsp90), such as 17-DMAG (17-dimethylamino-ethylamino-17-demethoxygeldanamycin).

In particular embodiments a squalene-based adjuvant can be used. Squalene is part of the group of molecules known as triterpenes, which are all hydrocarbons with 30 carbon molecules. Squalene can be derived from certain plant sources, such as rice bran, wheat germ, amaranth seeds, and olives, as well as from animal sources, such as shark liver oil. In particular embodiments, the squalene-based adjuvant is MF59® (Novartis, Basel, Switzerland). An example of a squalene-based adjuvant that is similar to MF59® but is designed for preclinical research use is Addavax™ (InvivoGen, San Diego, CA). MF59 has been FDA approved for use in an influenza vaccine, and studies indicate that it is safe for use during pregnancy (Tsai T, et al. Vaccine. 2010. 17:28(7): 1877-80; Heikkinen T, et al. American Journal of Obstetrics and Gynecology. 2012. 207(3):177). In particular embodiments, squalene-based adjuvants can include 0.1%-20% (v/v) squalene oil. In particular embodiments, squalene-based adjuvants can include 5% (v/v) squalene oil.

In particular embodiments the adjuvant alum can be used. Alum refers to a family of salts that contain two sulfate groups, a monovalent cation, and a trivalent metal, such as aluminum or chromium. Alum is an FDA approved adjuvant. In particular embodiments, vaccines can include alum in the amounts of 1-1000 μg/dose or 0.1 mg-10 mg/dose. In particular embodiments, the adjuvant Vaxfectin® (Vical, Inc., San Diego, CA) can be used. Vaxfectin® is a cationic lipid based adjuvant.

In particular embodiments, one or more STING agonists are used as a vaccine adjuvant. "STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein and is encoded by the gene TMEM173 in human. Activation of STING leads to production of Type I interferons (e.g. IFN-α and IFN-β), via the IRF3 (interferon regulatory factor 3) pathway; and to production of pro-inflammatory cytokines (e.g. TNF-a and IL-Iβ), via the NF-κB pathway and/or the NLRP3 inflammasome. Particular examples of STING agonists include c-AIMP; (3',2')c-AIMP; (2',2')c-AIMP; (2',3')c-AIMP; c-AIMP(S); c-(dAMP-dIMP); c-(dAMP-2'FdIMP); c-(2'FdAMP-2'FdIMP); (2',3')c-(AMP-2'FdIMP); c-[2'FdAMP(S)-2'FdIMP(S)]; c-[2'FdAMP(S)-2'FdIMP(S)](POM)2; and DMXAA. Additional examples of STING agonists are described in WO2016/145102.

Other immune stimulants can also be used as vaccine adjuvants. Additional exemplary small molecule immune stimulants include TGF-β inhibitors, SHP-inhibitors, STAT-3 inhibitors, and/or STAT-5 inhibitors. Exemplary siRNA capable of down-regulating immune-suppressive signals or oncogenic pathways (such as kras) can be used whereas any plasmid DNA (such as minicircle DNA) encoding immune-stimulatory proteins can also be used.

(vi). Compositions. The Env (in monomer or multimerized form (i.e., "active ingredients") can be provided as part of compositions formulated for administration to subjects with or without inclusion of an adjuvant in the composition.

In particular embodiments, active ingredients are provided as part of a composition that can include, for example, at least 0.1% w/v or w/w of active ingredient(s); at least 1% w/v or w/w of active ingredient(s); at least 10% w/v or w/w of active ingredient(s); at least 20% w/v or w/w of active ingredient(s); at least 30% w/v or w/w of active ingredient(s); at least 40% w/v or w/w of active ingredient(s); at least 50% w/v or w/w of active ingredient(s); at least 60% w/v or w/w of active ingredient(s); at least 70% w/v or w/w of active ingredient(s); at least 80% w/v or w/w of active ingredient(s); at least 90% w/v or w/w of active ingredient(s); at least 95% w/v or w/w of active ingredient(s); or at least 99% w/v or w/w of active ingredient(s).

The compositions disclosed herein can be formulated for administration by, for example, injection, inhalation, infusion, perfusion, lavage or ingestion. The compositions can further be formulated for, for example, intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Any composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

(vii) Kits. Combinations of active ingredients can also be provided as kits. Kits can include containers including one or more Env, engineered Env, Prime Env, Boost Env, and/or vaccine adjuvants described herein formulated individually, or in various combinations.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding preparation of components for administration; proper disposal of related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary medical supplies needed to use the kit effectively, such as syringes, ampules, tubing, facemask, an injection cap, sponges, sterile adhesive strips, Chloraprep, gloves, and the like. Variations in contents of any of the kits described herein can be made. The instructions of the kit will direct use of the active ingredients to effectuate a new clinical use described herein.

(viii) Methods of Use. Once formed, the compositions are used to effect sequential immunization strategies to guide the maturation of antibodies against HIV. In particular embodiments, the compositions elicit antibodies that recognize a full length Env protein. In particular embodiments, the compositions find use in the treatment of disease. "Treatment" refers to both therapeutic treatment and prophylactic treatment or preventative measures, wherein the object is to prevent, reduce the occurrence or severity of, or slow down or lessen a targeted pathologic condition or disorder. "Subjects" include those in need of treatment, such as, those with an infection, as well as those prone to have or develop an infection, or those in whom infection is to be prevented, such as those in a high-risk group for exposure to a pathogen.

Thus, in various exemplary embodiments, a subject can be a human subject. Other types of subjects include veterinary animals (dogs, cats, reptiles, birds, etc. and also including animals found within zoos), livestock (horses, cattle, goats, pigs, chickens, etc.), and research animals (monkeys, rats, mice, fish, etc.).

The compositions can be administered prophylactically in subjects who are at risk of developing HIV infection, or who have been exposed to HIV, to prevent, reduce, or delay the development of HIV infection or disease. For example, the compositions can be administered to a subject likely to have been exposed to HIV or to a subject who is at high risk for exposure to HIV.

In particular embodiments, compositions can be administered to a subject in a therapeutically effective amount. A "therapeutically effective amount" is an amount sufficient to produce a desired physiological effect and/or an amount capable of achieving a desired result, particularly for treatment of a disorder or disease condition, including reducing or eliminating one or more symptom of the disorder or disease or prevention or delaying the onset of at least one a disease symptom. Therapeutically effective amounts can provide therapeutic treatments and/or prophylactic treatments.

Particular uses of the compositions include use as prophylactic vaccines. Vaccines increase the immunity of a subject against a particular disease. Therefore, "HIV vaccine" can refer to a treatment that increases the immunity of a subject against HIV. Therefore, in some embodiments, a vaccine may be administered prophylactically, for example to a subject that is immunologically naive (e.g., no prior exposure or experience with HIV). In some embodiments, a vaccine may be administered therapeutically to a subject who has been exposed to HIV. In particular embodiments, the vaccine elicits antibodies that can bind a full length Env. In particular embodiments, a vaccine can be used to ameliorate a symptom associated with AIDS or HIV infection, such as a reduced T cell count.

In particular embodiments, an HIV vaccine is a therapeutically effective composition including one or more Env or engineered Env disclosed herein that induce an immune response in a subject against HIV. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

"Immune response" refers to a response of the immune system to an Env disclosed herein. In various exemplary embodiments, an immune response to an Env can be an innate and/or adaptive response. In some embodiments, an adaptive immune response can be a "primary immune response" which refers to an immune response occurring on the first exposure of a "naive" subject to an engineered Env that binds a gl BCR (e.g. a gl VRC01 BCR). For example, in the case of a primary antibody response, after a lag or latent period of from 3 to 14 days depending on, for example, the composition, dose, and subject, gl antibodies to the engineered prime Env can be produced. Generally, IgM production lasts for several days followed by IgG production and the IgM response can decrease. Antibody production can terminate after several weeks but memory cells can be produced. In some embodiments, an adaptive immune response can be a "secondary immune response", "anamnestic response," or "booster response" which refer to the immune response occurring on a second and subsequent exposure of a subject to a boost Env having an NLGS at position 276 disclosed herein.

In particular embodiments, an immune response against HIV will include antibody production against the gp120 domain of an engineered Env Antibodies that result from the disclosed sequential immunization strategies are induced by prime Env and a boost Env according to the methods disclosed herein. In some embodiments, an antibody can bind to a gp120 domain of an engineered Env. In some embodiments, an elicited antibody binds to gp120 (i.e., an etiologic agent of HIV). Without being bound by theory, in some embodiments, the binding of an antibody can substantially neutralize or inactivate autologous HIV gp120. Thus, antibodies are capable of reducing or eliminating a pathologic effect of HIV. That is, the binding of antibodies to gp120 of HIV may decrease or eliminate HIV infectivity and/or virulence factor activity, including replication, synthesis, and/or toxicity. In particular embodiments, at least a 25% decrease of one of these parameters is required to determine that a dose provides a therapeutically effective amount.

The actual dose amount of prime Env and boost Env administered to a particular subject as well as the timing between prime and boost administration can be determined by a physician, veterinarian, or researcher taking into account parameters such as physical and physiological factors including target, body weight, severity of infection, stage of infection, previous or concurrent therapeutic interventions, idiopathy of the subject, and route of administration.

For administration, therapeutically effective amounts (also referred to herein as doses) can be initially estimated based on results from in vitro assays and/or animal model studies. Exemplary doses include 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240 or 250 μg/kg body mass or mg/kg body mass although higher and/or lower doses can be used. The number of doses that can be administered as a function of time can be from 1, 2, 3, 4 or 5 doses over 1, 2, 3, 4, 5 or 6 weeks but can be increased or decreased depending at least in part on the immune status of a subject.

In particular embodiments, a composition can be administered initially, and thereafter maintained by further administration. For example, a composition can be administered by intravenous injection to bring blood levels to a suitable level. The subject's levels can then be maintained by an oral boost form, although other forms of administration, dependent upon the patient's condition, may be used. In the instance of a vaccine composition, the prime vaccine may be administered as a single dose, followed by one or more booster doses. For example, booster doses may guide the maturation of elicited antibodies to broadly neutralizing antibodies to provide bNAbs protective against multiple clades of HIV.

The engineered Env can be prepared by expressing polynucleotide sequences in vectors or other expression vehicles in compatible prokaryotic or eukaryotic host cells using standard molecular biology methods (e.g., Sambrook et al. 1989, Molecular Cloning a Laboratory Manual, Second Edition, Cold Spring Harbor Laboratory Press, Cold Spring Harbor, N.Y.; incorporated herein by reference).

Exemplary Embodiments. The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(ix) Exemplary Embodiments

1. A method of eliciting antibodies that bind full length glycosylated human immunodeficiency virus (HIV) envelope protein (Env) including administering to a subject:

(i) a prime immunization with an HIV Env that binds germline (gl) B cell receptors (BCR); and (ii) a boost immunization HIV Env with a glycosylated N276 wherein no Env are administered to the subject between the (i) prime immunization and (ii) boost immunization thereby eliciting antibodies that bind full length glycosylated HIV Env.

2. A method of embodiment 1, wherein a prime immunization HIV Env includes the 426c core including the sequence set forth in SEQ ID NO: 56.

3. A method of embodiment 1 or 2, wherein a prime immunization HIV Env includes: (i) mutations at one or more of: N460D; N463D; S278R; G471S; V65C; and S115C; (ii) removal of the V1 loop and the V2 loop; (iii) replacement of the V3 loop with a flexible linker; and (iv) an N-terminal truncation; wherein the HIV Env does not have a mutation at position 276.

4. A method of any of embodiments 1-3, wherein a prime immunization HIV Env includes mutations at N460D; N463D; S278R; G471S; V65C; and S115C.

5. A method of embodiments 3 or 4, wherein the N-terminal truncation is before residue 49, 48, 47, 46, 45, 44, 43, 42, 41, 40 or 39.

6. A method of embodiments 3 or 4, wherein the N-terminal truncation is before residue 44.

7. A method of any of embodiments 1-6, wherein a prime immunization HIV Env further includes a C-terminal truncation after residue 499, 498, 497, 496, 495, 494, 493, 492, 491, 490 or 389.

8. A method of embodiment 7, wherein the C-terminal truncation is after residue 494.

9. A method of any of embodiments 3-8, wherein the flexible linker includes a sequence set forth in a sequence selected from one or more of SEQ ID NOs: 57-68.

10. A method of any of embodiments 3-9, wherein the V3 loop includes residues 296-331.

11. A method of any of embodiments 3-10, wherein removal of the V1 loop includes removal of residues 131-152 and/or removal of the V2 loop includes removal of residues 161-196.

12. A method of any of embodiments 3-11, wherein removal of the V1 loop and removal of the V2 loop includes removal of residues 123-196.

13. A method of any of embodiments 1-12, wherein a prime immunization HIV Env retains glycosylation at N463 but lacks glycosylation at N276 and N460.

14. A method of any of embodiments 1-13, wherein a prime immunization HIV Env retains glycosylation at position 463.

15. A method of any of embodiments 1-14, wherein a prime immunization HIV Env includes a sequence set forth in a sequence selected from one or more of SEQ ID NOs: 69-112.

16. A method of any of embodiments 1-15, wherein a boost immunization HIV Env is selected from sequences including one or more of H×B2 core+3 NLGS, and the 45_01 dH5 core+3 NLGS.

17. A method of any of embodiments 1-16, wherein a boost immunization HIV Env includes the sequence set forth in SEQ ID NO: 183 and/or 119.

18. A method of any of embodiments 1-17, wherein a boost immunization HIV Env includes a sequence set forth in a sequence selected from one or more of SEQ ID NO. 69-SEQ ID NO. 79, SEQ ID NO. 82, SEQ ID NO. 107, SEQ ID NO. 113-118, and SEQ ID NO: 121-SEQ ID NO. 132.

19. A method of any of embodiments 1-18, wherein a prime immunization HIV Env and/or a boost immunization HIV Env are multimerized.

20. A method of any of embodiments 1-18, wherein a prime immunization HIV Env and a boost immunization HIV Env are multimerized.

21. A method of any of embodiments 1-18, wherein a prime immunization HIV Env and/or a boost immunization HIV Env are multimerized with ferritin.

22. A method of any of embodiments 1-18, wherein a prime immunization HIV Env and a boost immunization HIV Env are multimerized with ferritin.

23. A method of embodiments 21 or 22, wherein the ferritin includes a sequence set forth in a sequence selected from one or more of SEQ ID NOs: 51, or 133-136.

24. A method of any of embodiments 1-18, wherein a prime immunization HIV Env and/or a boost immunization HIV Env are multimerized with C4b.

25. A method of any of embodiments 1-18, wherein a prime immunization HIV Env and a boost immunization HIV Env are multimerized with C4b.

26. A method of embodiments 24 or 25, wherein the C4b includes a sequence set forth in a sequence selected from one or more of SEQ ID NOs: 50, or 138-170.

27. A method of any of embodiments 1-18, wherein a prime immunization HIV Env and/or a boost immunization HIV Env are multimerized into 5-mers, 6-mers, or 7-mers.

28. A method of any of embodiments 1-18, wherein a prime immunization HIV Env and a boost immunization HIV Env are multimerized into heptamers.

29. A method of embodiments 27 or 28, wherein the multimerization domain includes a sequence set forth in a sequence selected from one or more of SEQ ID NOs: 171-173.

30. A method of any of embodiments 1-18, wherein a prime immunization HIV Env and/or a boost immunization HIV Env are multimerized into 24-mers.

31. A method of any of embodiments 1-18, wherein a prime immunization HIV Env and a boost immunization HIV Env are multimerized into 24-mers.

32. A method of any of embodiments 1-31, wherein the prime immunization HIV Env and a boost immunization HIV Env are heterologous.

33. A method of any of embodiments 1-31, wherein the prime immunization HIV Env and a boost immunization HIV Env are autologous.

34. A method of any of embodiments 1-32, wherein a prime immunization HIV Env includes a 426c core+linker+ferritin construct.

35. A method of embodiment 34, wherein a prime immunization HIV Env includes the sequence set forth in SEQ ID NO: 137.

36. A method of any of embodiments 1-32, wherein a prime immunization HIV Env includes a 426c core+linker+C4b construct.

37. A method of embodiment 36, wherein a prime immunization HIV Env includes SEQ ID NO: 174 or 274.

38. A method of any of embodiments 1-37, wherein a boost immunization HIV Env includes a H×B2 core with all N276, N460, and N463 glycosylation.

39. A method of any of embodiments 1-38, wherein a prime immunization HIV Env includes a sequence set forth in a sequence selected from SEQ ID NO: 137, 174, or 274 and a boost immunization HIV Env includes a heterologous H×B2 core with N276 glycosylation.

40. A method of any of embodiments 1-39, wherein a prime immunization HIV Env includes a sequence set forth in a sequence selected from SEQ ID NO: 137, 174, or 274 and a boost immunization HIV Env includes a heterologous H×B2 core with N276, N460, and N463 glycosylation.

41. A method of any of embodiments 34-40, wherein a prime immunization HIV Env and a boost immunization HIV Env are 5-mers, 6-mers, or 7-mers.

42. A method of any of embodiments 1-41, wherein the gl BCR are gl VRC01 BCR.

43. A method of any of embodiments 1-42, further including administering a second boost immunization HIV Env.

44. A method of embodiment 43, wherein a second boost immunization HIV Env includes a wild-type HIV Env trimer.

45. A method of embodiment 43 or 44, wherein a second boost immunization HIV Env includes an HIV Env trimer with N276, N460, and N463 glycosylation.

46. A method of any of embodiments 43-45, wherein a second boost immunization HIV Env is autologous to a prime immunization HIV Env.

47. A method of any of embodiments 43-46, wherein a second boost immunization HIV Env is autologous to a boost immunization HIV Env.

48. A method of any of embodiments 43-47, wherein a second boost immunization HIV Env is heterologous to a prime immunization HIV Env.

49. A method of any of embodiments 43-48, wherein a second boost immunization HIV Env is heterologous to a boost immunization HIV Env.

50. A method of any of embodiments 43-49, wherein a second boost immunization HIV Env includes one or more of 426c WT SOSIP, BG505 WT SOSIP, and 426c dGly V5 SOSIP.

51. A method of any of embodiments 1-50, further including administering an adjuvant to the subject with the administration of the (i) prime immunization and/or (ii) boost immunization.

52. A method of embodiment 51, wherein the adjuvant includes one or more of PolyIC, Adjuplex, Alum, Ribi, or GLA-LSQ.

53. A kit including (i) a prime immunization HIV Env that binds germline (gl) B cell receptors (BCR); and (ii) a boost immunization HIV Env with a glycosylated N276; and instructions that no Env are to be administered to a subject between the (i) prime immunization with a prime immunization HIV Env and (ii) boost immunization with a boost immunization HIV Env.

54. A kit of embodiment 53, wherein a prime immunization HIV Env includes the 426c core with the sequence set forth in SEQ ID NO: 56.

55. A kit of embodiment 53 or 54, wherein a prime immunization HIV Env includes: (i) mutations at one or more of: N460D; N463D; S278R; G471S; V65C; and S115C; (ii) removal of the V1 loop and the V2 loop; (iii) replacement of the V3 loop with a flexible linker; and (iv) an N-terminal truncation; wherein the HIV Env does not have a mutation at position 276.

56. A kit of any of embodiments 53-55, wherein a prime immunization HIV Env includes mutations at N460D; N463D; S278R; G471S; V65C; and S115C.

57. A kit of embodiment 55 or 56, wherein the N-terminal truncation is before residue 49, 48, 47, 46, 45, 44, 43, 42, 41, 40 or 39.

58. A kit of any of embodiments 55-57, wherein the N-terminal truncation is before residue 44.

59. A kit of any of embodiments 53-58, wherein a prime immunization HIV Env further includes a C-terminal truncation after residue 499, 498, 497, 496, 495, 494, 493, 492, 491, 490 or 389.

60. A kit of embodiment 59, wherein the C-terminal truncation is after residue 494.

61. A kit of any of embodiments 55-60, wherein the flexible linker includes a sequence set forth in a sequence selected from one or more of SEQ ID NOs: 57-68.

62. A kit of any of embodiments 55-61, wherein the V3 loop includes residues 296-331.

63. A kit of any of embodiments 55-62, wherein removal of the V1 loop includes removal of residues 131-152 and/or removal of the V2 loop includes removal of residues 161-196.

64. A kit of any of embodiments 55-63, wherein removal of the V1 loop and removal of the V2 loop includes removal of residues 123-196.

65. A kit of any of embodiments 53-64, wherein a prime immunization HIV Env retains glycosylation at N463 but lacks glycosylation at N276 and N460.

66. A kit of any of embodiments 53-65, wherein a prime immunization HIV Env retains glycosylation at position 463.

67. A kit of any of embodiments 53-66, wherein a prime immunization HIV Env includes a sequence set forth in a sequence selected from one or more of SEQ ID NOs: 56, or 69-112. 68. A kit of any of embodiments 53-67, wherein a boost immunization HIV Env includes one or more of the H×B2 core+3 NLGS, and the 45_01 dH5 core+3 NLGS.

69. A kit of any of embodiments 53-68, wherein a boost immunization HIV Env includes SEQ ID NO.183.

70. A kit of any of embodiments 53-69, wherein the boost immunization HIV Env includes a sequence set forth in a sequence selected from one or more of SEQ ID NO. 69-SEQ ID NO. 79, SEQ ID NO. 82, SEQ ID NO. 107, SEQ ID NO. 113-118, and SEQ ID NO: 121-SEQ ID NO. 132.

71. A kit of any of embodiments 53-70, wherein a prime immunization HIV Env and/or a boost immunization HIV Env are multimerized.

72. A kit of any of embodiments 53-71, wherein a prime immunization HIV Env and a boost immunization HIV Env are multimerized.

73. A kit of any of embodiments 53-72, wherein a prime immunization HIV Env and/or a boost immunization HIV Env are multimerized with ferritin.

74. A kit of any of embodiments 53-73, wherein a prime immunization HIV Env and a boost immunization HIV Env are multimerized with ferritin.

75. A kit of embodiment 73 or 74, wherein the ferritin includes a sequence set forth in a sequence selected from one or more of SEQ ID NOs: 51, or 133-136.

76. A kit of any of embodiments 53-75, wherein a prime immunization HIV Env and/or a boost immunization HIV Env are multimerized with C4b.

77. A kit of any of embodiments 53-76, wherein a prime immunization HIV Env and a boost immunization HIV Env are multimerized with C4b.

78. A kit of embodiment 76 or 77, wherein the C4b includes a sequence set forth in a sequence selected from one or more of SEQ ID NOs: 50, or 138-170.

79. A kit of any of embodiments 53-78, wherein a prime immunization HIV Env and/or a boost immunization HIV Env are multimerized into 5-mers, 6-mers, or 7-mers.

80. A kit of any of embodiments 53-79, wherein a prime immunization HIV Env and a boost immunization HIV Env are multimerized into heptamers.

81. A kit of embodiment 79 or 80, wherein the multimerization domain includes a sequence set forth in a sequence selected from one or more of SEQ ID NOs: 171-173.

82. A kit of any of embodiments 53-81, wherein a prime immunization HIV Env and/or a boost immunization HIV Env are multimerized into 24-mers.

83. A kit of any of embodiments 53-82, wherein a prime immunization HIV Env and a boost immunization HIV Env are multimerized into 24-mers.

84. A kit of any of embodiments 53-83, wherein a prime immunization HIV Env and a boost immunization HIV Env are heterologous.

85. A kit of any of embodiments 53-84, wherein a prime immunization HIV Env and a boost immunization HIV Env are autologous.

86. A kit of any of embodiments 53-85, wherein a prime immunization HIV Env includes a 426c core+linker+ferritin construct.

87. A kit of any of embodiments 53-86, wherein a prime immunization HIV Env includes the sequence set forth in SEQ ID NO: 137.

88. A kit of any of embodiments 53-87, wherein a prime immunization HIV Env includes a 426c core+linker+C4b construct.

89. A kit of any of embodiments 53-88, wherein a prime immunization HIV Env includes the sequence set forth in SEQ ID NO: 174 or 274.

90. A kit of any of embodiments 53-89, wherein a boost immunization HIV Env includes a H×B2 core with N276, N460, and N463 glycosylation.

91. A kit of any of embodiments 53-90, wherein a prime immunization HIV Env includes a sequence set forth in a sequence selected from SEQ ID NO: 137, 174, or 274 and a boost immunization HIV Env includes a heterologous H×B2 core with N276 glycosylation.

92. A kit of any of embodiments 53-91, wherein a prime immunization HIV Env includes a sequence set forth in a sequence selected from SEQ ID NO: 137, 174, or 274 and a boost immunization HIV Env includes a heterologous H×B2 core with N276, N460, and N463 glycosylation.

93. A kit of any of any of embodiments 53-92, wherein a prime immunization HIV Env and a boost immunization HIV Env are 5-mers, 6-mers, or 7-mers.

94. A kit of any of embodiments 53-93, further including a second boost immunization HIV Env. 95. A kit of embodiment 94, wherein a second boost immunization HIV Env includes a wild-type HIV Env trimer.

96. A kit of embodiment 94 or 95, wherein a second boost immunization HIV Env includes an HIV Env trimer with N276, N460, and N463 glycosylation.

97. A kit of any of embodiments 94-96, wherein a second boost immunization HIV Env is autologous to a prime immunization HIV Env.

98. A kit of any of embodiments 94-97, wherein a second boost immunization HIV Env is autologous to a boost immunization HIV Env.

99. A kit of any of embodiments 94-98, wherein a second boost immunization HIV Env is heterologous to a prime immunization HIV Env.

100. A kit of any of embodiments 94-99, wherein a second boost immunization HIV Env is heterologous to a boost immunization HIV Env.

101. A kit of any of embodiments 94-100, wherein a second boost immunization HIV Env is selected from one or more of 426c WT SOSIP, BG505 WT SOSIP, and 426c dGly V5 SOSIP.

102. A kit of any of embodiments 53-101, further including an adjuvant.

103. A kit of embodiment 102, wherein the adjuvant includes one or more of PolyIC, Adjuplex, Alum, Ribi, or GLA-LSQ.

104. Any of the preceding embodiments wherein the 1$^{st}$ boost immunization following the prime immunization includes the sequence as set forth in SEQ ID NO: 119.

(x) Experimental Examples. Overcoming Steric Restrictions of VRC01 HIV-1 Neutralizing Antibodies through Immunization. VRC01-class antibodies are potent and broad HIV-1 neutralizing antibodies (bnAbs) that offer protection from experimental animal Simian (S)HIV infection in macaques and experimental HIV-1 infection in humanized mice (Balazs et al., 2014. Nature Medicine. 20, 296-300; Gautam et al., 2016. Nature 533, 105-109; Pegu et al., 2014. Science Translational Medicine 6, 243ra88; Shingai et al., 2014. Journal of Experimental Medicine. 211, 2061-2074). They have been isolated from several HIV-1-infected subjects and share key genetic origins: their heavy chain (HC) V genes are derived from the VH1-2*02 allele and are paired with light chains (LC) expressing rare, 5 amino acid long CDRL3 containing a hydrophobic residue at position 91 and a Glu96 (Scheid et al., 2011. Science 333, 1633-1637; Wu et al., 2010. Science 329, 856-861; Wu et al., 2011. Science 333, 1593-1602; Zhou et al., 2013. Immunity 39, 245-258; Zhou et al., 2015, Cell 161, 1280-1292). The VRC01-class bnAbs are extensively somatically hypermutated (30% amino acid difference from germline) and can be 50% divergent in amino acid sequence from one another (Scheid et al., 2011. Science 333, 1633-1637; Wu et al., 2010. Science 329, 856-861; Wu et al., 2011. Science 333, 1593-1602; Zhou et al., 2010. Science 329, 811-817; Zhou et al., 2015, Cell 161, 1280-1292). Despite this marked diversity, their CDR domains adopt similar overall structures and recognize the CD4-binding site (CD4-BS) of Env in a manner similar to that of CD4 (Zhou et al., 2010. Science 329, 811-817; Zhou et al., 2015, Cell 161, 1280-1292). Thus, despite their similar genetic origins, during chronic infection with different HIV-1 viruses, VRC01-class antibodies mature along different pathways but ultimately adopt similar structures that are associated with their broad neutralizing activity. The ‘structural convergent evolution’ observed during natural HIV-1 infection suggests that more than one evolutionary pathway will be available to develop VRC01-class bNAbs by immunization.

Although natural viral Env variants associated with the development of bnAbs against the Env apex region (Doria-Rose et al., 2014. Nature 209, 55-62) and of certain classes of anti-CD4-BS bnAbs have been identified (Bonsignori et al., 2016. Cell 165, 449-463; Liao et al., 2013. Nature 469-476), such natural Envs have yet to be identified for VRC01-class antibodies. Also, the inferred germline forms of VRC01-class antibodies (commonly referred to as glVRC01 Abs), do not display detectable reactivity to diverse recombinant Env-derived soluble proteins (Hoot et al., 2013. PLOS Pathogen 9, e1003106; Jardine et al., 2013. Science 340, 711-716; McGuire et al., 2013. Journal of Experimental Medicine 210, 655-663). In recent years, there have been reports on the design of ‘germline VRC01-targeting’ recombinant Env-derived proteins capable of binding glVRC01-class Abs (Jardine et al., 2013. Science 340, 711-716; Jardine et al., 2015. Science 351, 1458-1463; McGuire et al., 2013. Journal of Experimental Medicine 210, 655-663; McGuire et al., 2016. Nature Communications 7, 10618; Medina-Ramirez et al., 2017. Journal of Experimental Medicine 214, 2573-2590). A key feature of such immunogens is the absence of the conserved N linked glycosylation site (NLGS) at position 276 within Loop D of the gp 120 Env subunit, as the N276-associated glycans present a major barrier to glVRC01 Ab-binding, through steric obstruction of the germline-encoded CDRL1s (Borst et al., 2018. Elife. 7; McGuire et al., 2013. Journal of Experimental Medicine 210, 655-663; Zhou et al., 2013. Immunity 39, 245-258). Mature VRC01 bnAbs accommodate this glycan by either incorporating glycine residues in their CDRL1 domains or by shortening them during affinity maturation (Zhou et al., 2013. Immunity 39, 245-258).

Although VRC01 germline-targeting immunogens activate B cells engineered to express glVRC01-class BCRs in vitro and in vivo (Jardine et al., 2013. Science 340, 711-716; Jardine et al., 2015. Science 349, 156-161; McGuire et al., 2013. Journal of Experimental Medicine 210, 655-663; McGuire et al., 2014. Science 346, 1380-1283, McGuire et al., 2016. Nature Communications 7, 10618; Medina-Ramírez et al., 2017. Journal of Experimental Medicine 214, 2573-2590), these cells undergo limited somatic mutation and the secreted antibodies fail to bind in the presence of N276-associated glycans on wild type (WT) Envs (Dosenovic et al., 2015. Cell 161, 1505-1515; Jardine et al., 2015. Science 349, 156-161; McGuire et al., 2016. Nature Communications 7, 10618). Efforts to guide the maturation of VRC01-like antibody responses elicited by germline-targeting immunogens through subsequent immunizations with heterologous Env-derived proteins also lacking the N276 glycans, led to increased somatic mutations, in both the VH and VL antibody genes, but the antibodies still lack the ability to efficiently bypass the obstacle presented by the N276-associated glycans (Briney et al., 2016. Cell 166, 1459-1470.e11; Tian et al., 2016. Cell 166, 1471-1484.e18).

Herein, a two-step immunization scheme is reported. This two-step immunization scheme begins with a prime immunization with the VRC01 germline-targeting prime immunogen, 426c Core, that lacks the N276 NLGS, followed by a boost immunization with a heterologous Env-derived immunogen, harboring the 276 NLGS. The outcome of this immunization scheme was the production of VRC01-like antibodies capable of accommodating the steric block imposed by the glycans present at N276 and neutralizing the autologous, tier 2 426c virus.

Results. The 426c Core germline-targeting immunogen elicits potent plasma antibody responses against the VRC01 epitope in knock-in mice. There have been previous reports on the design of a recombinant protein derived from the inner and outer gp120 domains of the clade C Env 426c, lacking the variable domains 1, 2 and 3 as well as three NLGS at positions N276 (Loop D) and N460 and N463 (V5). That protein (TM4ΔV1-3, herein referred to as '426c Core' for simplicity) binds several of the known glVRC01-class antibodies (McGuire et al., 2016. Nature Communications 7, 10618). Here, two nanoparticle forms of the 426c Core were employed as immunogens: a 5-7-meric form (426c Core C4b) (Hofmeyer et al., 2013. Journal of Molecular Biology 425, 1302-1317; McGuire et al., 2016. Nature Communications, 7, 10618; Ogun et al., 2008. Immunity 76, 3817-3823) and a Ferritin-based 24-meric form (426c Core Fer) (Kanekiyo et al., 2013. Nature 499, 102-106; McGuire et al., 2016. Nature Communications, 7, 10618). One additional germline VRC01-targeting immunogen was investigated for its ability to engage B cells expressing glVRC01 BCRs in vivo: the 426c DS-SOSIP D3 (Borst et al., 2018. Elife 7; Joyce et al., 2017. Cell Reports 21, 2992-3002). It is derived from the clade C 426c virus (like the 426c Core) and was modified by eliminating the above-mentioned three NLGSs. An immunization was also performed with the non-germline targeting unmodified 426c WT gp 120 as a control.

Immunizations were performed in a knock-in mouse that is heterozygous for the glVRC01 HC whereas the LCs remain the endogenous mouse LCs (mLCs) (Jardine et al., 2015. Science 349, 156-161). 80% of naïve B cells express the glVRC01 HC and 0.1% of mLCs express 5 AA long CDRL3s. Thus, the overall estimated frequency of naïve B cells expressing potential glVRC01 BCRs in this mouse model is 0.08% (compared to 0.01% in humans (Arnaout et al., 2011. PLOS ONE 6, e22365; DeKosky et al., 2015. Nature Medicine 21, 86-91; Jardine et al., 2015. Science 349, 156-161)). The elicitation of VRC01-class bnAbs in this model requires overcoming at least two major obstacles: first, the germline-targeting immunogen must select for the B cells expressing extremely rare mLCs with a 5AA CDRL3 paired with the glVRC01 HC and second, the immunization regimen must lead to the accumulation of mutations that will allow the maturing B cells to bypass the obstacles presented by the N276 glycans on full length Envs.

Figure 4A:
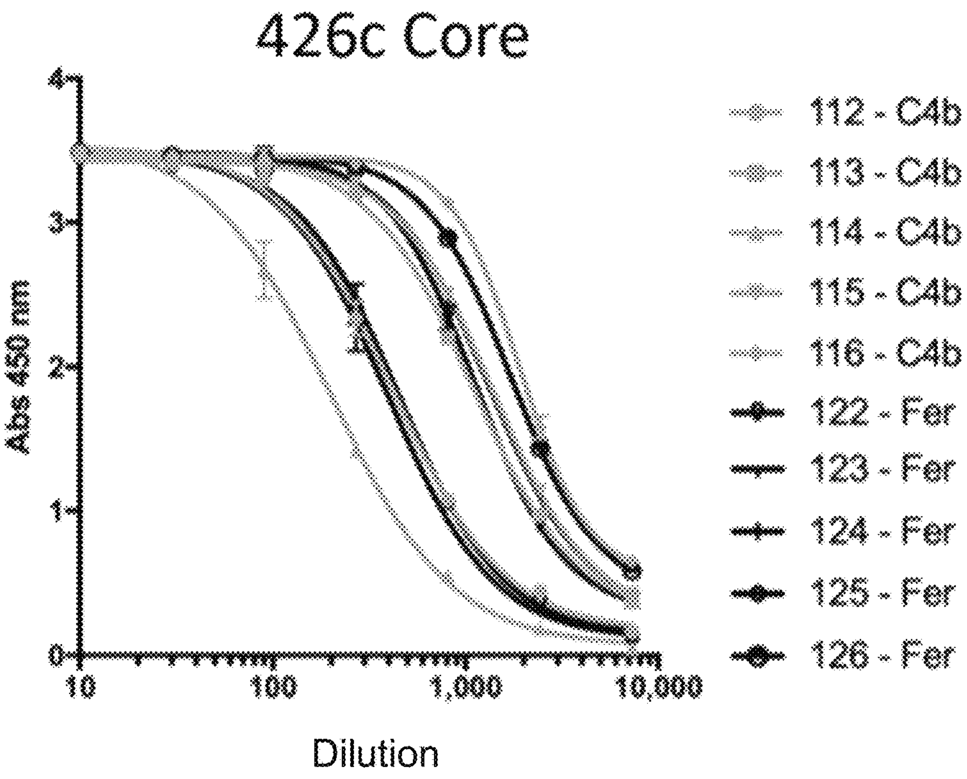
FIGS. 4A-4I. 426c Core elicited antibody and B cell response. Plasma from representative animals immunized with 426c Core C4b (gray) or 426c Core Fer (black) were tested for binding against (4A) 426c Core and its (B) CD4-BS KO form. (4B) Summarizes the data from one experiment with 10 animals in each group. A paired t-test was used to determine statistical significance between the mean EC50 titers against the 426c Core vs those against its CD4-BS KO. (4C) Summary of the animal frequencies per group of 426c Core immunized animals that developed anti-eOD-GT8 plasma antibody responses (OD 450 nm of ≥0.1 at 1:10 dilution; additional information is provided in FIG. 5A). The nanoparticle form and the adjuvant used is indicated. The number of animals that developed anti-eOD-GT8 responses out of the total immunized for each group is indicated within each bar. (4D-4G) Pie charts indicate heavy and light chain sequences from individually sorted B cells from immunized (3 independent experiments) and non-immunized animals (one experiment). The number of sequences analyzed is shown in the middle of each pie chart and the percentages of heavy- or light-chains with the indicated features are shown. (4D) Heavy chain sequences from naïve and immunized animals. (4E) Amino acid length of the CDRL3 domains in the sequences from the naïve and immunized animals. 5 amino acid long CDRL3s are shown in light gray and labeled. (4F) V-gene usage of the light chains from the sequences isolated from naïve and immunized animals. The 8-30*01 V-gene is shown in dark gray and labeled. (4G) Presence or absence of Glu96LC within the light chain sequences with 5 amino acid long CDRL3 domains. MAbs with VRC01 characteristics were generated from paired VH/VL sequences from class-switched B cells isolated following the prime immunization (indicated by 'P') with the 426c Core (4H). MAb binding to monomeric 426c Core and to monomeric 426c Core CD4-BS 30 KO. (4I) MAb binding to monomeric eOD-GT8 and to monomeric eOD-GT8 KO.
Figure 4B:
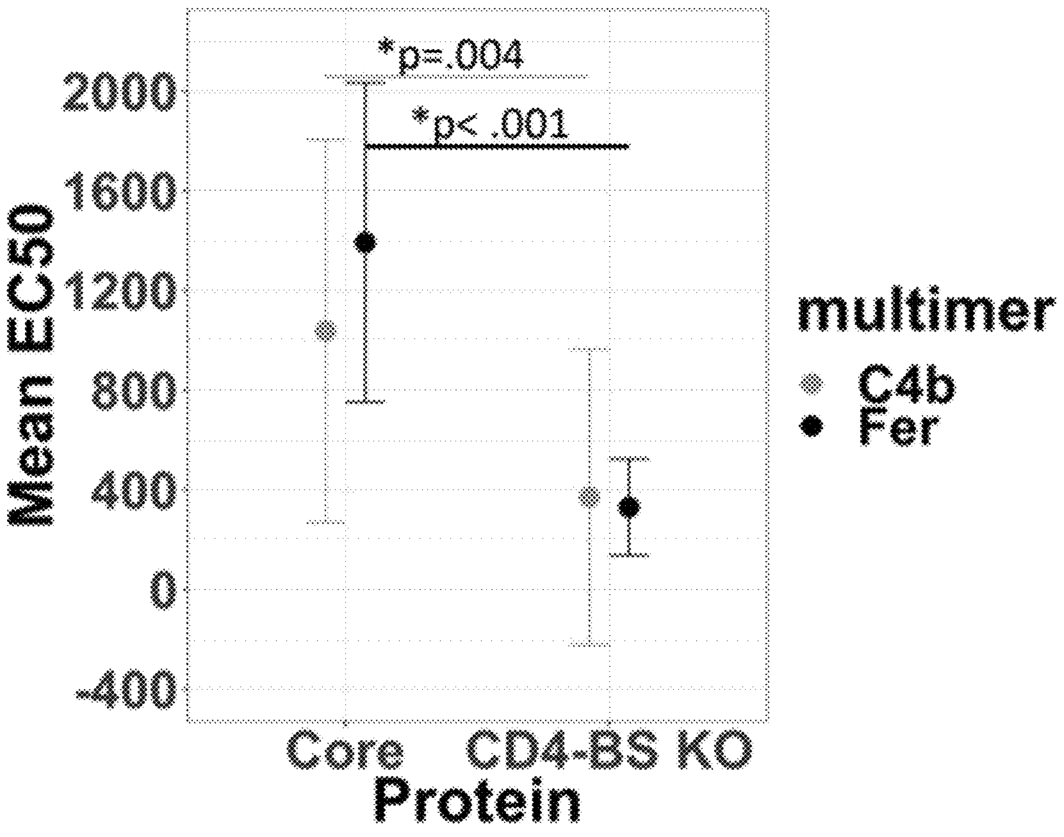
Figure 4C:
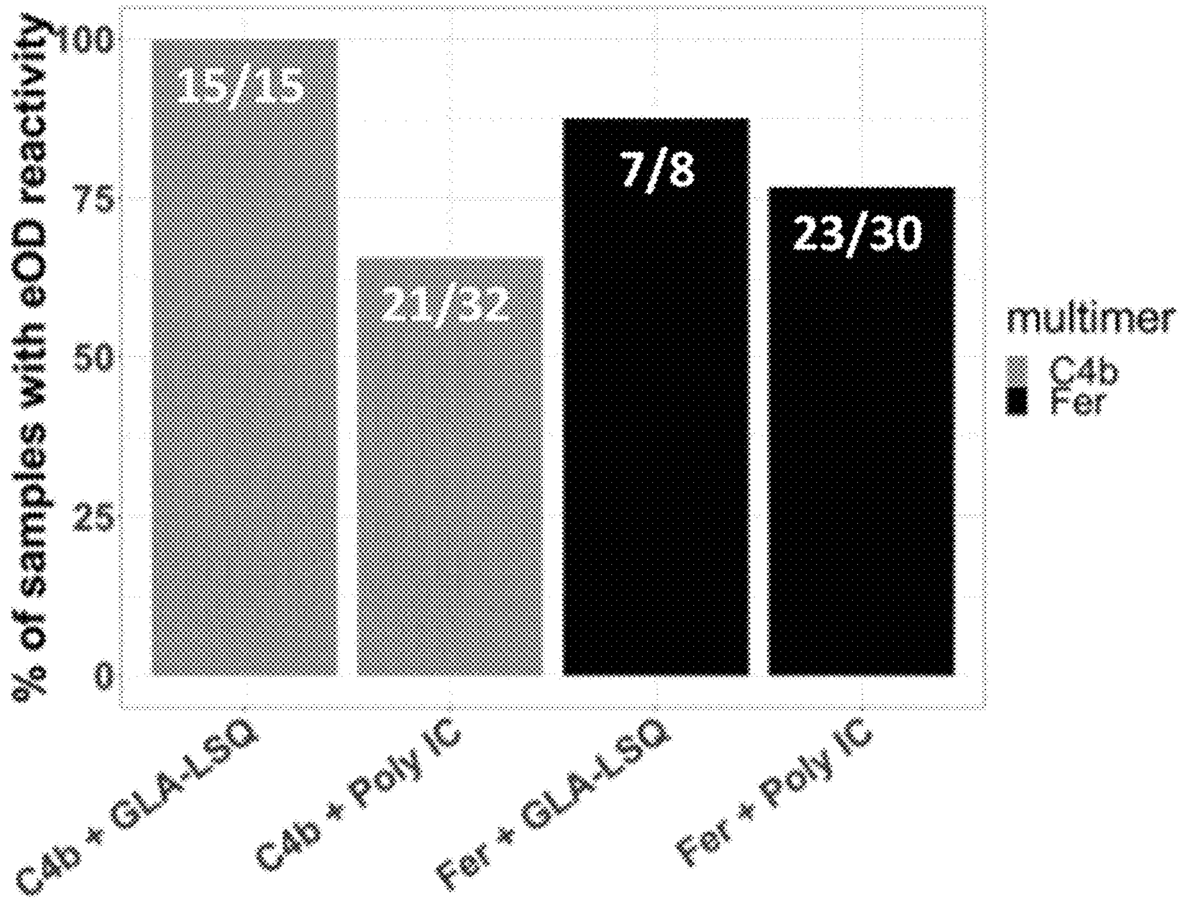
Figure 5A:
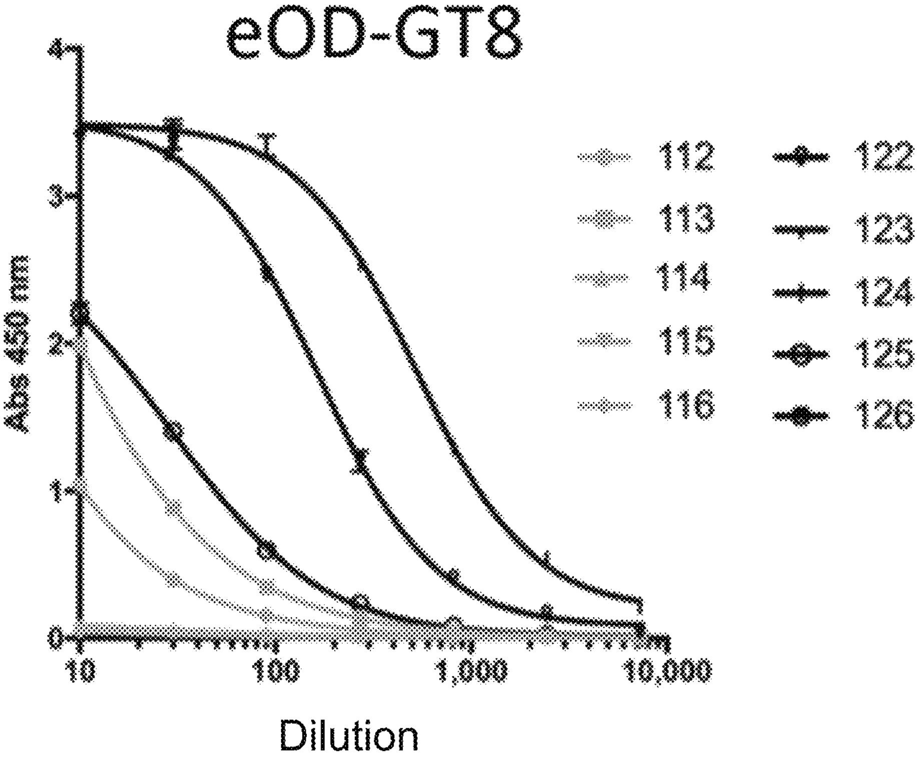
FIGS. 5A-5D. Plasma antibody responses elicited by the 426c Core, 426c WT gp 120 and 426c Core DS-SOSIP immunogens. Binding curves of plasma antibodies to eOD-GT8 (5A) and eOD-GT8 KO (5B) from the same animals shown in FIG. 4A, immunized with 426c Core Ferritin- or C4b-based nanoparticle forms. (5C) Plasma antibodies from four animals (13-16) immunized with the 426c DS-SOSIP D3 were tested for binding to the 426c Core, 426c Core KO, or eOD-GT8. (5D) Plasma antibodies from three animals (9-11) immunized with 426c WT gp120 (C4b nanoparticle form) were tested for binding to 426c WT gp120, eOD-GT8 and 426c Core.
Figure 5B:
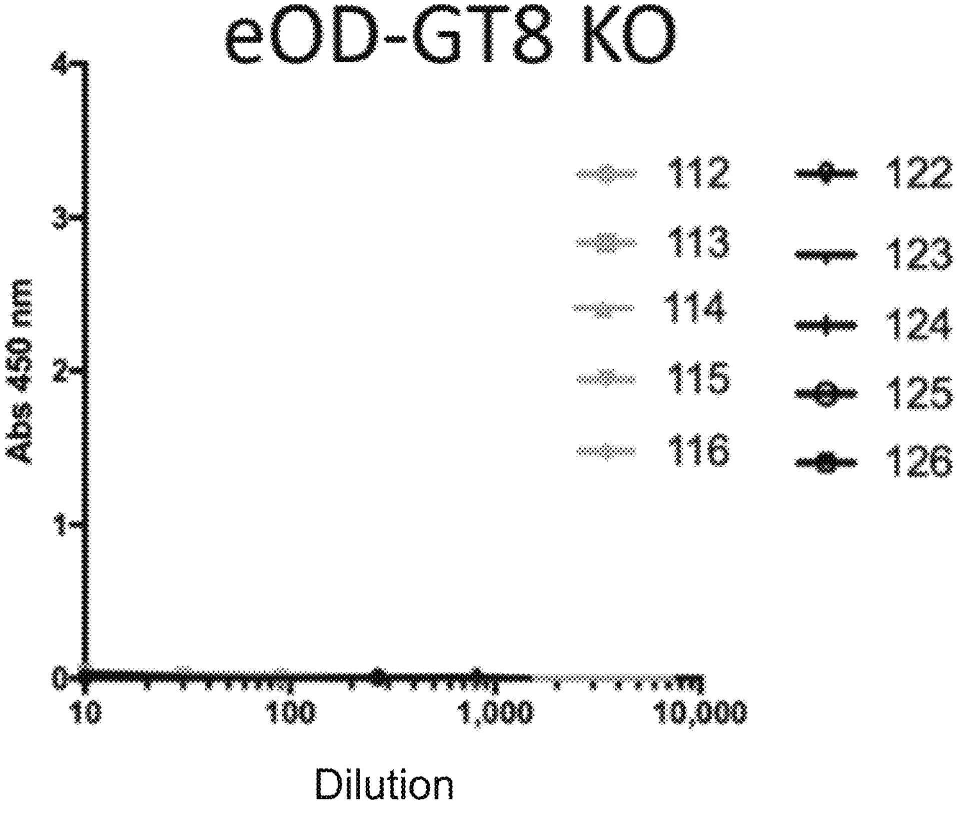
Figure 5C:
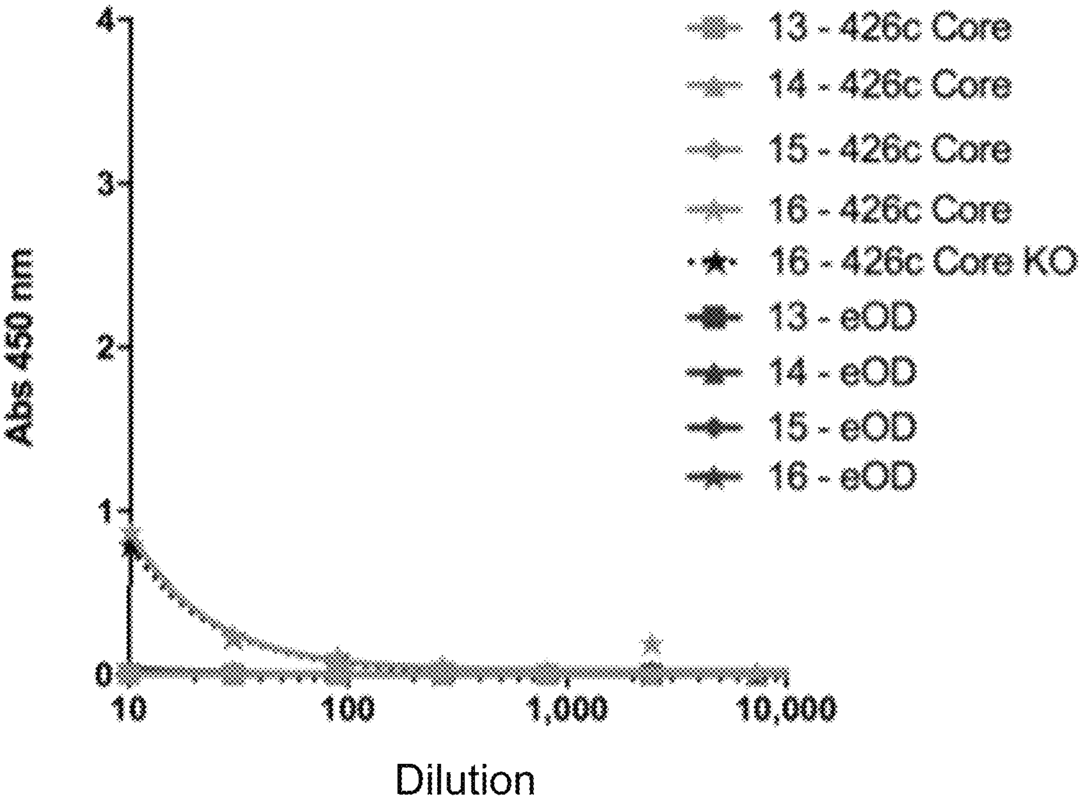
Figure 5D:
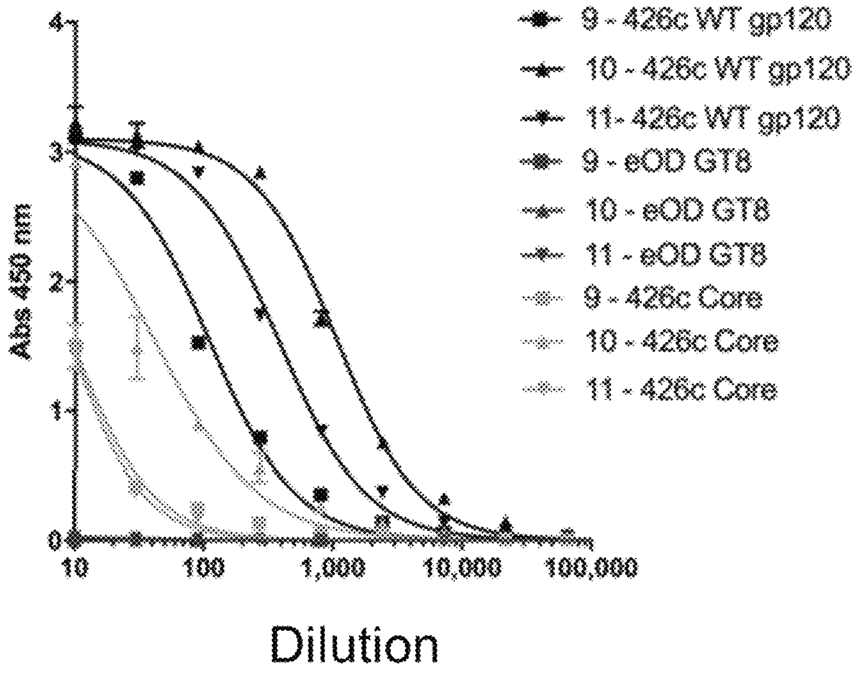
Figure 6A:
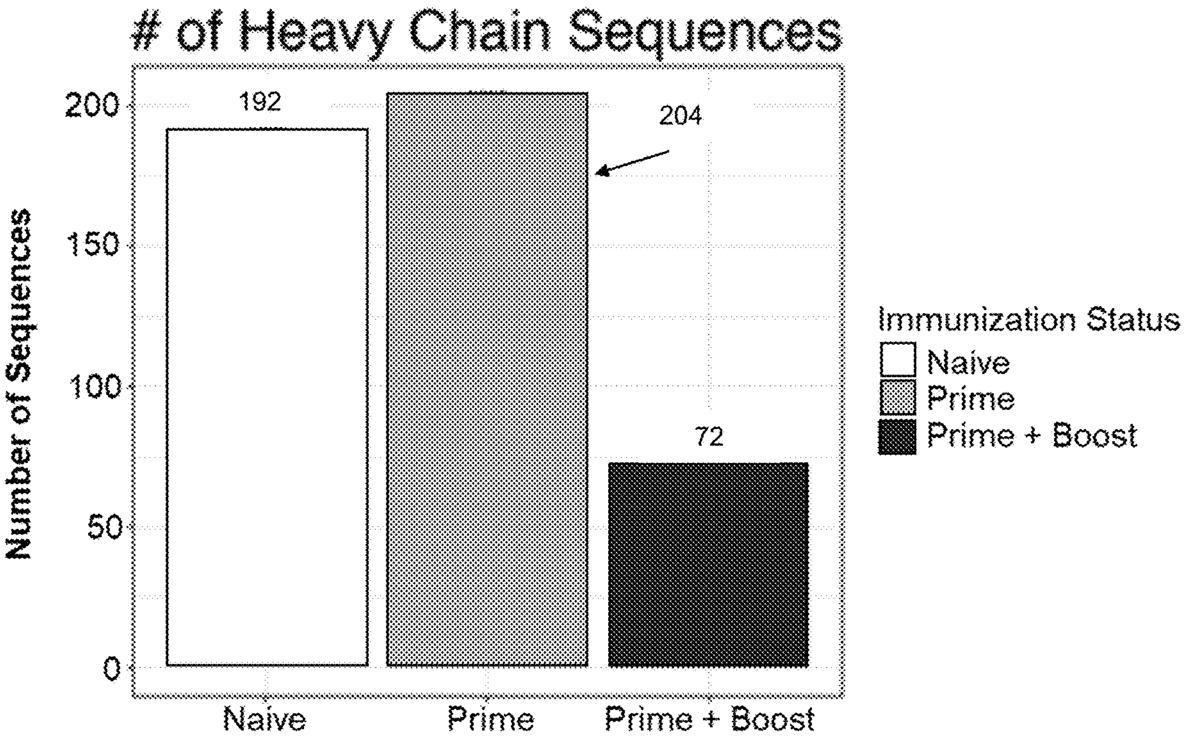
FIGS. 6A-6F. Characteristics of the heavy and light antibody chain sequences from unimmunized and immunized animals. B cells were isolated from unimmunized (naïve B cells) and from immunized animals (following the prime and following the boost immunization) as discussed in detail in the Experimental Examples section (section x). In the case of the unimmunized animals, spleens and lymph nodes (LNs) from three different animals were pooled and the B cells were then single-cell sorted. In the case of immunized animals, class-switched B cells were single cell sorted. The data following the prime are from three independent sorts and the data following the boost (prime+boost) are from two independent experiments. Data from animals immunized with C4b- or Ferritin-based nanoparticles and Poly (I:C) or GLA-LSQ are combined. (6A) The total number of heavy chain sequences and the (6B) V-gene usage of the heavy chain sequences. (6C) The total number of light chain sequences and the (6D) light chain V-usage. (6E) Frequencies of CDRL3 domains with the indicated lengths (the number of sequences with a particular CDRL3 length is indicated). (6F) frequency of five amino acid long CDRL domains with and without a Glu at position 96. The numbers of sequences with or without Glu 96 are also indicated.
Figure 6B:
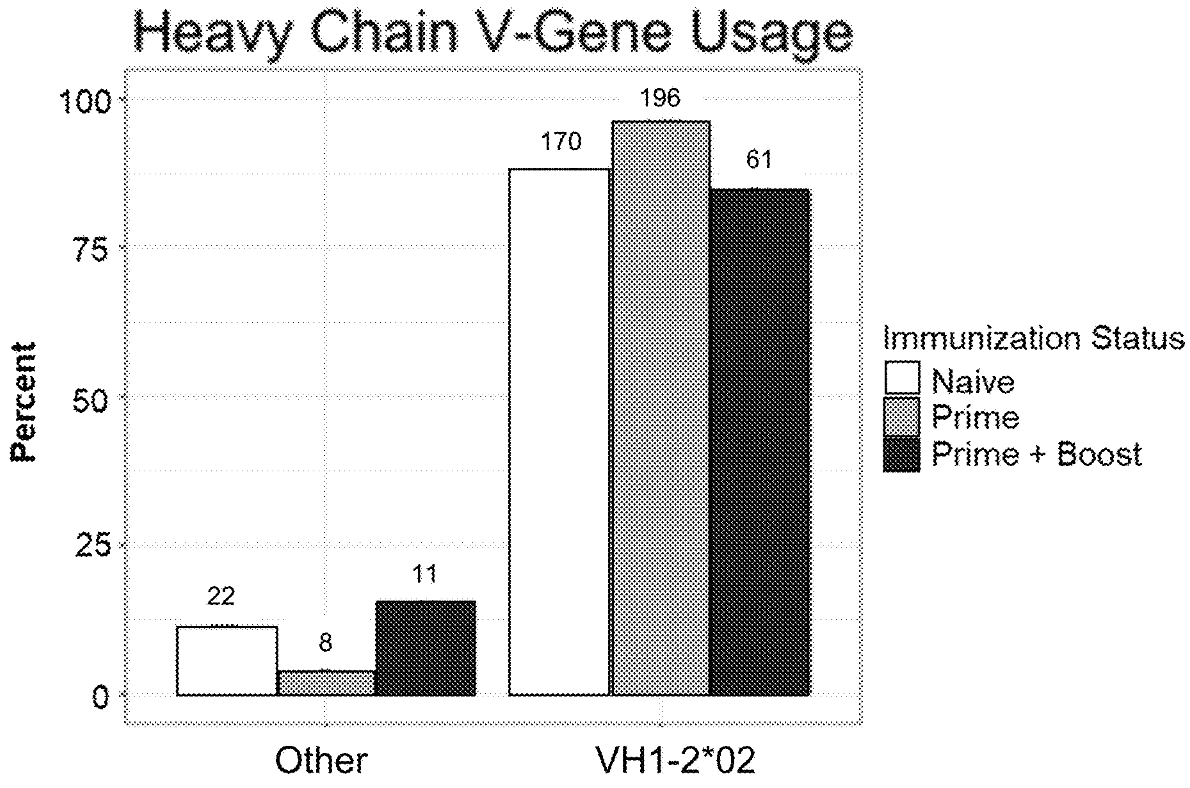
Figure 6C:
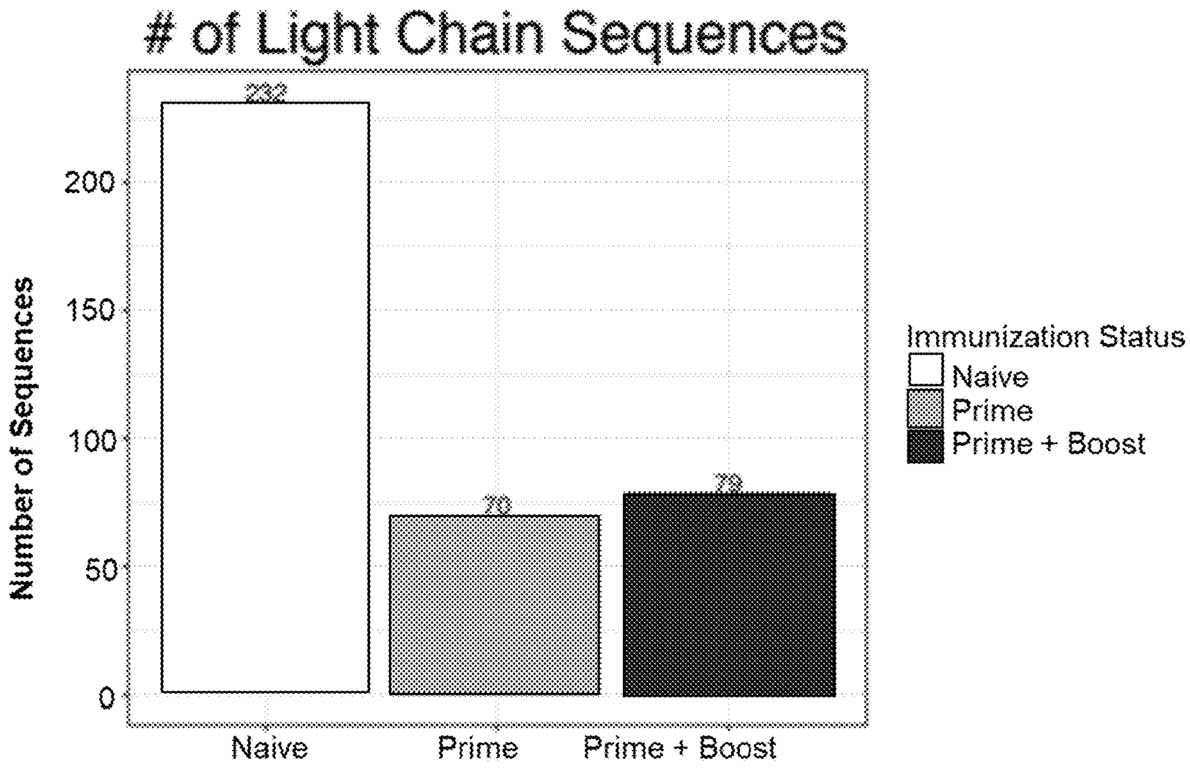
Figure 6D:
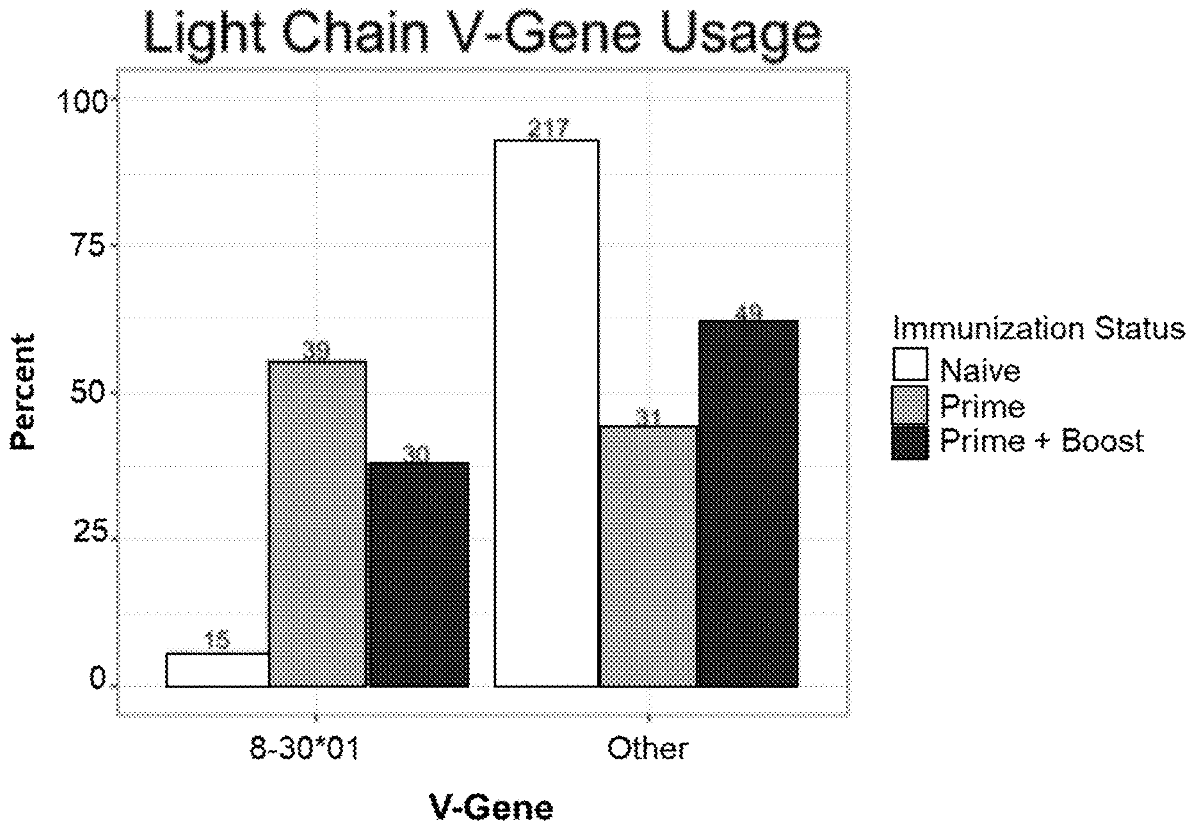
Figure 6E:
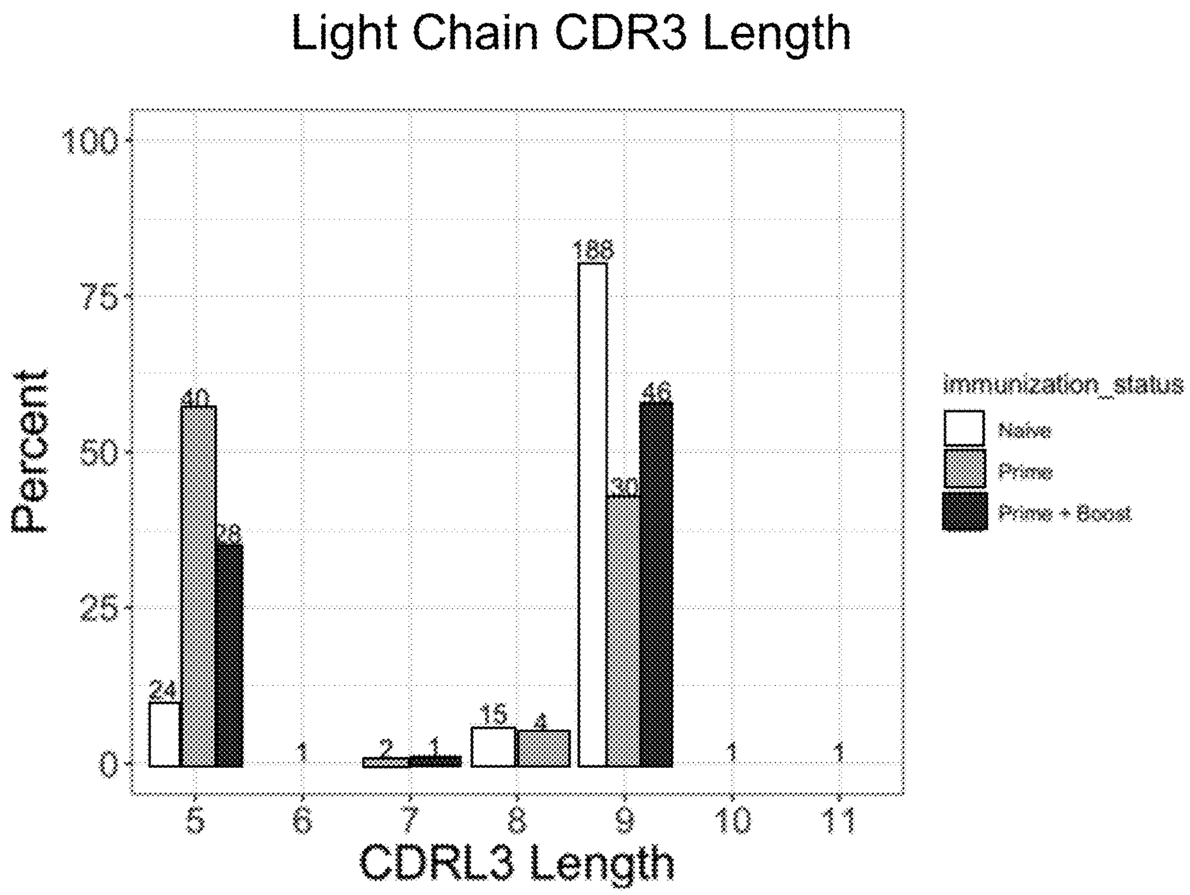
Figure 6F:
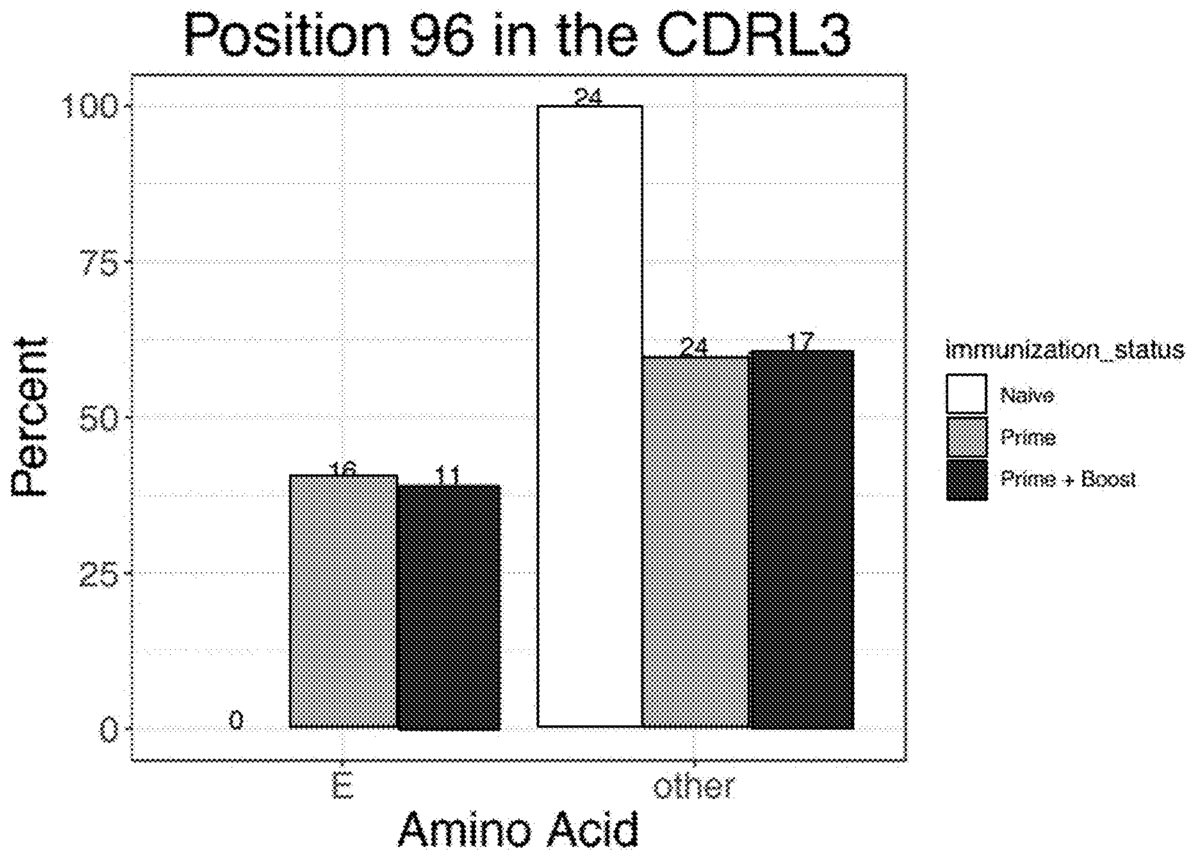

A single immunization with either nanoparticle form of 426c Core with two different adjuvants (Poly (I:C) or GLA-LSQ) elicits robust autologous plasma antibody responses (FIG. 4A), the majority of which target the CD4-BS (FIG. 4B). Plasma antibodies generated in 77% of the 426c Core-immunized animals (66 of 85), also recognized the heterologous VRC01 germline-targeting immunogen eOD-GT8 (FIG. 4C) in a VRC01 epitope-dependent manner (FIGS. 5A, 5B). eOD-GT8 is derived from the outer domain of the gp 120 subunit of the clade B H×B2 Env (Jardine et al., 2013. Science 340, 711-716; Jardine et al., 2015. Science 349, 156-161). Thus, antibodies elicited by the 426c Core that recognize eOD-GT8, but not the eOD-GT8 KO (not recognized by VRC01-class antibodies) are most likely VRC01 epitope-specific. In contrast, the 426c DS-SOSIP D3 germline-targeting immunogen elicited very weak autologous plasma antibody responses and only one animal elicited antibodies against the 426c Core, which were non-CD4-BS directed and did not recognize eOD-GT8 (FIG. 5C). Animals immunized with the non-germline-targeting Env 426c WT gp120 immunogen elicited strong autologous responses, but weak anti-426c Core antibody responses and no eOD-GT8 antibody response (FIG. 5D). These results indicate that the 426c Core immunogen elicits potent anti-CD4-BS antibody responses, which recognize the VRC01 epitope.

426c Core selects for key mutations in the antibody heavy and light chains. To directly demonstrate that the 426c Core expands VRC01-lineage B cells, two weeks after immunization, eOD-GT8+/eOD-GT8 KO− specific class-switched B cells from the spleens and lymph nodes (LNs) of mice displaying plasma antibody cross-reactivity to eOD-GT8 were sorted and their VH/VL genes were sequenced. eOD-GT8+/eOD-GT8 KO− B cells were also sorted from unimmunized animals (FIGS. 6A-6F). A total of 420 eOD-GT8+/eOD-GT8 KO-class-switched B cells were singly-sorted from the immunized animals and their VH and VL genes were amplified using PCR. 204 HC and 70 LCs were successfully sequenced.

Figure 4D:
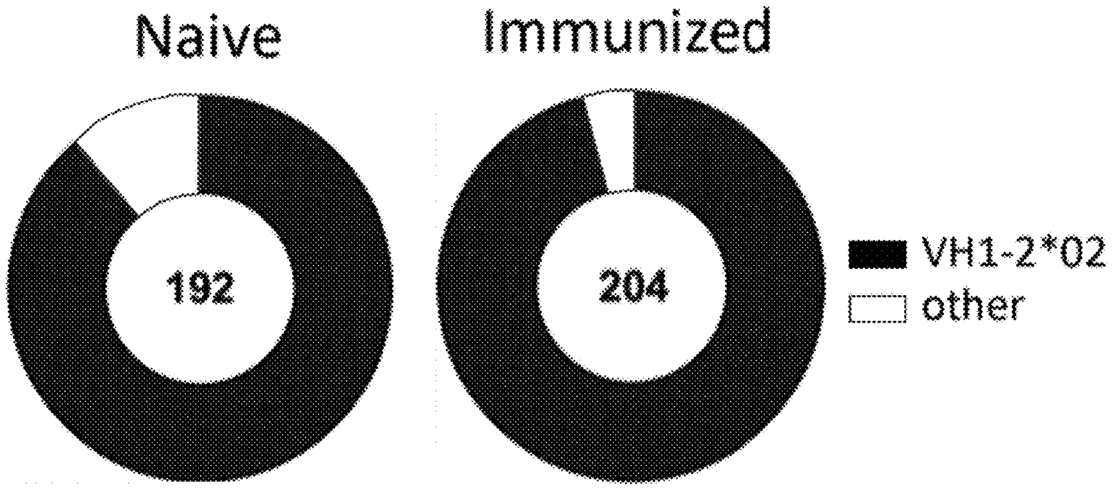

96% of sequenced HCs were VH1-2*02 (FIG. 4D). In 70% of 137 VH1-2*02 HCs isolated after the prime immunization, the histidine at position 35 in the CDRH1 domain was replaced by an asparagine (FIG. 7A). The H35N mutation, introduces an additional hydrogen bond with N100a in CDRH3 and increases the stability of interaction between CDRH1 and CDRH3 on VRC01-class antibodies (Jardine et al., 2015. Science 349, 156-161).

Figure 4E:
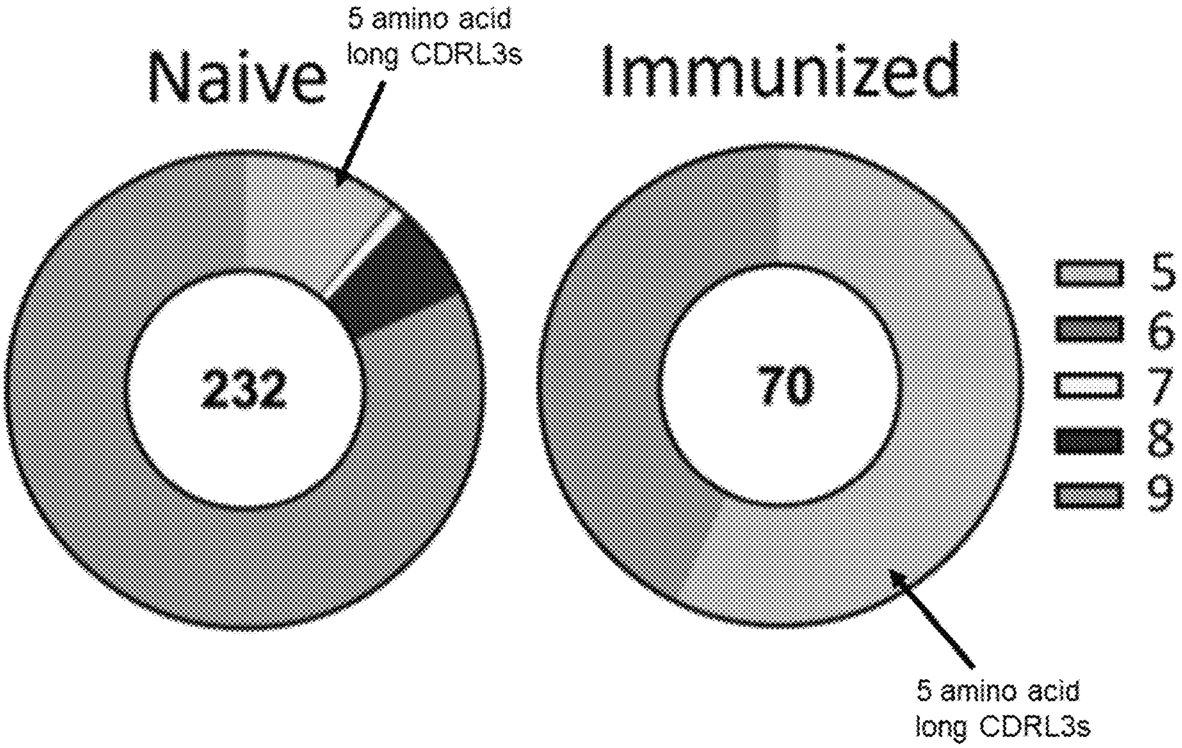
Figure 4F:
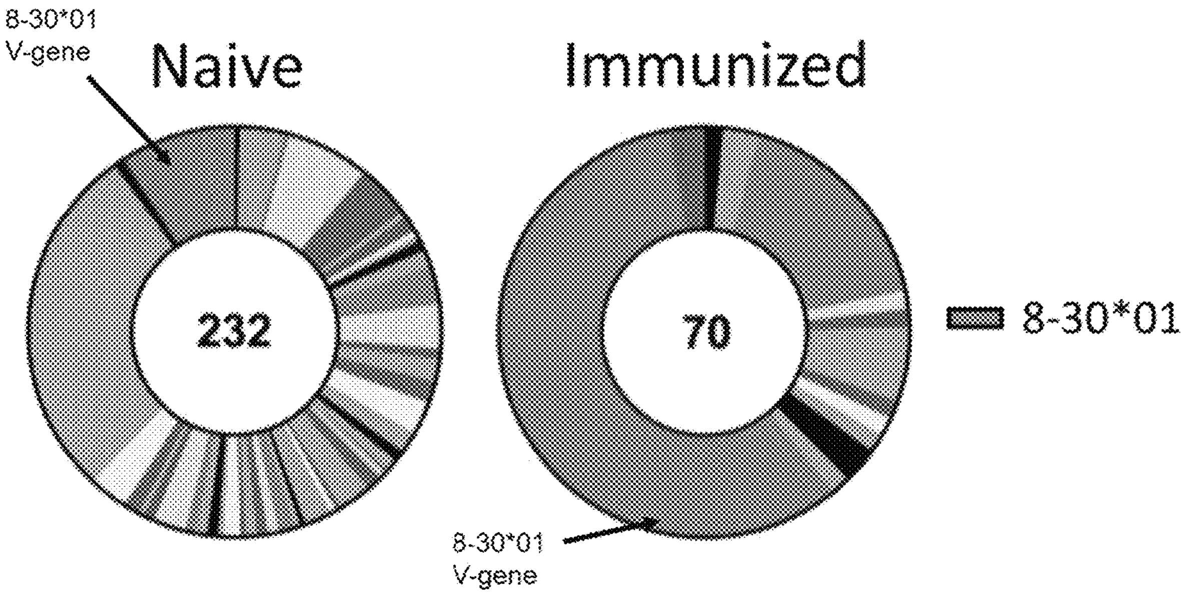
Figure 4G:
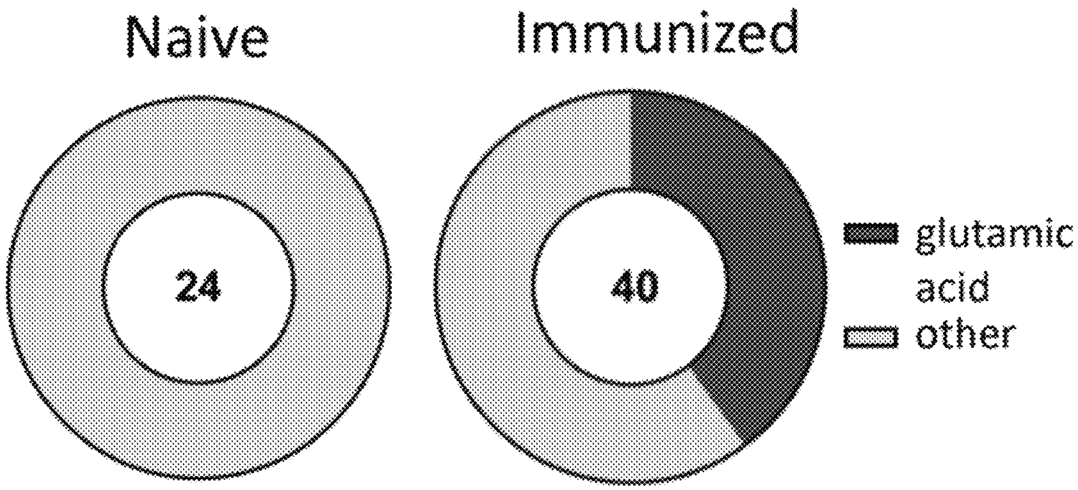

57% of sequenced mLCs contained 5 AA-long CDRL3s (FIG. 4E). The majority of the 5 AA CDRL3s are derived from the mouse 8-30*01 LC V gene, which is represented at 6% in the naïve eOD-GT8+/eOD-GT8 KO− B cell repertoire (FIG. 4F). All the identified 5 AA-long CDRL3s-containing mLCs were paired with gIVRC01 HCs. Immunization with the 426c Core therefore preferentially expanded B cells expressing mLCs with 5 AA-long CDRL3s. A large fraction (40%) of the 5 AA-long CDRL3s contained a Glu96LC (FIG. 4G), which is a key feature of mature VRC01-class antibodies and forms a hydrogen bond with Gly459gp120 at the N-terminus of the V5 region (West, A. P., et al., 2012. Proceedings of the National Academy of Sciences of the United States of America 109, E2083-E2090; Zhou, T., et al., 2013. Immunity 39, 245-258). In contrast, 5 AA-long CDRL3s with Glu96LC were detected in the mLC sequenced from naïve eOD-GT8+/eOD-GT8 KO− B cells (FIG. 4G).

Figure 4H:
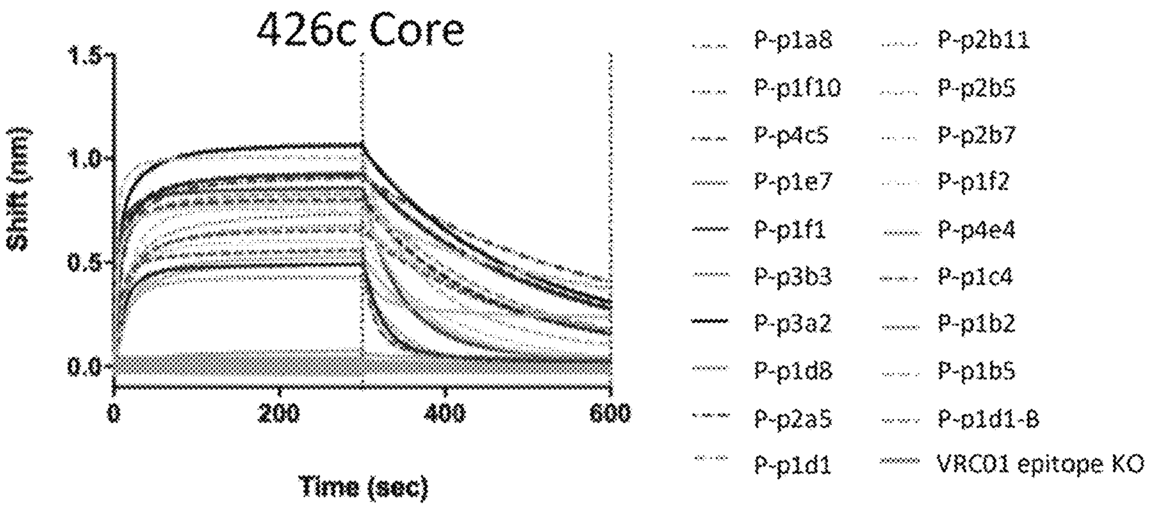
Figure 4I:
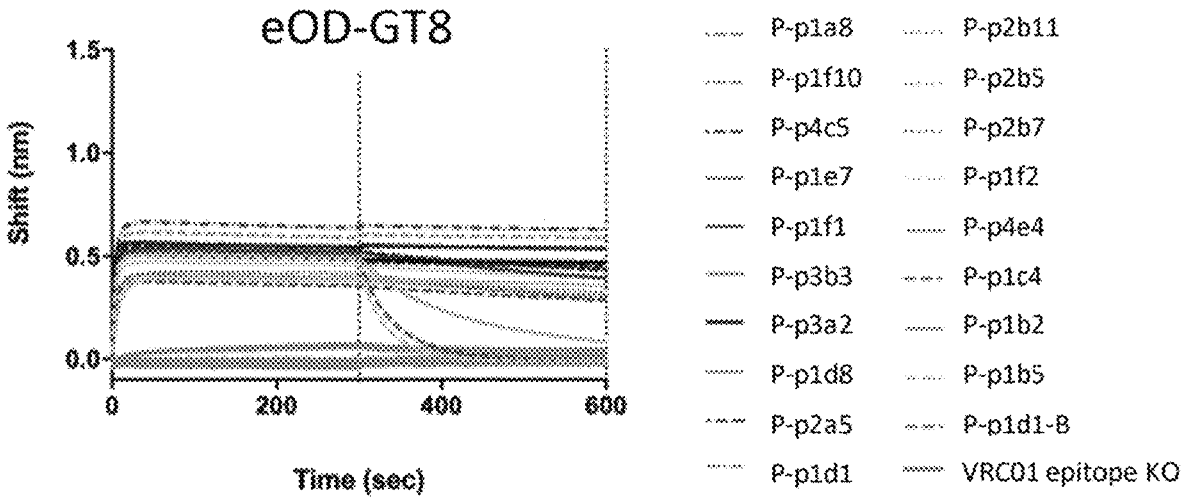

19 VH/VL pairs with VRC01 characteristics were expressed as IgGs (designated by 'P' to indicate they were isolated following the prime immunization). All bound 426c Core and displayed no reactivity with 426c Core CD4-BS KO (FIG. 4H). All 19 mAbs156 also bound the eOD-GT8 protein, but not the eOD-GT8 KO (FIG. 4I).

Figure 8A:
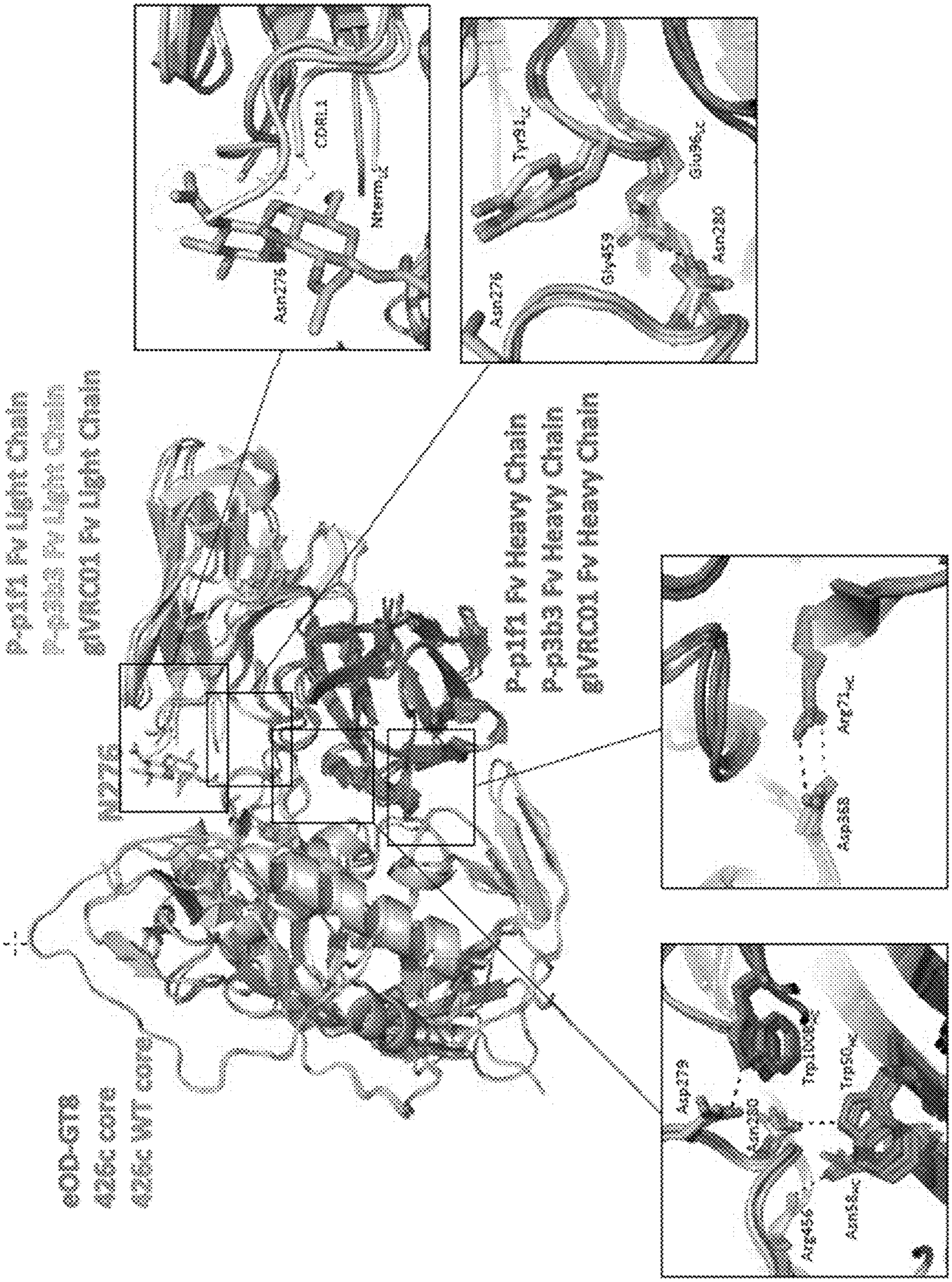

A 3.6 Å resolution crystal structure of antibody P-p3b3 bound to the 426c Core and a 3.2 Å resolution crystal structure of antibody P-p1f1 bound to eOD-GT8 were solved (FIG. 8A, FIG. 9). These antibodies bind 426c Core and eOD-GT8 with the same angles of approach that human gIVRC01 binds 426c WT Core (RMSD=0.334161 Å for gp120-Fv) (Borst et al., 2018. Elife 7) or eOD-GT6 (RMSD=0.765 Å for gp120-Fv) (Jardine et al., 2013. Science 340, 711-716) (FIG. 8A). Critical contacts, both in the HC (FIG. 8A) and in the LC (FIG. 8A), were maintained in these interactions: Trp 50HC, Asn 58HC, Arg71HC and Trp100BHC residues were not mutated in the mouse VRC01-like antibodies, adopted the same orientations, and participated in the same hydrogen bonding as observed with gIVRC01 (FIG. 8B). Similar to the human gIVRC01 antibody, the short 5 AA CDRL3 domains of the mouse VRC01-like antibodies facilitate the interactions with gp120 and Glu96LC maintains the hydrogen bonds with Gly459 and Asn280 of gp 120. Only a few residues in the LC seem to contact the gp 120 and they are located at the N170 terminus, the CDRL1 and CDRL3 domains. The mouse VRC01-like antibodies have longer CDRL1 than most human VRC01-class antibodies (17 vs 11-12 amino acids long based on the Kabat nomenclature), however several human VRC01-class antibodies, including VRC01c-HuGL2, have been isolated by sorting naïve B cells with eOD-GT8 that contain 17 amino acid long CDRL1 whose sequence is similar to that of the VRC01-like antibodies identified here (FIG. 8C) (Havenar-Daughton et al., 2018. Science Translational Medicine 10; Jardine et al., 2016. Science 351, 1458-1463). Whereas the shorter CDRL1 domain of the human inferred germline VRC01 Ab is well ordered in the complex of this antibody with eOD-GT6 (Jardine et al., 2013. Science 340, 711-716) or with WT 426c Core (Borst et al., 2018. Elife 7), the CDRL1 of the mouse VRC01-like antibodies bound to 426c Core or eOD-GT8 and that of VRC01c-HuGL2 bound to eOD-GT8 (Jardine et al., 2016. Science 351. 1458-1463) were disordered, indicating extensive CDRL1 flexibility. Such flexibility is likely necessary to accommodate glycans present on N276 in the presence of longer CDRL1. These data indicate that the 426c Core immunogen elicits antibodies with similar genetic and structural features of known human VRC01-class antibodies.

Figure 10A:
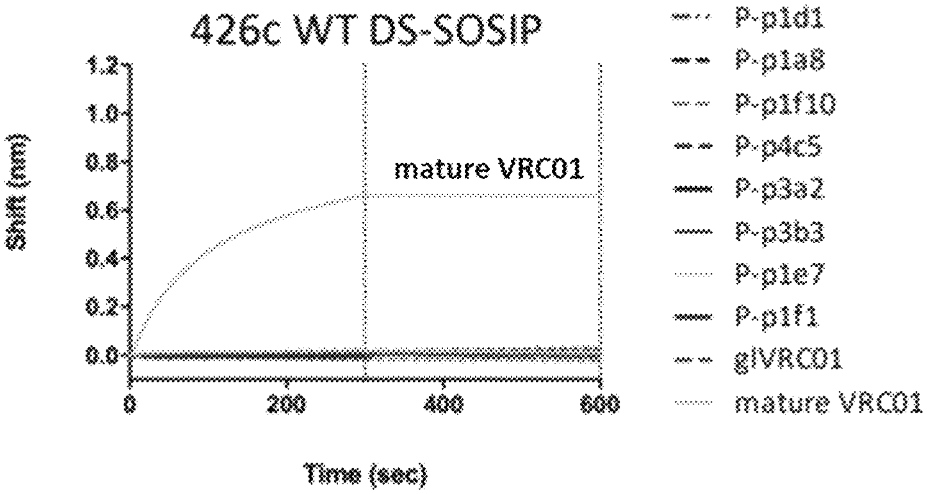
Figure 10B:
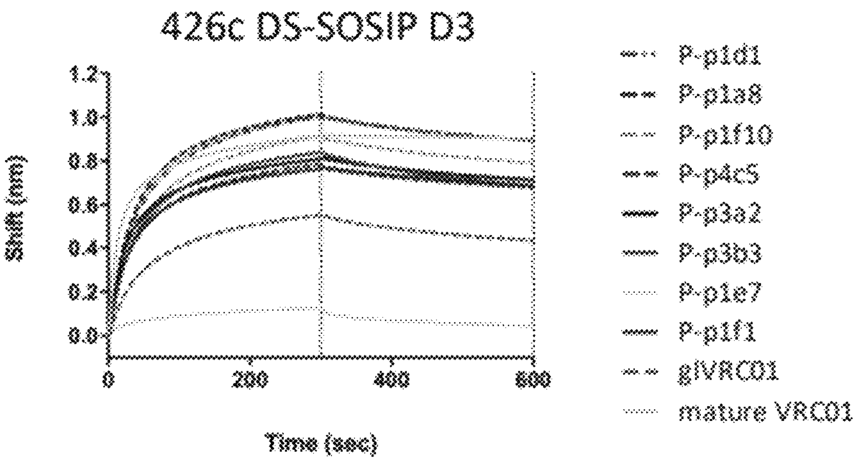
Figure 10C:
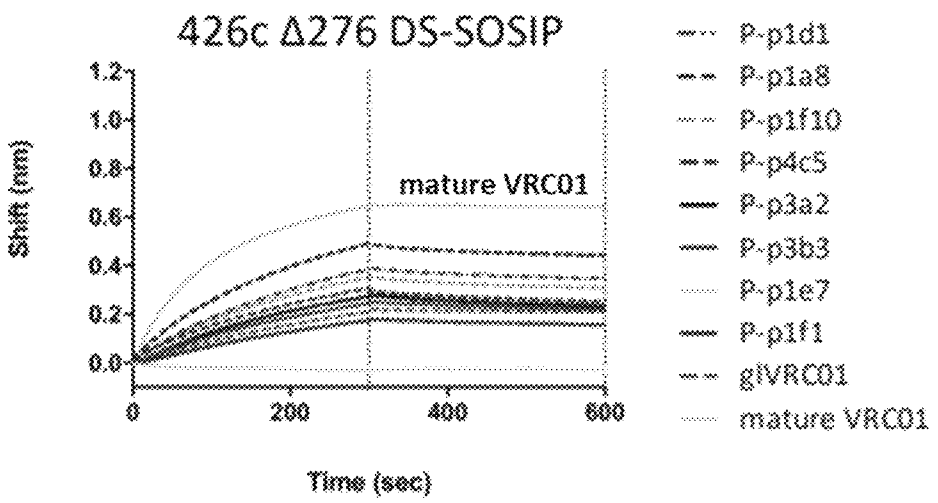
Figure 10D:
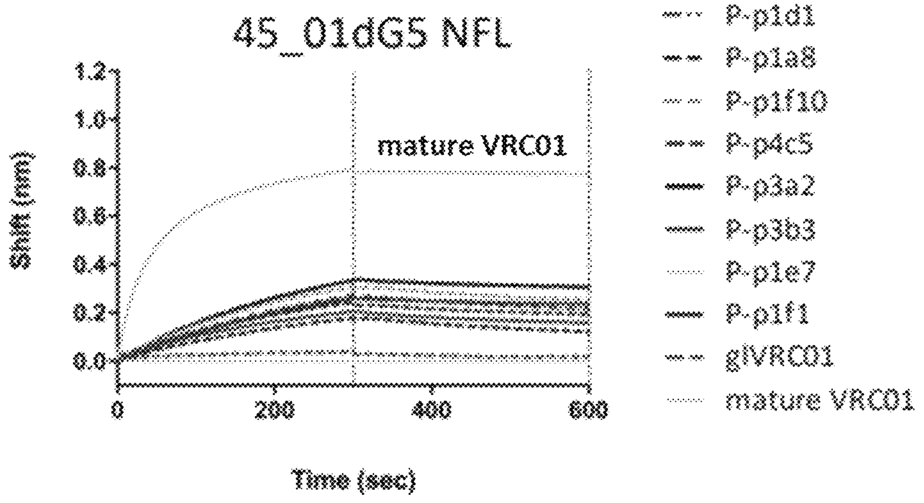

Antibodies elicited by the 426c Core neutralize the 426c virus lacking the N276 associated glycans. Eight of the above nineteen mAbs were tested for binding to stabilized soluble trimeric Envs (SOSIP or NFL). None bound the autologous 426c WT DS-SOSIP (FIG. 10A); however, all bound to the derivative lacking the 276, 460 and 463 NLGS (426c DS-SOSIP D3) (FIG. 10B) and seven bound the derivative only lacking the 276 NLGS (426c N276 DS-SOSIP) (FIG. 10C). Those seven mAbs also bound the heterologous 45_01 dG5 NFL TD-2CC+(DS+) trimer (FIG. 10D). 45_01 dG5 Env is derived from a virus that circulated in patient 45, from which several VRC01-class antibodies have been isolated (including VRC01), and naturally lacks the 276 and 460 NLGS (Lynch et al., 2015. Journal of Virology 89, 4201-4213). MAb P-p1e7 did not bind to autologous or N276 heterologous stabilized trimeric Envs and is the only antibody of those tested, that lacks Glu96LC (FIG. 7B).

The neutralizing potency of four mAbs were evaluated against the WT 426c virus or its 276 NLGS derivative (FIG. 10E) produced in either 293T or 293 GnTI −/− cells. Viruses produced in 293 GnTI −/− cells can be used to detect the presence of gIVRC01 class antibody neutralizing activities (Briney et al., 2016. Cell 166, 1459-1470.e11; LaBranche et al., 2018. PLOS Pathogens 14). In agreement with the binding data, the mAbs did not neutralize the WT 426c virus (regardless of whether it was produced in 293 or 293 GnTI −/− cells). However, three of four mAbs neutralized the GnTI −/− produced 276 NLGS virus. The fourth, non-neutralizing antibody, P-p1e7, is the one lacking Glu96LC (FIG. 7B).

These data indicate that the 426c Core immunogen elicits VRC01-like Abs that can recognize autologous and some heterologous soluble, stabilized Env trimers; avoiding clashes with variable regions 1, 2 and 3; and that the presence of Glu96LC appears to be important for these interactions. However, although these antibodies can avoid the glycans present on the V5 Env region, their binding is impaired by the glycan at position N276 in Loop D.

Figure 11A:
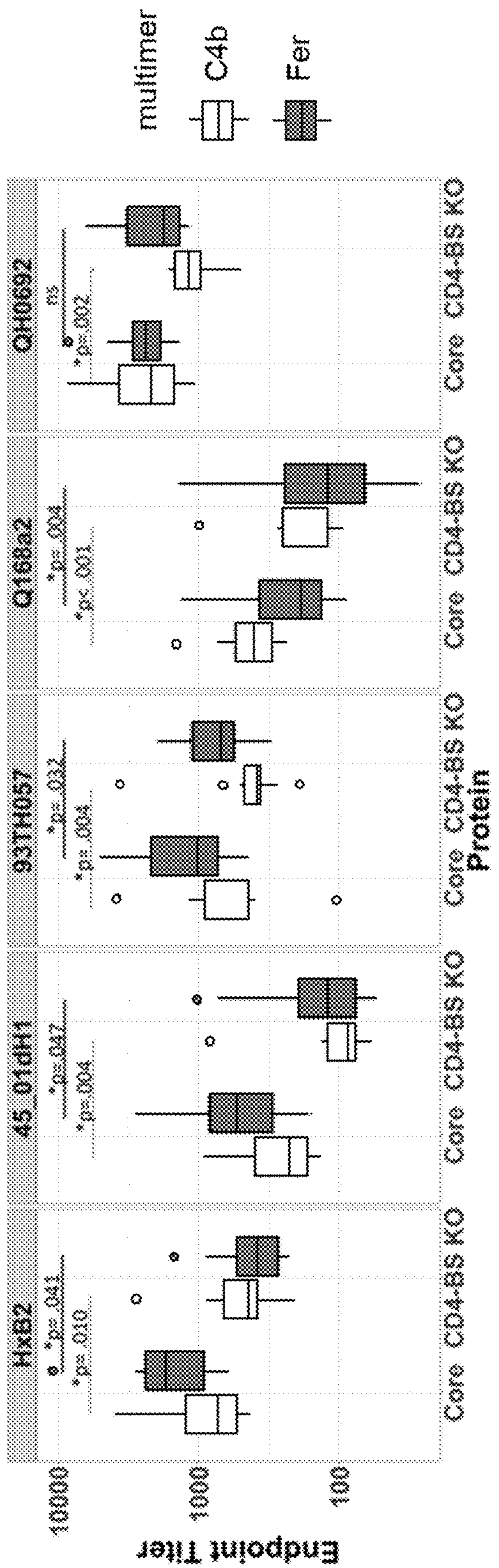
FIGS. 11A, 11B. Plasma antibodies elicited by the 426c Core recognize heterologous wild type gp 120 Core proteins. (11A) Plasma from animals (n=10 in each group) immunized with the 426c Core were tested for binding by ELISA against five heterologous wild type gp120 Core proteins and their CD4-BS KO derivatives. Data is shown as a box plot. Statistical values compare the plasma antibody endpoint titer of the indicated Core proteins to their CD4-BS KO derivatives. Statistical significance was calculated using a paired t-test. (11B) Amino acid alignment of the loop D and V5 loop sequences from these five Core proteins. The position of potential NLGS in these two envelope regions are highlighted in dark gray.
Figure 11B:
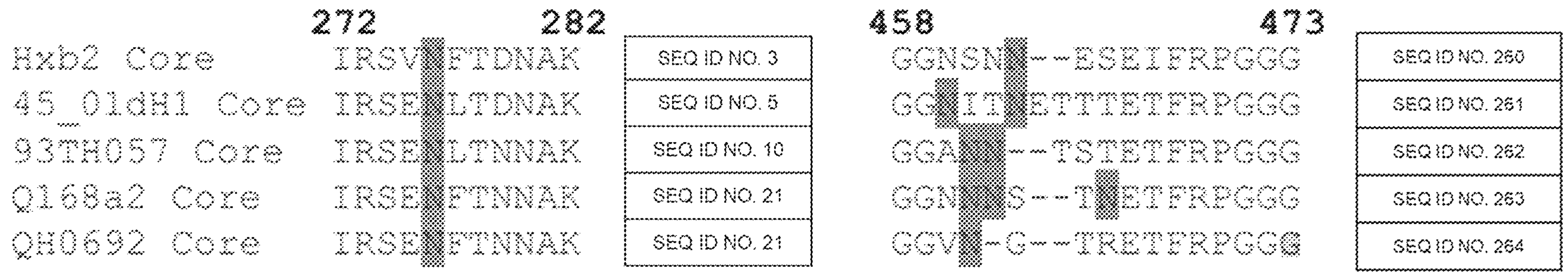

Antibodies elicited by the 426c Core accommodate the N276 associated glycans on heterologous Env Cores. Plasma antibodies from 426c Core-immunized animals displayed CD4-BS-dependent recognition of heterologous monomeric WT Core proteins derived from the H×B2 (clade B), 45_01 dH1 (clade B), 93TH057 (clade A/E), Q168a2 (clade A) and QH0692 (clade B) Envs (FIG. 11A). These gp120-derived proteins lack the variable domains 1, 2 and 3, but harbor the N-X-T/S sequons at position N276 and in the V5 loop (FIG. 11B). This observation suggested that the VRC01-like antibodies elicited by the 426c Core may bind heterologous Env Core proteins even in the presence of the N276-associated glycans.

Figure 12A:
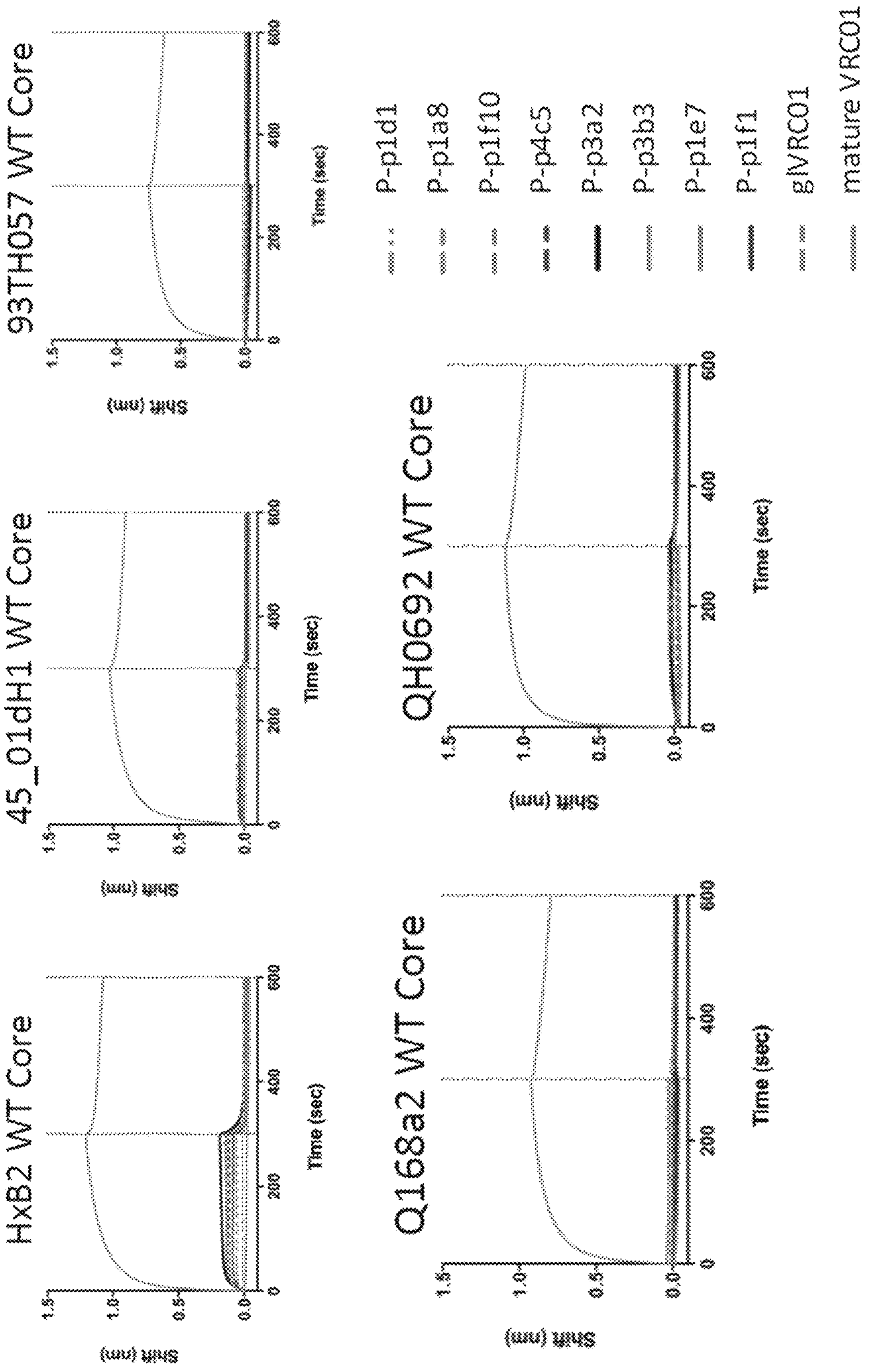
FIGS. 12A, 12B. VRC01-like antibodies elicited by the 426c Core germline-targeting immunogen recognize heterologous wild type Core Env proteins. BLI binding traces of the indicated mAbs to the indicated Env proteins in either monomeric (12A) or nanoparticle (C4b based) (12B) forms. Mature and germline VRC01 mAbs were used as controls.
Figure 12B:
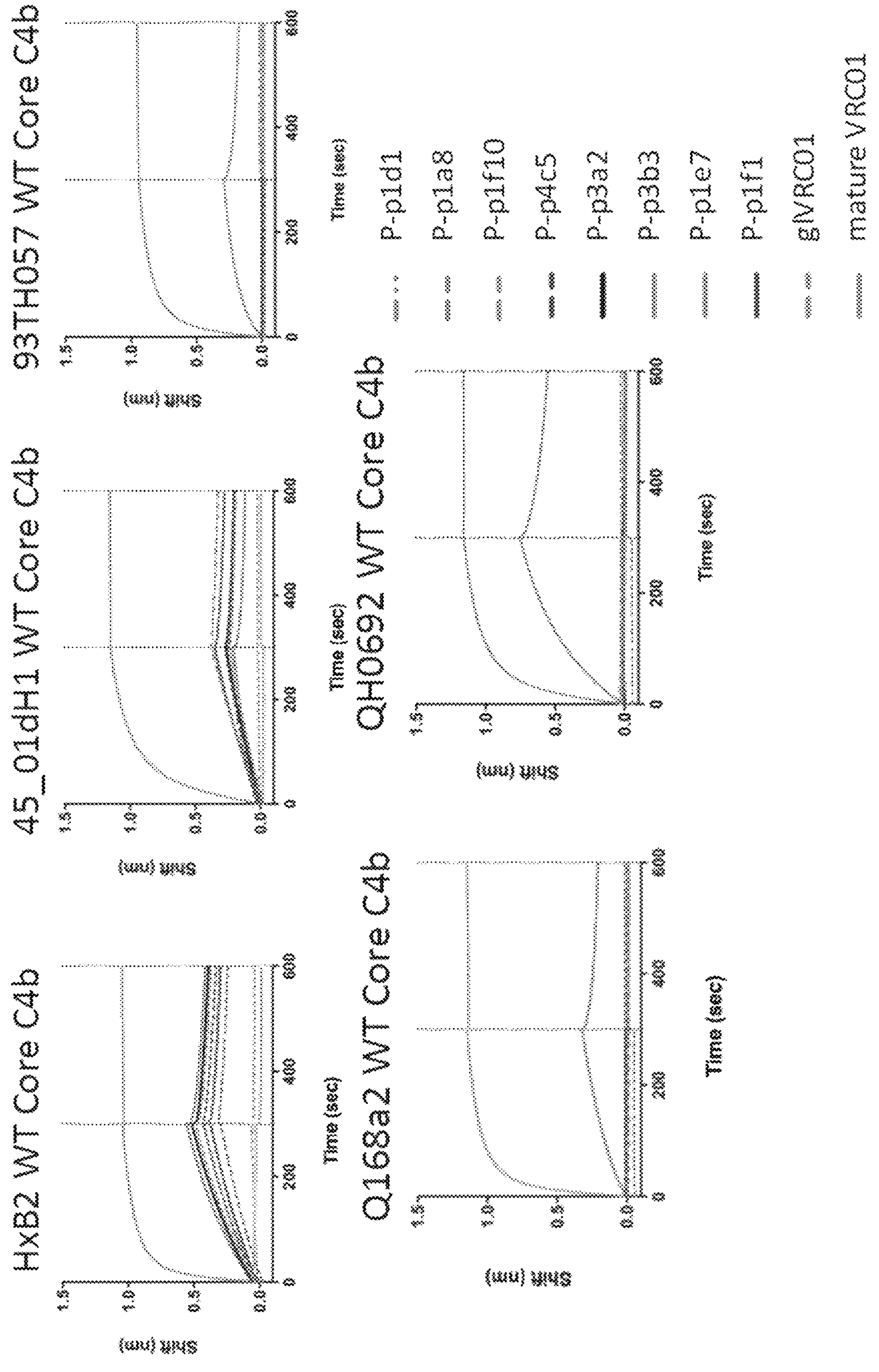

The binding of the above-mentioned VRC01-like mAbs was examined to both the monomeric and the multimeric (C4b based) forms of these Cores (FIGS. 12A, 7B). The mAbs exhibited weak binding to the monomeric form of H×B2, but not the other WT Cores (FIG. 12A). However, eight of nine mAbs tested bound the multimeric forms of the H×B2 and 45_01 dH1 WT Core proteins (P-p1e7 that lacks Glu96LC did not bind) (FIG. 12B), and one mAb (P-p3b3) also bound the multimeric forms of 93TH057 WT Core (FIG. 12B), Q168a2 WT Core (FIG. 12B), and QH0692 WT Core (FIG. 12B). Mature VRC01 recognized both the monomeric and multimerized forms of these Cores while germline VRC01 did not recognize either. Hence, the 426c Core-elicited VRC01 antibodies that display intermediate binding phenotypes in comparison to those of the germline and mature human VRC01 mAbs.

These data indicate that a single immunization with the 426c Core elicits VRC01-like antibodies that can bypass the N276 glycans on heterologous Envs as long as the variable domains are absent (i.e., gp120-Core forms).

Figure 13A:
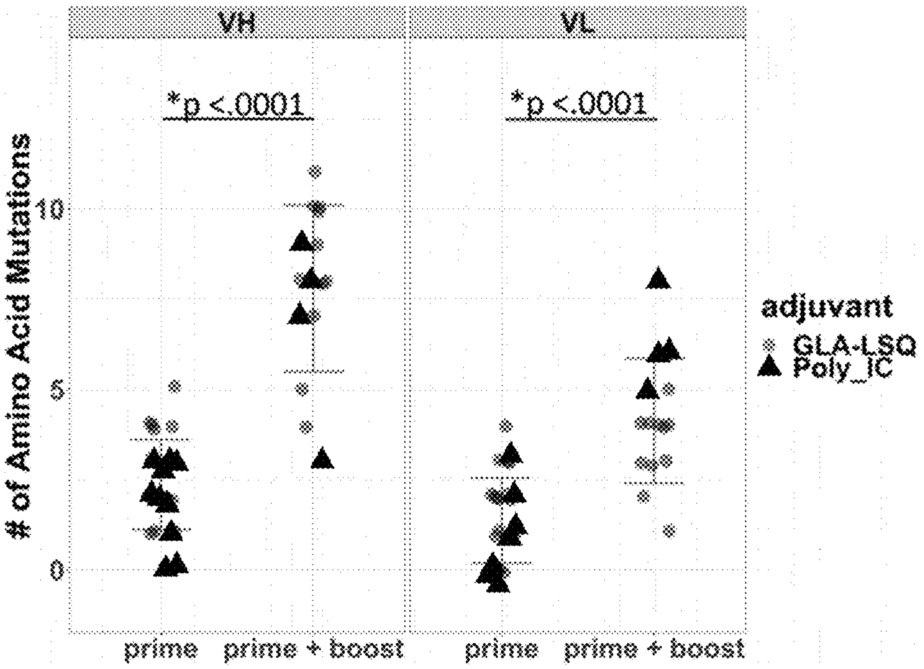
FIGS. 13A, 13B. VH/VL mutations and binding affinities of VRC01-like antibodies isolated throughout the immunization. (13A) The number of amino acid mutations per each VH and VL domains in mAbs generated from sequences isolated following the prime immunization with 426c Core and the boost immunization with H×B2 WT Core are shown (see FIG. 5B for VH and VL sequence alignments). Each dot represents a sequence. A Welch Two Sample t-test (unpaired t-test) was used to determine the statistical significance. Error bars show standard deviation from the mean. (13B) The binding affinities of antibodies (Fabs) isolated from naïve, non-immunized animals (black squares), antibodies generated after the prime immunization (gray circles) and following the boost immunization (white diamonds) are shown for the 426c WT Core and the H×B2 WT Core (binding traces and summary affinity information are shown in FIGS. 16A, 16B).

A heterologous boosting immunization improves the binding affinities of VRC01-like antibodies to Env. Based on the above observations, it was hypothesized that a boosting immunization with a heterologous Core Env expressing glycans at position N276 may expand the population of B cells that are capable of bypassing the N276-associated glycans. To test this hypothesis, a new group of animals were immunized first with the C4b nanoparticle form of 426c Core and four weeks later with the C4b nanoparticle form of the H×B2 WT Core Env. Env-specific B cells were isolated from the spleens and LNs two weeks following the boost immunization and analyzed as described above. A total of 160 eOD-GT8+/eOD-GT8 KO− B cells were isolated from these animals. 72 HCs and 79 LCs were successfully amplified and sequenced (FIGS. 6A-6F). The frequency of somatic mutation in the HC and LCs was higher in the antibodies isolated after the boost than after the prime (FIG. 13A and FIGS. 7A, 7B).

Figure 13B:
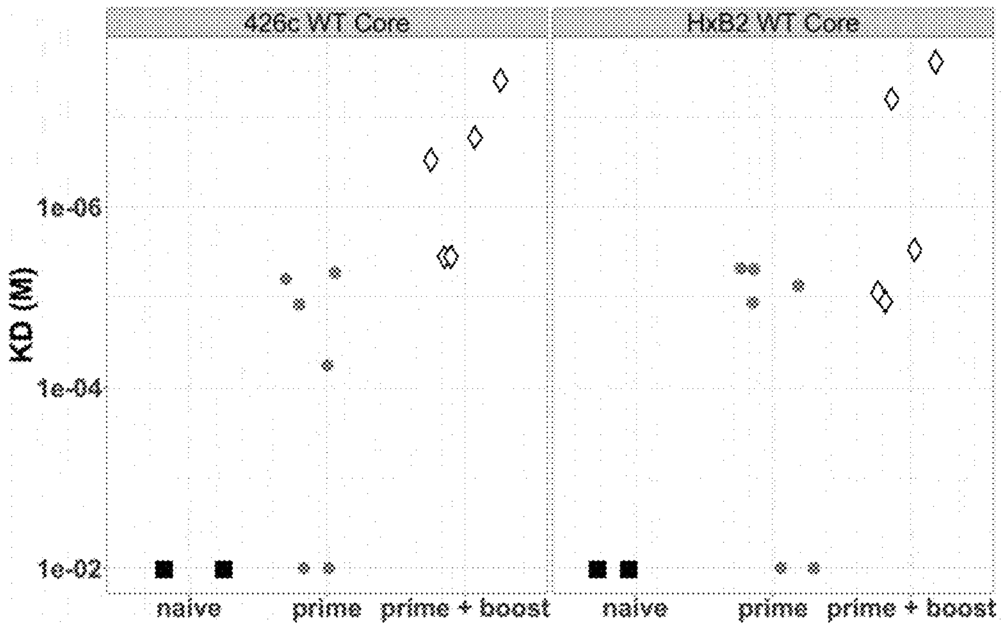
Figure 14A:
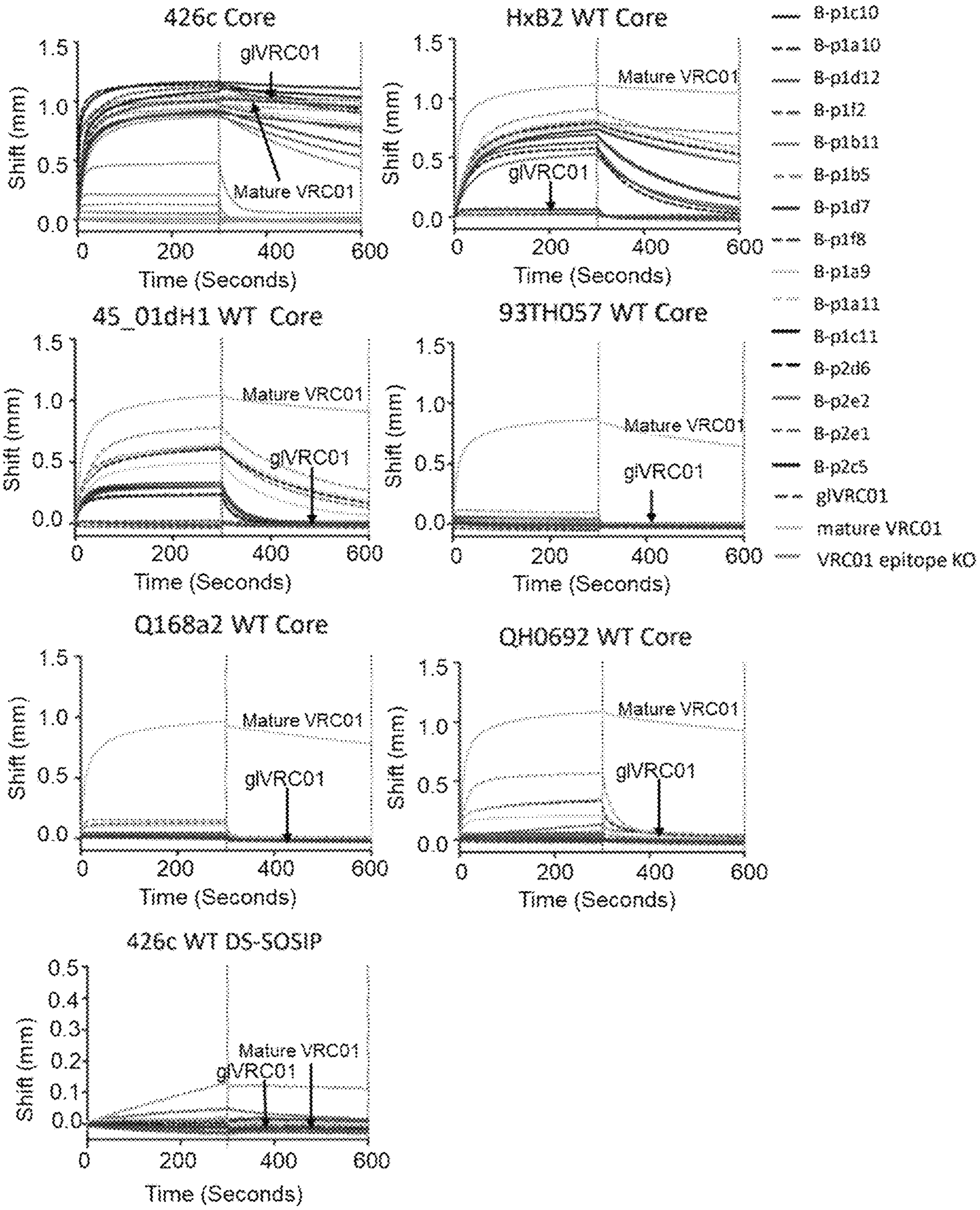
FIGS. 14A-14E. Env-recognition and neutralizing properties of VRC01-like antibodies isolated following the boost immunization with the H×B2 WT Core Env. BLI binding traces of the indicated VRC01-like mAbs isolated after the boost immunization (Prefix: B) to the indicated monomeric Env Core proteins and the 426c WT SOSIP trimeric Env (14A), monomeric eOD-GT8 (14B). Mature VRC01 (gray and marked) and germline VRC01 (dashed dark gray and marked) were used as controls. (14C) Negative stain EM analysis of the 426c WT DS-SOSIP/B-p1b5 complex. Raw micrographs (scale bar=200 nm) and 2D class averages (scale bar=90 Å) of B-p1b5 bound to 426c WT DS-SOSIP trimers following a mild glutaraldehyde crosslinking (0.25% GTA for 45 seconds followed by quenching with 1M Tris) to increase saturation of the 426c WT DS-SOSIP trimer. (14D) 3D reconstruction of the negatively stained 426c WT DS-SOSIP/B-p1b5 complex cross-linked with 0.25% GTA. Structures of the 426 DS-SOSIP trimer and germline VRC01 Fab were fit to the density as a reference (light gray envelope=negative stain EM density, dark gray=426c DS735 SOSIP, dotted circle=fab) (Borst et al., 2018. Elife 7). (14E) EC50 neutralizing titers (μg/ml) of indicated mAbs against the WT 426c virus grown in either 293T cells of 293S GnTI −/− cells. Mature and germline VRC01 mAbs were used as controls for the binding and neutralization assays.
Figure 14B:
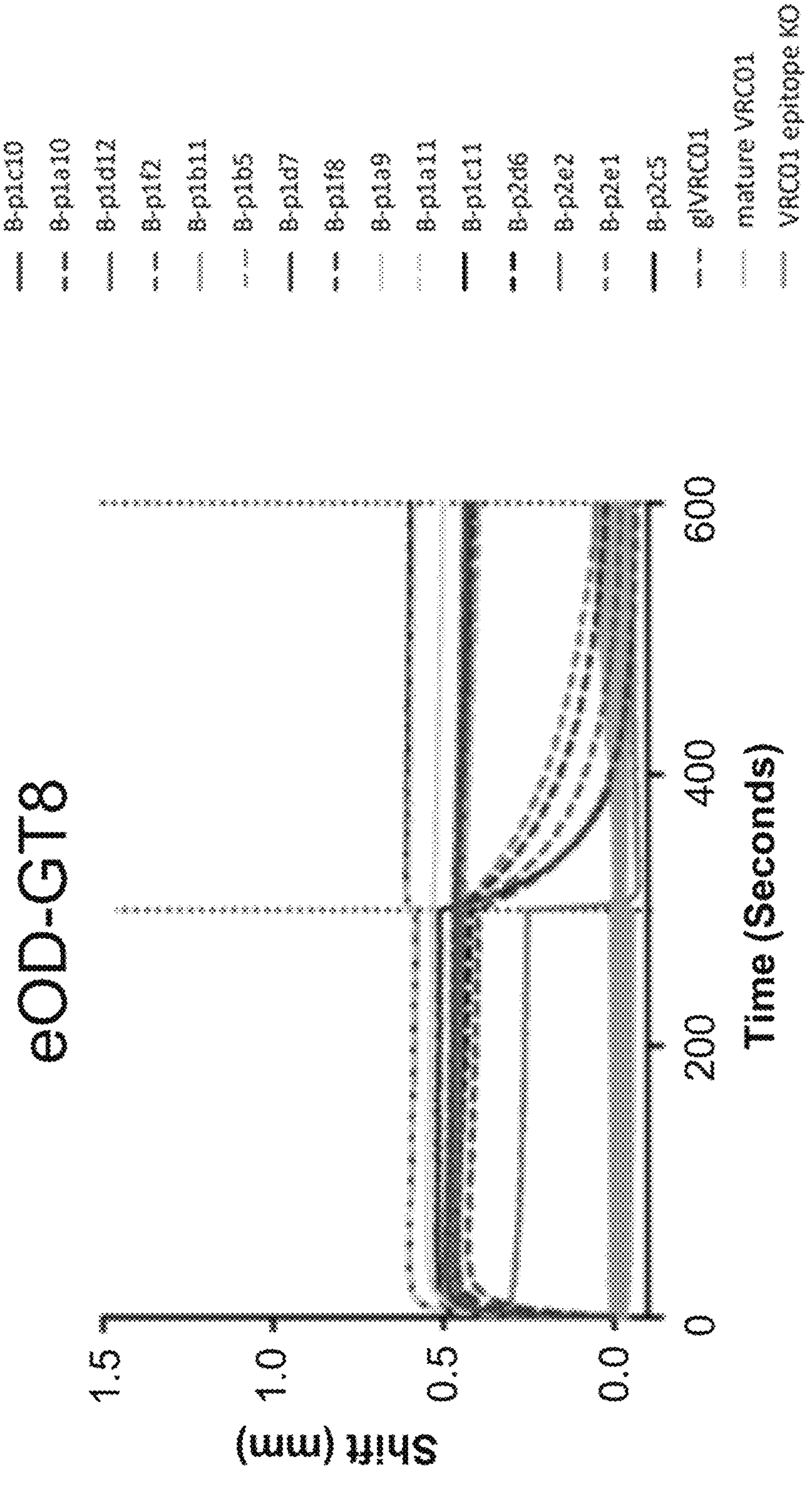
Figure 15:
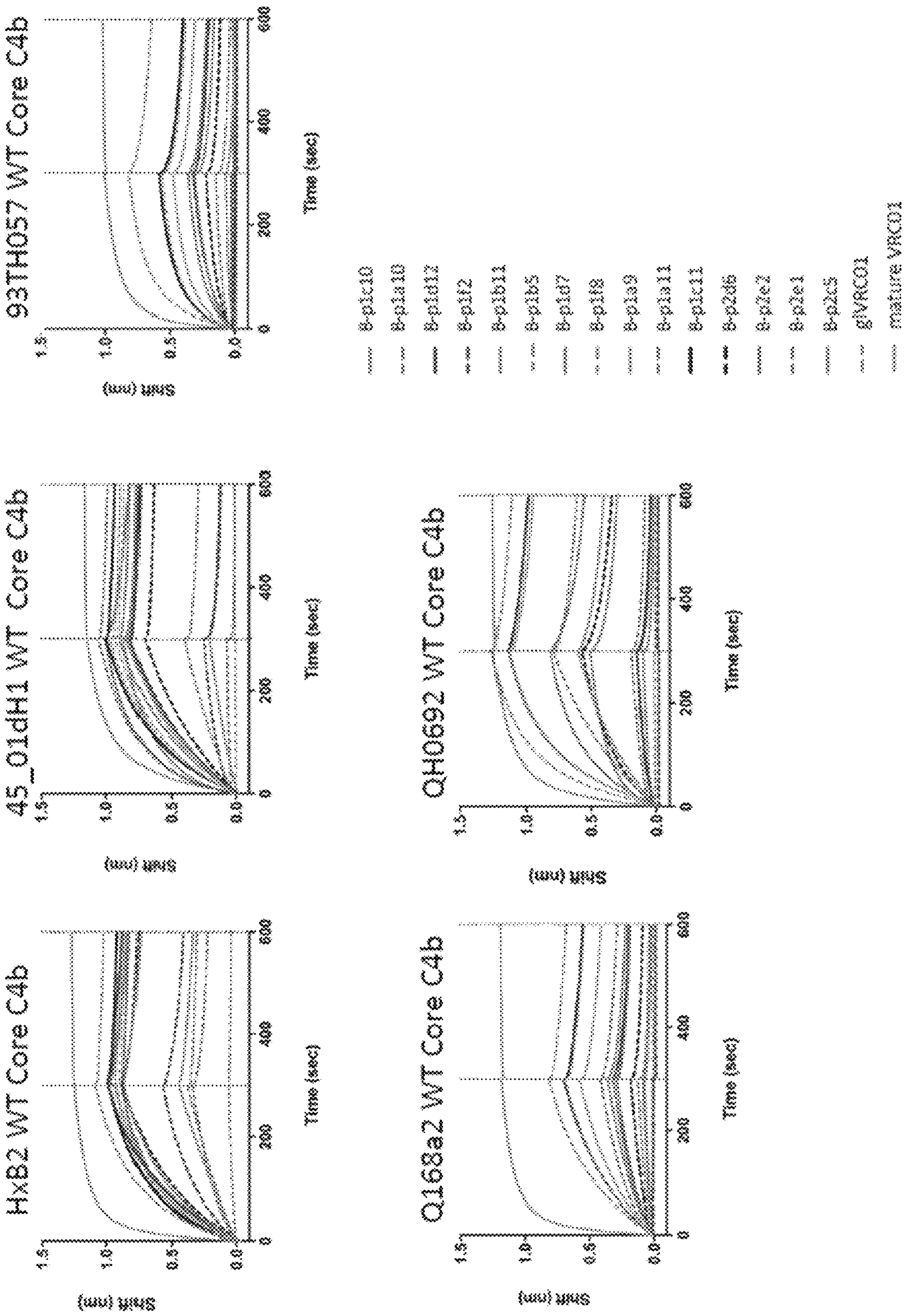
FIG. 15. Binding of MAbs isolated following the boost immunization to multimeric WT Core Env. BLI binding traces of the indicated MAbs isolated after the boost immunization to multimeric WT Core Env proteins.
Figure 16C:
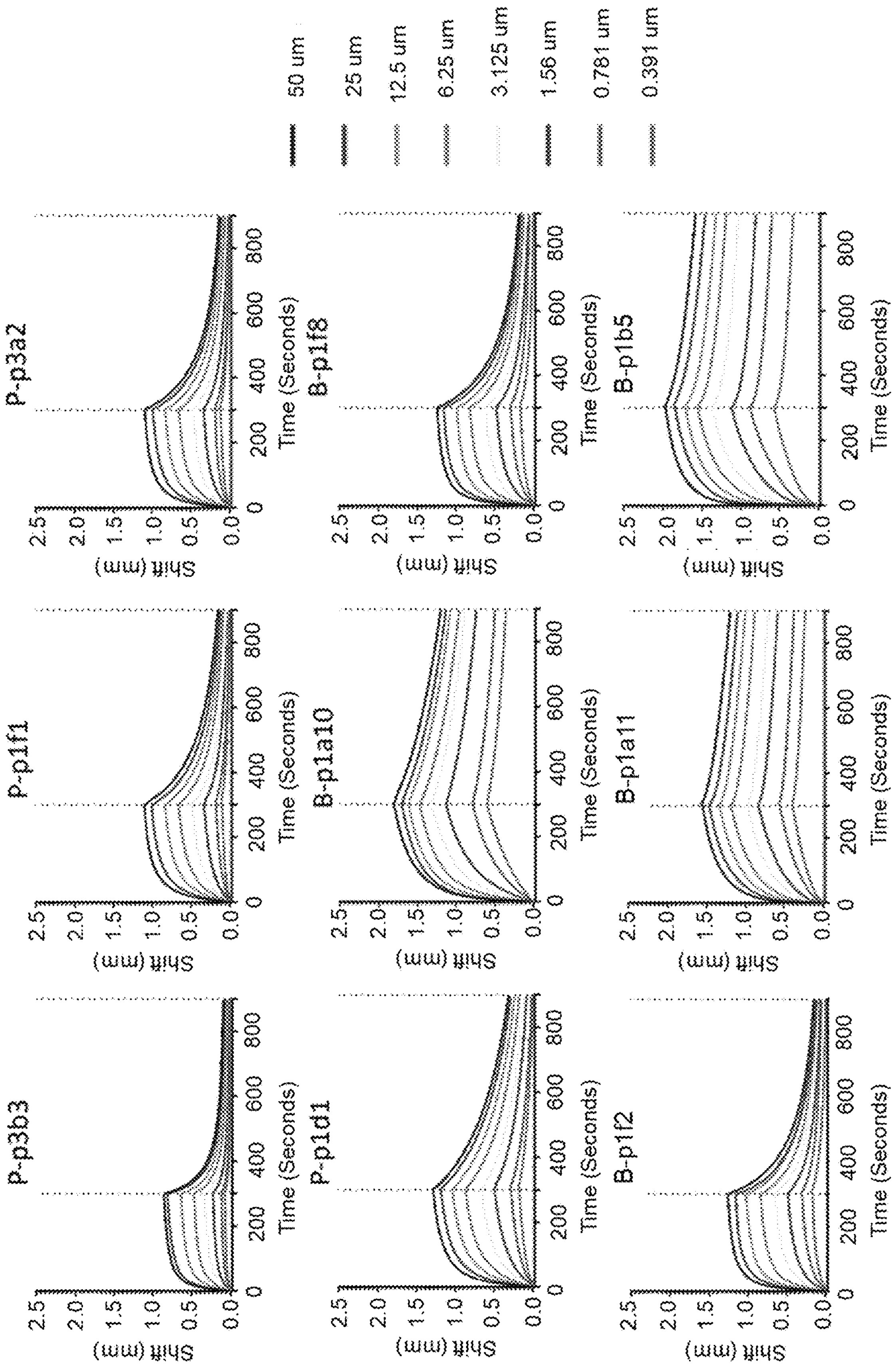
Figure 16D:
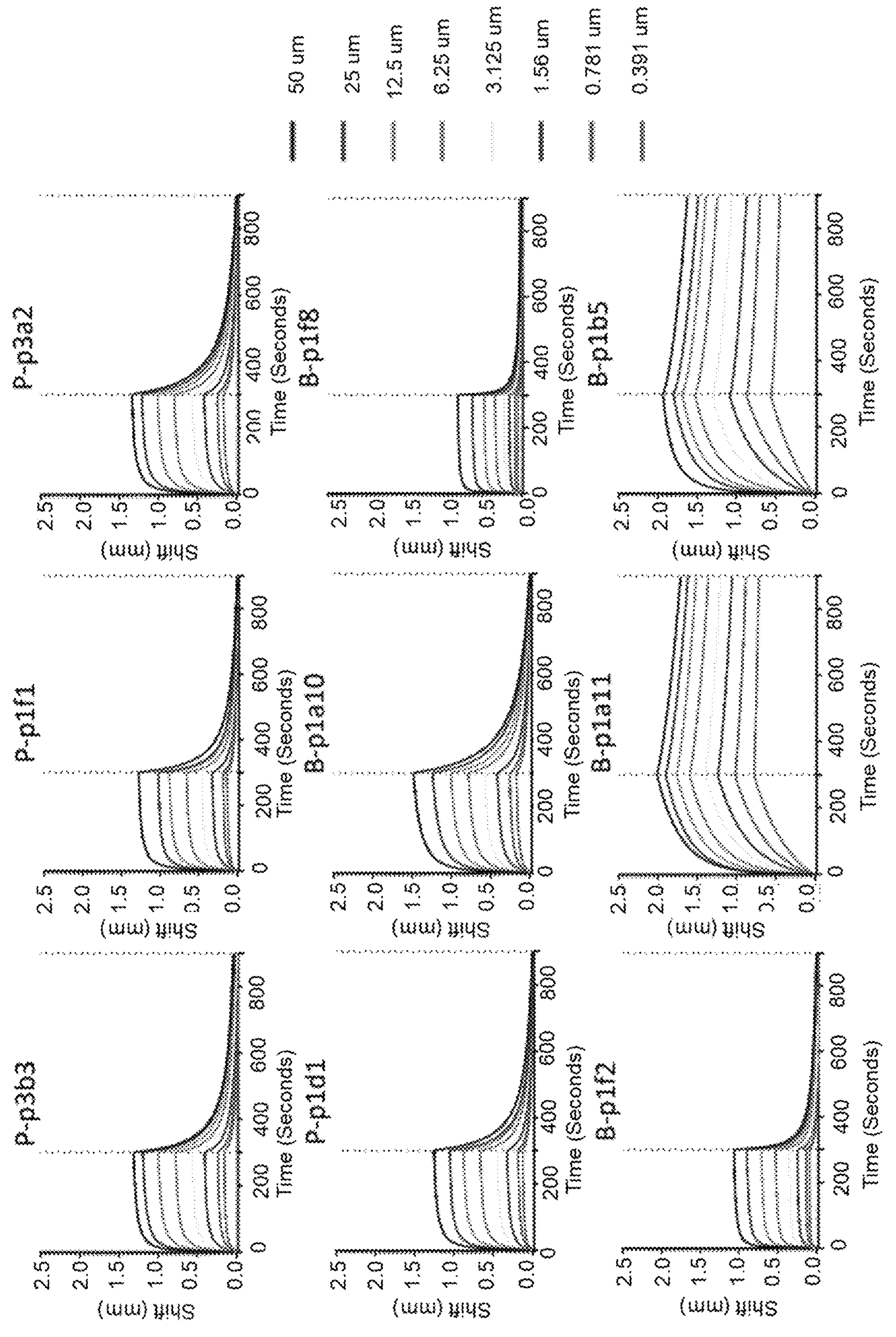

Thirteen antibodies (IgG) were generated from paired VH/VL sequences displaying VRC01-class antibody features. These are designated by 'B' to indicate they were isolated following the boost immunization. All mAbs recognized the 426c Core immunogen used during the prime in a CD4-BS-dependent manner (FIG. 14A). They also bound eOD-GT8 in a VRC01 epitope-dependent manner (FIG. 14B). While the VRC01-like antibodies elicited following the prime immunization displayed very weak binding to the monomeric H×B2 WT Core (FIG. 12A), antibodies elicited after the boost, bound more strongly to multiple monomeric (FIGS. 14A, 14B) and multimeric WT Cores (FIG. 15). Overall, the VRC01-like antibodies isolated after the boost have more mutations in both their HCs and LCs (FIG. 13A), and higher binding affinities (FIG. 13B and FIGS. 16A, 16B) than the antibodies isolated after the prime immunization.

Figure 14C:
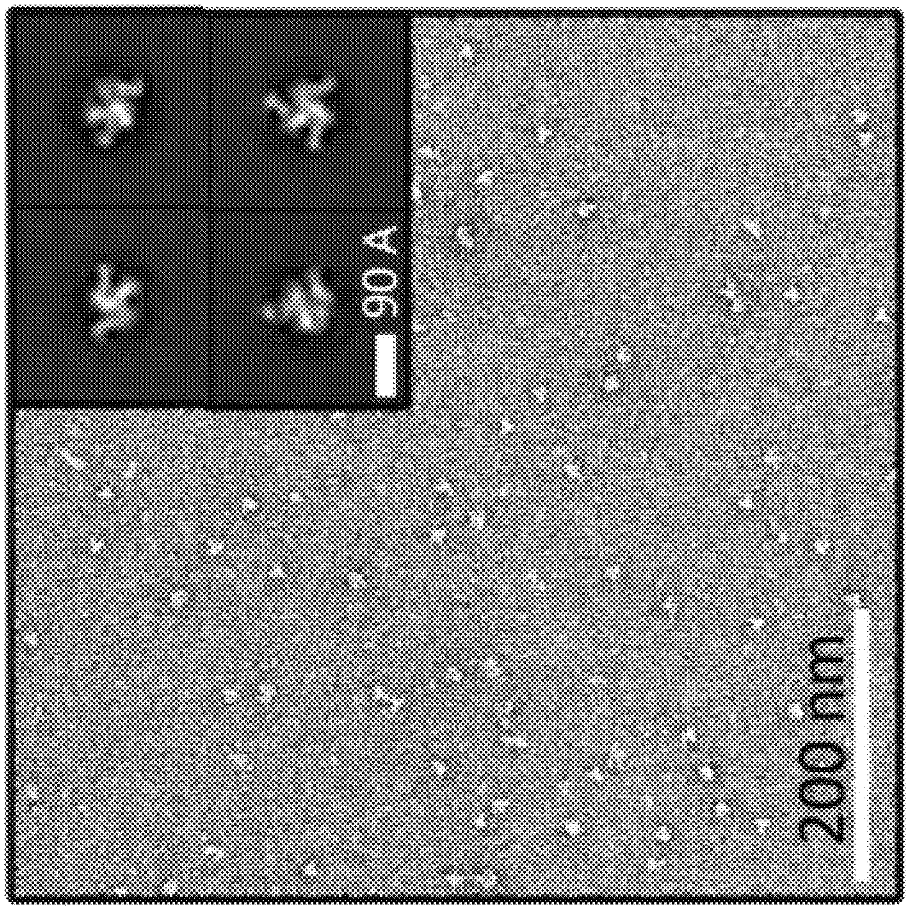
Figures 14D, 14E:
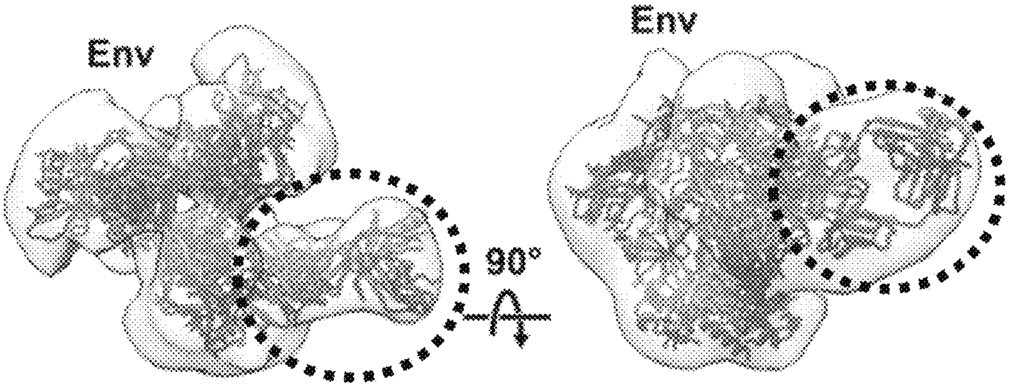

One of the 13 antibodies (MAb B-p1b5), displayed binding to the WT 426c DS257 SOSIP Env with an intact N276 glycan (FIG. 14A). The binding was confirmed using negative stain approaches, where 1-3 Fabs can be observed bound per trimer (FIG. 14C). Electron Microscopy (EM) negative stain 3D reconstruction of a 426c WT DS-SOSIP and B-p1b5 complex model that fits into the existing structure of 426c WT DS-SOSIP and glVRC01 in FIG. 14D (Borst et al., 2018. Elife 7). Weak binding of a second MAb, B-p2e2, was also observed to the WT 426c DS-SOSIP Env. Importantly, out of the four MAbs tested for neutralization, B-p1b5 neutralized the WT 426c virus (IC50 of 32.05 ug/ml) expressed in GnTI −/− cells (FIG. 14E). The human germline VRC01 MAb does not neutralize this virus suggesting that this mouse antibody is one step farther in the evolutionary pathway to VRC01. B-p1b5 also displays neutralizing activity against the heterologous tier 2 virus CH0505TF when produced in GnTI−/− cells, when the Loop D-associated 276 NLGS is absent (FIG. 17). The presence of V5 associated NLGS (positions 461/462) prevented B-p1b5 from neutralizing this virus. This position may not be glycosylated on the 426c virus (Borst et al., 2018. Elife 7). The neutralizing activity of B-p1b5 was abrogated by the D279K mutation, as is the case for known human VRC01-antibodies suggesting that B-p1b5 recognizes the Env gp120 subunit in a VRC01-like manner (Lynch et al., 2015. Journal Virology 89, 4201-4213). Thus, VRC01-like Abs isolated following the heterologous boost immunization have more mutations in their VH/VL domains and bind more efficiently to heterologous WT Core Envs than the antibodies isolated following the prime immunization with the 426c Core germline-targeting immunogen, and some also display autologous and heterologous tier 2 neutralizing activities.

Vaccine-elicited VRC01-like antibodies can avoid clashes with the N276-associated glycan. The results in the previous section suggested that the VRC01-like Abs isolated following the prime and boost immunization with 426c Core and H×B2 WT Core could more efficiently circumvent the steric hindrance imposed by the glycans at position N276 than those antibodies isolated following the prime immunization with the 'germline-targeting' 426c Core immunogen.

Figure 18A:
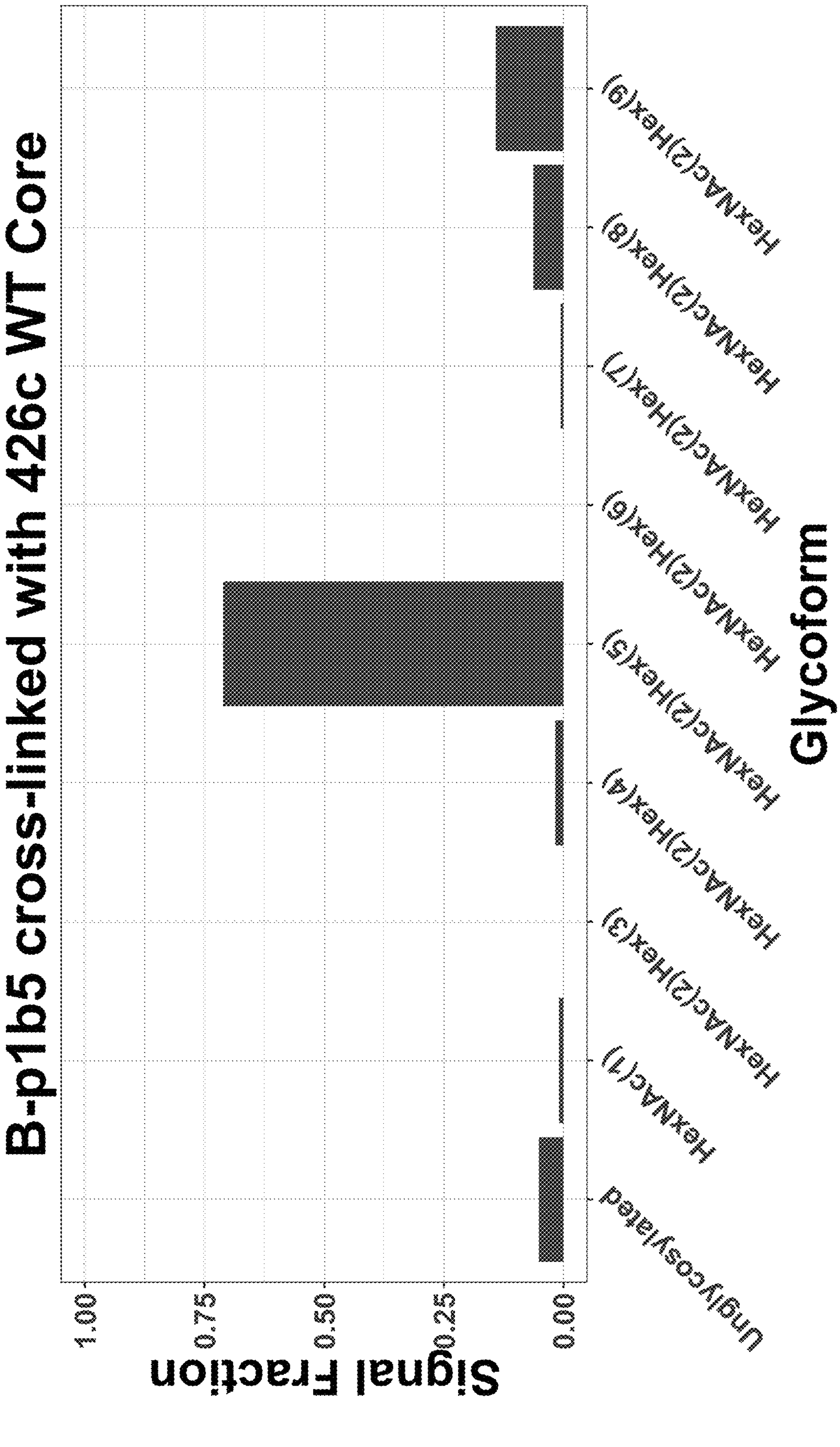
FIGS. 18A-18C. Vaccine elicited antibodies bind in to Env Core with glycans at N276. (18A) The 426c WT Core/B-p1b5 complex was generated in 293 GnTI−/− cells, purified and subjected to semi-quantitative LC-MS/MS analysis. Depicted here are the relative signal intensities of (glyco)peptides comprising the 276 NLGS. (18B) Binding of mAb 179NC75 to H×B2 WT Core or its derivative lacking the N276 NLGS ("H×B2 WT Core T278R"). (18C) Binding of the indicated mAbs to H×B2 WT Core that has been enriched for the glycan at 276 (eluted from a 179NC75 column) or the unenriched fraction.

To address this point directly, a series of complementary experiments were performed. In one experiment, B-p1b5 was co-expressed in GnTI−/− cells with the 426c WT Core (which expresses the N-X-S/T sequon at position N276) as a disulfide cross linked complex (Borst et al., 2018. Elife 7). The purified Ab-Env complex was further enzymatically treated with EndoH and Semi-quantitative mass spectrometry analysis of the 276 NLGS was performed (FIG. 18A). (N-linked mannose-5) Man-5 glycans were detected at position N276, confirming that B-p1b5 binds the 426c WT Core in the presence of N276-associated glycans and this interaction prevents the enzymatic activity of EndoH at that NLGS.

Figure 18B:
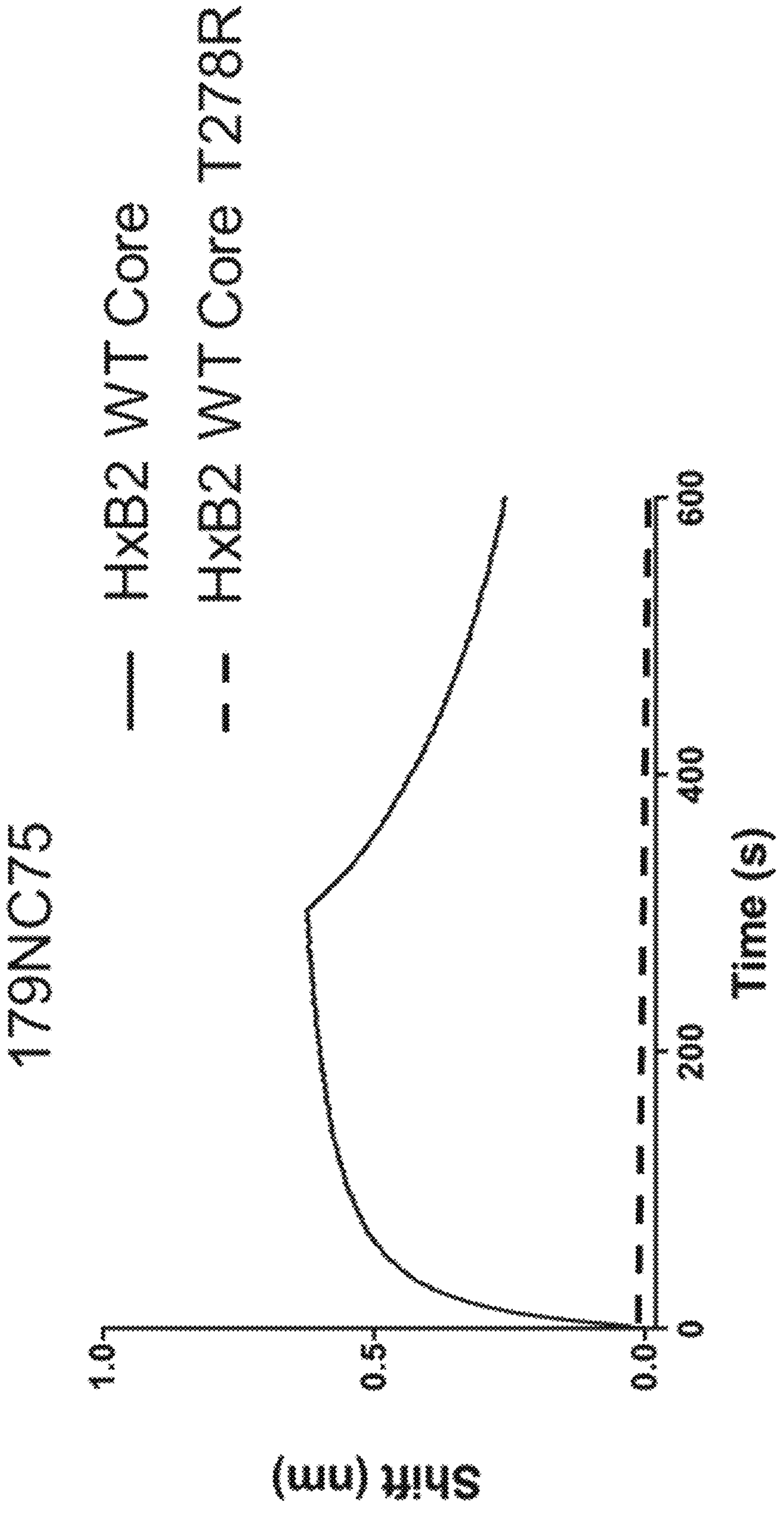
Figure 18C:
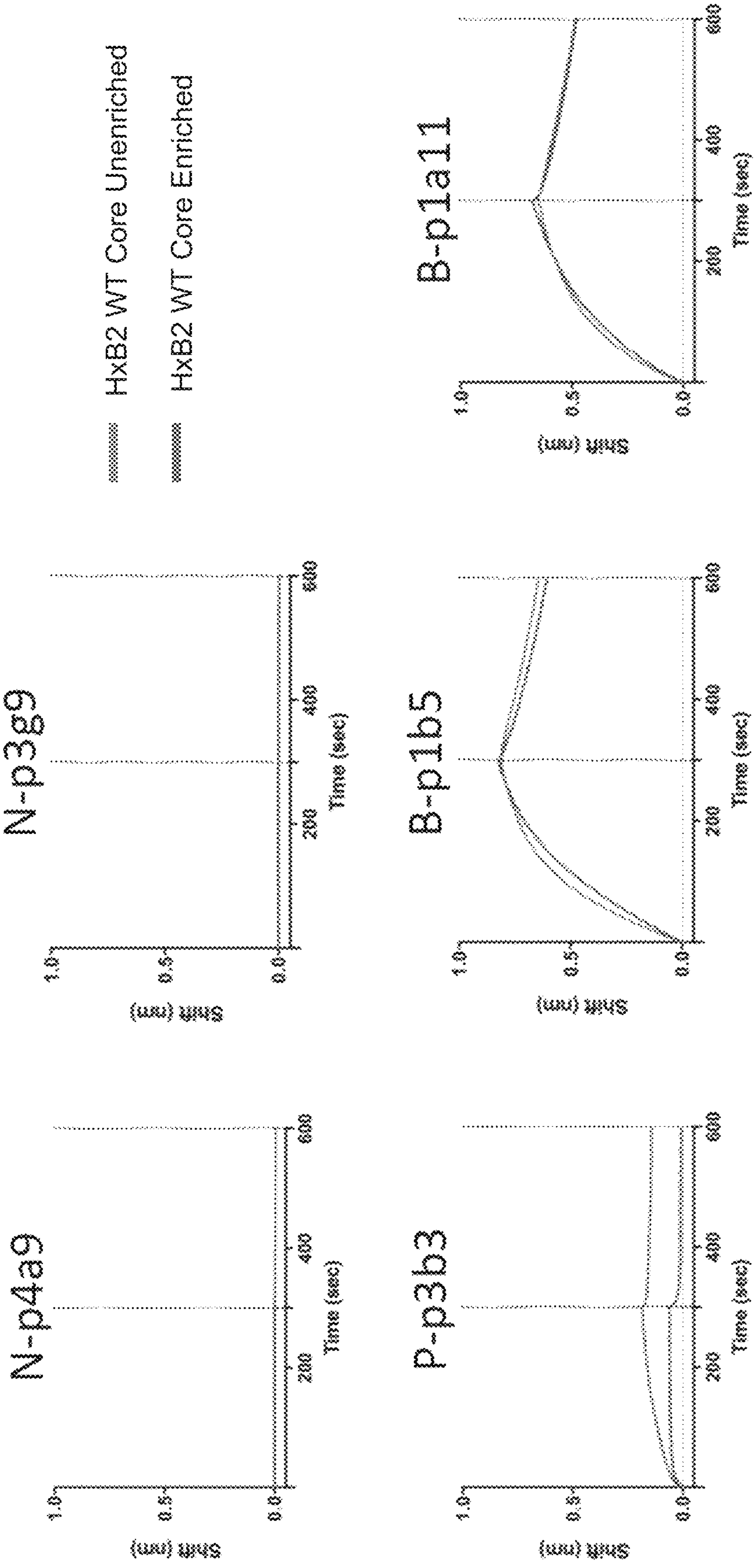

Additional experiments were performed to probe these interactions in the absence of disulfate crosslinking. In one such experiment, the 179NC75 N276-dependent mAb was used to purify the N276-glycosylated H×B2 WT Core Env (Freund et al., 2015. PLOS Pathogens, 11) (FIG. 18B). Purified monomeric H×B2 WT Core expressed in GnTI−/− cells was incubated with 179NC75 immobilized on magnetic beads and the bound Core molecules were eluted and tested for recognition by mouse VRC01 antibodies N-p4a9 and N-p3g9, isolated from unimmunized animals; P-p3b3, isolated following the prime immunization; and B-p1a11 and B-p1b5, isolated following the boost immunization. As expected, the antibodies isolated from unimmunized animals did not display H×B2 WT Core reactivity (FIG. 18C). P-p3b3 displayed marginal reactivity to H×B2 WT Core molecules expressing N276 glycans ("enriched") (FIG. 10E), while the two antibodies isolated after the boost, bound strongly to the H×B2 WT Core molecules expressing N276 glycans ("enriched") (FIG. 18C).

Figure 19A:
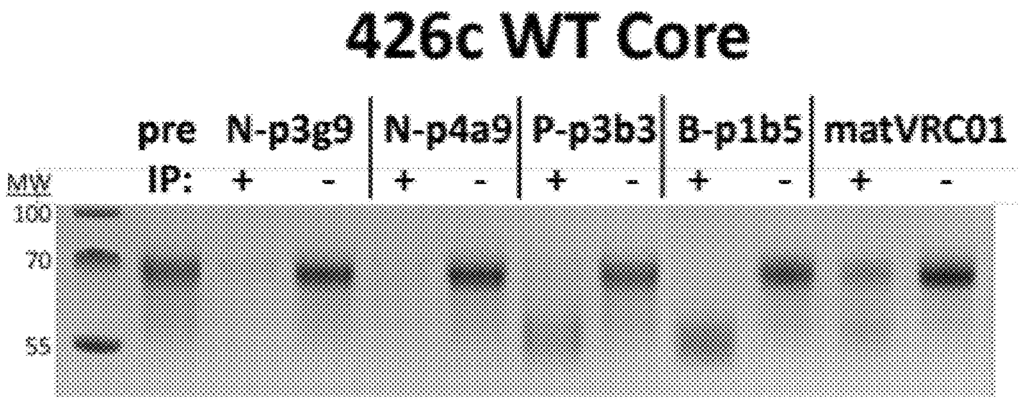
FIGS. 19A-19D. Immunoprecipitation of Env by bead-immobilized MAbs. MAbs generated from unimmunized animals (N-p3g9 and N-p4a9), from animals immunized with the 426c Core (P-p3b3), and from animals immunized with the 426c Core and the H×B2 WT Core (B-p1b5) were immobilized on beads. The beads were incubated with 426c WT Core or H×B2 WT Core proteins expressed in 293 GnTI−/− cells. Following co-immunoprecipitation, 426c WT Core (19A) and H×B2 WT Core (19B) were washed and eluted from the beads. (19A, 19B). A fraction of the unbound ("−") and the eluted ("+") material was subjected to SDS-PAGE gel electrophoresis. The eluted fractions were further subjected to semi-quantitative LC-MS/MS analysis to determine the presence of a glycan at position 276 on 426c WT Core (19C) and on H×B2 WT Core (19D). The quantity of material eluted from the beads after co-immunoprecipitation is shown in the middle of the pie charts which are scaled relative to the amount of material pulled-down with mature VRC01.
Figure 19B:
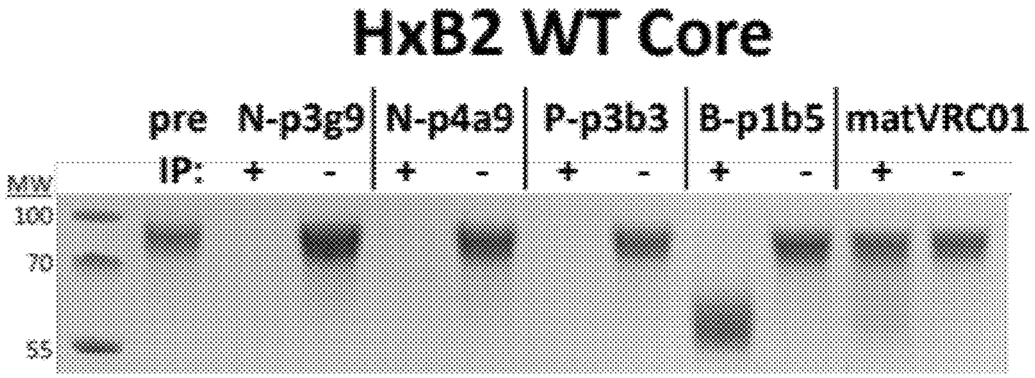
Figure 19C:
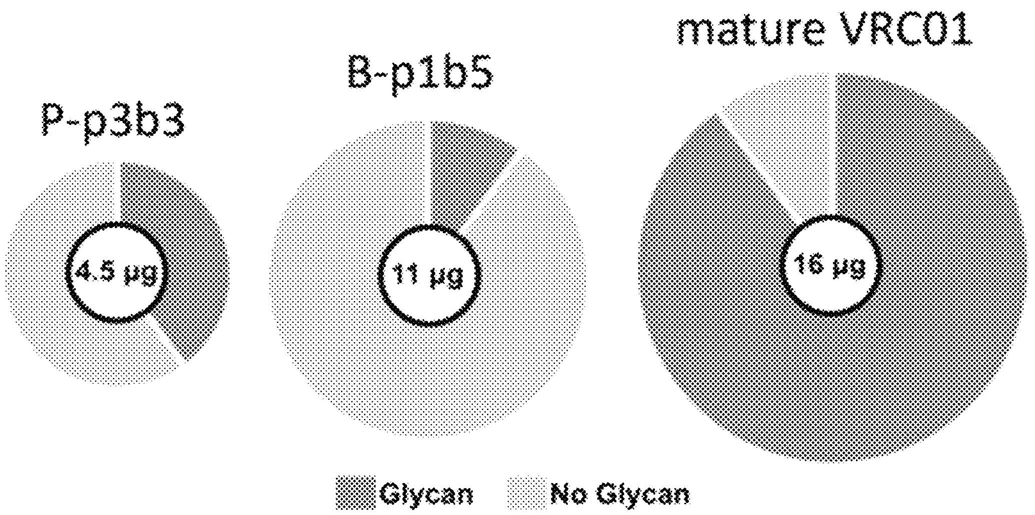
Figure 19D:
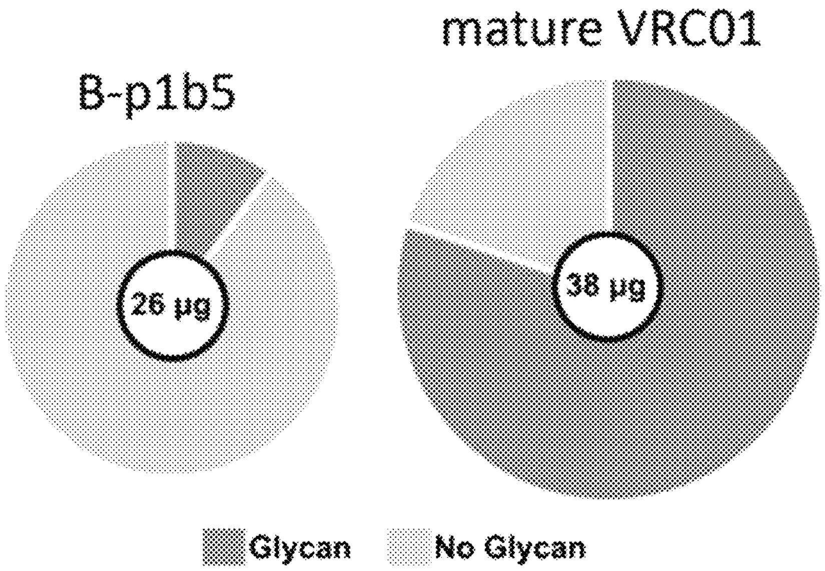

In another set of experiments, monomeric 426c WT Core and H×B2 WT Core proteins expressed in GnTI−/− cells were incubated with magnetic beads coated with the above-mentioned mouse VRC01-like antibodies. Following immunoprecipitation, the flow-through and eluted materials were subjected to gel electrophoresis (FIGS. 19A, 19B). As expected, neither 426c WT Core nor H×B2 WT Core proteins were immunoprecipitated by the N-p3g9 and N-p4a9 mAbs. 426c WT Core, but not H×B2 WT Core, was precipitated by P-p3b3. In contrast, both 426c WT Core and H×B2 WT Core were immunoprecipitated by B-p1b5. Semi-quantitative mass spectrometry analysis was performed to determine the presence of Man-5 glycans at position N276 in the immunoprecipitated material (FIGS. 19C, 19D). This analysis confirmed that the mouse VRC01-like antibodies isolated following the prime have the potential of recognizing 426c WT Core molecules expressing N276-associated glycans and that the antibodies isolated following the boost have the potential of recognizing both the 426c WT Core and H×B2 WT Core in the presence of N276 glycans. These antibodies preferentially immunoprecipitated Env molecules lacking the N276-associated glycans, a consequence of not yet being in a fully matured form following the prime-boost immunization scheme.

Collectively, the results confirm that the VRC01-like antibodies isolated following the boost immunization can accommodate N276-associated glycans.

Materials and Methods. Protein expression and purification. Recombinant Env proteins expressed in nanoparticle (Ferritin or C4b-based) and NFL forms were expressed and purified as previously described (Guenaga et al., 2015. Journal of Virology. 90, 2806-2817; McGuire et al., 2016. Nature Communications 7, 10618). Briefly, Envs were produced in 293E or 293F cells. Cell supernatants were purified by lectin affinity chromatography (*Galanthus nivalis*, Vector Labs), then subjected to Superdex 200 size exclusion chromatography (GE Healthcare). Ferritin nanoparticles underwent two rounds of size exclusion chromatography, first on a Superose 6 10/300GL column and then on a HiLoad 16/600 Superdex 200 pg column.

Soluble trimeric SOSIP-based Envs were expressed and purified as previously described (Borst et al., 2018. Elife 7). In short, Env-expressing and furin-expressing plasmids were co-transfected (at 5:1 DNA ratio) into 293E cells. The Envs were purified from the cell supernatants using a Ni-affinity column followed by a Streptactin affinity column. Proteins were then subjected to enzymatic cleavage to remove the his-tag.

Monomeric proteins were produced by transfecting 293E or GnTI−/− cells with Env encoding plasmid. Cells were cultured for 6 days at 37° C., 5% $CO_2$, 80% humidity, and shaking at 125 RPM. Cells were centrifuged at 3000 RPM for 30 minutes and the supernatant sterile filtered through at 0.22 uM filter. Protein was purified by passing the cellular supernatant over a 5 ml Fast Flow HisTrap column (Fisher Sci, Cat #45000326). The eluted protein was purified on size exclusion chromotagraphy as described above.

Core CD4-BS KO Env constructs contain the D368R and E370A mutations, while the eOD-GT8 KO contains the D368R mutation and the amino acids at positions 276-279 have been mutated to "NFTA".

Flow cytometry. Spleen and LN samples were thawed in a 37° C. water bath until a small ice pellet remained in the tube and warm RPMI was then added dropwise. B cells were isolated using a mouse B cell isolation kit (EasySep, Cat #: 19854). If the antigen-specific cells were infrequent, an antigen enrichment protocol was used during which tetramers and decoys were first added to the cells and then anti-PE microbeads (Miltenyi Biotech Cat #: 130-048-801) and anti-APC microbeads (Miltenyi Biotech Cat #: 130-090-855) were added. Stained cells were then flowed over Large Separation (LS) Columns (Miltenyi Biotec Cat #: 130-042-401) to separate the antigen-specific cells from the non-antigen specific cells. The B cells were then stained with a combination of the following antibodies: IgG1 FITC (BD Biosciences Cat #: 553443), IgG2b FITC (BD Biosciences Cat #: 553395), IgG2c FITC (Bio-Rad Cat #: STAR135F), IgG3 FITC (BD Biosciences Cat #: 553403), IgD PerCP-Cy5.5 (Biolegend Cat #: 405710), GL7 eFluor 450 (Affymetrix Cat #: 48-5902-80), Fixable viability stain BV510 (Affymetrix Cat #: 65-0866-14), CD3 BV510 (BD Biosceinces Ct #: 564024), CD4 BV510 (BD Biosciences Cat #: 563106), Ly-6G/Ly-6C BV510 (BD Biosciences Cat #:563040), F4/80 BV510 (BD Biosciences Cat #: 123135), IgM BV605 (Biolegend Cat #:406523), B220 BV786 (BD Bioscience Cat #: 563894), CD38 AF700 (Affymetrix Cat #: 56-0381-82), CD19 BUV395 (BD Biosciences Cat #: 563557) or CD19 BV650 (BD Bioscience Cat #: 563235). The cells were stained with either 426c DMRS Core/426c DMRS DREA (D368R and E279A) Core or eOD-GT8/eOD-GT8 KO tetramers to select for Env specific and CD4-BS specific B cells. Tetramers were made by combining biotinylated Env with Streptavidin conjugated to either a PE or APC fluorophore (Prozyme, PJFS25 and PJ27S). From the groups of immunized mice, only samples from animals which showed eOD-GT8 plasma cross-reactivity were used for sorting.

Single B cell sorting. Naïve, antigen-specific B cells were sorted as CD3−, CD4−, Gr-1−, F4/80−, B220+, CD19+, antigen+/antigen KO−. Class-switched IgG B cells from immunized animals were sorted based on the following markers: CD3−, CD4−, Gr-1−, F4/80−, B220+, CD19+, IgG1+, IgG2b+, IgG2c+, IgG3+, antigen+/antigen KO−. Individual B cells were sorted using the FACS ARIA II into a 96 well plate containing 20 μl of lysis buffer (20 U of RNAse out (Thermofisher, Cat #: 10777-019), 5 μl 5×Superscript IV RT buffer, 1.25 μl of 0.1M DTT, 0.625 μl of 10% Igepal, 13 μl nuclease free $H_2O$) in each well. Plates with the sorted cells were stored at −80° C. until further processing.

PCR amplification and sequencing of VH and VL genes. RNA was reverse transcribed to cDNA. For the reverse transcription reaction, 0.1 μl of Random Primers (3 μg/μl, Thermofisher Cat #: 48190011), 2 μl 10 mM GeneAmp dNTP Blend (Thermofisher, Cat #: N8080261), 1 μl SuperScript IV RT (200 U, Thermofisher Cat #: 18090200), and 2.9 μl of nuclease free $H_2O$ was added to the wells containing lysed cells. The reaction was run on a thermocycler for 10 minutes at 42° C., 10 minutes at 25° C., 60 minutes at 50° C., and 5 min at 94° C. Following reverse transcription, the cDNA was diluted 1:2. Two rounds of PCR were employed to amplify both VH and VL genes. Each PCR reaction contains: 7 μl of cDNA, 2.4 units of HotStar Taq Plus (Qiagen, Cat #: 203607), 240 nM of 5' and 3' primer, 350 UM GeneAmp dNTP Blend (Thermofisher, Cat #: N8080261), 4 μl of 10×buffer, and 27.8 μl nuclease free $H_2O$. All primers and cycling conditions can be found in FIG. 20 and FIG. 21. After the second round of PCR, samples were subjected to electrophoresis on a 1.5% agarose gel containing 0.1% Gel Red Nucleic Acid Stain (Biotium, Cat #: 41002). cDNA was purified using the enzyme ExoSap905 IT (Affymetrix, Cat #: 78201). The purification reaction contained 5 μl of second round PCR product and 2 μl of ExoSap-IT (ThermoFisher). This reaction was run on a thermocycler for 15 min at 37° C. followed by 15 min at 80° C. Following enzymatic purification, 5 μl of 5 uM second round 5' primer was added to the sample and 3 μl of nuclease free water. Samples underwent Sanger sequencing to identify the DNA sequence (Genewiz, Seattle, WA). Upon receiving the sequence, IMGT/V-QUEST was used to assign V, D, and J gene identity to the sequences (Giudicelli et al., 2011. Cold Spring Harbor Protocols 2011, pdb.prot5633-pdb.prot5633).

Amino acid mutations were identified by aligning the VH/VL gene sequences to the corresponding germline genes (IMGT Repertoire) using the Geneious Software (Version 8.1.9). For VL, mutations were counted beginning at the 5' end of the V-gene to the 3' end of the FW3. For VH, mutations were counted beginning at the 5' end of the V-gene to the end of the KI gene. To quantify the number of amino acid mutations, the sequence alignments were exported from Geneious and imported into R Studio (Version 1.0.153) for analysis. This analysis uses the packages Biostrings (Pagès et al., 2017. Biostrings), seqinr (Charif and Lobry, 2007. Seqinr) and tidyverse (Wickham, 2017. tidyverse).

VH and VL cloning and antibody expression. Gene-specific PCR was used to amplify the DNA product from the first round PCR using primers designed to anneal to the gene of interest as well as add ligation sites to facilitate insertion of the DNA fragment into the human IgG1 vector [ptt3 k for kappa (Snijder et al., 2018. Immunity 48, 799-811.e9), and PMN 4-341 for gamma (Mouquet et al., 2010. Nature 467, 582 591-595)]. Each gene specific PCR reaction contained 0.5 μl each of 10 μM 5' and 3' primer, 22.5 μl Accuprime Pfx Supermix (Cat #: 12344040), and 1.5 μl of 1st or 2nd 928 round PCR product. The gene-specific PCR product was infused into the cut IgG1 vector in a reaction containing 12.5 ng of cut vector, 50 ng of insert, 0.5 μl of 5× Infusion enzyme (InFusion HD Cloning Kit, Cat #: 639649), and nuclease-free water to bring the volume to 2.5 μl. The entire reaction was used to transform competent *E. coli* cells and plated on agar plates containing ampicillin. In some cases, gBlocks were synthesized to make the VH or VL containing plasmid (GenScript). 60 ng of gBlock was added to 15 ng of cut vector and 0.5 μl of 5× In-Fusion enzyme (Takara, Cat #: 1805251A). This reaction was run on the thermocycler for 15 min at 50° C. The entire reaction was used to transform competent *E. coli* cells (New England Biolabs, Cat #: C2987HI) and plated on agar plates containing ampicillin. Once a colony containing the insert sequence was identified, it was grown in Luria-Bertani (LB) broth containing ampicillin. DNA was prepared using QIAprep Spin Miniprep Kit (Qiagen, Cat #: 27106). Equal amounts of heavy and light chain DNA and 293F transfection reagent (Millipore Sigma, Cat #: 72181) were used to transfect 293E cells. 5-7 days post transfection, cell supernatants were collected, and the antibodies were purified using Pierce Protein A agarose beads (ThermoFisher, Cat #: 20334). The antibodies were eluted using 0.1 M Citric Acid into a tube containing 1 M Tris. The antibodies were buffer exchanged into 1XPBS using an amicon centrifugal filter.

To make Fabs, the IgG was cleaved overnight at 37° C. to generate antigen binding fragment (Fab) with Endoproteinase Lys-C(NEB). To remove undigested IgG and IgG Fc fragments, the mixture was incubated with Protein A Agarose Resin for 1 hour at room temperature. Beads were washed with 1×PBS to remove excess Fab. Fab was further purified on SEC using a HiLoad 16/600 Superdex 200 pg (GE) column.

Protein production for structural studies. P-p1f1Fab and eOD-GT8. eOD-GT8 was expressed in human embryonic kidney 293 cells (HEK293S) GnTI−/− cells. Cells were cultured in suspension and transfected using 500 μg eOD-GT8 plasmid with 293 Free Transfection Reagent (Novagen) in 1 L. After 6 days, cells were centrifuged at 4,500 rpm for 20 min and supernatant was filter-sterilized. A His-tag was utilized for purification by adding His60 Ni957 Superflow Resin (Takara, Cat #:636660) in the supernatant at 4° C. overnight. Ni Resin was washed with a solution of 150 mM NaCl, 20 mM Tris pH 8.0, 20 mM Imidazole pH 7.0 and eluted with a solution of 300 mM NaCl, 50 mM Tris pH 8.0, 250 mM Imidazole pH 7.0. Protein was further purified using SEC as previously described. Complexes of eOD-GT8 and P-p1f1Fab were made by mixing equal molar ratio of both proteins for 1 hour at room temperature. Complexes were then mixed with EndoH (NEB, Cat #: P0702S) for 1 hour at 37° C. SEC was used to remove any uncomplexed protein and EndoH. Complexes were concentrated to 10 mgs/mL for crystallization trials.

P-p3b3Fab and 426c Core. P-p3b3Fab crosslinked to 426c Core was expressed in HEK293S GnTI−/− cells. Cells were cultured in suspension and transfected with equal parts of 426c Core G459C, P968 p3b3Fab-A60C heavy chain, and P-p3b3 light chain plasmids (500 μg total/L) as previously described (Borst et al., 2018. Elife 7). Complexes were purified with a His tag on the Fab heavy chain C-terminus followed by SEC to remove nonspecific proteins and excess unliganded Fab. An SDS gel was run on the complex to confirm the disulfide bond formation between the P-p3b3fab and the 426c Core. Complexes were treated with EndoH (New England Biolabs, Cat #: P0702S) for 1 hr at 37° C. and run on SEC to remove EndoH. Complexes were concentrated to 10 mgs/mL for crystallization trials.

Crystallization. Crystallization conditions were screened and monitored with an NT8 drop setter and Rock Imager (Formulatrix). Screening was done with Rigaku Wizard Precipitant Synergy block no. 2 (MD15-PS-B), Molecular Dimensions Proplex screen HT-96 (MD1-38), and Hampton Research Crystal Screen HT (HR2-130) using the sitting drop vapor diffusion method. P-p1f1fab+eOD-GT8 crystals were further optimized with hanging drop trays using the vapor diffusion method. Final crystals for P-p1f1fab+eODGT8 were grown in 22.5% PEG 3350, 13.5% Isopropanol, and 0.18M Ammonium Citrate pH 4.0. Final crystals for P-p3b3fab+426c Core were grown in 0.67% polyethylene glycol 4000, and 0.67M Ammonium Citrate, pH 5.5. P-p1f1fab+eODGT8 crystal were cryo protected in a solution of 20% molar excess of the crystallization condition and 20% Ethylene Glycol. P-p3b3fab+426c Core were cryoprotected in the original crystallization condition. P3b3fab+426c and P-p1f1fab+eODGT8 were sent to ALS 5.0.2 and diffraction data was collected to 3.59 Å and 3.2 Å respectively. Data was processed using HKL2000 (Otwinowski and Minor, 1997. Enzymology 276, 307-326).

Structure solution and refinement. The structure of P-p1f1Fab+eOD-GT8 was solved by molecular replacement using PDB ID: 4JPK as a search model in Phaser in Phenix. The structure of P-p3b3Fab+426c Core was solved by molecular replacement using PDB ID: 6MFT as a search. The structures were further refined with COOT (Emsley and Cowtan, 2004. Crystallography. 60, 2126-2132) and Phenix (Adams et al., 2004. Journal of Synchrotron Radiation). The refinement statistics are summarized in FIG. 9.

Negative-stain electron microscopy. The 426c WT DS-SOSIP/P1B5 complex was formed by co-incubating P1B5 Fab to 426c WT DS-SOSIP trimer at a 2:1 ratio at 10 minutes at 4° C. Samples treated with glutaraldehyde were cross-linked in 0.25% GTA for 45 seconds followed by quenching with 1M Tris, followed by purification of bound complexes via a Superdex 200 10/300 GL Increase column. Examined 426c WT DS-SOSIP/P1B5 Fab complexes (3 μL) were negatively stained at a final concentration of 0.010 mg/mL using Gilder Grids overlaid with a thin layer of carbon and 2% uranyl formate (Electron Microscopy Sciences, Cat #: 22451) as previously described (Veesler et al., 2014. Proceedings of the National Academy of Sciences of the United States of America 111, 8815-8819). Data was collected on an FEI Technai 12 Spirit 120 kV electron microscope equipped with a Gatan Ultrascan 4000 CCD camera. A total of 300 images were collected per sample by using a random defocus range of 1.1-2.0 μm with a total exposure of 45 e-/A2. Data was automatically acquired using Leginon (Suloway et al., 2005. Journal of Structural Biology 151, 41-60), and data processing was carried out using Appion (Lander et al., 2009. Journal of Structural Biology 166-95-102). The parameters of the contrast transfer function (CTF) were estimated using CTFFIND4 (Mindell and Grigorieff, 2003. Journal of Structural Biology 142, 334-347), and particles were picked in a reference-free manner using DoG picker (Voss et al., 2009. Journal of Structural Biology 166, 205-213). Particles were extracted with a binning factor of 2 after correcting for the effect of the CTF by flipping the phases of each micrograph with EMAN 1.9 (Ludtke et al., 1999. Journal of Structural Biology 128, 82-97). The GTA cross-linked 426c WT DS-SOSIP P1B5 Fab stack was pre-processed in RELION/2.1 (Kimanius et al., 2016. eLife 5, 1-21; Scheres, 2012. Journal of Structural Biology 180, 519-530; Scheres 2012. Journal of Molecular Biology 415, 406-418) with an additional binning factor of 2 applied, resulting in a final pixel size of 6.4 Å. Resulting particles were sorted by reference-free 2D classification over 25 iterations. The best particles were chosen for 3D classification into 2 classes using C1 symmetry in RELION/2.1 (Kimanius et al., 2016. eLife 5, 1-21). The best class of particles were refined using RELION/3.0 (Zivanov et al., 2018. eLife 7).

Biolayer Interferometry (BLI). Antibody binding to recombinant Env proteins was determined using BLI on the Octet Red 96 (ForteBio, Inc, Menlo Park, CA), as previously described (Yacoob et al., 2016. Cell Reports 17, 1560-1570). Briefly, anti-human Fc capture biosensors (ForteBio, Cat #: 18-5063) were activated by immersion into 1× Kinetics Buffer (1× PBS, 0.1% BSA, 0.02% Tween-20, 0.005% NaN3) for 10 minutes. Antibodies were loaded onto an anti-human Fc capture probe at 20 μg/ml. The probes were then dipped into solutions containing recombinant Env: 2 uM for monomeric gp120-derived Envs or 1 uM for trimeric Env (SOSIP or NFL designs). Parameters for all BLI assays were: 30 seconds of baseline measurement, 240 seconds to load the antibody onto the anti-human Fc capture probe, 60 seconds of baseline measurement, 300 seconds of association, 300 seconds of dissociation. All measurements of Env-Ab binding were corrected by subtracting the background signal obtained from env traces generated with an irrelevant negative control IgG.

Kinetic analyses were performed by BLI as described above using recombinant Fabs loaded onto FAB2G biosensors (ForteBio, Cat #: 18-5126) (at 40 μg/in 1XPBS) and 2-fold dilutions of envelope monomers (ranging from 50 uM-391 nM), and by extending the dissociation phase of binding to 600 seconds. Curve fitting to determine relative apparent antibody affinities for envelope was performed using a 1:1 binding model and the data analysis software (ForteBio). Mean $k_{on}$, $k_{off}$, and KD values were determined by averaging all binding curves within a dilution series having $R^2$ values of greater than 95% confidence level.

Enzyme linked immunosorbent assays. Plasma samples were heat-inactivated at 56° C. for 1 hour, centrifuged at 13000 RPM for 10 min and stored at 4° C. or −20° C. ELISAs were performed in either a 96 well or 384 well plate format. For a 384 well plate ELISA, 30 μl of protein at 0.1 μM in coating buffer (0.1M sodium bicarbonate, pH: 9.4-9.6) was added to each well and incubated a room temperature overnight. Plates were washed 4× with ELISA wash buffer (1XPBS+0.2% Tween®-20). 80 μl of blocking buffer (1×PBS+10% non-fat milk+0.03% Tween®-20) was added to the plates and they were incubated at 37° C. for 1-2 hours. Plates were then washed 4× with ELISA wash buffer. Plasma was diluted 1:10 in blocking buffer and diluted 1:3 across or down the plate. His tag control started at 1 mg/ml. The plates were incubated for 1 hour at 37° C. The plates were washed 4× with ELISA wash buffer. 30 μl of secondary antibody was added to each well. The plates were incubated for an hour at 37° C. Plates were washed 4× with ELISA wash buffer. Following washing 30 μl of SureBlue Reserve TMB Microwell Peroxidase Substrate: KPL (Cat #: 53-00-02) was added to each well. The plates were incubated for 5 minutes at room temperature. 30 μl of 1N $H_2SO_4$ was added to each well. Plates were read immediately on the SpectraMax M2 microplate reader (Molecular Devices) at 450 nm. Blank wells were used to subtract the background signal in the analysis. 96 well plate ELISAs followed a similar protocol but used 50 μl of volume for the coating of protein, dilution volumes, secondary antibody volume, and development steps. 120 μl of blocking buffer was used to block the plates.

Neutralization assays. Neutralizing antibody activity was measured in 96-well culture plates by using Tat1064 regulated luciferase (Luc) reporter gene expression to quantify reductions in virus infection in TZM-bl cells. TZM-bl cells were obtained from the NIH AIDS Research and Reference Reagent Program, as contributed by John Kappes and Xiaoyun Wu. Assays were performed with HIV-1 Env-pseudotyped viruses as described previously (Montefiori, 2009. Methods in Molecular Biology 485, 395-405). For the assays, purified mouse IgG or monoclonal antibodies (mAbs) were used at 100 μg/ml or the highest concentration possible and test sera were diluted 1:20 using cell culture medium. Samples were then diluted over seven 3-fold dilutions and preincubated with virus (150,000 relative light unit equivalents) for 1 hr at 37° C. before addition of cells. Following an additional 48 hr incubation, cells were lysed and Luc activity determined using a microtiter plate luminometer and BriteLite Plus Reagent (Perkin Elmer, Cat #: 6066766). Neutralization titers are the antibody concentration at which relative luminescence units (RLU) were reduced by 50% compared to RLU in virus control wells after subtraction of background RLU in cell control wells. Serum samples were heat-inactivated at 56° C. for 15 minutes prior to assay.

Immunoprecipitation. Purified recombinant IgGs were covalently coupled to MyOne Tosylactivated Dynabeads (Life Technologies, Cat #: 65501). Coupling and Env-immunoprecipitation were carried out according to the manufacturer's protocol. Briefly, 5 mg of Env produced in HEK293S GnTI 1082 −/−were incubated with 200 μg of IgG-beads for 30 min. The IgG-Env protein complexes were then precipitated using magnetic separation and washed 3-4×before performing acidic elution and PH neutralization of the bound material. Env-samples of the original input of 426c WT Core or H×B2 WT Core, and bead-bound/eluted and unbound fractions were subjected to sodium dodecyl sulfate (SDS) polyacrylamide gel electrophoresis under reducing conditions. A sample of the bound fractions were subjected to Liquid Chromatography with tandem mass spectrometry (LC-MS/MS) analysis or used for BLI.

Mass spectrometry. For analysis of the N-linked glycosylation profile of the cross-linked 426c WT Core-P1B5 complex, 250 pmol of sample was denatured, reduced, and alkylated by dilution to 5 μM in 50 μL of buffer containing 100 mM Tris (pH 8.5), 10 mM Tris (2-carboxyethylphosphine (TCEP), 40 mM iodoacetamide or 40 mM iodoacetic acid, and 2% (wt/vol) sodium deoxycholate. Samples were first heated to 95° C. for 5 min and then incubated for an additional 25 min at room temperature in the dark. The samples were digested with trypsin (ThermoFisher Scientific, Cat #: 90057), by diluting 20 μL of sample to a total volume of 100 UL of buffer containing 50 mM ammonium bicarbonate (pH 8.5). Trypsin was added in a ratio of 1:50 (w/w) before incubation at 37° C. overnight. Subsequently, 2 μL of formic acid was added to precipitate the sodium deoxycholate from the solution. Following centrifugation at 17,000×g for 25 min, 85 μL of the supernatant was collected and centrifuged again at 17,000×g for 5 min to ensure removal of any residual precipitated deoxycholate. 80 μL of this supernatant was collected. For each sample, 8 μL was injected on a Thermo Scientific Orbitrap Fusion Tribrid mass spectrometer. A 35 cm analytical column and a 3 cm trap column filled with ReproSil-Pur C18AQ 5 μM beads were used. Nanospray LC-MS/MS was used to separate peptides over a 90 minute gradient from 5% to 30% acetonitrile with 0.1% formic acid. A positive spray voltage of 2100 was used with an ion transfer tube temperature of 350° C. An electron-transfer/higher-energy collision dissociation ion-fragmentation scheme (Frese et al., 2013. Journal of Proteome Research 12, 1520-1525) was used with calibrated charge-dependent entity-type definition parameters and supplemental higher-energy collision dissociation energy of 0.15. A resolution setting of 120,000 with an automatic gain control target of $2\times10^5$ was used for MS1, and a resolution setting of 30,000 with an AGC target of $1\times10^5$ was used for MS2. Data was searched with the Protein Metrics Byonic software (Bern et al., 2012. Current Protocols in Bioinformatics Chapter 13), using a small custom database of recombinant protein sequences including the proteases used to prepare the glycopeptides. Reverse decoy sequences were also included in the search. Specificity of the search was set to C-terminal cleavage at R/K (trypsin), allowing up to three missed cleavages, with EthcD fragmentation (b/y- and c/z-type ions). A precursor mass and product mass tolerance of 12 ppm and 24 ppm were used, respectively. Carbamidomethylation of cysteines was set as fixed modification, carbamidomethylation of lysines was set as a variable modification, methionine oxidation as variable modification, and a concatenated N-linked glycan database (derived from the four software-included databases) was used to identify glycopeptides. All analyzed glycopeptide hits were manually inspected to ensure their quality and accuracy.

Semi-quantitative LC-MS/MS of P-p3b3, B-p1b5 and VRC01-immunoprecipitation experiments were performed using Skyline (MacLean et al., 2010. Bioinformatics 26, 966-968) with peak integration and LC-MS/MS searches imported from Byonic, as previously described (Borst et al., 2018. Elife 7). Missed cleavages and post-translational modifications listed above for qualitative LC-MS/MS searches were included in the quantification of glycopeptides. All MS1 peak areas used for integration were manually inspected. Each fraction was performed as part of two technical replicates and was subsequently averaged. Calculations and plots for glycoform enrichment graphs were generated by subtracting the relative signal values of the input Core fraction from the unbound or bound Core fractions.

Quantification and statistical methods. Mean and standard deviations were calculated using R Studio. Statistical analyses were calculated using R Studio and GraphPad Prism. Descriptions of the statistical methods used for each data set are described in the figure legends. The tidyverse packages (Wickham, 2017. tidyverse) were used in R Studio to manipulate data and create graphs in addition to GraphPad Prism.

Data Software and Availability. The sequences of monoclonal antibodies reported here have been deposited on GenBank, Accession numbers: MN087228-MN087315 and in the GitHub repository. Multimeric and monomeric heterologous Env sequences have been deposited under GenBank, Accession numbers: MN179660-MN179671. Coordinates and structure factors are in the process of being deposited in the Protein Data Bank. The mass spec data was uploaded to the PRIDE database with the accompanying accession number PXD015168.

Discussion A major challenge to the successful maturation of the germline forms of VRC01 antibodies towards their broadly neutralizing forms is the steric hindrance imposed by glycan molecules present on the conserved Loop D 276 NLGS. As the present germline targeting Env-based immunogens are designed to specifically lack the 276 NLGS (Jardine et al., 2013. Science 340, 711-716; Jardine et al., 2015. Science 349, 156-161; McGuire et al., 2013. Journal of Experimental Medicine 210, 655-663; McGuire et al., 2014. Science 346, 1380-1383, McGuire et al., 2016. Nature Communications 7, 10618; Medina-Ramírez et al., 2017. Journal of Experimental Medicine 214, 2573-2590), they are expected to preferentially activate BCRs that recognize the VRC01 epitope when N276-associated glycans are absent. Efforts to guide the maturation of such antibodies through the sequential immunization with Env constructs also lacking 276 NLGS have so far met limited success (Briney et al., 2016. Cell 166, 1459-1470; Tian et al., 2016. Cell 166, 1471-1484.e18).

Herein, an alternative immunization scheme was tested, during which the prime immunization with the 426c Core germline-targeting immunogen is directly followed by an immunization with a heterologous Core that expresses N276-associated glycans. This scheme was selected because it was observed that a fraction of the VRC01-like antibodies elicited by the 426c Core immunogen display weak binding to heterologous Cores with N276 glycans. Indeed, the boost immunization improved the ability of the elicited VRC01-like antibodies to bypass the N276-associated glycans. These observations are in agreement with reports by Escolano et al., where germline PGT121 B cell receptors were activated upon immunization with very low affinity Env-derived immunogen (Escolano et al., 2016. Cell 166, 1445-1458.e12.; Escolano et al., 2019. Nature).

The 426c Core immunogen selects for VRC01-like antibodies with key features. The H35N mutation in the CDRH1 domain leads to an increased stability between the CDRH1 and CDRH3 domains of the HC, whereas the selection of the Glu96LC allows for the formation of a hydrogen bond with Gly459gp 120 at the N-terminus of the V5 region (West et al., 2012. Proceedings of the National Academy of Sciences of the United States of America 109, E2083-2090; Zhou et al., 2013. Immunity 39, 245-258). These data indicate that within the five amino acid long CDRL3 domains, the presence of Glu96LC appears to be important for the antibody interactions with autologous and heterologous Core proteins. LCs with five amino acid long CDRL3s are identifiable from naïve B cells in this mouse model. However light chains with five amino acid long CDRL3 containing a Glu96LC in the BCR repertoire analysis of naive B cells from the unimmunized mice have not yet been identified. Either these LCs are present at extremely low frequencies and the present germline-targeting immunogen selects for them, or Glu96LC is the result of somatic hypermutation and subsequent selection in the germinal center following immunization with the 426c Core immunogen.

As compared to the rest of the VL domains, the CDRL1 regions appear to be under intense selective pressure to accumulate negatively charged amino acids (FIG. 7B). For instance, in most sequences, Lys30LC is replaced by a glutamic acid and additional negatively charged amino acids (Asp or Glu) are also introduced in that same general region of CDRL1. Although it was confirmed that the mouse VRC01-like antibodies elicited by the vaccination strategy recognize the VRC01 epitope in the presence of N276-associated glycans, the disordered CDRL1 structures provide some question into exactly how the introduction of negatively charged amino acids allow these LCs to accommodate these glycans. Affinity maturation of the antibodies outside of the CDRL1 region may have compensated for the entropic cost of binding in the presence of the N276-associated glycan as has been observed in the VRC08 antibody lineage, which has a long rigid CDRL1 (Bonsignori et al., 2018. Immunity 49, 1162-1174.e8). VRC01-like antibodies that do not express k8-30*01 derived VL domains were also isolated after the prime immunization (FIG. 7B). VRC01-like antibodies that do not express k8-30*01derived VL domains were also isolated after the prime immunization (FIG. 7B). These express shorter CDRL1 domains ($10^{-11}$ amino acids), but in contrast to the k8-30*01 expressing antibodies, they were not mutated from germline, nor did they contain Glu96. So far, the neutralizing activities of mAbs isolated following the prime-boost immunization are evident against the 426c-derived virus lacking the 276 NLGS and against the heterologous CH0505TF-derived virus that not only lacks the N276 NLGS but also V5-associated NLGS (positions 461/462) (FIG. 17). The observation that the D279K mutation abolished the neutralizing activity of mouse VRC01-like antibodies indicates that this activity is indeed targeting the VRC01 epitope. In that case, the absence of V5-associated NLGS appears to be required for neutralization. In all cases, the potency of neutralization was higher when the target virus was expressed in 293 GnTI −/− cells, an indication that the mouse VRC01 antibodies have not yet accumulated the necessary mutations to accommodate complex glycans surrounding the CD4-BS.

The data presented here inform how VRC01-class antibody responses may be generated during natural HIV-1 infection. It suggests that although viral Env species that initiated the expansion of precursor VRC01-class BCRs in the context of infection may either lack N276-associated glycans or have short N276-associated glycans, the subsequent viral Envs that guide the maturation of these antibodies to bypass the N276-associated glycans most likely express glycans at N276. Indeed, sequence analysis of viral Envs in patient 45 (Lynch et al., 2015. Journal of Virology 89, 4201-4213), from which VRC01 was isolated from (Wu et al., 2010. Science 329, 1593-1602), indicate the early presence of viral variants lacking N276-associated glycans which were gradually replaced by viral Env variants expressing N276-associated glycans.

These data inform on how to guide the maturation of glVRC01-class antibodies during immunization, so that the immunogens employed during the boost select for antibodies with mutations that allow them to accommodate the N276-associated glycan. These results are relevant to current and upcoming clinal trials directed to germline-targeting immunogens to elicit cross-reactive VRC01-class antibody responses.

(xi) Closing Paragraphs. Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile(+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile(−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a CAR binding domain or a nanoparticle selected cell targeting ligand) to its cognate binding molecule with an affinity or Ka (i.e., an equilibrium association constant of a particular binding interaction with units of 1/M) equal to or greater than 105 M−1, while not significantly associating with any other molecules or components in a relevant environment sample. "Specifically binds" is also referred to as "binds" herein. Binding domains may be classified as "high affinity" or "low affinity". In particular embodiments, "high affinity" binding domains refer to those binding domains with a Ka of at least 107 M−1, at least 108 M−1, at least 109 M 1, at least 1010 M−1, at least 1011 M−1, at least 1012 M−1, or at least 1013 M−1. In particular embodiments, "low affinity" binding domains refer to those binding domains with a Ka of up to 107 M−1, up to 106 M−1, up to 105 M−1. Alternatively, affinity may be defined as an equilibrium dissociation constant (Kd) of a particular binding interaction with units of M (e.g., 10-5 M to 10-13 M). In certain embodiments, a binding domain may have "enhanced affinity," which refers to a selected or engineered binding domains with stronger binding to a cognate binding molecule than a wild type (or parent) binding domain. For example, enhanced affinity may be due to a Ka (equilibrium association constant) for the cognate binding molecule that is higher than the reference binding domain or due to a Kd (dissociation constant) for the cognate binding molecule that is less than that of the reference binding domain, or due to an off-rate (Koff) for the cognate binding molecule that is less than that of the reference binding domain. A variety of assays are known for detecting binding domains that specifically bind a particular cognate binding molecule as well as determining binding affinities, such as Western blot, ELISA, and BIACORE® (GE Healthcare, United States) analysis (see also, e.g., Scatchard, et al., 1949, Ann. N.Y. Acad. Sci. 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995);

Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in ability of elicited antibodies to neutralize autologous virus.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value. In particular embodiments, the residue numbering of mutation and deletion positions of Env is precise, rather than approximate.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A kit comprising (i) a prime immunization comprising a multimerized 426c core HIV-1 Env; and (ii) a boost immunization HIV Env with a glycosylated N276; and instructions that no Env are to be administered to a subject between the (i) prime immunization and the (ii) boost immunization, wherein residue numbering of the HIV-1 Env is according to Hxb2.

2. A kit of claim 1, wherein the multimerized 426c core HIV-1 Env has the sequence set forth in SEQ ID NO. 56.

3. A kit of claim 1, wherein the multimerized 426c core HIV-1 Env comprises: (i) mutations at one or more of: N460D; N463D; S278R; G471S; V65C; and S115C; (ii) removal of the V1 loop and the V2 loop; (iii) replacement of the V3 loop with a flexible linker; and (iv) an N-terminal truncation; wherein the HIV Env does not have a mutation at position 276, and wherein residue numbering of the HIV-1 Env is according to Hxb2.

4. A kit of claim 3, wherein the multimerized 426c core HIV-1 Env comprises mutations at N460D, N463D, S278R, and G471S; or N460D, N463D, S278R, G471S, V65C, and S115C, wherein residue numbering of the HIV-1 Env is according to Hxb2.

5. A kit of claim 3, wherein the N-terminal truncation is before residue 49, 48, 47, 46, 45, 44, 43, 42, 41, 40 or 39, wherein residue numbering of the HIV-1 Env is according to Hxb2.

6. A kit of claim 3, wherein the N-terminal truncation is before residue 44, wherein residue numbering of the HIV-1 Env is according to Hxb2.

7. A kit of claim 3, wherein the multimerized 426c core HIV-1 Env further comprises a C-terminal truncation after residue 499, 498, 497, 496, 495, 494, 493, 492, 491, 490 or 389, wherein residue numbering of the HIV-1 Env is according to Hxb2.

8. A kit of claim 7, wherein the C-terminal truncation is after residue 494, wherein residue numbering of the HIV-1 Env is according to Hxb2.

9. A kit of claim 3, wherein the flexible linker has a sequence set forth in a sequence selected from SEQ ID NOs. 57-68.

10. A kit of claim 3, wherein the V3 loop comprises residues 296-331, wherein residue numbering of the HIV-1 Env is according to Hxb2.

11. A kit of claim 3, wherein removal of the V1 loop comprises removal of residues 131-152 and/or removal of the V2 loop comprises removal of residues 161-196, wherein residue numbering of the HIV-1 Env is according to Hxb2.

12. A kit of claim 3, wherein removal of the V1 loop and removal of the V2 loop comprises removal of residues 123-196, wherein residue numbering of the HIV-1 Env is according to Hxb2.

13. A kit of claim 1, wherein the multimerized 426c core HIV-1 Env retains glycosylation at N463 but lacks glycosylation at N276 and N460, wherein residue numbering of the HIV-1 Env is according to Hxb2.

14. A kit of claim 1, wherein the multimerized 426c core HIV-1 Env retains glycosylation at position 463, wherein residue numbering of the HIV-1 Env is according to Hxb2.

15. A kit of claim 1, wherein the multimerized 426c core HIV-1 Env has a sequence set forth in a sequence selected from SEQ ID NOs. 69-112.

16. A kit of claim 1, wherein the boost immunization HIV Env is selected from the HxB2 core+3 NLGS, the 45_01dH5 core+3 NLGS, or a C4b-multimerized HxB2 wildtype core glycosylated at N276 and having the sequence set forth in SEQ ID NO: 119, wherein residue numbering of the HIV-1 Env is according to Hxb2.

17. A kit of claim 1, wherein the boost immunization HIV Env has the sequence set forth in SEQ ID NO. 183.

18. A kit of claim 1, wherein the boost immunization HIV Env has a sequence set forth in a sequence selected from SEQ ID NO. 69-SEQ ID NO. 79, SEQ ID NO. 82, SEQ ID NO. 107, SEQ ID NO. 113-118, and SEQ ID NO: 121-SEQ ID NO. 132.

19. A kit of claim 1, wherein the boost immunization HIV Env is multimerized.

20. A kit of claim 1, wherein the multimerized 426c core HIV-1 Env and the boost immunization HIV Env are multimerized with ferritin.

* * * * *

SEQUENCE LISTING

```
Sequence total quantity: 275
SEQ ID NO: 1            moltype = AA  length = 121
FEATURE                 Location/Qualifiers
source                  1..121
                        mol_type = protein
                        organism = synthetic construct
SEQUENCE: 1
QVQLVQSGAE VKKPGASVKV SCKASGYTFT GYYMNWVRQA PGQGPEWMGW INPNSGGTNY  60
AQKFQGRVIM TRDTSISTAY MELSRLRSDD TVVYYCARGK NSDYNWDFQH WGQGTLVTVS  120
S                                                                  121

SEQ ID NO: 2            moltype = AA  length = 121
FEATURE                 Location/Qualifiers
source                  1..121
                        mol_type = protein
                        organism = synthetic construct
SEQUENCE: 2
QVQLVQSGAE VKKPGASVKV SCKASGYTFT GYYMNWVRQA PGQGLEWMGW INPKSGGTNY  60
AQKFQGRVTM TRDTSISTAY MELSRLRSDD TAVYYCARGK NSDYNWDFQH WGQGTLVTVS  120
S                                                                  121

SEQ ID NO: 3            moltype = AA  length = 11
FEATURE                 Location/Qualifiers
source                  1..11
                        mol_type = protein
                        organism = synthetic construct
SEQUENCE: 3
IRSVNFTDNA K                                                       11

SEQ ID NO: 4            moltype = AA  length = 121
FEATURE                 Location/Qualifiers
source                  1..121
                        mol_type = protein
                        organism = synthetic construct
SEQUENCE: 4
QVQLVQSGAE VKKPGASVKV SCKASGYTFT GYYMNWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                  121

SEQ ID NO: 5            moltype = AA  length = 11
FEATURE                 Location/Qualifiers
source                  1..11
                        mol_type = protein
                        organism = synthetic construct
SEQUENCE: 5
IRSENLTDNA K                                                       11

SEQ ID NO: 6            moltype = AA  length = 121
FEATURE                 Location/Qualifiers
source                  1..121
                        mol_type = protein
                        organism = synthetic construct
SEQUENCE: 6
QVQLVQSGAE VKKPGASVKV SCKASGYTFT GYYIHWVRQA PGQGLEWMGW INPNRGGTNY  60
AQKFQGRVTM TRDTSISTAY MELSRLRSDD TAVYYCARGI NSDYTWDFQH WGQGTLVTVS  120
S                                                                  121

SEQ ID NO: 7            moltype = AA  length = 121
FEATURE                 Location/Qualifiers
source                  1..121
                        mol_type = protein
                        organism = synthetic construct
SEQUENCE: 7
QVQLVQSGAE VKKPGASVKV SCKASGYTFT GYYMNWVRQA PGQGLEWMGW INPKSGGTNY  60
AQKFQGRVTM TRDTSISTAY MELSRLRSDD TAVYYCARGK TSDYNWDFQH WGQGTLVTVS  120
S                                                                  121

SEQ ID NO: 8            moltype = AA  length = 121
FEATURE                 Location/Qualifiers
source                  1..121
                        mol_type = protein
                        organism = synthetic construct
SEQUENCE: 8
```

```
QVQLVQSGAE VKKPGASVKV SCKASGYTFT GYFLHWVRQA PGQGLEWMGW INPYSGGTNY  60
PQKFQGRVTM TRDTSISTVY MELSRLRSDD TAVYYCARGK NSDYNWDFQH WGQGTLVTVS  120
S                                                                 121

SEQ ID NO: 9           moltype = AA  length = 121
FEATURE                Location/Qualifiers
source                 1..121
                       mol_type = protein
                       organism = synthetic construct
SEQUENCE: 9
QVQLVQSGAE VKKPGASVKV SCKASGYTFT GYYMNWVRQA PGQGLEWMGW INPNSGGTNY  60
AQKFQGRVTM IRDTSISTAY MELSRLRSDD TAVYYCARGK NSDYNWDFQH WGQGTLVTVS  120
S                                                                 121

SEQ ID NO: 10          moltype = AA  length = 11
FEATURE                Location/Qualifiers
source                 1..11
                       mol_type = protein
                       organism = synthetic construct
SEQUENCE: 10
IRSENLTNNA K                                                      11

SEQ ID NO: 11          moltype = AA  length = 121
FEATURE                Location/Qualifiers
source                 1..121
                       mol_type = protein
                       organism = synthetic construct
SEQUENCE: 11
QVQLVQSGAE VKKPGASVKV SCEASGYTFI GYYMNWVRQA PGQGLEWMGW INPNSGGTNY  60
AQKFQGRVTM TRDTSISTVY MELSRLRSDD TAVYYCARGK NSDYNWDFQH WGQGTLVTVS  120
S                                                                 121

SEQ ID NO: 12          moltype = AA  length = 121
FEATURE                Location/Qualifiers
source                 1..121
                       mol_type = protein
                       organism = synthetic construct
SEQUENCE: 12
QVQLVQSGAE VKKPGASVKV SCKASGYTFT GYYMNWVRQA PGQGLEWMGW INPNSGGTNY  60
AQKFQGRVTM TRDTSISTVY MELSRLRSDD TAVYYCARGK NSDYNWDFQH WGQGTLVTVS  120
S                                                                 121

SEQ ID NO: 13          moltype = AA  length = 121
FEATURE                Location/Qualifiers
source                 1..121
                       mol_type = protein
                       organism = synthetic construct
SEQUENCE: 13
QVQLVQSGAE VKKPGASVRV SCKATGYTFT GYYINWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                 121

SEQ ID NO: 14          moltype = AA  length = 121
FEATURE                Location/Qualifiers
source                 1..121
                       mol_type = protein
                       organism = synthetic construct
SEQUENCE: 14
QVQLVQSGAE VKKPGASVKV SCKATGYTFT GYYINWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                 121

SEQ ID NO: 15          moltype = AA  length = 121
FEATURE                Location/Qualifiers
source                 1..121
                       mol_type = protein
                       organism = synthetic construct
SEQUENCE: 15
QVQLVQSGAE VKKPGASVKV SCKASGYTFT GYYMDWVRQA PGQGLEWMGW INPNGGGTNY  60
AQKFQGRVTM TRDTSISTAY MELSRLRSDD TAVYYCARGK NSDYNWDFQH WGQGTLVTVS  120
S                                                                 121

SEQ ID NO: 16          moltype = AA  length = 121
FEATURE                Location/Qualifiers
source                 1..121
                       mol_type = protein
                       organism = synthetic construct
SEQUENCE: 16
QVQLVQSGAE VKKPGASVKV SCKASGYTFT GYYMNWVRQA PGQGLEWMGW INPKSGGTNY  60
```

```
AQKFQGRITM TRDTSISTAY MELSRLRSDD TAVYYCARGK NSDYNWDFQH WGQGTLVTVS  120
S                                                                  121

SEQ ID NO: 17          moltype = AA  length = 121
FEATURE                Location/Qualifiers
source                 1..121
                       mol_type = protein
                       organism = synthetic construct
SEQUENCE: 17
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARGK DTDYIWDFQH WGQGTLVTVS  120
S                                                                  121

SEQ ID NO: 18          moltype = AA  length = 121
FEATURE                Location/Qualifiers
source                 1..121
                       mol_type = protein
                       organism = synthetic construct
SEQUENCE: 18
QVQLVQSGAE VKKPGASVKV SCKASGYTFT GYYLHWVRQA PGQGLEWMGW INPNNGGTNY  60
AQKFQGRVTM TRDTSISTAY MELSRLRSDD TAVYYCARGK NSDYTWDFQH WGQGTLVTVS  120
S                                                                  121

SEQ ID NO: 19          moltype = AA  length = 121
FEATURE                Location/Qualifiers
source                 1..121
                       mol_type = protein
                       organism = synthetic construct
SEQUENCE: 19
QVQLVQSGAE VKKPGASVKV SCKASGYTFT GQYMNWVRQA PGQGLEWMGW INPNRGGTNY  60
AQKFQGRVTM TRDTSISTAY MELSRLRSDD TAVYYCARGK NSDYNWDFQH WGQGTLVTVS  120
S                                                                  121

SEQ ID NO: 20          moltype = AA  length = 121
FEATURE                Location/Qualifiers
source                 1..121
                       mol_type = protein
                       organism = synthetic construct
SEQUENCE: 20
QVQLVQSGAE VKKPGASVKV SCKASGYTFT GYYMNWVRQA PGQGLEWMGW INPHSGGTNY  60
AQKFQGRVTM TRDTSISTAY MELSRLRSDD TAVYYCARGK NSDYNWDFQH WGQGTLVTVS  120
S                                                                  121

SEQ ID NO: 21          moltype = AA  length = 11
FEATURE                Location/Qualifiers
source                 1..11
                       mol_type = protein
                       organism = synthetic construct
SEQUENCE: 21
IRSENFTNNA K                                                       11

SEQ ID NO: 22          moltype = DNA  length = 24
FEATURE                Location/Qualifiers
source                 1..24
                       mol_type = other DNA
                       organism = synthetic construct
SEQUENCE: 22
gatggtggga agatggatac agtt                                         24

SEQ ID NO: 23          moltype = DNA  length = 30
FEATURE                Location/Qualifiers
source                 1..30
                       mol_type = other DNA
                       organism = synthetic construct
SEQUENCE: 23
gccaccgtac gtttgatttc cagcttggtg                                   30

SEQ ID NO: 24          moltype = DNA  length = 30
FEATURE                Location/Qualifiers
source                 1..30
                       mol_type = other DNA
                       organism = synthetic construct
SEQUENCE: 24
gccaccgtac gttttatttc cagcttggtc                                   30

SEQ ID NO: 25          moltype = AA  length = 121
FEATURE                Location/Qualifiers
source                 1..121
                       mol_type = protein
```

```
                         organism = synthetic construct
SEQUENCE: 25
QVQLVQSGAE VKKPGASVKV SCKASGYTFT GYYMDWVRQA PGQGLEWMGW INPKSGGTNY  60
AQKFQGRVTM TRDTSISTAY MELSRLRSDD TAVYYCARGK DSDYNWDFQH WGQGTLVTVS  120
S                                                                  121

SEQ ID NO: 26            moltype = AA  length = 121
FEATURE                  Location/Qualifiers
source                   1..121
                         mol_type = protein
                         organism = synthetic construct
SEQUENCE: 26
QVQLVQSGAE VKKPGASVKV SCKASGYTFT GYHMNWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                  121

SEQ ID NO: 27            moltype = AA  length = 121
FEATURE                  Location/Qualifiers
source                   1..121
                         mol_type = protein
                         organism = synthetic construct
SEQUENCE: 27
QVQLVQSGAE VKKPGASVKV SCKASGYTFT GYYMNWVRQA PGQGLEWMGW INPNNGGTNY  60
AQKFQGRVTM TRDTSISTAY MELSRLRSDD TAVYYCARGK NSDYNWDFQH WGQGTLVTVS  120
S                                                                  121

SEQ ID NO: 28            moltype = AA  length = 121
FEATURE                  Location/Qualifiers
source                   1..121
                         mol_type = protein
                         organism = synthetic construct
SEQUENCE: 28
QVQLVQSGAE VKKPGASVKV SCKTSGYTII DYYMNWVRQA PGQGLEWMGW INPNRGGTNY  60
ARKFQGRVTM TRDTSINTVY LELSRLRSDD TAVYYCARGK NSDYNWDFQH WGQGTLVTVS  120
S                                                                  121

SEQ ID NO: 29            moltype = AA  length = 121
FEATURE                  Location/Qualifiers
source                   1..121
                         mol_type = protein
                         organism = synthetic construct
SEQUENCE: 29
QVQLVQSGAE VKKPGASMRV SCKASGYTFT DYYVNWVRQA PGQGLEWMGW INPTRGGINY  60
AQKFQGRVTM TRDTSISTAY MELSRLRSDD TAVYFCAREK NSDYNWDFQH WGQGTLVTVS  120
S                                                                  121

SEQ ID NO: 30            moltype = AA  length = 121
FEATURE                  Location/Qualifiers
source                   1..121
                         mol_type = protein
                         organism = synthetic construct
SEQUENCE: 30
QVQLVQSGAE VKKPGASVKV SCKTSGYTII DYYMNWVRQA PGQGLEWMGW INPNRGGTNY  60
ARKFQGRVTM TRDTSINTVY LELNRLRSDD TAVYYCARGK NSDYNWDFQH WGQGTLVTVS  120
S                                                                  121

SEQ ID NO: 31            moltype = AA  length = 121
FEATURE                  Location/Qualifiers
source                   1..121
                         mol_type = protein
                         organism = synthetic construct
SEQUENCE: 31
QVQLVQSGAE VKKPGAAVKV SCKAFGYTFT GYYMNWVRQA PGQGLEWMGW INPNRGGTNY  60
AQKFQGRVTM TRDTSISTVY LELSRLRSDD TAVYYCARGK NSDFNWDFQH WGQGTLVTVS  120
S                                                                  121

SEQ ID NO: 32            moltype = AA  length = 121
FEATURE                  Location/Qualifiers
source                   1..121
                         mol_type = protein
                         organism = synthetic construct
SEQUENCE: 32
QVQLVQSGAE VKKPGASVKV SCKTSGYTII DYYMNWVRQA PGQGLEWMGW INPNRGGTNY  60
AQKFQGRVTM TRDTSISTVY SELSRLRSDD TAVYYCARGK NSDYNWDFQH WGQGTLVTVS  120
S                                                                  121

SEQ ID NO: 33            moltype = AA  length = 121
FEATURE                  Location/Qualifiers
source                   1..121
```

```
                         mol_type = protein
                         organism = synthetic construct
SEQUENCE: 33
QVQLVQSGAE VKKPGASMRV SCKASGYTFT DYYVNWVRQA PGQGLEWMGW INPTRGGVNY  60
AQKFQGRVTM TRDTSISTAY MELSRLRSDD TAVYFCARGK NSDYNWDFQH WGQGTLVTVS  120
S                                                                 121

SEQ ID NO: 34            moltype = AA  length = 121
FEATURE                  Location/Qualifiers
source                   1..121
                         mol_type = protein
                         organism = synthetic construct
SEQUENCE: 34
QVQLVQSGAE VKKPGASVKV SCKASGYTFT GYYMNWVRQA PGQGLEWMGW INPTRGGTNY  60
AQKFQGRVTM TRDTSISTAY MELSRLRSDD TAVYFCARGK NSDYNWDFQH WGQGTLVTVS  120
S                                                                 121

SEQ ID NO: 35            moltype = AA  length = 121
FEATURE                  Location/Qualifiers
source                   1..121
                         mol_type = protein
                         organism = synthetic construct
SEQUENCE: 35
QVQLVQSGAE VKKPGASVKV SCKASGYTFT GYYMNWVRQA PGQGLEWMGW INPNRGGTNY  60
AQKFQGRVTM TRDTSINTAY MELTRLRSDD TAVYYCARGK TSDYNWDFQH WGQGTLVTVS  120
S                                                                 121

SEQ ID NO: 36            moltype = AA  length = 121
FEATURE                  Location/Qualifiers
source                   1..121
                         mol_type = protein
                         organism = synthetic construct
SEQUENCE: 36
QVQLVQSGAE VKKPGASVKV SCKTSGYTFI AYYMNWVRQA PGQGLEWMGW INPFRGGTNY  60
AQKFQGRVTM TRDTSISTVF LELSSLRSDD TAVYYCARGK NSDYNWDFQH WGQGTLVTVS  120
S                                                                 121

SEQ ID NO: 37            moltype = AA  length = 121
FEATURE                  Location/Qualifiers
source                   1..121
                         mol_type = protein
                         organism = synthetic construct
SEQUENCE: 37
QVQLVQSGAE VKKPGASVKV SCKTSGYTFI AYYMNWVRQA PGQGLEWMGW INPFRGGTNY  60
AQKFQGRVTM TRDTSISTVY LELSRLRSDD TAVYYCARGK NSDYNWDFQH WGQGTLVTVS  120
S                                                                 121

SEQ ID NO: 38            moltype = DNA  length = 30
FEATURE                  Location/Qualifiers
source                   1..30
                         mol_type = other DNA
                         organism = synthetic construct
SEQUENCE: 38
gccaccgtac gttttatttc caactttgtc                                  30

SEQ ID NO: 39            moltype = AA  length = 372
FEATURE                  Location/Qualifiers
source                   1..372
                         mol_type = protein
                         organism = synthetic construct
SEQUENCE: 39
MDAMKRGLCC VLLLCGAVFV SPSASVWKEA KTTLFCASDA KAYEKECHNV WATHACVPTD  60
PNPQEVVLEN VTENFNMWKN DMVDQMQEDV ISIWDQCLKP CVKLTNTSTL TQACPKVTFD  120
PIPIHYCAPA GYAILKCNNK TFNGKGPCNN VSTVQCTHGI KPVVSTQLLL NGSLAEEEIV  180
IRSKNLSDNA KIIIVQLNKS VEIVCTRPNN GGSGSGGDIR QAYCNISGRN WSEAVNQVKK  240
KLKEHFPHKN ISFQSSSGGD LEITTHSFNC GGEFFYCNTS GLFNDTISNA TIMLPCRIKQ  300
IINMWQEVGK AIYAPPIKGN ITCKSDITGL LLLRDGGNTT NNTEIFRPGG GDMRDNWRSE  360
LYKYKVVEIK PL                                                     372

SEQ ID NO: 40            moltype = AA  length = 197
FEATURE                  Location/Qualifiers
source                   1..197
                         mol_type = protein
                         organism = synthetic construct
SEQUENCE: 40
MDAMKRGLCC VLLLCGAVFV SPSASDTITL PCRPAPPPHC SSNITGLILT RQGGYSNDNT  60
VIFRPSGGDW RDIARCQIAG TVVSTQLFLN GSLAEEEVVI RSEDWRDNAK SICVQLNTSV  120
EINCTGAGHC NISRAKWNNT LKQIASKLRE QYGNKTIIFK PSSGGDPEFV NHSFNCGGEF  180
FYCDSTQLFN STWFNST                                                197
```

```
SEQ ID NO: 41          moltype = AA  length = 650
FEATURE                Location/Qualifiers
source                 1..650
                       mol_type = protein
                       organism = synthetic construct
SEQUENCE: 41
MPMGSLQPLA TLYLLGMLVA SVLAAENLWV TVYYGVPVWK EAKTTLFCAS DAKAYEKEVH  60
NVWATHACVP TDPNPQEVVL ENVTENFNMW KNDMVDQMQE DVISIWDQSL KPCVKLTPLC  120
VTLNCTNVNV TSNSTNVNSS STDNTTLGEI KNCSFDITTE IRDKTRKEYA LFYRLDIVPL  180
DNSSNPNSSN TYRLINCNTS TCTQACPKVT FDPIPIHYCA PAGYAILKCN NKTFNGKGPC  240
NNVSTVQCTH GIKPVVSTQL LLNGSLAEEE IVIRSKNLSD NAKIIIVQLN KSVEIVCTRP  300
NNNTRRSIRI GPGQTFYATD IIGDIRQAYC NISGRNWSEA VNQVKKKLKE HFPHKNISFQ  360
SSSGGDLEIT THSFNCGGEF FYCNTSGLFN DTISNATIML PCRIKQIINM WQEVGKCIYA  420
PPIKGNITCK SDITGLLLLR DGGNTTNNTE IFRPGGGDMR DNWRSELYKY KVVKIEPLGV  480
APTRCKRRVV GRRRRRRAVG IGAVFLGFLG AAGSTMGAAS MTLTVQARNL LSGIVQQQSN  540
LLRAPEAQQH LLKLTVWGIK QLQARVLAVE RYLRDQQLLG IWGCSGKLIC CTNVPWNSSW  600
SNRNLSEIWD NMTWLQWDKE ISNYTQIIYG LLEESQNQQE KNEQDLLALD             650

SEQ ID NO: 42          moltype = AA  length = 650
FEATURE                Location/Qualifiers
source                 1..650
                       mol_type = protein
                       organism = synthetic construct
SEQUENCE: 42
MPMGSLQPLA TLYLLGMLVA SVLAAENLWV TVYYGVPVWK EAKTTLFCAS DAKAYEKEVH  60
NVWATHACVP TDPNPQEVVL ENVTENFNMW KNDMVDQMQE DVISIWDQSL KPCVKLTPLC  120
VTLNCTNVNV TSNSTNVNSS STDNTTLGEI KNCSFDITTE IRDKTRKEYA LFYRLDIVPL  180
DNSSNPNSSN TYRLINCNTS TCTQACPKVT FDPIPIHYCA PAGYAILKCN NKTFNGKGPC  240
NNVSTVQCTH GIKPVVSTQL LLNGSLAEEE IVIRSKNLAD NAKIIIVQLN KSVEIVCTRP  300
NNNTRRSIRI GPGQTFYATD IIGDIRQAYC NISGRNWSEA VNQVKKKLKE HFPHKNISFQ  360
SSSGGDLEIT THSFNCGGEF FYCNTSGLFN DTISNATIML PCRIKQIINM WQEVGKCIYA  420
PPIKGNITCK SDITGLLLLR DGGNTANNAE IFRPGGGDMR DNWRSELYKY KVVKIEPLGV  480
APTRCKRRVV GRRRRRRAVG IGAVFLGFLG AAGSTMGAAS MTLTVQARNL LSGIVQQQSN  540
LLRAPEAQQH LLKLTVWGIK QLQARVLAVE RYLRDQQLLG IWGCSGKLIC CTNVPWNSSW  600
SNRNLSEIWD NMTWLQWDKE ISNYTQIIYG LLEESQNQQE KNEQDLLALD             650

SEQ ID NO: 43          moltype = AA  length = 648
FEATURE                Location/Qualifiers
source                 1..648
                       mol_type = protein
                       organism = synthetic construct
SEQUENCE: 43
MGSLQPLATL YLLGMLVASV LAAENLWVTV YYGVPVWKEA KTTLFCASDA KAYEKEVHNV  60
WATHACVPTD PNPQEVVLEN VTENFNMWKN DMVDQMQEDV ISIWDQSLKP CVKLTPLCVT  120
LNCTNVNVTS NSTNVNSSST DNTTLGEIKN CSFDITTEIR DKTRKEYALF YRLDIVPLDN  180
SSNPNSSNTY RLINCNTSTC TQACPKVTFD PIPIHYCAPA GYAILKCNNK TFNGKGPCNN  240
VSTVQCTHGI KPVVSTQLLL NGSLAEEEIV IRSKNLADNA KIIIVQLNKS VEIVCTRPNN  300
NTRRSIRIGP GQTFYATDII GDIRQAYCNI SGRNWSEAVN QVKKKLKEHF PHKNISFQSS  360
SGGDLEITTH SFNCGGEFFY CNTSGLFNDT ISNATIMLPC RIKQIINMWQ EVGKCIYAPP  420
IKGNITCKSD ITGLLLLRDG GNTTNNTEIF RPGGGDMRDN WRSELYKYKV VKIEPLGVAP  480
TRCKRRVVGR RRRRRAVGIG AVFLGFLGAA GSTMGAASMT LTVQARNLLS GIVQQQSNLL  540
RAPEAQQHLL KLTVWGIKQL QARVLAVERY LRDQQLLGIW GCSGKLICCT NVPWNSSWSN  600
RNLSEIWDNM TWLQWDKEIS NYTQIIYGLL EESQNQQEKN EQDLLALD               648

SEQ ID NO: 44          moltype = AA  length = 385
FEATURE                Location/Qualifiers
source                 1..385
                       mol_type = protein
                       organism = synthetic construct
SEQUENCE: 44
MDAMKRGLCC VLLLCGAVFV SPSASVWKEA TATLFCASDA KAYETECHNV WATHACVPTD  60
PNPQEVVLEN VTENFNMWKN NMVEQMHEDI ISLWDQCLKP CVKLTNTSVI TQACPKISFE  120
PIPIHYCAPA GFAILKCNDK KFNGTGPCTN VSTVQCTHGI RPVVSTQLLL NGSLAEEEIV  180
IRSENIKDNA KIIIVQLNET VEINCTRPNN GGSGSGGDIR QAHCNISKAK WENTLKQIAR  240
KLREHFKNET IAFNQSSGGD PEIVMHSFNC GGEFFYCNST QLFNSTWTWN DTEVVNNTEK  300
NINITLPCRI KQIINMWQEV GKAMYAPPIK GQIRCSSNIT GLLLTRDGGS STNGTTETFR  360
PGGGDMRDNW RSELYKYKVV KIEPL                                        385

SEQ ID NO: 45          moltype = AA  length = 385
FEATURE                Location/Qualifiers
source                 1..385
                       mol_type = protein
                       organism = synthetic construct
SEQUENCE: 45
MDAMKRGLCC VLLLCGAVFV SPSASVWKEA STTLFCASDA KAYDTECHNV WATHACVPTD  60
PNPQEVVLEN VTEKFNMWKN NMVEQMHEDI ISLWDQCLKP CVKLTNTSVI TQACPKISFE  120
PIPIHYCAPA GFAILKCNDK KFNGTGKCTN VSTVQCTHGI RPVVSTQLLL NGSLAEEEII  180
IRSENLTDNA KTLIVQLNET VAINCTRPNN GGSGSGGNIR QAHCNISETD WNNTLKQVAR  240
```

```
KLRELFNKTI VFNQSSGGDP EIVMHSFNCG GEFFYCNTTQ LFNSTWHGNE TEESSITKDN  300
KTITLPCRIK QIVNRWQEVG KAMYAPPIEG LIRCSSNITG LLLTRDGGNI TNETTTETFR  360
PGGGNMRDNW RSELYKYKVV KIEPL                                        385

SEQ ID NO: 46          moltype = AA  length = 648
FEATURE                Location/Qualifiers
source                 1..648
                       mol_type = protein
                       organism = synthetic construct
SEQUENCE: 46
MGSLQPLATL YLLGMLVASV LAAENLWVTV YYGVPVWKEA KTTLFCASDA KAYEKEVHNV  60
WATHACVPTD PNPQEVVLEN VTENFNMWKN DMVDQMQEDV ISIWDQSLKP CVKLTPLCVT  120
LNCTNVNVTS NSTNVNSSST DNTTLGEIKN CSFDITTEIR DKTRKEYALF YRLDIVPLDN  180
SSNPNSSNTY RLINCNTSTC TQACPKVTFD PIPIHYCAPA GYAILKCNNK TFNGKGPCNN  240
VSTVQCTHGI KPVVSTQLLL NGSLAEEEIV IRSKNLSDNA KIIIVQLNKS VEIVCTRPNN  300
NTRRSIRIGP GQTFYATDII GDIRQAYCNI SGRNWSEAVN QVKKKLKEHF PHKNISFQSS  360
SGGDLEITTH SFNCGGEFFY CNTSGLFNDT ISNATIMLPC RIKQIINMWQ EVGKCIYAPP  420
IKGNITCKSD ITGLLLLRDG GNTANNAEIF RPGGGDMRDN WRSELYKYKV VKIEPLGVAP  480
TRCKRRVVGR RRRRRAVGIG AVFLGFLGAA GSTMGAASMT LTVQARNLLS GIVQQQSNLL  540
RAPEAQQHLL KLTVWGIKQL QARVLAVERY LRDQQLLGIW GCSGKLICCT NVPWNSSWSN  600
RNLSEIWDNM TWLQWDKEIS NYTQIIYGLL EESQNQQEKN EQDLLALD              648

SEQ ID NO: 47          moltype = AA  length = 387
FEATURE                Location/Qualifiers
source                 1..387
                       mol_type = protein
                       organism = synthetic construct
SEQUENCE: 47
MDAMKRGLCC VLLLCGAVFV SPSASVWKEA TTTLFCASDA KAYDTECHNV WATHACVPTD  60
PNPQEVVLVN VTENFNMWKN DMVEQMHEDI ISLWDQCLKP CVKLTNTSVI TQACPKVSFE  120
PIPIHYCAPA GFAILKCNNK TFNGTGPCTN VSTVQCTHGI RPVVSTQLLL NGSLAEEEVV  180
IRSVNFTDNA KTIIVQLNTS VEINCTRPNN GGSGSGGNMR QAHCNISRAK WNNTLKQIAS  240
KLREQFGNNK TIIFKQSSGG DPEIVTHSFN CGGEFFYCNS TQLFNSTWFN STWSTEGSNN  300
TEGSDTITLP CRIKQIINMW QKVGKAMYAP PISGQIRCSS NITGLLLTRD GGNSNNESEI  360
FRPGGGDMRD NWRSELYKYK VVKIEPL                                      387

SEQ ID NO: 48          moltype = AA  length = 386
FEATURE                Location/Qualifiers
source                 1..386
                       mol_type = protein
                       organism = synthetic construct
SEQUENCE: 48
MDAMKRGLCC VLLLCGAVFV SPSASVWKEA TTTLFCASDA KAYETECHNV WATHACVPTD  60
PNPQEVVLGN VTENFNMWKN NMVEQMHEDI ISLWDECLKP CVKLTNTSVI TQACPKVSFE  120
PIPIHYCAPA GFAILKCNNK TFNGTGPCTN VSTVQCTHGI RPVVSTQLLL NGSLAEEEVV  180
IRSENFTNNA KTIIVHLKKS VEINCTRPGN GGSGSGGDIR QAHCNLSSVQ WNDTLKQIVI  240
KLGEQFGTNK TIAFNQSSGG DPEIVMHSFN CGGEFFYCNT TQLFNSTWEF HGNWTRSNFT  300
ESNSTTITLP CRIKQIVNMW QEVGKAMYAP PIRGQIRCSS NITGLLLTRD GGVNGTRETF  360
RPGGGDMRDN WRSELYKYKV VKIEPL                                       386

SEQ ID NO: 49          moltype = AA  length = 405
FEATURE                Location/Qualifiers
source                 1..405
                       mol_type = protein
                       organism = synthetic construct
SEQUENCE: 49
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LSDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGNTTNNTEI FRPGGGDMRD NWRSELYKYK VVEIKPLGSS KKQGDADVCG  360
EVAYIQSVVS DCHVPTAELR TLLEIRKLFL EIQKLKVELQ GLSKE                  405

SEQ ID NO: 50          moltype = AA  length = 56
FEATURE                Location/Qualifiers
source                 1..56
                       mol_type = protein
                       organism = synthetic construct
SEQUENCE: 50
SKKQGDADVC GEVAYIQSVV SDCHVPTAEL RTLLEIRKLF LEIQKLKVEL QGLSKE      56

SEQ ID NO: 51          moltype = AA  length = 175
FEATURE                Location/Qualifiers
source                 1..175
                       mol_type = protein
                       organism = synthetic construct
SEQUENCE: 51
ESQVRQQFSK DIEKLLNEQV NKEMQSSNLY MSMSSWCYTH SLDGAGLFLF DHAAEEYEHA  60
```

-continued

```
KKLIIFLNEN NVPVQLTSIS APEHKFEGLT QIFQKAYEHE QHISESINNI VDHAIKSKDH  120
ATFNFLQWYV AEQHEEEVLF KDILDKIELI GNENHGLYLA DQYVKGIAKS RKSGS       175

SEQ ID NO: 52           moltype = AA  length = 121
FEATURE                 Location/Qualifiers
source                  1..121
                        mol_type = protein
                        organism = synthetic construct
SEQUENCE: 52
QVQLVQSGAE VKKPGASMRV SCKASGYTFT DYYVNWVRQA PGQGLEWMGW INPTRGGVNY  60
AQKFQGRVTM TRDTSISTAY MELSRLRSDD TAVYFCARGK NSDYNWDFQH WGQGTLVTVS  120
S                                                                  121

SEQ ID NO: 53           moltype = AA  length = 109
FEATURE                 Location/Qualifiers
source                  1..109
                        mol_type = protein
                        organism = synthetic construct
SEQUENCE: 53
DIVMSQSPSP LAVSVGEKVT MSCKSSQNLL YSSNEENYLA WYQQKPGQSP KLLIYWASTR  60
ESGVPDRFTG SGSGTDFTLT ISSVKAEDLA VYYCQQYETF GGGTKLEIK             109

SEQ ID NO: 54           moltype = AA  length = 847
FEATURE                 Location/Qualifiers
source                  1..847
                        mol_type = protein
                        organism = synthetic construct
SEQUENCE: 54
MRVKGIRKSY QYLWKGGTLL LGILMICSAV EKLWVTVYYG VPVWKEATTT LFCASDAKAY  60
DTEVHNVWAT HACVPTDPNP QEVVLENVTE HFNMWKNNMV EQMQEDIISL WDQSLKPCVK  120
LTPLCVTLNC KDVNATNTTN DSEGTMERGE IKNCSFNITT SIRDEVQKEY ALFYKLDVVP  180
IDNNNTSYRL ISCDTSVITQ ACPKISFEPI PIHYCAPAGF AILKCNDKTF NGKGPCKNVS  240
TVQCTHGIRP VVSTQLLLNG SLAEEEVVIR SDNFTNNAKT IIVQLKESVE INCTRPNNNT  300
RKSIHIGPGR AFYTTGEIIG DIRQAHCNIS RAKWNDTLKQ IVIKLREQFE NKTIVFNHSS  360
GGDPEIVMHS FNCGGEFFYC NSTQLFNSTW NNNTEGSNNT EGNTITLPCR IKQIINMWQE  420
VGKAMYAPPI RGQIRCSSNI TGLLLTRDGG INENGTEIFR PGGGDMRDNW RSELYKYKVV  480
KIEPLGVAPT KAKRRVVQRE KRAVGIGAVF LGFLGAAGST MGAASMTLTV QARLLLSGIV  540
QQQNNLLRAI EAQQRMLQLT VWGIKQLQAR VLAVERYLGD QQLLGIWGCS GKLICTTAVP  600
WNASWSNKSL DRIWNNMTWM EWEREIDNYT SEIYTLIEES QNQQEKNEQE LLELDKWASL  660
WNWFDITKWL WYIKIFIMIV GGLVGLRLVF TVLSIVNRVR QGYSPLSFQT LLPAPRGPDR  720
PEGIEEEGGE RDRDRSGRLV NGFLALIWVD LRSLCLFSYH RLRDLLLTVT RIVELLGRRG  780
WEVLKYWWNL LQYWSQELKN SAVSLLNATA IAVAEGTDRI IEALQRTYRA ILHIPTRIRQ  840
GLERALL                                                            847

SEQ ID NO: 55           moltype = AA  length = 856
FEATURE                 Location/Qualifiers
source                  1..856
                        mol_type = protein
                        organism = synthetic construct
SEQUENCE: 55
MRVKEKYQHL WRWGWRWGTM LLGMLMICSA TEKLWVTVYY GVPVWKEATT TLFCASDAKA  60
YDTEVHNVWA THACVPTDPN PQEVVLVNVT ENFNMWKNDM VEQMHEDIIS LWDQSLKPCV  120
KLTPLCVSLN CTDLKNDTNT NSSSGRMIME KGEIKNCSFN ISTSIRGKVQ KEYAFFYKLD  180
IIPIDNDTTS YTLTSCNTSV ISQACPKVSF EPIPIHYCAP AGFAILKCNN KTFNGTGPCT  240
NVSTVQCTHG IRPVVSTQLL LNGSLAEEEV VIRSVNFMDN AKTIIVQLNT SVEINCTRPS  300
NNTIKRIRIQ RGPGRAFVTM GKIGDMRQAH CNISRAKWNN TLKQIASKLR EQFGNNKTII  360
FKQSSGGDPE IVTHSFNCGG EFFYCNSTQL FNSTWFNSTW STEGSNNTEG SDTITLPCRI  420
KQIINMWQKV GKAMYAPPIS GQIRCSSNIT GLLLTRDGGK GNNESEIFRP GGGDMRDNWR  480
SELYKYKVVK IEPLGVAPTK AKRRVVQREK RAVGIGALFL GFLGAAGSTM GAASMTLTVQ  540
ARQLLSGIVQ QQNNLLRAIE AQQHLLQLTV WGIKQLQARI LAVERYLKDQ QLLGIWGCSG  600
KLICTTAVPW NASWSNKSLE QIWNHMTWME WDREINNYTS LIHSLIEESQ NQQEKNEQEL  660
LELDKWASLW NWFDITNWLW YIKLFIMIVG GLVGLRIVFA VLSIVNRVRQ GYSPLSFQTH  720
LPTPRGPDRP EGIEEEGGER DRDRSIRLVN GSLALIWDDL RSLCLFSYHR LRDLLLIVTR  780
IVELLGRRGW EALKYWWNLL QYWSQELKNS AVSLLNATAI AVAEGTDRVI EVVQGACRAI  840
RHIPRRIRQG LERILL                                                  856

SEQ ID NO: 56           moltype = AA  length = 347
FEATURE                 Location/Qualifiers
source                  1..347
                        mol_type = protein
                        organism = synthetic construct
SEQUENCE: 56
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LRDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGDTTDNTEI FRPSGGDMRD NWRSELYKYK VVEIKPL                347
```

```
SEQ ID NO: 57          moltype = AA  length = 6
FEATURE                Location/Qualifiers
source                 1..6
                       mol_type = protein
                       organism = synthetic construct
SEQUENCE: 57
GGSGSG                                                     6

SEQ ID NO: 58          moltype = AA  length = 4
FEATURE                Location/Qualifiers
source                 1..4
                       mol_type = protein
                       organism = synthetic construct
MOD_RES                1
                       note = Acetylation
SEQUENCE: 58
CGGG                                                       4

SEQ ID NO: 59          moltype = AA  length = 18
FEATURE                Location/Qualifiers
source                 1..18
                       mol_type = protein
                       organism = synthetic construct
SEQUENCE: 59
GSTSGSGKPG SGEGSTKG                                        18

SEQ ID NO: 60          moltype = AA  length = 7
FEATURE                Location/Qualifiers
source                 1..7
                       mol_type = protein
                       organism = synthetic construct
SEQUENCE: 60
SGRAHAG                                                    7

SEQ ID NO: 61          moltype = AA  length = 10
FEATURE                Location/Qualifiers
source                 1..10
                       mol_type = protein
                       organism = synthetic construct
VARIANT                2..10
                       note = Any one or all of amino acids 2-10 can be either
                        present or absent
SEQUENCE: 61
GGGGGGGGGG                                                 10

SEQ ID NO: 62          moltype = AA  length = 10
FEATURE                Location/Qualifiers
source                 1..10
                       mol_type = protein
                       organism = synthetic construct
VARIANT                2..10
                       note = Any one or all of amino acids 2-10 can be either
                        present or absent
SEQUENCE: 62
SSSSSSSSSS                                                 10

SEQ ID NO: 63          moltype = AA  length = 10
FEATURE                Location/Qualifiers
source                 1..10
                       mol_type = protein
                       organism = synthetic construct
VARIANT                2..10
                       note = Any one or all of amino acids 2-10 can be either
                        present or absent
SEQUENCE: 63
AAAAAAAAAA                                                 10

SEQ ID NO: 64          moltype = AA  length = 20
FEATURE                Location/Qualifiers
source                 1..20
                       mol_type = protein
                       organism = synthetic construct
VARIANT                3..20
                       note = Any one or all of amino acids 3 to 20 can either be
                        present or  absent
SEQUENCE: 64
GSGSGSGSGS GSGSGSGSGS                                      20

SEQ ID NO: 65          moltype = AA  length = 40
```

```
FEATURE                Location/Qualifiers
source                 1..40
                       mol_type = protein
                       organism = synthetic construct
VARIANT                5..40
                       note = Any one or all of amino acids 5 to 40 can be either
                        present or absent
SEQUENCE: 65
GSSGGSSGGS SGGSSGGSSG GSSGGSSGGS SGGSSGGSSG                        40

SEQ ID NO: 66          moltype = AA  length = 30
FEATURE                Location/Qualifiers
source                 1..30
                       mol_type = protein
                       organism = synthetic construct
VARIANT                4..30
                       note = Any one or all of amino acids 4 to 30 can be either
                        present or absent
SEQUENCE: 66
GSGGSGGSGG SGGSGGSGGS GGSGGSGGSG                                   30

SEQ ID NO: 67          moltype = AA  length = 30
FEATURE                Location/Qualifiers
source                 1..30
                       mol_type = protein
                       organism = synthetic construct
VARIANT                4..30
                       note = Any one or all of amino acids 4 to 30 can be either
                        present or absent
SEQUENCE: 67
GSSGSSGSSG SSGSSGSSGS SGSSGSSGSS                                   30

SEQ ID NO: 68          moltype = AA  length = 20
FEATURE                Location/Qualifiers
source                 1..20
                       mol_type = protein
                       organism = synthetic construct
VARIANT                3..20
                       note = Any one or all of amino acids 3 to 20 can be either
                        present or absent
SEQUENCE: 68
GAGAGAGAGA GAGAGAGAGA                                              20

SEQ ID NO: 69          moltype = AA  length = 183
FEATURE                Location/Qualifiers
source                 1..183
                       mol_type = protein
                       organism = synthetic construct
SEQUENCE: 69
RPVVSTQLLL NGSLAEEEVV IRSVNFTDNA KTIIVQLNTS VEINCTGAGH CNISRAKWNN  60
TLKQIASKLR EQFGNNKTII FKQSSGGDPE IVTHSFNCGG EFFYCDSTQL FNSTWFNSTW  120
STEGSNNTEG SDTITLPCRP APPPHCSSNI TGLLLTRDGG NSNNESEIFR PGGGDMRDNW  180
RSE                                                                183

SEQ ID NO: 70          moltype = AA  length = 183
FEATURE                Location/Qualifiers
source                 1..183
                       mol_type = protein
                       organism = synthetic construct
SEQUENCE: 70
RPVVSTQLLL NGSLAEEEVV IRSVNFTDNA KTIIVQLNTS VEINCTGAGH CNISRAKWNN  60
TLKQIASKLR EQFGNNKTII FKQSSGGDPE IVTHSFNCGG EFFYCNSTQL FNSTWFNSTW  120
STEGSNNTEG SDTITLPCRP APPPHCSSNI TGLLLTRDGG NSNNESEIFR PGGGDMRDNW  180
RSE                                                                183

SEQ ID NO: 71          moltype = AA  length = 175
FEATURE                Location/Qualifiers
source                 1..175
                       mol_type = protein
                       organism = synthetic construct
SEQUENCE: 71
DTITLPCRPA PPPHCSSNIT GLLLTRDGGN SNNESEIFRP GGGDMRDNWR SGLSGPVVST  60
QLLLNGSLAE EEVVIRSVNF TDNAKTIIVQ LNTSVEINCT GAGHCNISRA KWNNTLKQIA  120
SKLREQFGNN KTIIFKQSSG GDPEIVTHSF NCGGEFFYCD STQLFNSTWF NSTWS       175

SEQ ID NO: 72          moltype = AA  length = 185
FEATURE                Location/Qualifiers
source                 1..185
                       mol_type = protein
```

```
                          organism = synthetic construct
SEQUENCE: 72
GEFFYCDSTQ LFNSTWFNST WSTEGSNNTE GSDTITLPCR PAPPPHCSSN ITGLLLTRDG  60
GNSNNESEIF RPGGGDMRDN WRSGLSGPVV STQLLLNGSL AEEEVVIRSV NFTDNAKTII  120
VQLNTSVEIN CTGAGHCNIS RAKWNNTLKQ IASKLREQFG NNKTIIFKQS SGGDPEIVTH  180
SFNCG                                                              185

SEQ ID NO: 73             moltype = AA  length = 175
FEATURE                   Location/Qualifiers
source                    1..175
                          mol_type = protein
                          organism = synthetic construct
SEQUENCE: 73
DTITLPCRPA PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCD STQLFNSTWF NSTWS       175

SEQ ID NO: 74             moltype = AA  length = 175
FEATURE                   Location/Qualifiers
source                    1..175
                          mol_type = protein
                          organism = synthetic construct
SEQUENCE: 74
DTITLPCRPA PPPHCSSNIT GLILTRDGGN SNNESEIFRP GGGDMRDIAR CQIAGTVVST  60
QLLLNGSLAE EEVVCRSVNF TDNAKSICVQ LNTSVEINCT GAGHCNISRA KWNNTLKQIA  120
SCLREQFGNN KTIIFKQSSG GDPEIVTHSF NCGGEFFYCD STQLFNSTWF NSTWS       175

SEQ ID NO: 75             moltype = AA  length = 168
FEATURE                   Location/Qualifiers
source                    1..168
                          mol_type = protein
                          organism = synthetic construct
SEQUENCE: 75
DTITLPCRPA PPPHCSSNIT GLILTRDGGN SNNESEIFRP GGGDMAGMPR CGGGAVSTQL  60
LLNGSLAEEE VVCRSVNFTD NAKSICVQLN TSVEINCTGA GHCNISRAKW NNTLKQIASC  120
LREQFGNNKT IIFKQSSGGD PEIVTHSFNC GGEFFYCDST QLFNSTWF               168

SEQ ID NO: 76             moltype = AA  length = 175
FEATURE                   Location/Qualifiers
source                    1..175
                          mol_type = protein
                          organism = synthetic construct
SEQUENCE: 76
DTITLPCRPA PPPHCSSNIT GLILTRDGGN SNDESEIFRP GGGDMRDIAR CQIAGTVVST  60
QLLLNGSLAE EEVVIRSVDF TDNAKSICVQ LDTSVEIDCT GAGHCDISRA KWDNTLKQIA  120
SKLREQFGND KTIIFKQSSG GDPEIVTHSF NCGGEFFYCD STQLFDSTWF DSTWS       175

SEQ ID NO: 77             moltype = AA  length = 185
FEATURE                   Location/Qualifiers
source                    1..185
                          mol_type = protein
                          organism = synthetic construct
SEQUENCE: 77
GEFFYCDSTQ LFNSTWFNST WSTEGSNNTE GSDTITLPCR PAPPPHCSSN ITGLILTRDG  60
GNSNNESEIF RPGGGDMRDI ARCQIAGTVV STQLLLNGSL AEEEVVIRSV NFTDNAKSIC  120
VQLNTSVEIN CTGAGHCNIS RAKWNNTLKQ IASKLREQFG NNKTIIFKQS SGGDPEIVTH  180
SFNCG                                                              185

SEQ ID NO: 78             moltype = AA  length = 185
FEATURE                   Location/Qualifiers
source                    1..185
                          mol_type = protein
                          organism = synthetic construct
SEQUENCE: 78
GEFFYCDSTQ LFNSTWFNST WSTEGSNNTE GSDTITLPCR PAPPPHCSSN ITGLILTRDG  60
GNSNNESEIF RPGGGDMRCG ARSGIAGTVV STQLLLNGSL AEEEVVIRSV NFTDNAKCII  120
VQLNTSVEIN CTGAGHCNIS RAKWNNTLKQ IASKLREQFG NNKTIIFKQS SGGDPEIVTH  180
SFNCG                                                              185

SEQ ID NO: 79             moltype = AA  length = 185
FEATURE                   Location/Qualifiers
source                    1..185
                          mol_type = protein
                          organism = synthetic construct
SEQUENCE: 79
GEFFYCDSTQ LFNSTWFNST WSTEGSNNTE GSDTITLPCR PAPPPHCSSN ITGLILTRDG  60
GNSNNESEIF RPGGGDMRDI ARCQIAGTVV STQLLLNGSL AEEEVVCRSV NFTDNAKSIC  120
VQLNTSVEIN CTGAGHCNIS RAKWNNTLKQ IASCLREQFG NNKTIIFKQS SGGDPEIVTH  180
SFNCG                                                              185
```

```
SEQ ID NO: 80           moltype = AA  length = 174
FEATURE                 Location/Qualifiers
source                  1..174
                        mol_type = protein
                        organism = synthetic construct
SEQUENCE: 80
DTITLPCRPA PPPHCSSNIT GLILTRDGGT SDDKTEIFRP GGGDMRDIAR CQIAGTVVST  60
QLLLNGSLAE EEVVIRSEDF RDNAKSICVQ LNTSVEINCT GAGHCNISRA KWNNTLKQIA  120
SKLREQFGNK TIIFKQSSGG DPEFVTHSFN CGGEFFYCDS TQLFDSTWFD STWS        174

SEQ ID NO: 81           moltype = AA  length = 174
FEATURE                 Location/Qualifiers
source                  1..174
                        mol_type = protein
                        organism = synthetic construct
SEQUENCE: 81
DTITLPCRPA PPPHCSSNIT GLILTRGGGI SDDKTEIFRP GGGDMRDIAR CQIAGTVVST  60
QLLLNGSLAE EEVVIRSEDF RDNSKSICVQ LNTSVEINCT GAGHCNISRA KWNNTLKQIA  120
SKLREQFGNK TIIFSQSLGG DPEFVTHSFN CGGEFFYCDS TQLFDSTWFD STWS        174

SEQ ID NO: 82           moltype = AA  length = 174
FEATURE                 Location/Qualifiers
source                  1..174
                        mol_type = protein
                        organism = synthetic construct
SEQUENCE: 82
DTITLPCRPA PPPHCSSNIT GLILTRGGGI SDDKTEIFRP GGGDMRDIAR CQIAGTVVST  60
QLLLNGSLAE EEVVIRSENF TDNSKSICVQ LNTSVEINCT GAGHCNISRA KWNNTLKQIA  120
SKLREQFGNK TIIFSQSLGG DPEFVTHSFN CGGEFFYCDS TQLFDSTWFD STWS        174

SEQ ID NO: 83           moltype = AA  length = 173
FEATURE                 Location/Qualifiers
source                  1..173
                        mol_type = protein
                        organism = synthetic construct
SEQUENCE: 83
DTITLPCRPA PPPHCSSNIT GLILTRGGGI SDDKTEIFRP SGGDMRDIAR CQIAGTVVST  60
QLLLNGSLAE EEVVIRSEDF RDNSKSICVQ LNTSVEINCT GAGHCNISRA KWNNTLKQIA  120
SKLREQFGNK TIIFSQSLGG DPEFVTHSFN CGGEFFYCDS TQLFDSTWFD STW         173

SEQ ID NO: 84           moltype = AA  length = 173
FEATURE                 Location/Qualifiers
source                  1..173
                        mol_type = protein
                        organism = synthetic construct
SEQUENCE: 84
DTITLPCRPA PPPHCSSNIT GLILTRGGGI SDDKTEIFRP GGGDMRDIAR CQIAGTVVST  60
QLLLNGSLAE EEVVIRSEDF RDNSKSICVQ LNTSVEINCT GAGHCNISRA KWNNTLKQIA  120
SKLREQFGNR TIIFSQSLGG DPEFVTHSFN CGGEFFYCDS TQLFDSTWFD STW         173

SEQ ID NO: 85           moltype = AA  length = 173
FEATURE                 Location/Qualifiers
source                  1..173
                        mol_type = protein
                        organism = synthetic construct
SEQUENCE: 85
DTITLPCRPA PPPHCSSNIT GLILTRGGGI SDDDTEIFRP SGGDMRDIAR CQIAGTVVST  60
QLFLNGSLAE EEVVIRSEDF RDNSKSICVQ LNTSVEINCT GAGHCNISRA KWNNTLKQIA  120
SKLREQFGNR TIIFSQSLGG DPEFVTHSFN CGGEFFYCDS TQLFDSTWFD STW         173

SEQ ID NO: 86           moltype = AA  length = 173
FEATURE                 Location/Qualifiers
source                  1..173
                        mol_type = protein
                        organism = synthetic construct
SEQUENCE: 86
DTITLPCRPA PPPHCSSNIT GLILTRAGGI SDDNTEIFRP SGGDMRDIAR CQIAGTVVST  60
QLFLNGSLAE EEVVIRSEDF RDNSKSICVQ LNTSVEINCT GAGHCNISRA KWNNTLKQIA  120
SKLREQFGNR TIIFSQSLGG DPEFVTHSFN CGGEFFYCDS TQLFDSTWFD STW         173

SEQ ID NO: 87           moltype = AA  length = 173
FEATURE                 Location/Qualifiers
source                  1..173
                        mol_type = protein
                        organism = synthetic construct
SEQUENCE: 87
DTITLPCRPA PPPHCSSNIT GLILTRGGGI SDDNTEIFRP SGGDMRDIAR CQIAGTVVST  60
QLLLNGSLAE EEVVIRSEDF RDNSKSICVQ LNTSVEINCT GAGHCNISRA KWNNTLKQIA  120
```

```
SKLREQFGNR TIIFSQSLGG DPEFVTHSFN CGGEFFYCDS TQLFDSTWFD STW         173

SEQ ID NO: 88          moltype = AA  length = 173
FEATURE                Location/Qualifiers
source                 1..173
                       mol_type = protein
                       organism = synthetic construct
SEQUENCE: 88
DTITLPCRPA PPPHCSSNIT GLILTRGGGV SDDDTEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFSQSSGG DPEFVTHSFN CGGEFFYCDS TQLFDSTWFD STW         173

SEQ ID NO: 89          moltype = AA  length = 173
FEATURE                Location/Qualifiers
source                 1..173
                       mol_type = protein
                       organism = synthetic construct
SEQUENCE: 89
DTITLPCRPA PPPHCSSNIT GLILTRGGGV SDDDTEIFRP AGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFSQSSGG DPEFVTHSFN CGGEFFYCDS TQLFDSTWFD STW         173

SEQ ID NO: 90          moltype = AA  length = 170
FEATURE                Location/Qualifiers
source                 1..170
                       mol_type = protein
                       organism = synthetic construct
SEQUENCE: 90
DTITLPCRPA PPPHCSSNIT GLILTRGGGV SDDDTEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFSQSSGG DPEFVTHSFN CGGEFFYCDS TQLFDSTWFD             170

SEQ ID NO: 91          moltype = AA  length = 172
FEATURE                Location/Qualifiers
source                 1..172
                       mol_type = protein
                       organism = synthetic construct
SEQUENCE: 91
DTITLPCRPA PPPHCSSNIT GLILTRDGGV SNDETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 92          moltype = AA  length = 172
FEATURE                Location/Qualifiers
source                 1..172
                       mol_type = protein
                       organism = synthetic construct
SEQUENCE: 92
DTITLPCRPA PPPHCSSNIT GLILTRDGGN SNDETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 93          moltype = AA  length = 172
FEATURE                Location/Qualifiers
source                 1..172
                       mol_type = protein
                       organism = synthetic construct
SEQUENCE: 93
DTITLPCRPA PPPHCSSNIT GLILTRDGGV SNDESEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 94          moltype = AA  length = 172
FEATURE                Location/Qualifiers
source                 1..172
                       mol_type = protein
                       organism = synthetic construct
SEQUENCE: 94
DTITLPCRPA PPPHCSSNIT GLILTRDGGV SNDETEIFRP GGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 95          moltype = AA  length = 172
FEATURE                Location/Qualifiers
source                 1..172
                       mol_type = protein
                       organism = synthetic construct
SEQUENCE: 95
DTITLPCRPA PPPHCSSNIT GLILTRDGGV SNDETEIFRP SGGDMRDIAR CQIAGTVVST  60
```

```
QLLLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 96          moltype = AA  length = 172
FEATURE                Location/Qualifiers
source                 1..172
                       mol_type = protein
                       organism = synthetic construct
SEQUENCE: 96
DTITLPCRPA PPPHCSSNIT GLILTRDGGV SNDETEIFRP SGGDMRDIAR CQIAGTVVST  60
QLFLNGSLAE EEVVIRSVDF TDNAKSICVQ LNTSVEINCT GAGHCNISRA KWNNTLKQIA  120
SKLREQFGNR TIIFKQSSGG DPEFVTHSFN CGGEFFYCDS TQLFNSTWFN ST          172

SEQ ID NO: 97          moltype = AA  length = 172
FEATURE                Location/Qualifiers
source                 1..172
                       mol_type = protein
                       organism = synthetic construct
SEQUENCE: 97
DTITLPCRPA PPPHCSSNIT GLILTRDGGV SNDETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNK TIIFKQSSGG DPEFVTHSFN CGGEFFYCDS TQLFNSTWFN ST          172

SEQ ID NO: 98          moltype = AA  length = 172
FEATURE                Location/Qualifiers
source                 1..172
                       mol_type = protein
                       organism = synthetic construct
SEQUENCE: 98
DTITLPCRPA PPPHCSSNIT GLILTRDGGV SNDETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEIVTHSFN CGGEFFYCDS TQLFNSTWFN ST          172

SEQ ID NO: 99          moltype = AA  length = 172
FEATURE                Location/Qualifiers
source                 1..172
                       mol_type = protein
                       organism = synthetic construct
SEQUENCE: 99
DTITLPCRPA PPPHCSSNIT GLILTRDGGV SNDETEIFRP SGGDMRDIAR CQIAGTVVST  60
QLFLNGSLAE EEVVIRSVDF RDNAKSICVQ LDTSVEIDCT GAGHCDISRA KWDNTLKQIA  120
SKLREQFGDR TIIFKQSSGG DPEFVTHSFN CGGEFFYCDS TQLFDSTWFD ST          172

SEQ ID NO: 100         moltype = AA  length = 172
FEATURE                Location/Qualifiers
source                 1..172
                       mol_type = protein
                       organism = synthetic construct
SEQUENCE: 100
DTITLPCRPA PPPHCSSNIT GLILTRDGGV SNNETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 101         moltype = AA  length = 172
FEATURE                Location/Qualifiers
source                 1..172
                       mol_type = protein
                       organism = synthetic construct
SEQUENCE: 101
DTITLPCRPA PPPHCSSNIT GLILTRDGGN SNNETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 102         moltype = AA  length = 172
FEATURE                Location/Qualifiers
source                 1..172
                       mol_type = protein
                       organism = synthetic construct
SEQUENCE: 102
DTITLPCRPA PPPHCSSNIT GLILTRDGGV SNNETEIFRP GGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 103         moltype = AA  length = 172
FEATURE                Location/Qualifiers
source                 1..172
                       mol_type = protein
                       organism = synthetic construct
SEQUENCE: 103
```

```
DTITLPCRPA PPPHCSSNIT GLILTRDGGV SNNETEIFRP SGGDMRDIAR CQIAGTVVST  60
QLLLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 104         moltype = AA  length = 172
FEATURE                Location/Qualifiers
source                 1..172
                       mol_type = protein
                       organism = synthetic construct
SEQUENCE: 104
DTITLPCRPA PPPHCSSNIT GLILTRDGGV SNNETEIFRP SGGDMRDIAR CQIAGTVVST  60
QLFLNGSLAE EEVVIRSVDF TDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 105         moltype = AA  length = 172
FEATURE                Location/Qualifiers
source                 1..172
                       mol_type = protein
                       organism = synthetic construct
SEQUENCE: 105
DTITLPCRPA PPPHCSSNIT GLILTRDGGV SNNETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNK TIIFKQSSGG DPEFVTHSFN CGGEFFYCNS TQLFNSTWFN ST          172

SEQ ID NO: 106         moltype = AA  length = 172
FEATURE                Location/Qualifiers
source                 1..172
                       mol_type = protein
                       organism = synthetic construct
SEQUENCE: 106
DTITLPCRPA PPPHCSSNIT GLILTRDGGV SNNETEIFRP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEIVTHSFN CGGEFFYCNS TQLFNSTWFN ST          172

SEQ ID NO: 107         moltype = AA  length = 172
FEATURE                Location/Qualifiers
source                 1..172
                       mol_type = protein
                       organism = synthetic construct
SEQUENCE: 107
DTITLPCRPA PPPHCSSNIT GLILTRDGGV SNNETEIFRP SGGDMRDIAR CQIAGTVVST  60
QLFLNGSLAE EEVVIRSVNF TDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 108         moltype = AA  length = 172
FEATURE                Location/Qualifiers
source                 1..172
                       mol_type = protein
                       organism = synthetic construct
SEQUENCE: 108
DTITLPCRPA PPPHCSSNIT GLILTRAGGV SDNNTEIFFP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFSQSTGG DPEFVTHSFN CGGEFFYCNS TQLFNSTWFN ST          172

SEQ ID NO: 109         moltype = AA  length = 173
FEATURE                Location/Qualifiers
source                 1..173
                       mol_type = protein
                       organism = synthetic construct
SEQUENCE: 109
DTITLPCRPA PPPHCSSNIT GLILGRAGGA SDDNTEIFYP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFSQSTGG DPEIVTHSFN CGGEFFYCNS TQLFNSTWFN STW         173

SEQ ID NO: 110         moltype = AA  length = 172
FEATURE                Location/Qualifiers
source                 1..172
                       mol_type = protein
                       organism = synthetic construct
SEQUENCE: 110
DTITLPCRPA PPPHCSSNIT GLILTRAGGV SNNETEIFFP SGGDMRDIAR CQIAGTVVST  60
QLFLNGSLAE EEVVIRSVDF RDNAKSICVQ LNTSVEINCT GAGHCNISRA KWNNTLKQIA  120
SKLREQFGNR TIIFKQSSGG DPEFVTHSFN CGGEFFYCNS TQLFNSTWFN ST          172

SEQ ID NO: 111         moltype = AA  length = 355
FEATURE                Location/Qualifiers
source                 1..355
                       mol_type = protein
                       organism = synthetic construct
```

```
SEQUENCE: 111
VWKEATTTLF CASDAKAYDT EVHNVWATHA CVPTDPNPQE VELENVTENF NMWKNNMVEQ  60
MHEDIISLWD QSLKPCVKLT GGSVITQACP KISFEPIPIH YCAPAGFAIL KCKDKKFNGK  120
GPCSNVSTVQ CTHGIRPVVS TQLLLNGSLA EEEVVIRSEN FADNAKTIIV QLNESVEINC  180
TRPNNGGSGS GGDIRQAHCN LSRAKWNDTL NKIVIKLREQ FGNKTIVFKH SSGGDPEIVT  240
HSFNCGGEFF YCNSTQLFNS TWNVTEESNN TVENNTITLP CRIKQIINMW QKVGRAMYAP  300
PIRGQIRCSS NITGLLLTRD GGPEDNKTEV FRPGGGDMRD NWRSELYKYK VVKIE       355

SEQ ID NO: 112          moltype = AA  length = 299
FEATURE                 Location/Qualifiers
source                  1..299
                        mol_type = protein
                        organism = synthetic construct
SEQUENCE: 112
VWKDATTTLF CASDAKAHET EVHNVWATHA CVPTDPNPQE VELKNVTENF NMWKNNMVEQ  60
MHEDIISLWD QSLKPCVKLT GGSVITQACP KVSFEPIPIH YCAPAGFAIL KCKDKKFNGK  120
GPCSNVSTVQ CTHGIRPVVS TQLLLNGSLA EEEVVIRSED FRNNAKIIIV QLNESVEINC  180
TGAGHCNLSR AKWNDTLNKI VIKLREQFGN KTIVFKHSSG GDPEIVTHSF NCGGEFFYCN  240
STQLFNSTWN VTEESNNTVE NNTITLPCRI KQIINMWQEV GRAMYAPPIR GQIRCSSNI   299

SEQ ID NO: 113          moltype = AA  length = 175
FEATURE                 Location/Qualifiers
source                  1..175
                        mol_type = protein
                        organism = synthetic construct
SEQUENCE: 113
DTITLPCRPA PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS        175

SEQ ID NO: 114          moltype = AA  length = 175
FEATURE                 Location/Qualifiers
source                  1..175
                        mol_type = protein
                        organism = synthetic construct
SEQUENCE: 114
DTITLPCRPA PPPHCSSNIT GLILTRDGGN SNNESEIFRP GGGDMRDIAR CQIAGTVVST  60
QLFLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS        175

SEQ ID NO: 115          moltype = AA  length = 175
FEATURE                 Location/Qualifiers
source                  1..175
                        mol_type = protein
                        organism = synthetic construct
SEQUENCE: 115
DTITLPCRPA PPPHCSSNIT GLILTRDGGN SNNESEIFRP GGGDMRDNAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS        175

SEQ ID NO: 116          moltype = AA  length = 174
FEATURE                 Location/Qualifiers
source                  1..174
                        mol_type = protein
                        organism = synthetic construct
SEQUENCE: 116
DTITLPCRPA PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNK TIIFKQSSGG DPEIVTHSFN CGGEFFYCNS TQLFNSTWFN STWS         174

SEQ ID NO: 117          moltype = AA  length = 175
FEATURE                 Location/Qualifiers
source                  1..175
                        mol_type = protein
                        organism = synthetic construct
SEQUENCE: 117
DTITLPCRPA PPPHCSSNIT GLILTRDGGN SNNESEIFRP GGGDMRDIAR CQIAGTVVST  60
QLLLNGSLAE EEIVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS        175

SEQ ID NO: 118          moltype = AA  length = 175
FEATURE                 Location/Qualifiers
source                  1..175
                        mol_type = protein
                        organism = synthetic construct
SEQUENCE: 118
DTITLPCRPA PPPHCSSNIT GLILTRDGGN SNNESEIFRP GGGDMRDIAR CQIAGTVVSS  60
QLFLNGSLAE EEVVIRSVNF TDNAKSICVQ LNTSVEINCT GAGHCNISRA KWNNTLKQIA  120
SKLREQFGNN KTIIFKQSSG GDPEIVTHWF NCGGEFFYCN STQLFNSTWF NSTWS        175
```

```
SEQ ID NO: 119         moltype = AA  length = 420
FEATURE                Location/Qualifiers
source                 1..420
                       mol_type = protein
                       organism = synthetic construct
SEQUENCE: 119
VWKEATTTLF CASDAKAYDT ECHNVWATHA CVPTDPNPQE VVLVNVTENF NMWKNDMVEQ  60
MHEDIISLWD QCLKPCVKLT NTSVITQACP KVSFEPIPIH YCAPAGFAIL KCNNKTFNGT  120
GPCTNVSTVQ CTHGIRPVVS TQLLLNGSLA EEEVVIRSVN FTDNAKTIIV QLNTSVEINC  180
TRPNNGGSGS GGNMRQAHCN ISRAKWNNTL KQIASKLREQ FGNNKTIIFK QSSGGDPEIV  240
THSFNCGGEF FYCNSTQLFN STWFNSTWST EGSNNTEGSD TITLPCRIKQ IINMWQKVGK  300
AMYAPPISGQ IRCSSNITGL LLTRDGGNSN NESEIFRPGG GDMRDNWRSE LYKYKVVKIE  360
PLGSSKKQGD ADVCGEVAYI QSVVSDCHVP TAELRTLLEI RKLFLEIQKL KVELQGLSKE  420

SEQ ID NO: 120         moltype = AA  length = 7
FEATURE                Location/Qualifiers
source                 1..7
                       mol_type = protein
                       organism = synthetic construct
SEQUENCE: 120
GGSGSGG                                                            7

SEQ ID NO: 121         moltype = AA  length = 175
FEATURE                Location/Qualifiers
source                 1..175
                       mol_type = protein
                       organism = synthetic construct
SEQUENCE: 121
DTITLPCRPA PPPHCSSNIT GLILTRDGGN SNNESEIFRP GGGDMRDIAN CSIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS       175

SEQ ID NO: 122         moltype = AA  length = 175
FEATURE                Location/Qualifiers
source                 1..175
                       mol_type = protein
                       organism = synthetic construct
SEQUENCE: 122
DTITLPCRPA PPPHCSSNIT GLILTRDGGN SNNESEIFRP GGGDMRDIAR CQNASTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS       175

SEQ ID NO: 123         moltype = AA  length = 175
FEATURE                Location/Qualifiers
source                 1..175
                       mol_type = protein
                       organism = synthetic construct
SEQUENCE: 123
DTITLPCRPA PPPHCSSNIT GLILTRDGGN SNNESEIFRP GGGDMRDIAR CQIAGNVTST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS       175

SEQ ID NO: 124         moltype = AA  length = 175
FEATURE                Location/Qualifiers
source                 1..175
                       mol_type = protein
                       organism = synthetic construct
SEQUENCE: 124
DTITLPCRPA PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLRENFSNN KTIIFKQSSG GDPEIVTHSF NCGGEFFYCN STQLFNSTWF NSTWS       175

SEQ ID NO: 125         moltype = AA  length = 175
FEATURE                Location/Qualifiers
source                 1..175
                       mol_type = protein
                       organism = synthetic construct
SEQUENCE: 125
DTITLPCNPS PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS       175

SEQ ID NO: 126         moltype = AA  length = 175
FEATURE                Location/Qualifiers
source                 1..175
                       mol_type = protein
                       organism = synthetic construct
SEQUENCE: 126
```

```
DTITLPCRNA TPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGGEFFYCN STQLFNSTWF NSTWS       175

SEQ ID NO: 127         moltype = AA  length = 175
FEATURE                Location/Qualifiers
source                 1..175
                       mol_type = protein
                       organism = synthetic construct
SEQUENCE: 127
DTITLPCRPA PPPHCSSNIT GLILTRDGGN SNNESEIFRP GGGDMRDIAR CQIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGNETFYCN STQLFNSTWF NSTWS       175

SEQ ID NO: 128         moltype = AA  length = 175
FEATURE                Location/Qualifiers
source                 1..175
                       mol_type = protein
                       organism = synthetic construct
SEQUENCE: 128
DTITLPCNPS PPPHCSSNIT GLILTRDGGN SNNESEIFRP GGGDMRDIAR CQNASTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGNETFYCN STQLFNSTWF NSTWS       175

SEQ ID NO: 129         moltype = AA  length = 175
FEATURE                Location/Qualifiers
source                 1..175
                       mol_type = protein
                       organism = synthetic construct
SEQUENCE: 129
DTITLPCNPS PPPHCSSNIT GLILTRDGGN SNNESEIFRP GGGDMRDIAN CSIAGTVVST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGNETFYCN STQLFNSTWF NSTWS       175

SEQ ID NO: 130         moltype = AA  length = 175
FEATURE                Location/Qualifiers
source                 1..175
                       mol_type = protein
                       organism = synthetic construct
SEQUENCE: 130
DTITLPCNPS PPPHCSSNIT GLILTRDGGN SNNESEIFRP GGGDMRDIAN CSIAGNVTST  60
QLLLNGSLAE EEVVIRSVNF TDNAKSICVQ LNTSVEINCT GAGHCNISRA KWNNTLKQIA  120
SKLREQFGNN KTIIFKQSSG GDPEIVTHSF NCGNETFYCN STQLFNSTWF NSTWS       175

SEQ ID NO: 131         moltype = AA  length = 175
FEATURE                Location/Qualifiers
source                 1..175
                       mol_type = protein
                       organism = synthetic construct
SEQUENCE: 131
DTITLPCNPS PPPHCSSNIT GLILTRDGGN SNNESEIFRP GGGDMRDIAN CSIAGTVVST  60
QLLLNGSLAE EEVVIRSVNF TDNAKSICVQ LNTSVEINCT GAGHCNISRA KWNNTLKQIA  120
SKLRENFSNN KTIIFKQSSG GDPEIVTHSF NCGNETFYCN STQLFNSTWF NSTWS       175

SEQ ID NO: 132         moltype = AA  length = 175
FEATURE                Location/Qualifiers
source                 1..175
                       mol_type = protein
                       organism = synthetic construct
SEQUENCE: 132
DTITLPCNPS PPPHCSSNIT GLILTRDGGN SNNESEIFRP GGGDMRDIAN CSIAGNVTST  60
QLLLNGSLAE EEVVIRSVNF TDNAKSICVQ LNTSVEINCT GAGHCNISRA KWNNTLKQIA  120
SKLRENFSNN KTIIFKQSSG GDPEIVTHSF NCGNETFYCN STQLFNSTWF NSTWS       175

SEQ ID NO: 133         moltype = AA  length = 528
FEATURE                Location/Qualifiers
source                 1..528
                       mol_type = protein
                       organism = synthetic construct
SEQUENCE: 133
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LRDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGDTTDNTEI FRPSGGDMRD NWRSELYKYK VVEIKPLGSG GSGESQVRQQ  360
FSKDIEKLLN EQVNKEMQSS NLYMSMSSWC YTHSLDGAGL FLFDHAAEEY EHAKKLIIFL  420
NENNVPVQLT SISAPEHKFE GLTQIFQKAY EHEQHISESI NNIVDHAIKS KDHATFNFLQ  480
WYVAEQHEEE VLFKDILDKI ELIGNENHGL YLADQYVKGI AKSRKSGS              528
```

```
SEQ ID NO: 134         moltype = AA  length = 163
FEATURE                Location/Qualifiers
source                 1..163
                       mol_type = protein
                       organism = synthetic construct
SEQUENCE: 134
DIIKLLNEQV NKEMNSSNLY MSMSSWCYTH SLDGAGLFLF DHAAEEYEHA KKLIIFLNEN  60
NVPVQLTSIS APEHKFEGLT QIFQKAYEHE QHISESINNI VDHAIKSKDH ATFNFLQWYV  120
AEQHEEEVLF KDILDKIELI GNENHGLYLA DQYVKGIAKS RKS                   163

SEQ ID NO: 135         moltype = AA  length = 158
FEATURE                Location/Qualifiers
source                 1..158
                       mol_type = protein
                       organism = synthetic construct
SEQUENCE: 135
LNEQVNKEMN SSNLYMSMSS WCYTHSLDGA GLFLFDHAAE EYEHAKKLII FLNENNVPVQ  60
LTSISAPEHK FEGLTQIFQK AYEHEQHISE SINNIVDHAI KSKDHATFNF LQWYVAEQHE  120
EEVLFKDILD KIELIGNENH GLYLADQYVK GIAKSRKS                        158

SEQ ID NO: 136         moltype = AA  length = 163
FEATURE                Location/Qualifiers
source                 1..163
                       mol_type = protein
                       organism = synthetic construct
SEQUENCE: 136
DIIKLLNEQV NKEMQSSNLY MSMSSWCYTH SLDGAGLFLF DHAAEEYEHA KKLIIFLNEN  60
NVPVQLTSIS APEHKFEGLT QIFQKAYEHE QHISESINNI VDHAIKSKDH ATFNFLQWYV  120
AEQHEEEVLF KDILDKIELI GNENHGLYLA DQYVKGIAKS RKS                   163

SEQ ID NO: 137         moltype = AA  length = 528
FEATURE                Location/Qualifiers
source                 1..528
                       mol_type = protein
                       organism = synthetic construct
SEQUENCE: 137
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LRDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGDTTDNTEI FRPSGGDMRD NWRSELYKYK VVEIKPLGSG GSGESQVRQQ  360
FSKDIEKLLN EQVNKEMQSS NLYMSMSSWC YTHSLDGAGL FLFDHAAEEY EHAKKLIIFL  420
NENNVPVQLT SISAPEHKFE GLTQIFQKAY EHEQHISESI NNIVDHAIKS KDHATFNFLQ  480
WYVAEQHEEE VLFKDILDKI ELIGNENHGL YLADQYVKGI AKSRKSGS              528

SEQ ID NO: 138         moltype = AA  length = 68
FEATURE                Location/Qualifiers
source                 1..68
                       mol_type = protein
                       organism = synthetic construct
SEQUENCE: 138
SGRAHAGWET PEGCEQVLTG KRLMQCLPNP EDVKMALEVY KLSLEIEQLE LQRDSARQST  60
LDKELVPR                                                         68

SEQ ID NO: 139         moltype = AA  length = 55
FEATURE                Location/Qualifiers
source                 1..55
                       mol_type = protein
                       organism = synthetic construct
SEQUENCE: 139
KKQGDADVCG EVAYIQSVVS DCHVPTAELR TLLEIRKLFL EIQKLKVELQ GLSKE       55

SEQ ID NO: 140         moltype = AA  length = 57
FEATURE                Location/Qualifiers
source                 1..57
                       mol_type = protein
                       organism = synthetic construct
SEQUENCE: 140
ETPEGCEQVL TGKRLMQCLP NPEDVKMALE VYKLSLEIEQ LELQRDSARQ STLDKEL     57

SEQ ID NO: 141         moltype = AA  length = 58
FEATURE                Location/Qualifiers
source                 1..58
                       mol_type = protein
                       organism = synthetic construct
SEQUENCE: 141
WETPEGCEQV LTGKRLMQCL PNPEDVKMAL EVYKLSLEIE QLELQRDSAR QSTLDKEL    58
```

```
SEQ ID NO: 142          moltype = AA  length = 52
FEATURE                 Location/Qualifiers
source                  1..52
                        mol_type = protein
                        organism = synthetic construct
SEQUENCE: 142
CEQVLTGKRL MQCLPNPEDV KMALEVYKLS LEIEQLELQR DSARQSTLDK EL          52

SEQ ID NO: 143          moltype = AA  length = 57
FEATURE                 Location/Qualifiers
source                  1..57
                        mol_type = protein
                        organism = synthetic construct
SEQUENCE: 143
ETPEGCEQVL TGKRLMQCLP NPEDVKMALE VYKLSLEIEQ LELQRDSARQ YTLDKEL     57

SEQ ID NO: 144          moltype = AA  length = 57
FEATURE                 Location/Qualifiers
source                  1..57
                        mol_type = protein
                        organism = synthetic construct
SEQUENCE: 144
ETPEGCEQVL AGKRLMQCLP NPEDVKMALE VYKLSLEIEQ LELQRDRARQ STLDKEL     57

SEQ ID NO: 145          moltype = AA  length = 57
FEATURE                 Location/Qualifiers
source                  1..57
                        mol_type = protein
                        organism = synthetic construct
SEQUENCE: 145
ETPEGCEQVL AGKRLMQCLP NPEDVKMALE VYKLSLEIEQ LELQRDRARQ STWDKEL     57

SEQ ID NO: 146          moltype = AA  length = 57
FEATURE                 Location/Qualifiers
source                  1..57
                        mol_type = protein
                        organism = synthetic construct
SEQUENCE: 146
EVPEGCEQVQ AGRRLMQCLA DPYEVKMALE VYKLSLEIEL LELQRDKARK SSVLRQL     57

SEQ ID NO: 147          moltype = AA  length = 57
FEATURE                 Location/Qualifiers
source                  1..57
                        mol_type = protein
                        organism = synthetic construct
SEQUENCE: 147
VVPEGCEHIL KGRKTMQCLP NPEDVKMALE IYKLSLDIEL LELQRDRAKE STVQSPV     57

SEQ ID NO: 148          moltype = AA  length = 55
FEATURE                 Location/Qualifiers
source                  1..55
                        mol_type = protein
                        organism = synthetic construct
SEQUENCE: 148
EVPKDCEHVF AGKKLMQCLP NSNDVKMALE VYKLTLEIKQ LQLQIDKAKH VDREL       55

SEQ ID NO: 149          moltype = AA  length = 57
FEATURE                 Location/Qualifiers
source                  1..57
                        mol_type = protein
                        organism = synthetic construct
SEQUENCE: 149
EYPEDCEQVH EGKKLMQCLP NLEEIKLALE LYKLSLETKL LELQIDKEKK AKAKYSI     57

SEQ ID NO: 150          moltype = AA  length = 57
FEATURE                 Location/Qualifiers
source                  1..57
                        mol_type = protein
                        organism = synthetic construct
SEQUENCE: 150
EYPEDCEQVH EGKKLMECLP TLEEIKLALA LYKLSLETNL LELQIDKEKK AKAKYST     57

SEQ ID NO: 151          moltype = AA  length = 57
FEATURE                 Location/Qualifiers
source                  1..57
                        mol_type = protein
                        organism = synthetic construct
SEQUENCE: 151
```

```
EIAEGCEQVL AGRKIMQCLP KPEDVRTALE LYKLSLEIKQ LEKKLEKEEK CTPEVQE     57

SEQ ID NO: 152         moltype = AA  length = 67
FEATURE                Location/Qualifiers
source                 1..67
                       mol_type = protein
                       organism = synthetic construct
SEQUENCE: 152
EYPEGCEQVV TGRKLLQCLS RPEEVKLALE VYKLSLEIEI LQTNKLKKEA FLLREREKNV  60
TCDFNPE                                                            67

SEQ ID NO: 153         moltype = AA  length = 52
FEATURE                Location/Qualifiers
source                 1..52
                       mol_type = protein
                       organism = synthetic construct
SEQUENCE: 153
EYPEGCEQVV TGRKLLKCLS RPEEVKLALE VYKLSLEIAL LELQIDKPKD AS          52

SEQ ID NO: 154         moltype = AA  length = 52
FEATURE                Location/Qualifiers
source                 1..52
                       mol_type = protein
                       organism = synthetic construct
SEQUENCE: 154
EVPENCEQVI VGKKLMKCLS NPDEAQMALQ LYKLSLEAEL LRLQIVKARQ GS          52

SEQ ID NO: 155         moltype = AA  length = 54
FEATURE                Location/Qualifiers
source                 1..54
                       mol_type = protein
                       organism = synthetic construct
SEQUENCE: 155
EASEDLKPAL TGNKTMQYVP NSHDVKMALE IYKLTLEVEL LQLQIQKEKH TEAH        54

SEQ ID NO: 156         moltype = AA  length = 51
FEATURE                Location/Qualifiers
source                 1..51
                       mol_type = protein
                       organism = synthetic construct
SEQUENCE: 156
VSAEVCEAVF KGQKLLKCLP NAMEVKMALE VYKLSLEIEK LEQEKRKLEI A           51

SEQ ID NO: 157         moltype = AA  length = 66
FEATURE                Location/Qualifiers
source                 1..66
                       mol_type = protein
                       organism = synthetic construct
SEQUENCE: 157
EVPEECKQVA AGRKLLECLP NPSDVKMALE VYKLSLEIEQ LEKEKYVKIQ EKFSKKEMKQ  60
LTSALH                                                             66

SEQ ID NO: 158         moltype = AA  length = 59
FEATURE                Location/Qualifiers
source                 1..59
                       mol_type = protein
                       organism = synthetic construct
SEQUENCE: 158
EVLEDCRIVS RGAQLLHCLS SPEDVHRALK VYKLFLEIER LEHQKEKWIQ LHRKPQSMK   59

SEQ ID NO: 159         moltype = AA  length = 63
FEATURE                Location/Qualifiers
source                 1..63
                       mol_type = protein
                       organism = synthetic construct
SEQUENCE: 159
EGPEDCEIVN KGRQLLQCLS SPEDVQRALE VYKLSLEIER LEQQREKRTS VHRKAHYTKV  60
DGP                                                                63

SEQ ID NO: 160         moltype = AA  length = 67
FEATURE                Location/Qualifiers
source                 1..67
                       mol_type = protein
                       organism = synthetic construct
SEQUENCE: 160
EAPEGCEQVL TGRKLMQCLP SPEDVKVALE VYKLSLEIKQ LEKERDKLMN THQKFSEKEE  60
MKDLFFP                                                            67

SEQ ID NO: 161         moltype = AA  length = 52
```

```
FEATURE                Location/Qualifiers
source                 1..52
                       mol_type = protein
                       organism = synthetic construct
SEQUENCE: 161
EVPEGCEQVL TGKKLMQCLP NPEDVKMALE VYKLSLEIEL LELQIDKARQ GS          52

SEQ ID NO: 162         moltype = AA  length = 47
FEATURE                Location/Qualifiers
source                 1..47
                       mol_type = protein
                       organism = synthetic construct
SEQUENCE: 162
GCEQVLTGKR LMQCLPNPED VKMALEVYKL SLEIEQLELQ RDSARQS                47

SEQ ID NO: 163         moltype = AA  length = 51
FEATURE                Location/Qualifiers
source                 1..51
                       mol_type = protein
                       organism = synthetic construct
SEQUENCE: 163
ETPEGCEQVL TGKRLMQCLP NPEDVKMALE VYKLSLEIEQ LELQRDSARQ S           51

SEQ ID NO: 164         moltype = AA  length = 53
FEATURE                Location/Qualifiers
source                 1..53
                       mol_type = protein
                       organism = synthetic construct
SEQUENCE: 164
GSEQVLTGKR LMQSLPNPED VKMALEVYKL SLEIEQLELQ RDSARQSTLD KEL         53

SEQ ID NO: 165         moltype = AA  length = 57
FEATURE                Location/Qualifiers
source                 1..57
                       mol_type = protein
                       organism = synthetic construct
SEQUENCE: 165
ETPEGCEQVL TGKRLMQCLP NPEDVKMALE IYKLTLEIEQ LELQRDSARQ STLDKEL     57

SEQ ID NO: 166         moltype = AA  length = 57
FEATURE                Location/Qualifiers
source                 1..57
                       mol_type = protein
                       organism = synthetic construct
SEQUENCE: 166
ETPEGCEQVL TGKRLMQCLP NPEDVKMALE IYKLSLEIKQ LELQRDSARQ STLDKEL     57

SEQ ID NO: 167         moltype = AA  length = 50
FEATURE                Location/Qualifiers
source                 1..50
                       mol_type = protein
                       organism = synthetic construct
SEQUENCE: 167
EGCEQILTGK RLMQCLPDPE DVKMALEIYK LSLEIKQLEL QRDRARQSTL             50

SEQ ID NO: 168         moltype = AA  length = 57
FEATURE                Location/Qualifiers
source                 1..57
                       mol_type = protein
                       organism = synthetic construct
SEQUENCE: 168
ETPEGCEQVL TGKRLMQCLP NPEDVKMALE VYKLSLEIKQ LELQRDRARQ STLDKEL     57

SEQ ID NO: 169         moltype = AA  length = 52
FEATURE                Location/Qualifiers
source                 1..52
                       mol_type = protein
                       organism = synthetic construct
SEQUENCE: 169
EGCEQILTGK RLMQCLPNPE DVKMALEIYK LSLEIEQLEL QRDRARQSTL DK          52

SEQ ID NO: 170         moltype = AA  length = 61
FEATURE                Location/Qualifiers
source                 1..61
                       mol_type = protein
                       organism = synthetic construct
SEQUENCE: 170
WETPEGCEQV LTGKRLMQCL PNPEDVKMAL EVYKLSLEIE QLELQRDSAR QSTLDKELVP  60
R                                                                  61
```

```
SEQ ID NO: 171          moltype = AA  length = 62
FEATURE                 Location/Qualifiers
source                  1..62
                        mol_type = protein
                        organism = synthetic construct
SEQUENCE: 171
AHAGWETPEG CEQVLTGKRL MQCLPNPEDV KMALEVYKLS LEIEQLELQR DSARQSTLDK  60
EL                                                                 62

SEQ ID NO: 172          moltype = AA  length = 56
FEATURE                 Location/Qualifiers
source                  1..56
                        mol_type = protein
                        organism = synthetic construct
SEQUENCE: 172
SKKQGDADVC GEVAYIQSVV SDCHVPTEDV KTLLEIRKLF LEIQKLKVEL QGLSKE      56

SEQ ID NO: 173          moltype = AA  length = 55
FEATURE                 Location/Qualifiers
source                  1..55
                        mol_type = protein
                        organism = synthetic construct
SEQUENCE: 173
SKKQGDADVC GEVAYIQSVV SDCHVPTAEL RTLLEIRKLF LEIQKLKVEL QGLSK       55

SEQ ID NO: 174          moltype = AA  length = 415
FEATURE                 Location/Qualifiers
source                  1..415
                        mol_type = protein
                        organism = synthetic construct
SEQUENCE: 174
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LRDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGDTTDNTEI FRPSGGDMRD NWRSELYKYK VVEIKPLSGR AHAGWETPEG  360
CEQVLTGKRL MQCLPNPEDV KMALEVYKLS LEIEQLELQR DSARQSTLDK ELVPR       415

SEQ ID NO: 175          moltype = AA  length = 347
FEATURE                 Location/Qualifiers
source                  1..347
                        mol_type = protein
                        organism = synthetic construct
SEQUENCE: 175
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LSDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGNTTNNTEI FRPGGGDMRD NWRSELYKYK VVEIKPL                347

SEQ ID NO: 176          moltype = AA  length = 172
FEATURE                 Location/Qualifiers
source                  1..172
                        mol_type = protein
                        organism = synthetic construct
SEQUENCE: 176
DTITLPCRPA PPPHCSSNIT GLILTRQGGY SNDNTVIFRP SGGDWRDIAR CQIAGTVVST  60
QLFLNGSLAE EEVVIRSEDW RDNAKSICVQ LNTSVEINCT GAGHCNISRA KWNNTLKQIA  120
SKLREQYGNK TIIFKPSSGG DPEFVNHSFN CGGEFFYCDS TQLFNSTWFN ST          172

SEQ ID NO: 177          moltype = AA  length = 625
FEATURE                 Location/Qualifiers
source                  1..625
                        mol_type = protein
                        organism = synthetic construct
SEQUENCE: 177
ENLWVTVYYG VPVWKEAKTT LFCASDAKAY EKEVHNVWAT HACVPTDPNP QEVVLENVTE  60
NFNMWKNDMV DQMQEDVISI WDQSLKPCVK LTPLCVTLNC TNVNVTSNST NVNSSSTDNT  120
TLGEIKNCSF DITTEIRDKT RKEYALFYRL DIVPLDNSSN PNSSNTYRLI NCNTSTCTQA  180
CPKVTFDPIP IHYCAPAGYA ILKCNNKTFN GKGPCNNVST VQCTHGIKPV VSTQLLLNGS  240
LAEEEIVIRS KNLSDNAKII IVQLNKSVEI VCTRPNNNTR RSIRIGPGQT FYATDIIGDI  300
RQAYCNISGR NWSEAVNQVK KKLKEHFPHK NISFQSSSGG DLEITTHSFN CGGEFFYCNT  360
SGLFNDTISN ATIMLPCRIK QIINMWQEVG KCIYAPPIKG NITCKSDITG LLLLRDGGNT  420
TNNTEIFRPG GGDMRDNWRS ELYKYKVVKI EPLGVAPTRC KRRVVGRRRR RRAVGIGAVF  480
LGFLGAAGST MGAASMTLTV QARNLLSGIV QQQSNLLRAP EAQQHLLKLT VWGIKQLQAR  540
VLAVERYLRD QQLLGIWGCS GKLICCTNVP WNSSWSNRNL SEIWDNMTWL QWDKEISNYT  600
```

```
QIIYGLLEES QNQQEKNEQD LLALD                                  625

SEQ ID NO: 178          moltype = AA  length = 625
FEATURE                 Location/Qualifiers
source                  1..625
                        mol_type = protein
                        organism = synthetic construct
SEQUENCE: 178
ENLWVTVYYG VPVWKEAKTT LFCASDAKAY EKEVHNVWAT HACVPTDPNP QEVVLENVTE  60
NFNMWKNDMV DQMQEDVISI WDQSLKPCVK LTPLCVTLNC TNVNVTSNST NVNSSSTDNT  120
TLGEIKNCSF DITTEIRDKT RKEYALFYRL DIVPLDNSSN PNSSNTYRLI NCNTSTCTQA  180
CPKVTFDPIP IHYCAPAGYA ILKCNNKTFN GKGPCNNVST VQCTHGIKPV VSTQLLLNGS  240
LAEEEIVIRS KNLADNAKII IVQLNKSVEI VCTRPNNNTR RSIRIGPGQT FYATDIIGDI  300
RQAYCNISGR NWSEAVNQVK KKLKEHFPHK NISFQSSSGG DLEITTHSFN CGGEFFYCNT  360
SGLFNDTISN ATIMLPCRIK QIINMWQEVG KCIYAPPIKG NITCKSDITG LLLLRDGGNT  420
ANNAEIFRPG GGDMRDNWRS ELYKYKVVKI EPLGVAPTRC KRRVVGRRRR RRAVGIGAVF  480
LGFLGAAGST MGAASMTLTV QARNLLSGIV QQQSNLLRAP EAQQHLLKLT VWGIKQLQAR  540
VLAVERYLRD QQLLGIWGCS GKLICCTNVP WNSSWSNRNL SEIWDNMTWL QWDKEISNYT  600
QIIYGLLEES QNQQEKNEQD LLALD                                  625

SEQ ID NO: 179          moltype = AA  length = 625
FEATURE                 Location/Qualifiers
source                  1..625
                        mol_type = protein
                        organism = synthetic construct
SEQUENCE: 179
ENLWVTVYYG VPVWKEAKTT LFCASDAKAY EKEVHNVWAT HACVPTDPNP QEVVLENVTE  60
NFNMWKNDMV DQMQEDVISI WDQSLKPCVK LTPLCVTLNC TNVNVTSNST NVNSSSTDNT  120
TLGEIKNCSF DITTEIRDKT RKEYALFYRL DIVPLDNSSN PNSSNTYRLI NCNTSTCTQA  180
CPKVTFDPIP IHYCAPAGYA ILKCNNKTFN GKGPCNNVST VQCTHGIKPV VSTQLLLNGS  240
LAEEEIVIRS KNLADNAKII IVQLNKSVEI VCTRPNNNTR RSIRIGPGQT FYATDIIGDI  300
RQAYCNISGR NWSEAVNQVK KKLKEHFPHK NISFQSSSGG DLEITTHSFN CGGEFFYCNT  360
SGLFNDTISN ATIMLPCRIK QIINMWQEVG KCIYAPPIKG NITCKSDITG LLLLRDGGNT  420
TNNTEIFRPG GGDMRDNWRS ELYKYKVVKI EPLGVAPTRC KRRVVGRRRR RRAVGIGAVF  480
LGFLGAAGST MGAASMTLTV QARNLLSGIV QQQSNLLRAP EAQQHLLKLT VWGIKQLQAR  540
VLAVERYLRD QQLLGIWGCS GKLICCTNVP WNSSWSNRNL SEIWDNMTWL QWDKEISNYT  600
QIIYGLLEES QNQQEKNEQD LLALD                                  625

SEQ ID NO: 180          moltype = AA  length = 360
FEATURE                 Location/Qualifiers
source                  1..360
                        mol_type = protein
                        organism = synthetic construct
SEQUENCE: 180
VWKEATATLF CASDAKAYET ECHNVWATHA CVPTDPNPQE VVLENVTENF NMWKNNMVEQ  60
MHEDIISLWD QCLKPCVKLT NTSVITQACP KISFEPIPIH YCAPAGFAIL KCNDKKFNGT  120
GPCTNVSTVQ CTHGIRPVVS TQLLLNGSLA EEEIVIRSEN IKDNAKIIIV QLNETVEINC  180
TRPNNGGSGS GGDIRQAHCN ISKAKWENTL KQIARKLREH FKNETIAFNQ SSGGDPEIVM  240
HSFNCGGEFF YCNSTQLFNS TWTWNDTEVV NNTEKNINIT LPCRIKQIIN MWQEVGKAMY  300
APPIKGQIRC SSNITGLLLT RDGGSSTNGT TETFRPGGGD MRDNWRSELY KYKVVKIEPL  360

SEQ ID NO: 181          moltype = AA  length = 360
FEATURE                 Location/Qualifiers
source                  1..360
                        mol_type = protein
                        organism = synthetic construct
SEQUENCE: 181
VWKEASTTLF CASDAKAYDT ECHNVWATHA CVPTDPNPQE VVLENVTEKF NMWKNNMVEQ  60
MHEDIISLWD QCLKPCVKLT NTSVITQACP KISFEPIPIH YCAPAGFAIL KCNDKKFNGT  120
GKCTNVSTVQ CTHGIRPVVS TQLLLNGSLA EEEIIIRSEN LTDNAKTLIV QLNETVAINC  180
TRPNNGGSGS GGNIRQAHCN ISETDWNNTL KQVARKLREL FNKTIVFNQS SGGDPEIVMH  240
SFNCGGEFFY CNTTQLFNST WHGNETEESS ITKDNKTITL PCRIKQIVNR WQEVGKAMYA  300
PPIEGLIRCS SNITGLLLTR DGGNITNETT TETFRPGGGN MRDNWRSELY KYKVVKIEPL  360

SEQ ID NO: 182          moltype = AA  length = 625
FEATURE                 Location/Qualifiers
source                  1..625
                        mol_type = protein
                        organism = synthetic construct
SEQUENCE: 182
ENLWVTVYYG VPVWKEAKTT LFCASDAKAY EKEVHNVWAT HACVPTDPNP QEVVLENVTE  60
NFNMWKNDMV DQMQEDVISI WDQSLKPCVK LTPLCVTLNC TNVNVTSNST NVNSSSTDNT  120
TLGEIKNCSF DITTEIRDKT RKEYALFYRL DIVPLDNSSN PNSSNTYRLI NCNTSTCTQA  180
CPKVTFDPIP IHYCAPAGYA ILKCNNKTFN GKGPCNNVST VQCTHGIKPV VSTQLLLNGS  240
LAEEEIVIRS KNLSDNAKII IVQLNKSVEI VCTRPNNNTR RSIRIGPGQT FYATDIIGDI  300
RQAYCNISGR NWSEAVNQVK KKLKEHFPHK NISFQSSSGG DLEITTHSFN CGGEFFYCNT  360
SGLFNDTISN ATIMLPCRIK QIINMWQEVG KCIYAPPIKG NITCKSDITG LLLLRDGGNT  420
ANNAEIFRPG GGDMRDNWRS ELYKYKVVKI EPLGVAPTRC KRRVVGRRRR RRAVGIGAVF  480
LGFLGAAGST MGAASMTLTV QARNLLSGIV QQQSNLLRAP EAQQHLLKLT VWGIKQLQAR  540
```

```
VLAVERYLRD QQLLGIWGCS GKLICCTNVP WNSSWSNRNL SEIWDNMTWL QWDKEISNYT  600
QIIYGLLEES QNQQEKNEQD LLALD                                        625

SEQ ID NO: 183         moltype = AA  length = 362
FEATURE                Location/Qualifiers
source                 1..362
                       mol_type = protein
                       organism = synthetic construct
SEQUENCE: 183
VWKEATTTLF CASDAKAYDT ECHNVWATHA CVPTDPNPQE VVLVNVTENF NMWKNDMVEQ  60
MHEDIISLWD QCLKPCVKLT NTSVITQACP KVSFEPIPIH YCAPAGFAIL KCNNKTFNGT  120
GPCTNVSTVQ CTHGIRPVVS TQLLLNGSLA EEEVVIRSVN FTDNAKTIIV QLNTSVEINC  180
TRPNNGGSGS GGNMRQAHCN ISRAKWNNTL KQIASKLREQ FGNNKTIIFK QSSGGDPEIV  240
THSFNCGGEF FYCNSTQLFN STWFNSTWST EGSNNTEGSD TITLPCRIKQ IINMWQKVGK  300
AMYAPPISGQ IRCSSNITGL LLTRDGGNSN NESEIFRPGG GDMRDNWRSE LYKYKVVKIE  360
PL                                                                 362

SEQ ID NO: 184         moltype = AA  length = 361
FEATURE                Location/Qualifiers
source                 1..361
                       mol_type = protein
                       organism = synthetic construct
SEQUENCE: 184
VWKEATTTLF CASDAKAYET ECHNVWATHA CVPTDPNPQE VVLGNVTENF NMWKNNMVEQ  60
MHEDIISLWD ECLKPCVKLT NTSVITQACP KVSFEPIPIH YCAPAGFAIL KCNNKTFNGT  120
GPCTNVSTVQ CTHGIRPVVS TQLLLNGSLA EEEVVIRSEN FTNNAKTIIV HLKKSVEINC  180
TRPGNGGSGS GGDIRQAHCN LSSVQWNDTL KQIVIKLGEQ FGTNKTIAFN QSSGGDPEIV  240
MHSFNCGGEF FYCNTTQLFN STWEFHGNWT RSNFTESNST TITLPCRIKQ IVNMWQEVGK  300
AMYAPPIRGQ IRCSSNITGL LLTRDGGVNG TRETFRPGGG DMRDNWRSEL YKYKVVKIEP  360
L                                                                  361

SEQ ID NO: 185         moltype = AA  length = 11
FEATURE                Location/Qualifiers
source                 1..11
                       mol_type = protein
                       organism = synthetic construct
SEQUENCE: 185
RASQSVSSYL A                                                       11

SEQ ID NO: 186         moltype = AA  length = 7
FEATURE                Location/Qualifiers
source                 1..7
                       mol_type = protein
                       organism = synthetic construct
SEQUENCE: 186
DASNRAT                                                            7

SEQ ID NO: 187         moltype = AA  length = 5
FEATURE                Location/Qualifiers
source                 1..5
                       mol_type = protein
                       organism = synthetic construct
SEQUENCE: 187
QQYEF                                                              5

SEQ ID NO: 188         moltype = AA  length = 11
FEATURE                Location/Qualifiers
source                 1..11
                       mol_type = protein
                       organism = synthetic construct
SEQUENCE: 188
QASQDISNYL N                                                       11

SEQ ID NO: 189         moltype = AA  length = 7
FEATURE                Location/Qualifiers
source                 1..7
                       mol_type = protein
                       organism = synthetic construct
SEQUENCE: 189
DASNLET                                                            7

SEQ ID NO: 190         moltype = AA  length = 5
FEATURE                Location/Qualifiers
source                 1..5
                       mol_type = protein
                       organism = synthetic construct
SEQUENCE: 190
AVLEF                                                              5
```

```
SEQ ID NO: 191          moltype = AA  length = 5
FEATURE                 Location/Qualifiers
source                  1..5
                        mol_type = protein
                        organism = synthetic construct
SEQUENCE: 191
QQYET                                                              5

SEQ ID NO: 192          moltype = AA  length = 12
FEATURE                 Location/Qualifiers
source                  1..12
                        mol_type = protein
                        organism = synthetic construct
SEQUENCE: 192
RASQSVSSSY LA                                                      12

SEQ ID NO: 193          moltype = AA  length = 7
FEATURE                 Location/Qualifiers
source                  1..7
                        mol_type = protein
                        organism = synthetic construct
SEQUENCE: 193
GASSRAT                                                            7

SEQ ID NO: 194          moltype = AA  length = 5
FEATURE                 Location/Qualifiers
source                  1..5
                        mol_type = protein
                        organism = synthetic construct
SEQUENCE: 194
QQLEF                                                              5

SEQ ID NO: 195          moltype = AA  length = 14
FEATURE                 Location/Qualifiers
source                  1..14
                        mol_type = protein
                        organism = synthetic construct
SEQUENCE: 195
TGTSSDVGGY NYVS                                                    14

SEQ ID NO: 196          moltype = AA  length = 7
FEATURE                 Location/Qualifiers
source                  1..7
                        mol_type = protein
                        organism = synthetic construct
SEQUENCE: 196
EVSNRPS                                                            7

SEQ ID NO: 197          moltype = AA  length = 5
FEATURE                 Location/Qualifiers
source                  1..5
                        mol_type = protein
                        organism = synthetic construct
SEQUENCE: 197
SSYEF                                                              5

SEQ ID NO: 198          moltype = AA  length = 121
FEATURE                 Location/Qualifiers
source                  1..121
                        mol_type = protein
                        organism = synthetic construct
SEQUENCE: 198
QVQLVQSGAE VKKPGASVKV SCKASGYTFT DYYMNWVRQA PGQGLEWMGL INPKTGGPIY  60
AQKFQGRVTM TRDTSISTAY MELSRLRSDD TAIYYCARGK NSDYNWDFQH WGQGTLVTVS  120
S                                                                  121

SEQ ID NO: 199          moltype = AA  length = 121
FEATURE                 Location/Qualifiers
source                  1..121
                        mol_type = protein
                        organism = synthetic construct
SEQUENCE: 199
QVQLVQSGAE VKKPGASVKV SCKASGYTFT DYYMNWVRQA PGQGLEWMGL INPKTGGPNY  60
ARKFQGRVTM TRDTSISTAY MELSRLRFDD TAIYYCARGK NSDYNWDFQH WGQGTLVTVS  120
S                                                                  121

SEQ ID NO: 200          moltype = AA  length = 121
FEATURE                 Location/Qualifiers
source                  1..121
```

```
                        mol_type = protein
                        organism = synthetic construct
SEQUENCE: 200
QVQLVQSGAE VKKPGASVKV SCKASGYTFT GYYMNWVRQA PGQGLEWMGW INPNRGGTNY  60
AQKFQGRVTM TRDTSSSTAY MELSRLRSDD TAVYYCARGK NSDYNWDFQH WGQGTLVTVS  120
S                                                                  121

SEQ ID NO: 201          moltype = AA  length = 121
FEATURE                 Location/Qualifiers
source                  1..121
                        mol_type = protein
                        organism = synthetic construct
SEQUENCE: 201
QVQLVQSGAE VKKPGASVKV SCKASGYTFT DYYMNWVRQA PGQGLEWMGL INPKTGGPNY  60
AQKFQGRVTM TRDTSISTAY MELSRLRSDD TAIYYCARGK NSDYNWDFQH WGQGTLVTVS  120
S                                                                  121

SEQ ID NO: 202          moltype = AA  length = 121
FEATURE                 Location/Qualifiers
source                  1..121
                        mol_type = protein
                        organism = synthetic construct
SEQUENCE: 202
QVQLVQSGAE VKKPGASVKA SCKASGYTFT GYYMHWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                  121

SEQ ID NO: 203          moltype = DNA  length = 30
FEATURE                 Location/Qualifiers
source                  1..30
                        mol_type = other DNA
                        organism = synthetic construct
SEQUENCE: 203
gccaccgtac gtttcagctc cagcttggtc                                   30

SEQ ID NO: 204          moltype = AA  length = 99
FEATURE                 Location/Qualifiers
source                  1..99
                        mol_type = protein
                        organism = synthetic construct
SEQUENCE: 204
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYYS                         99

SEQ ID NO: 205          moltype = AA  length = 99
FEATURE                 Location/Qualifiers
source                  1..99
                        mol_type = protein
                        organism = synthetic construct
SEQUENCE: 205
DIVMSQSPSS LAVSVGEKVT MNCKSSQSLL YSTNQENYLA WYQQKPGQSP KLLIYWASTR  60
ESGVPDRFTG SGSGTDFTLT ISSVKAEDLA VYYCQQYET                         99

SEQ ID NO: 206          moltype = AA  length = 99
FEATURE                 Location/Qualifiers
source                  1..99
                        mol_type = protein
                        organism = synthetic construct
SEQUENCE: 206
DIVMSQSPSS LAVSVGEKVT MSCKSSQSPL YSNNQKNYLA WYQQKPGQSP KLLIYWASTR  60
ESGVPDRFTG SGSGTDFTLT ISSVKAEDLA VYYCQQYET                         99

SEQ ID NO: 207          moltype = AA  length = 99
FEATURE                 Location/Qualifiers
source                  1..99
                        mol_type = protein
                        organism = synthetic construct
SEQUENCE: 207
DIVMSQSPSS LVVSVGEKVT MSCKSSQSLL YSSNQKNYLA WYQQKPGQSP KLLIYWASTR  60
ESGVPDRFTG SGSGTDFTLT ISSVKAEDQA VYYCQQYET                         99

SEQ ID NO: 208          moltype = AA  length = 99
FEATURE                 Location/Qualifiers
source                  1..99
                        mol_type = protein
                        organism = synthetic construct
SEQUENCE: 208
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYYK                         99
```

```
SEQ ID NO: 209         moltype = AA  length = 99
FEATURE                Location/Qualifiers
source                 1..99
                       mol_type = protein
                       organism = synthetic construct
SEQUENCE: 209
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYEM                         99

SEQ ID NO: 210         moltype = AA  length = 99
FEATURE                Location/Qualifiers
source                 1..99
                       mol_type = protein
                       organism = synthetic construct
SEQUENCE: 210
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYET                         99

SEQ ID NO: 211         moltype = AA  length = 99
FEATURE                Location/Qualifiers
source                 1..99
                       mol_type = protein
                       organism = synthetic construct
SEQUENCE: 211
DIVMSQSPSS LAVSVGEKVT MSCKSSQSPL YSTNQKNYLA WYQQKPGQSP KLLIYWASTR  60
ESGVPDRFTG SGSGTDFTLT ISSVKAEDLA VYYCQQYET                         99

SEQ ID NO: 212         moltype = AA  length = 99
FEATURE                Location/Qualifiers
source                 1..99
                       mol_type = protein
                       organism = synthetic construct
SEQUENCE: 212
DIVMSQSPSS LAVSVGEKVT MSCKSSQSLL YSSDQENYLA WYQRKPGQSP KLLIYWASTR  60
ESGVPDRFTG SGSGTDFTLT ISSVKAEDLA VYYCQQYET                         99

SEQ ID NO: 213         moltype = AA  length = 99
FEATURE                Location/Qualifiers
source                 1..99
                       mol_type = protein
                       organism = synthetic construct
SEQUENCE: 213
DIVMSQSPSS LAVSVGEKVT MSCKSSQSLL YSSNQENYLA WYQQKPGQSP KLLIYWASTR  60
ESGVPDRFTG SGSGTDFTLT ISSVKAEDLA VYYCQQYYK                         99

SEQ ID NO: 214         moltype = AA  length = 99
FEATURE                Location/Qualifiers
source                 1..99
                       mol_type = protein
                       organism = synthetic construct
SEQUENCE: 214
DIVMSQSPSS LAVSVGEKVT MSCKSSQSLL YSSDQKNYLA WYQQKPGQSP KLLIYWASAR  60
ESGVPDRFTG SGSGTDFTLT ISSVKAEDLA VYYCQQYEM                         99

SEQ ID NO: 215         moltype = AA  length = 99
FEATURE                Location/Qualifiers
source                 1..99
                       mol_type = protein
                       organism = synthetic construct
SEQUENCE: 215
DIVMSQSPSS LAVSVGEKVT MSCKSSQSLL YSSNQENYLA WYQQKPGQSP KLLIYWASTR  60
ESGVPDRFTG SGSGTDFTLT ISSVKAEDLA VYYCQQYYK                         99

SEQ ID NO: 216         moltype = AA  length = 99
FEATURE                Location/Qualifiers
source                 1..99
                       mol_type = protein
                       organism = synthetic construct
SEQUENCE: 216
DIVMSQSPSS LAVSVGEKVT MSCKSSQSLL DSSNQKNYLA WYQQKPGQSP KLLIYWASTR  60
ESGVPDRFTG SESGTDFTLT ISSVKAEDLA VYYCQQYYK                         99

SEQ ID NO: 217         moltype = AA  length = 99
FEATURE                Location/Qualifiers
source                 1..99
                       mol_type = protein
                       organism = synthetic construct
SEQUENCE: 217
```

```
DIVMSQSPSS LGVSVGEKVT MSCKSSQSLL DSCNQENYLA WYQQKPGQSP KLLIYWASTR  60
ESGVPDRFTG SGSGTDFTLT ISSVKAEDLA VYYCQQYYK                         99

SEQ ID NO: 218          moltype = DNA  length = 24
FEATURE                 Location/Qualifiers
source                  1..24
                        mol_type = other DNA
                        organism = synthetic construct
SEQUENCE: 218
gayattgtgm tsacmcarwc tmca                                         24

SEQ ID NO: 219          moltype = AA  length = 99
FEATURE                 Location/Qualifiers
source                  1..99
                        mol_type = protein
                        organism = synthetic construct
SEQUENCE: 219
DIVMSQSPSS LAVSVGEKVT MSCKSSQSLL YSSNQENYLA WYQQKPGQSP KLLIYWASTR  60
ESGVPDRFTG SGSGTDFTLT ISSVKAEDLA VYYCQQYYS                         99

SEQ ID NO: 220          moltype = AA  length = 99
FEATURE                 Location/Qualifiers
source                  1..99
                        mol_type = protein
                        organism = synthetic construct
SEQUENCE: 220
DIVMSQSPSS LAVSVGEKIT MSCKSSQSLL YGSNQKNYLA WYQQKPGQSP KLLIYWASTW  60
ESGVPDRFTG SGSGTDFTLT ISSVKAEDLA VYYCQQYYK                         99

SEQ ID NO: 221          moltype = AA  length = 99
FEATURE                 Location/Qualifiers
source                  1..99
                        mol_type = protein
                        organism = synthetic construct
SEQUENCE: 221
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYET                         99

SEQ ID NO: 222          moltype = AA  length = 99
FEATURE                 Location/Qualifiers
source                  1..99
                        mol_type = protein
                        organism = synthetic construct
SEQUENCE: 222
DIVMSQSPSS LAVSVGEKVT MSCKSSQSLL YSSNEENYLA WYQQKPGQSP KLLIYWASTR  60
ESGAPDRFTG SGSGTDFTLT ISSVKAEDLA VYYCQQYYK                         99

SEQ ID NO: 223          moltype = AA  length = 99
FEATURE                 Location/Qualifiers
source                  1..99
                        mol_type = protein
                        organism = synthetic construct
SEQUENCE: 223
DIVMSQSPSS LAVSVGEKVT MSCKSSQSLL YSSNQKNYLA WYQQKPGQSP KLLIYWASTR  60
ESGVPDRFTG SGSGTDFTLT ISSVKTEDLA VYYCQQYYK                         99

SEQ ID NO: 224          moltype = DNA  length = 31
FEATURE                 Location/Qualifiers
source                  1..31
                        mol_type = other DNA
                        organism = synthetic construct
SEQUENCE: 224
ctcttcctcc tgtcagtaac tgaaggtgtc c                                 31

SEQ ID NO: 225          moltype = AA  length = 99
FEATURE                 Location/Qualifiers
source                  1..99
                        mol_type = protein
                        organism = synthetic construct
SEQUENCE: 225
DIVMSQSPSS LAVSVGEKVT MSCKSSQSLL YSSNEKNYLA WYQQKPGQSP KLLIYWASTR  60
ESGVPDRFTG SGSGTDFTLT ISSVKAEDLA VYYCQQYET                         99

SEQ ID NO: 226          moltype = AA  length = 99
FEATURE                 Location/Qualifiers
source                  1..99
                        mol_type = protein
                        organism = synthetic construct
SEQUENCE: 226
```

```
DIVMSQSPSS LAVSVGEKVT MSCKSSQSLL YSSNQKNYLA WYQQKPGQSP KLLIYWASTR  60
ESGVPDRFTA SGSGTDFTLT ISSVKAEDLA LYYCQQYYK                         99

SEQ ID NO: 227         moltype = AA  length = 99
FEATURE                Location/Qualifiers
source                 1..99
                       mol_type = protein
                       organism = synthetic construct
SEQUENCE: 227
DIVMSQSPSS LAVSIGEKVT MSCKSSQSLL YSSNQKNYLA WYQQKPGQSP KLLIYWASTR  60
ESGVPDRFTG SGSGTDFTLT ISSVKAEDLA VYYCQQYET                         99

SEQ ID NO: 228         moltype = AA  length = 99
FEATURE                Location/Qualifiers
source                 1..99
                       mol_type = protein
                       organism = synthetic construct
SEQUENCE: 228
DIVMSQSPSS LAVSVGEKVT MSCKSSQSLL YSSNQENYLA WYQQKPGQSP KLLIYWASTR  60
ESGVPDRFTG SGSGTDFTLT ISSVKAEDLA VYYCQQYYK                         99

SEQ ID NO: 229         moltype = AA  length = 99
FEATURE                Location/Qualifiers
source                 1..99
                       mol_type = protein
                       organism = synthetic construct
SEQUENCE: 229
DIVMSQSPSS LAVSVGEKVT MNCKSSQSLL YSSNQENYLA WYQQKPGQSP KLLIYWASTR  60
ESGVPDRFTG SGSGTDFTLT ISSVKAEDLA VYYCQQYYK                         99

SEQ ID NO: 230         moltype = AA  length = 99
FEATURE                Location/Qualifiers
source                 1..99
                       mol_type = protein
                       organism = synthetic construct
SEQUENCE: 230
DIVMSQSPSS LAVSVGEKVT MSCKSSQSLL YSSNQKNYLA WYQQKPGQSP KLLIYWASSR  60
ESGVPDRFTG SGSGTDFTLT ISSVKAEDLA VYYCQQYET                         99

SEQ ID NO: 231         moltype = AA  length = 99
FEATURE                Location/Qualifiers
source                 1..99
                       mol_type = protein
                       organism = synthetic construct
SEQUENCE: 231
DIVMSQSPSS LAVSVGEKVT MSCKSSQNLL YSSNEENYLA WYQQKPGQSP KLLIYWASTR  60
ESGVPDRFTG SGSGTDFTLT ISSVKVEDLA VYYCQQYET                         99

SEQ ID NO: 232         moltype = AA  length = 99
FEATURE                Location/Qualifiers
source                 1..99
                       mol_type = protein
                       organism = synthetic construct
SEQUENCE: 232
DIVMSQSPSS LAVSVGEKVT MSCKSSQSLF YSSNQKNYLA WYQQKPGQSP KLLIYWASSR  60
ESGVPDRFTG SGSGTDFTLT ISSVKAEDLA VYYCQQYET                         99

SEQ ID NO: 233         moltype = AA  length = 99
FEATURE                Location/Qualifiers
source                 1..99
                       mol_type = protein
                       organism = synthetic construct
SEQUENCE: 233
DIVMSQSPSS LAVSVGEKVT LSCKSSQSLS YSNNEKNYLA WYQQKPGQSP KLLIYWASTR  60
ESGVPDRFTG SGSGTDFTLT ISSVKAEDLA VYYCQQYYK                         99

SEQ ID NO: 234         moltype = AA  length = 99
FEATURE                Location/Qualifiers
source                 1..99
                       mol_type = protein
                       organism = synthetic construct
SEQUENCE: 234
DIVMSQSPSS LAVSIGEKVT LSCKSSQSLL YSSNQKNYLA WYQQKPGQSP KLLIYWASTR  60
ESGVPDRFIG SGSGTDFTLT ISSVEAEDLA VYYCQQYET                         99

SEQ ID NO: 235         moltype = AA  length = 99
FEATURE                Location/Qualifiers
source                 1..99
                       mol_type = protein
```

```
                        organism = synthetic construct
SEQUENCE: 235
DIVMSQSPSP LAVSVGEKVT MSCKSSQNLL YSSNEENYLA WYQQKPGQSP KLLIYWASTR  60
ESGVPDRFTG SGSGTDFTLT ISSVKAEDLA VYYCQQYET                        99

SEQ ID NO: 236          moltype = AA  length = 99
FEATURE                 Location/Qualifiers
source                  1..99
                        mol_type = protein
                        organism = synthetic construct
SEQUENCE: 236
DIVMSQSPSS LAVSVGEKVT MSCKSSQSLL YSSNENNYLA WYQQKPGQSP KLLIYWASTR  60
ESGVPDRFTG SGSGTDFTLT ISSVKAEDLV VYYCQQYET                        99

SEQ ID NO: 237          moltype = AA  length = 99
FEATURE                 Location/Qualifiers
source                  1..99
                        mol_type = protein
                        organism = synthetic construct
SEQUENCE: 237
DIVMSQSPSS LAVSVGEKVT MNCKSSQNVL YSSDQKNYLA WYQQKPGQSP KLLIYWASIR  60
ESGVPDRFTG SGSGTDFTLT ISSVKAEDLA VYYCQQYYK                        99

SEQ ID NO: 238          moltype = AA  length = 99
FEATURE                 Location/Qualifiers
source                  1..99
                        mol_type = protein
                        organism = synthetic construct
SEQUENCE: 238
DIVMSQSPSS LAVSVGEKVT MSCKSSQSLL YSSNQKNYLA WYQQKPGQSP KLLIYWASSR  60
ESGVPERFTG SGSGTDFTLT ISSVKTEDLA VYYCQQYET                        99

SEQ ID NO: 239          moltype = DNA  length = 24
FEATURE                 Location/Qualifiers
source                  1..24
                        mol_type = other DNA
                        organism = synthetic construct
SEQUENCE: 239
tgaggagacg gtgaccaggg tgcc                                        24

SEQ ID NO: 240          moltype = AA  length = 99
FEATURE                 Location/Qualifiers
source                  1..99
                        mol_type = protein
                        organism = synthetic construct
SEQUENCE: 240
DIVMSQSPSS LAVSVGEKVT MSCKSSQNLL YSSNEENYLA WYQQKPGQSP KLLIYWASTR  60
ESGVPDRFTG SGSGTDFTLT ISSVKVEDLA VYYCQQYET                        99

SEQ ID NO: 241          moltype = AA  length = 99
FEATURE                 Location/Qualifiers
source                  1..99
                        mol_type = protein
                        organism = synthetic construct
SEQUENCE: 241
DIVMSQSPSS LAVSVGEKVT MSCKSSLSLL DNNNQKNYLA WYQQKPGQSP KLLIYWAFIR  60
ESGVPDRFTG SGSGTDFTLT ISSVKAEDLA VYYCQQYYQ                        99

SEQ ID NO: 242          moltype = AA  length = 99
FEATURE                 Location/Qualifiers
source                  1..99
                        mol_type = protein
                        organism = synthetic construct
SEQUENCE: 242
DIVMSQSPSS LTVSVGEKVT MSCKSSLSLL DNNNQKNYLA WYQQKPGQSP KLLIYWASSR  60
ESGVPDRFTG SGSGTDFTLT ISSVKAEDLA VYYCQQYYQ                        99

SEQ ID NO: 243          moltype = AA  length = 99
FEATURE                 Location/Qualifiers
source                  1..99
                        mol_type = protein
                        organism = synthetic construct
SEQUENCE: 243
DIVMSQSPSS LVVSLGEKVT LSCKSSQSLL YSSNQENYLA WYQQKPGQSP KLLIYSASTR  60
ESGVPDRFTG SGSGTDFTLT ISSVKAEDLA VYYCQQYET                        99

SEQ ID NO: 244          moltype = DNA  length = 23
FEATURE                 Location/Qualifiers
source                  1..23
```

```
                        mol_type = other DNA
                        organism = synthetic construct
SEQUENCE: 244
caggtgcagc tggtgcagtc tgg                                          23

SEQ ID NO: 245          moltype = AA  length = 99
FEATURE                 Location/Qualifiers
source                  1..99
                        mol_type = protein
                        organism = synthetic construct
SEQUENCE: 245
DIVMSQSPSS LAVSVGEKVT MSCKSSQSLL YSSNQKNYLA WYQQKPGQSP KLLIYWASTR  60
ESGVPDRFTG SGSGTDFTLT ISSVKAEDLA VYYCQQYWT                         99

SEQ ID NO: 246          moltype = AA  length = 95
FEATURE                 Location/Qualifiers
source                  1..95
                        mol_type = protein
                        organism = synthetic construct
SEQUENCE: 246
QIVLSQSPAI LSASPGEKVT MTCRASSSVS YMHWYQQKPG SSPKPWIYAT SNLASGVPAR  60
FSGSGSGTSY SLTISRVEAE DAATYYCQQW SSNPP                             95

SEQ ID NO: 247          moltype = AA  length = 92
FEATURE                 Location/Qualifiers
source                  1..92
                        mol_type = protein
                        organism = synthetic construct
SEQUENCE: 247
QIVLSQSPAI LSASPGEKVT MTCRASSSVS YMHWYQQKPG SSPKPWIYAT SNLASGVPAR  60
FSGSGSGTSY SLTISRVEAE DAATYYCQQW ST                                92

SEQ ID NO: 248          moltype = AA  length = 93
FEATURE                 Location/Qualifiers
source                  1..93
                        mol_type = protein
                        organism = synthetic construct
SEQUENCE: 248
DIQMTQSPAS LSVSVGETVT ITCRASENIY SNLAWYQQKQ GKSPQLLVYA ATNLADGVPS  60
RFSGSGSGTQ YSLKINSLQS EDFGSYYCQH FWG                               93

SEQ ID NO: 249          moltype = AA  length = 93
FEATURE                 Location/Qualifiers
source                  1..93
                        mol_type = protein
                        organism = synthetic construct
SEQUENCE: 249
DIQMTQSPAS LSVSVGETVT ITCRASENIY SNLAWYQQKQ GKSPQLLVYA ATNLADGVPS  60
RFSGSGSGTQ YSLKINSLQS EDFGSYYCQH FYT                               93

SEQ ID NO: 250          moltype = AA  length = 93
FEATURE                 Location/Qualifiers
source                  1..93
                        mol_type = protein
                        organism = synthetic construct
SEQUENCE: 250
DIQMTQSPAS LSASVGETVT ITCRASENIY SYLAWYQQKQ GKSPQLLVYN AKTLAEGVPS  60
RFSGSGSGTQ FSLKINSLQP EDFGSYYCQH HYG                               93

SEQ ID NO: 251          moltype = AA  length = 93
FEATURE                 Location/Qualifiers
source                  1..93
                        mol_type = protein
                        organism = synthetic construct
SEQUENCE: 251
DIVMSQSPAS LSASVGETVT ITCRASENIY SYLAWYQQKQ GKSPQLLVYN AKTLAEGVPS  60
RFSGSGSGTQ FSLKINSLQP EDFGSYYCQH HYG                               93

SEQ ID NO: 252          moltype = AA  length = 118
FEATURE                 Location/Qualifiers
source                  1..118
                        mol_type = protein
                        organism = synthetic construct
SEQUENCE: 252
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARGK NSDYNWDFQH WGQGTLVT    118

SEQ ID NO: 253          moltype = AA  length = 118
FEATURE                 Location/Qualifiers
```

```
source                  1..118
                        mol_type = protein
                        organism = synthetic construct
SEQUENCE: 253
QVQLVQSGAE VKKPGASVKV SCKASGYTFT GYYMNWVRQA PGQGLEWMGW INPNSGGTNY  60
AQKFQGRVTM TRDTSISTAY MELSRLRSDD TAVYYCARGK NSDYNWDFQH WGQGTLVT    118

SEQ ID NO: 254          moltype = AA  length = 118
FEATURE                 Location/Qualifiers
source                  1..118
                        mol_type = protein
                        organism = synthetic construct
SEQUENCE: 254
QVQLVQSGAE VKKPGASVKV SCKASGYTFT GYYIHWVRQA PGQGLEWMGW INPNRGGTNY  60
CQKFQGRVTM TRDTSISTAY MELSRLRSDD TAVYYCARGI NSDYTWDFQH WGQGTLVT    118

SEQ ID NO: 255          moltype = AA  length = 115
FEATURE                 Location/Qualifiers
source                  1..115
                        mol_type = protein
                        organism = synthetic construct
SEQUENCE: 255
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARKI SGDYSQDWGQ GTLVT       115

SEQ ID NO: 256          moltype = AA  length = 102
FEATURE                 Location/Qualifiers
source                  1..102
                        mol_type = protein
                        organism = synthetic construct
SEQUENCE: 256
EIVLTQSPGT LSLSPGERAT LSCRASQSVS SSYLAWYQQK PGQAPRLLIY GASSRATGIP  60
DRFSSGSGTD FTLTISRLEP EDFAVYYCQQ YEFFGQGTKL EI                     102

SEQ ID NO: 257          moltype = AA  length = 107
FEATURE                 Location/Qualifiers
source                  1..107
                        mol_type = protein
                        organism = synthetic construct
SEQUENCE: 257
DIVMSQSPSS LAVSVGEKVT MSCKSSQSLL YSSNQKNYLA WYQQKPGQSP KLLIYWASTR  60
ESGVPDRFTS GSGTDFTLTI SRVKAEDLAV YYCQQYEMFG GGTKLEI                107

SEQ ID NO: 258          moltype = AA  length = 107
FEATURE                 Location/Qualifiers
source                  1..107
                        mol_type = protein
                        organism = synthetic construct
SEQUENCE: 258
DIVMSQSPSS LAVSVGEKVT MSCKSSQSLL YSSNQKNYLA WYQQKPGQSP KLLIYWASTR  60
ESGVPDRFTS GSGTDFTLTI SRVKAEDLAV YYCQQYETLG SGTKLEI                107

SEQ ID NO: 259          moltype = AA  length = 107
FEATURE                 Location/Qualifiers
source                  1..107
                        mol_type = protein
                        organism = synthetic construct
SEQUENCE: 259
DIVMTQSPDS LAVSLGERAT INCKSSQSVL YSSNNKNYLA WYQQKPGQPP KLLIYWASTR  60
RSGVPDRFSS GSGTDFTLTI SRLQAEDVAV YYCQQYYSFG GGTKLEI                107

SEQ ID NO: 260          moltype = AA  length = 16
FEATURE                 Location/Qualifiers
source                  1..16
                        mol_type = protein
                        organism = synthetic construct
SEQUENCE: 260
GGNSNNESEI FRPGGG                                                  16

SEQ ID NO: 261          moltype = AA  length = 18
FEATURE                 Location/Qualifiers
source                  1..18
                        mol_type = protein
                        organism = synthetic construct
SEQUENCE: 261
GGNITNETTT ETFRPGGG                                                18

SEQ ID NO: 262          moltype = AA  length = 16
FEATURE                 Location/Qualifiers
```

```
source                  1..16
                        mol_type = protein
                        organism = synthetic construct
SEQUENCE: 262
GGANNTSTET FRPGGG                                                    16

SEQ ID NO: 263          moltype = AA  length = 16
FEATURE                 Location/Qualifiers
source                  1..16
                        mol_type = protein
                        organism = synthetic construct
SEQUENCE: 263
GGNNNSTNET FRPGGG                                                    16

SEQ ID NO: 264          moltype = AA  length = 15
FEATURE                 Location/Qualifiers
source                  1..15
                        mol_type = protein
                        organism = synthetic construct
SEQUENCE: 264
GGVNGTRETF RPGGG                                                     15

SEQ ID NO: 265          moltype = DNA  length = 21
FEATURE                 Location/Qualifiers
source                  1..21
                        mol_type = other DNA
                        organism = synthetic construct
SEQUENCE: 265
tgctgctgct ctgggttcca g                                              21

SEQ ID NO: 266          moltype = DNA  length = 21
FEATURE                 Location/Qualifiers
source                  1..21
                        mol_type = other DNA
                        organism = synthetic construct
SEQUENCE: 266
attwtcagct tcctgctaat c                                              21

SEQ ID NO: 267          moltype = DNA  length = 21
FEATURE                 Location/Qualifiers
source                  1..21
                        mol_type = other DNA
                        organism = synthetic construct
SEQUENCE: 267
ttttgctttt ctggattyca g                                              21

SEQ ID NO: 268          moltype = DNA  length = 21
FEATURE                 Location/Qualifiers
source                  1..21
                        mol_type = other DNA
                        organism = synthetic construct
SEQUENCE: 268
tcgtgttkct stggttgtct g                                              21

SEQ ID NO: 269          moltype = DNA  length = 20
FEATURE                 Location/Qualifiers
source                  1..20
                        mol_type = other DNA
                        organism = synthetic construct
SEQUENCE: 269
atggaatcac agrcycwggt                                                20

SEQ ID NO: 270          moltype = DNA  length = 21
FEATURE                 Location/Qualifiers
source                  1..21
                        mol_type = other DNA
                        organism = synthetic construct
SEQUENCE: 270
tcttgttgct ctggttycca g                                              21

SEQ ID NO: 271          moltype = DNA  length = 24
FEATURE                 Location/Qualifiers
source                  1..24
                        mol_type = other DNA
                        organism = synthetic construct
SEQUENCE: 271
cagttcctgg ggctcttgtt gttc                                           24

SEQ ID NO: 272          moltype = DNA  length = 19
```

-continued

```
FEATURE                 Location/Qualifiers
source                  1..19
                        mol_type = other DNA
                        organism = synthetic construct
SEQUENCE: 272
ctcactagct cttctcctc                                            19

SEQ ID NO: 273          moltype = AA  length = 121
FEATURE                 Location/Qualifiers
source                  1..121
                        mol_type = protein
                        organism = synthetic construct
SEQUENCE: 273
QVQLVQSGAE VKKPGASVKV SCKASGYTFT GYYMHWVRQA PGQGLEWMGW INPNSGGTNY  60
AQKFQGRVTM TRDTSISTAY MELSRLRSDD TAVYYCARGK NSDYNWDFQH WGQGTLVTVS  120
S                                                                  121

SEQ ID NO: 274          moltype = AA  length = 405
FEATURE                 Location/Qualifiers
source                  1..405
                        mol_type = protein
                        organism = synthetic construct
SEQUENCE: 274
VWKEAKTTLF CASDAKAYEK ECHNVWATHA CVPTDPNPQE VVLENVTENF NMWKNDMVDQ  60
MQEDVISIWD QCLKPCVKLT NTSTLTQACP KVTFDPIPIH YCAPAGYAIL KCNNKTFNGK  120
GPCNNVSTVQ CTHGIKPVVS TQLLLNGSLA EEEIVIRSKN LRDNAKIIIV QLNKSVEIVC  180
TRPNNGGSGS GGDIRQAYCN ISGRNWSEAV NQVKKKLKEH FPHKNISFQS SSGGDLEITT  240
HSFNCGGEFF YCNTSGLFND TISNATIMLP CRIKQIINMW QEVGKAIYAP PIKGNITCKS  300
DITGLLLLRD GGDTTDNTEI FRPSGGDMRD NWRSELYKYK VVEIKPLGSS KKQGDADVCG  360
EVAYIQSVVS DCHVPTAELR TLLEIRKLFL EIQKLKVELQ GLSKE                  405

SEQ ID NO: 275          moltype = AA  length = 99
FEATURE                 Location/Qualifiers
source                  1..99
                        mol_type = protein
                        organism = synthetic construct
SEQUENCE: 275
DIVMTQSPSS LVVSVGEKVT MSCKSSLSLL DNNNQKNYLA WYQQKPGQSP KLLIYWAFIR  60
ESGVPDRFTG SGSGTDFTLT ISSVKAEDLA VYYCQQYYQ                         99
```